United States Patent
Dyckman et al.

(10) Patent No.: US 11,447,466 B2
(45) Date of Patent: *Sep. 20, 2022

(54) SUBSTITUTED INDOLE COMPOUNDS USEFUL AS INHIBITORS OF TLR7/8/9

(71) Applicant: BRISTOL-MYERS SQUIBB COMPANY, Princeton, NJ (US)

(72) Inventors: Alaric J. Dyckman, Lawrenceville, NJ (US); Dharmpal S. Dodd, Princeton, NJ (US); Tasir Shamsul Haque, Yardley, PA (US); Brian K. Whiteley, Lebanon, NJ (US); John L. Gilmore, Yardley, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 12 days.

This patent is subject to a terminal disclaimer.

(21) Appl. No.: 16/635,593

(22) PCT Filed: Aug. 3, 2018

(86) PCT No.: PCT/US2018/045082
§ 371 (c)(1),
(2) Date: Jan. 31, 2020

(87) PCT Pub. No.: WO2019/028302
PCT Pub. Date: Feb. 7, 2019

(65) Prior Publication Data
US 2020/0239437 A1     Jul. 30, 2020

Related U.S. Application Data

(60) Provisional application No. 62/541,335, filed on Aug. 4, 2017.

(51) Int. Cl.
*A61K 31/4545*     (2006.01)
*A61P 29/00*      (2006.01)
(Continued)

(52) U.S. Cl.
CPC ......... *C07D 401/14* (2013.01); *C07D 405/14* (2013.01); *C07D 409/14* (2013.01)

(58) Field of Classification Search
CPC .. C07D 401/14; C07D 405/14; C07D 409/14; C07D 413/14; A61P 29/00; A61P 37/00; A61K 31/4545
See application file for complete search history.

(56) References Cited

U.S. PATENT DOCUMENTS 6,867,200 B1   3/2005   Allen et al.
7,410,975 B2   8/2008   Lipford et al.
(Continued)

FOREIGN PATENT DOCUMENTS

EP    2738172 A1       6/2014
WO    WO2006113458 A1  10/2006
(Continued)

OTHER PUBLICATIONS

International Preliminary Report on Patentability No. PCT/US2018/045082, dated Feb. 4, 2020.
(Continued)

*Primary Examiner* — Brenda L Coleman
(74) *Attorney, Agent, or Firm* — Gary Greenblatt

(57) ABSTRACT

Disclosed are compounds of Formula (I) or a salt thereof, wherein: Y is Formula (II), or Formula (III); $R_1$, $R_2$, $R_{2a}$, $R_{2b}$, $R_{2c}$, $R_3$, $R_4$, $R_5$, m, and n are defined herein. Also disclosed are methods of using such compounds as inhibitors of signaling through Toll-like receptor 7, or 8, or 9, and pharmaceutical compositions comprising such compounds. These compounds are useful in treating inflammatory and autoimmune diseases.

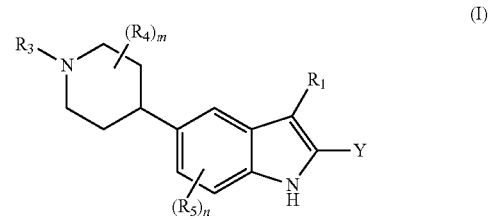

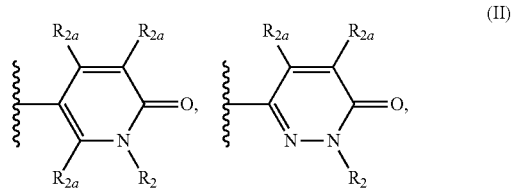

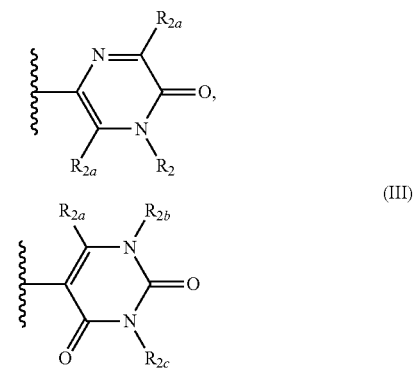

7 Claims, No Drawings

(51) Int. Cl.
  *A61P 37/00*   (2006.01)
  *C07D 401/14*  (2006.01)
  *C07D 405/14*  (2006.01)
  *C07D 409/14*  (2006.01)
  *C07D 413/14*  (2006.01)

(56) References Cited

U.S. PATENT DOCUMENTS

| | | |
|---|---|---|
| 8,138,187 B2 | 3/2012 | Zemolka et al. |
| 8,354,400 B2 | 1/2013 | Zheng et al. |
| 9,126,996 B2 | 9/2015 | Lipford et al. |
| 9,126,999 B2 | 9/2015 | Bolvin et al. |
| 9,241,991 B2 | 1/2016 | Ji et al. |
| 9,353,115 B2 | 5/2016 | Lipford et al. |
| 9,376,398 B2 | 6/2016 | Hori et al. |
| 9,428,495 B2 | 8/2016 | Carlson et al. |
| 9,643,967 B2 | 5/2017 | Koul et al. |
| 2006/0235037 A1* | 10/2006 | Purandare ............ C07D 401/14 514/278 |
| 2010/0160314 A1 | 6/2010 | Lipford et al. |
| 2011/0009444 A1 | 1/2011 | Dubois et al. |
| 2011/0015219 A1 | 1/2011 | Trawick et al. |
| 2011/0275631 A1 | 11/2011 | Abeywardane et al. |
| 2013/0045986 A1 | 2/2013 | Nagarathnam et al. |
| 2014/0066432 A1 | 3/2014 | Howbert et al. |
| 2014/0088085 A1 | 3/2014 | Burgess et al. |
| 2014/0242121 A1 | 8/2014 | Lipford et al. |
| 2016/0096833 A1 | 4/2016 | Emmitte et al. |
| 2021/0087174 A1* | 3/2021 | Dyckman ............ C07D 401/10 |

FOREIGN PATENT DOCUMENTS

| | | |
|---|---|---|
| WO | WO2007115306 A2 | 10/2007 |
| WO | WO2008065198 A1 | 6/2008 |
| WO | WO2008152471 A1 | 12/2008 |
| WO | WO2009030996 A1 | 3/2009 |
| WO | WO2010149769 A1 | 12/2010 |
| WO | WO2013010904 A1 | 1/2013 |
| WO | WO2013181579 A2 | 12/2013 |
| WO | WO2015088045 A1 | 6/2015 |
| WO | WO2016029077 A1 | 2/2016 |
| WO | WO2018005586 A1 | 1/2018 |
| WO | WO2018026620 A1 | 2/2018 |
| WO | WO2018049089 A1 | 3/2018 |

OTHER PUBLICATIONS

Kawai, Taro, et al., "The role of pattern-recognition receptors in innate immunity: update on Toll-like receptors", Nature Immunology, 2010, vol. 11, No. 5, pp. 373-384.

Lamphier, M. et al., "Novel Small Molecule Inhibitors of TLR7 and TLR9: Mechanism of Action and Efficacy in Vivo", Mol Pharmacol, 2014, 85:429-440.

Patra, Mahesh Chandra, et al., "Recent Progress in the Development of Toll-like Receptor (TLR) antagonists", Exp. Opin. on Therapeutic Patents, 2016, vol. 26, No. 6, 719-730.

Roy, et al., "Design and developmen of benzoxazole derivatives with toll-like receptor 9 antagonism", Eur J Med Chem, 2017, vol. 134, 334-347.

Sims, et al., "The IL-1 Family: Regulators of Immunity", Nature Rev. Immunol., 2010, 10, 89-102.

* cited by examiner

SUBSTITUTED INDOLE COMPOUNDS USEFUL AS INHIBITORS OF TLR7/8/9

CROSS REFERENCE TO RELATED APPLICATIONS

This application is a national phase application under 35 U.S.C. § 371 of International Patent Application No. PCT/US2018/045082, filed Aug. 3, 2018, which claims priority to U.S. Provisional Application Ser. No. 62/541,335, filed Aug. 4, 2017, the contents of which are specifically incorporated fully herein by reference.

The present invention generally relates to substituted indole compounds useful as inhibitors of signaling through Toll-like receptor 7, 8, or 9 (TLR7, TLR8, TLR9) or combinations thereof. Provided herein are substituted indole compounds, compositions comprising such compounds, and methods of their use. The invention further pertains to pharmaceutical compositions containing at least one compound according to the invention that are useful for the treatment of conditions related to TLR modulation, such as inflammatory and autoimmune diseases, and methods of inhibiting the activity of TLRs in a mammal.

Toll/IL-1 receptor family members are important regulators of inflammation and host resistance. The Toll-like receptor family recognizes molecular patterns derived from infectious organisms including bacteria, fungi, parasites, and viruses (reviewed in Kawai, T. et al., Nature Immunol., 11:373-384 (2010)). Ligand binding to the receptor induces dimerization and recruitment of adaptor molecules to a conserved cytoplasmic motif in the receptor termed the Toll/IL-1 receptor (TIR) domain. With the exception of TLR3, all TLRs recruit the adaptor molecule MyD88. The IL-1 receptor family also contains a cytoplasmic TIR motif and recruits MyD88 upon ligand binding (reviewed in Sims, J. E. et al., Nature Rev. Immunol., 10:89-102 (2010)).

Toll-like receptors (TLRs) are a family of evolutionarily conserved, transmembrane innate immune receptors that participate in the first-line defense. As pattern recognition receptors, the TLRs protect against foreign molecules, activated by pathogen associated molecular patterns (PAMPs), or from damaged tissue, activated by danger associated molecular patterns (DAMPs). A total of 13 TLR family members have been identified, 10 in human, that span either the cell surface or the endosomal compartment. TLR7-9 are among the set that are endosomally located and respond to single-stranded RNA (TLR7 and TLR8) or unmethylated single-stranded DNA containing cytosine-phosphate-guanine (CpG) motifs (TLR9).

Activation of TLR7/8/9 can initiate a variety of inflammatory responses (cytokine production, B cell activation and IgG production, Type I interferon response). In the case of autoimmune disorders, the aberrant sustained activation of TLR7/8/9 leads to worsening of disease states. Whereas overexpression of TLR7 in mice has been shown to exacerbate autoimmune disease, knockout of TLR7 in mice was found to be protective against disease in lupus-prone MRL/lpr mice. Dual knockout of TLR7 and 9 showed further enhanced protection.

As numerous conditions may benefit by treatment involving modulation of cytokines, IFN production and B cell activity, it is immediately apparent that new compounds capable of modulating TLR7 and/or TLR8 and/or TLR9 and methods of using these compounds could provide substantial therapeutic benefits to a wide variety of patients.

The present invention relates to a new class of substituted indole compounds found to be effective inhibitors of signaling through TLR7/8/9. These compounds are provided to be useful as pharmaceuticals with desirable stability, bioavailability, therapeutic index, and toxicity values that are important to their drugability.

SUMMARY OF THE INVENTION

The present invention provides compounds of Formula (I) that are useful as inhibitors of signaling through Toll-like receptor 7, 8, or 9 and are useful for the treatment of proliferative diseases, allergic diseases, autoimmune diseases and inflammatory diseases, or stereoisomers, tautomers, pharmaceutically acceptable salts, solvates or prodrugs thereof.

The present invention also provides pharmaceutical compositions comprising a pharmaceutically acceptable carrier and at least one of the compounds of the present invention or stereoisomers, tautomers, pharmaceutically acceptable salts, solvates, or prodrugs thereof.

The present invention also provides a method for inhibition of Toll-like receptor 7, 8, or 9 comprising administering to a host in need of such treatment a therapeutically effective amount of at least one of the compounds of the present invention or stereoisomers, tautomers, pharmaceutically acceptable salts, solvates, or prodrugs thereof.

The present invention also provides a method for treating proliferative, metabolic, allergic, autoimmune and inflammatory diseases, comprising administering to a host in need of such treatment a therapeutically effective amount of at least one of the compounds of the present invention or stereoisomers, tautomers, pharmaceutically acceptable salts, solvates, or prodrugs thereof.

The present invention provides a method for treating inflammatory and autoimmune diseases. Particular, inflammatory and autoimmune diseases include, but are not limited to, Crohn's disease, ulcerative colitis, asthma, graft versus host disease, allograft rejection, chronic obstructive pulmonary disease, rheumatoid arthritis, systemic lupus erythematosus, lupus nephritis, cutaneous lupus, psoriasis, adult onset Still's disease, systemic onset juvenile idiopathic arthritis, multiple sclerosis.

DETAILED DESCRIPTION

The first aspect of the present invention provides at least one compound of Formula (I):

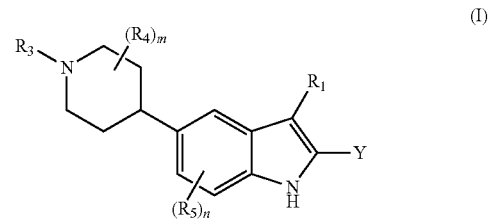

or a salt thereof, wherein:
Y is

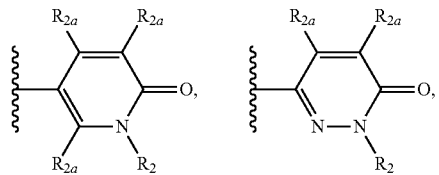

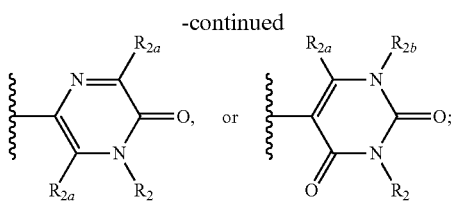

R₁ is H, Cl, —CN, C₁₋₄ alkyl, C₁₋₃ fluoroalkyl, C₁₋₃ hydroxy-fluoroalkyl, —CR_z=CH₂, C₃₋₆ cycloalkyl, —CH₂(C₃₋₆ cycloalkyl), —C(O)O(C₁₋₃ alkyl), or tetrahydropyranyl;

R₂ is C₁₋₆ alkyl, C₁₋₃ fluoroalkyl, C₁₋₆ hydroxyalkyl, C₁₋₃ aminoalkyl, —(CH₂)₀₋₄O(C₁₋₃ alkyl), C₃₋₆ cycloalkyl, —(CH₂)₁₋₃C(O)NR_xR_x, —CH₂(C₃₋₆ cycloalkyl), —CH₂(phenyl), tetrahydrofuranyl, tetrahydropyranyl, or phenyl;

each R₂ₐ is independently H, halo, —CN, —NR_xR_x, C₁₋₆ alkyl, C₁₋₃ fluoroalkyl, C₁₋₃ hydroxyalkyl, C₁₋₃ fluoroalkoxy, —(CH₂)₀₋₂O(C₁₋₃ alkyl), —(CH₂)₀₋₃C(O)NR_xR_x, —(CH₂)₁₋₃(C₃₋₆ cycloalkyl), —C(O)O(C₁₋₃ alkyl), —C(O)NR_x(C₁₋₃ alkyl), —CR_x=CR_xR_x, —CR_x=CH(C₃₋₆ cycloalkyl), —C(O)(pyrrolidinyl), or a cyclic group selected from pyrrolidinyl, pyrazolyl, phenyl, pyridinyl, and pyrimidinyl, each substituted with zero, 1, or 2 R_y;

each R_y is independently F, Cl, —CN, C₁₋₃ alkyl, C₁₋₃ fluoroalkyl, C₁₋₃ alkoxy, —NR_xC(O)(C₁₋₃ alkyl), —C(O)NR_xR_x, C₃₋₆ cycloalkyl, piperidinyl, or morpholinyl;

R₂ᵦ is R₂ or R₂ₐ;

R₂c is R₂ or R₂ₐ; provided that one of R₂ᵦ and R₂c is R₂, and the other of R₂ᵦ and R₂c is R₂ₐ; R₃ is (a) -L₁-A; or (b) H, C₁₋₆ alkyl, C₁₋₆ fluoroalkyl, C₁₋₆ hydroxyalkyl, C₁₋₃ cyanoalkyl, —(CH₂)₀₋₄O(C₁₋₃ alkyl), —(CH₂CH₂O)₂₋₃O(C₁₋₃ alkyl), —CH₂CH₂NR_xR_x, —CR_xR_xC(O)OH, —(CR_xR_x)₀₋₂C(O)NR_xR_x, —CH₂C(O)NR_x(C₁₋₃ alkyl), —CH₂C(O)NR_x(C₁₋₄ hydroxyalkyl), —(CR_xR_x)₀₋₂S(O)₂(C₁₋₃ alkyl), —C(O)(C₁₋₃ alkyl), —C(O)(C₁₋₃ fluoroalkyl), —C(O)CR_xR_xNR_xR_x, —C(O)(C₁₋₆ hydroxyalkyl), or —NR_xC(O)(C₁₋₃ alkyl);

L₁ is a bond, —(CR_xR_x)₁₋₂—, —(CR_xR_x)₁₋₂CR_x(OH)—, —(CR_xR_x)₁₋₂O—, —CR_xR_xC(O)—, —(CR_xR_x)₂NR_x(CR_xR_x)₀₋₁—, —CR_xR_xC(O)NR_x(CR_xR_x)₀₋₄—, —C(O)(CR_xR_x)₀₋₃—, —C(O)(CR_xR_x)₀₋₂NR_x(CR_xR_x)₀₋₂—, —C(O)(CR_xR_x)₀₋₂NR_x(CR_xR_x)₁₋₂CR_x(OH)—, —C(O)(CR_xR_x)₁₋₂C(O)NR_x—, —(CR_xR_x)₀₋₂C(O)NR_x(CR_xR_x)₁₋₂ CR_x(OH)—, —C(O)(CR_xR_x)₀₋₁O—, —C(O)(CR_xR_x)₁₋₂NHS(O)₂—, —C(O)NR_x(CR_xR_x)₁₋₂—, or —S(O)₂(CR_xR_x)₀₋₂—;

A is adamantanyl, azepanyl, azetidinyl, C₃₋₆ cycloalkyl, diazepanyl, dihydroinonyl, dihydropyrimidinonyl, dioxidoisothiazolidinyl, dioxidothiazinanyl, dioxotetrahydrothiophenyl, dioxotetrahydrothiopyranyl, dioxothiomorpholinyl, furanyl, imidazolyl, imidazolidinonyl, indolyl, isoquinolinyl, isoxazolyl, morpholinyl, morpholinonyl, naphthalenyl, oxazolidinonyl, oxadiazolyl, oxetanyl, oxazolyl, phenyl, piperidinyl, piperidinonyl, piperazinyl, piperazinonyl, pyrazinyl, pyrazolyl, pyrazolidinonyl, pyridazinonyl, pyridinonyl, pyridinyl, pyrimidinyl, pyrrolidinonyl, pyrrolidin-dionyl, pyrrolidinyl, pyrrolyl, quinolinyl, quinolizinonyl, tetrahydrofuranyl, tetrahydrofuranonyl, tetrahydropyranyl, tetrazolyl, thiadiazolyl, thiazolyl, or triazolyl, each substituted with zero, 1, or 2 R₃ₐ;

each R₃ₐ is independently F, Cl, —OH, —NH₂, C₁₋₃ alkyl, C₁₋₂ fluoroalkyl, or —C(O)NR_xR_x;

each R₄ is independently F, —OH, C₁₋₂ alkyl, or —OCH₃; or two R₄ attached to the same carbon atom form =O;

each R₅ is independently F, Cl, —CN, C₁₋₂ alkyl, C₁₋₂ fluoroalkyl, or —OCH₃;

each R_x is independently H or —CH₃;

R_z is H, C₁₋₂ alkyl, or C₁₋₂ fluoroalkyl;

m is zero, 1, 2, 3, or 4; and n is zero, 1, 2, or 3.

One embodiment provides a compound of Formula (I) or a salt thereof, wherein Y is

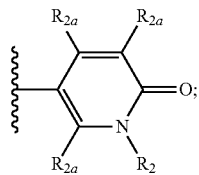

and R₁, R₂, R₂ₐ, R₃, R₄, R₅, m, and n are defined in the first aspect. Compounds of this embodiment have the structure of Formula (Ia):

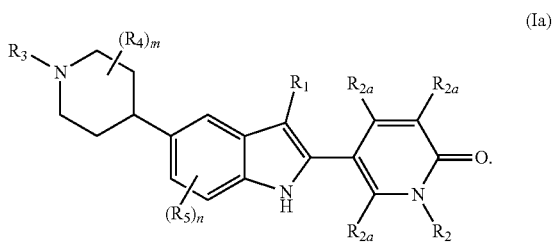

Included in this embodiment are compounds in which R₁ is —CH(CH₃)₂.

One embodiment provides a compound of Formula (I) or a salt thereof, wherein Y is

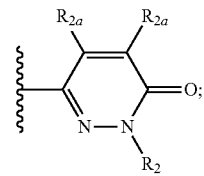

and R₁, R₂, R₂ₐ, R₃, R₄, R₅, m, and n are defined in the first aspect.

Compounds of this embodiment have the structure of Formula (Ib):

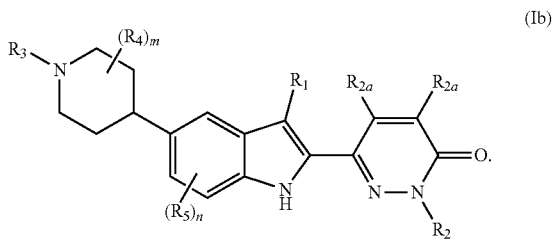

Included in this embodiment are compounds in which $R_1$ is —CH(CH$_3$)$_2$.

One embodiment provides a compound of Formula (I) or a salt thereof, wherein Y is

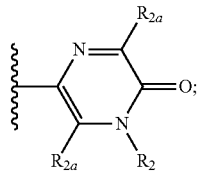

and $R_1$, $R_2$, $R_{2a}$, $R_3$, $R_4$, $R_5$, m, and n are defined in the first aspect. Compounds of this embodiment have the structure of Formula (Ic):

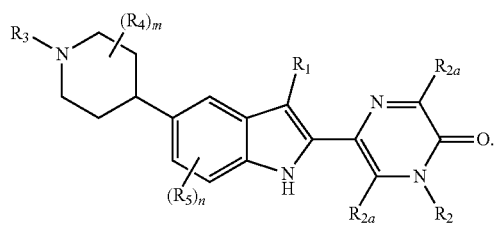

Included in this embodiment are compounds in which $R_1$ is —CH(CH$_3$)$_2$.

One embodiment provides a compound of Formula (I) or a salt thereof, wherein Y is

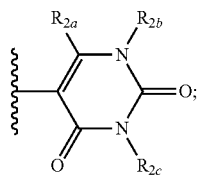

and $R_1$, $R_2$, $R_{2a}$, $R_3$, $R_4$, $R_5$, m, and n are defined in the first aspect. Compounds of this embodiment have the structure of Formula (Id):

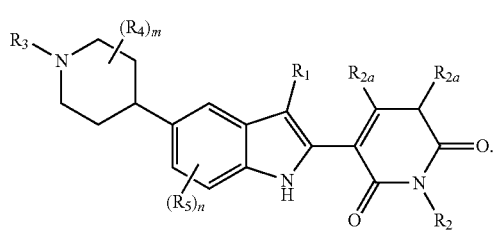

Included in this embodiment are compounds in which $R_1$ is —CH(CH$_3$)$_2$.

One embodiment provides a compound of Formula (I) or a salt thereof, wherein Y is

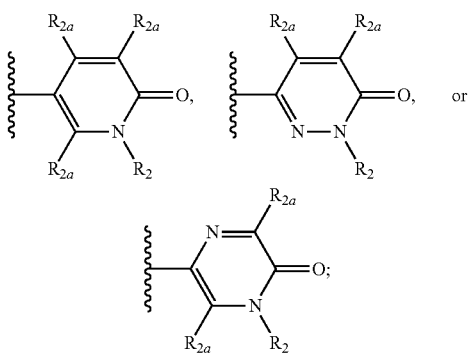

and $R_1$, $R_2$, $R_{2a}$, $R_3$, $R_4$, $R_5$, m, and n are defined in the first aspect. Included in this embodiment are compounds in which Y is

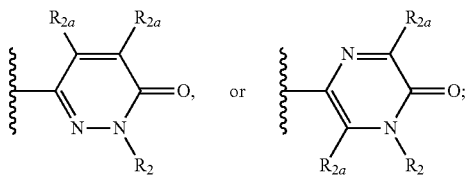

Also included in this embodiment are compounds in which $R_1$ is —CH(CH$_3$)$_2$.

One embodiment provides a compound of Formula (I) or a salt thereof, wherein Y is

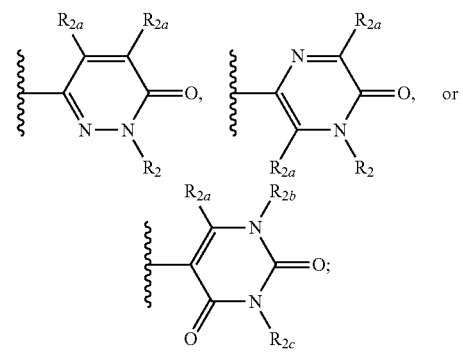

and $R_1$, $R_2$, $R_{2a}$, $R_{2b}$, $R_{2c}$, $R_3$, $R_4$, $R_5$, m, and n are defined in the first aspect. Included in this embodiment are compounds in which $R_1$ is —CH(CH$_3$)$_2$.

One embodiment provides a compound of Formula (I) or a salt thereof, wherein Y is

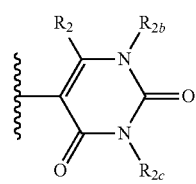

and $R_1$, $R_2$, $R_{2a}$, $R_{2b}$, $R_{2c}$, $R_3$, $R_4$, $R_5$, m, and n are defined in the first aspect. Included in this embodiment are compounds in which $R_{2b}$ is R. Also included in this embodiment are compounds in which $R_{2b}$ is $R_{2a}$. Additionally, included in this embodiment are compounds in which $R_1$ is —CH(CH$_3$)$_2$.

One embodiment provides a compound of Formula (I) or a salt thereof, wherein $R_1$ is H, Cl, —CN, $C_{1-4}$ alkyl, $C_{1-3}$ fluoroalkyl, $C_{1-3}$ hydroxy-fluoroalkyl, $C_{3-6}$ cycloalkyl, —CH$_2$($C_{3-6}$ cycloalkyl), —C(O)O($C_{1-3}$ alkyl), or tetrahydropyranyl; and $R_2$, $R_{2a}$, $R_{2b}$, $R_{2c}$, $R_3$, $R_4$, $R_5$, m, and n are defined in the first aspect. Included in this embodiment are compounds in which $R_1$ is H, $C_{1-4}$ alkyl, $C_{1-3}$ fluoroalkyl, or $C_{3-6}$ cycloalkyl. Also included in this embodiment are compounds in which $R_1$ is —CH$_2$CH$_3$ or —CH(CH$_3$)$_2$. Additionally, included in this embodiment are compounds in which $R_1$ is —CH(CH$_3$)$_2$.

One embodiment provides a compound of Formula (I) or a salt thereof, wherein $R_2$ is $C_{1-4}$ alkyl, $C_{1-3}$ fluoroalkyl, $C_{1-4}$ hydroxyalkyl, $C_{1-2}$ aminoalkyl, —(CH$_2$)$_{0-4}$O($C_{1-2}$ alkyl), $C_{3-6}$ cycloalkyl, —(CH$_2$)$_{1-2}$C(O)NR$_x$R$_x$, —CH$_2$($C_{3-6}$ cycloalkyl), —CH$_2$(phenyl), tetrahydrofuranyl, tetrahydropyranyl, or phenyl; and Y, $R_1$, $R_{2a}$, $R_{2b}$, $R_{2c}$, $R_3$, $R_4$, $R_5$, $R_x$, m, and n are defined in the first aspect. Included in this embodiment are compounds in which $R_2$ is $C_{1-4}$ alkyl, $C_{1-2}$ fluoroalkyl, $C_{1-4}$ hydroxyalkyl, —(CH$_2$)$_{1-3}$OCH$_3$, $C_{3-6}$ cycloalkyl, —CH$_2$C(O)NR$_x$R$_x$, —CH$_2$($C_{3-6}$ cycloalkyl), —CH$_2$(phenyl), tetrahydrofuranyl, or phenyl. Also included in this embodiment are compounds in which $R_2$ is —CH$_3$, —CH$_2$CH$_3$, —CH(CH$_3$)$_2$, —CH$_2$CH(CH$_3$)$_2$, —CH$_2$CH$_2$OH, —CH$_2$CH$_2$CH$_2$OH, —CH$_2$C(CH$_3$)$_2$OH, —CH$_2$CHF$_2$, —CH$_2$CF$_3$, —CH$_2$CH$_2$OCH$_3$, —CH$_2$(cyclopropyl), —CH$_2$(phenyl), —CH$_2$C(O)NH$_2$, tetrahydrofuranyl, or phenyl.

One embodiment provides a compound of Formula (I) or a salt thereof, wherein $R_1$ is —CH(CH$_3$)$_2$; $R_2$ is —CH$_3$, —CH$_2$CH$_3$, —CH(CH$_3$)$_2$, —CH$_2$CH(CH$_3$)$_2$, —CH$_2$CH$_2$OH, —CH$_2$CH$_2$CH$_2$OH, —CH$_2$C(CH$_3$)$_2$OH, —CH$_2$CHF$_2$, —CH$_2$CF$_3$, —CH$_2$CH$_2$OCH$_3$, —CH$_2$(cyclopropyl), —CH$_2$(phenyl), —CH$_2$C(O)NH$_2$, tetrahydrofuranyl, or phenyl; and $R_{2a}$, $R_{2b}$, $R_{2c}$, $R_3$, $R_4$, $R_5$, $R_x$, m, and n are defined in the first aspect. Included in this embodiment are compounds in which Y is

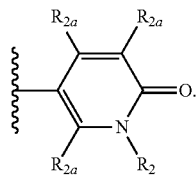

One embodiment provides a compound of Formula (I) or a salt thereof, wherein each $R_{2a}$ is independently H, F, Cl, —CN, —NR$_x$R$_x$, $C_{1-6}$ alkyl, $C_{1-2}$ fluoroalkyl, $C_{1-3}$ hydroxyalkyl, $C_{1-3}$ fluoroalkoxy, —(CH$_2$)$_{0-2}$O($C_{1-3}$ alkyl), —(CH$_2$)$_{0-3}$C(O)NR$_x$R$_x$, —(CH$_2$)$_{1-3}$($C_{3-6}$ cycloalkyl), —C(O)O($C_{1-3}$ alkyl), —C(O)NR$_x$($C_{1-3}$ alkyl), —CR$_x$=CR$_x$R$_x$, —CR$_x$=CH($C_{3-6}$ cycloalkyl), —C(O)(pyrrolidinyl), or a cyclic group selected from pyrrolidinyl, pyrazolyl, phenyl, pyridinyl, and pyrimidinyl, each substituted with zero, 1, or 2 R$_y$; and Y, $R_1$, $R_2$, $R_{2b}$, $R_{2c}$, $R_3$, $R_4$, $R_5$, $R_x$, $R_y$, m, and n are defined in the first aspect. Included in this embodiment are compounds in which each $R_{2a}$ is independently H, F, Cl, —CN, —NR$_x$R$_x$, $C_{1-6}$ alkyl, $C_{1-2}$ fluoroalkyl, $C_{1-3}$ hydroxyalkyl, —(CH$_2$)$_{0-2}$O($C_{1-2}$ alkyl), —(CH$_2$)$_{0-2}$C(O)NR$_x$R$_x$,
—(CH$_2$)$_{1-3}$(cyclopropyl), —C(O)O($C_{1-2}$ alkyl), —C(O)NR$_x$($C_{1-3}$ alkyl), —CR$_x$=CH$_2$, —CH=CH($C_{3-6}$ cycloalkyl), —C(O)(pyrrolidinyl), or a cyclic group selected from pyrrolidinyl, pyrazolyl, phenyl, pyridinyl, and pyrimidinyl, each substituted with zero, 1, or 2 R$_y$. Also included in this embodiment are compounds in which each $R_{2a}$ is independently H, F, Cl, —CN, —NH$_2$, $C_{1-5}$ alkyl, —CF$_3$, —CH$_2$OH, —OCH$_3$, —CH$_2$OCH$_3$, —CH$_2$CH$_2$(cyclopropyl), —C(O)OCH$_3$, —C(O)N(CH$_3$)$_2$, —C(O)NH(CH$_2$CH$_2$CH$_3$), —CH=CH$_2$, —C(CH$_3$)=CH$_2$, —CH=CH(cyclopropyl), —C(O)(pyrrolidinyl), or a cyclic group selected from pyrrolidinyl, pyrazolyl, phenyl, pyridinyl, and pyrimidinyl, each substituted with zero, 1, or 2 R$_y$.

One embodiment provides a compound of Formula (I) or a salt thereof, wherein each $R_{2a}$ is independently H, F, Cl, —CN, —NR$_x$R$_x$, $C_{1-6}$ alkyl, $C_{1-2}$ fluoroalkyl, $C_{1-3}$ hydroxyalkyl, $C_{1-3}$ fluoroalkoxy, —(CH$_2$)$_{0-2}$O($C_{1-3}$ alkyl), —(CH$_2$)$_{0-3}$C(O)NR$_x$R$_x$, —(CH$_2$)$_{1-3}$($C_{3-6}$ cycloalkyl), —C(O)O($C_{1-3}$ alkyl), —C(O)NR$_x$($C_{1-3}$ alkyl), —CR$_x$=CR$_x$R$_x$, —CR$_x$=CH($C_{3-6}$ cycloalkyl), —C(O)(pyrrolidinyl), or a cyclic group selected from pyrrolidinyl, pyrazolyl, phenyl, pyridinyl, and pyrimidinyl, each substituted with zero, 1, or 2 R$_y$; each R$_y$ is independently F, Cl, —CN, $C_{1-2}$ alkyl, $C_{1-2}$ alkoxy, —NR$_x$C(O)($C_{1-2}$ alkyl), —C(O)NR$_x$R$_x$, $C_{3-6}$ cycloalkyl, or morpholinyl; and Y, $R_1$, $R_2$, $R_{2b}$, $R_{2c}$, $R_3$, $R_4$, $R_5$, $R_x$, m, and n are defined in the first aspect. Included in this embodiment are compounds in which each $R_{2a}$ is independently H, F, Cl, —CN, —NR$_x$R$_x$, $C_{1-6}$ alkyl, $C_{1-2}$ fluoroalkyl, $C_{1-3}$ hydroxyalkyl, —(CH$_2$)$_{0-2}$O($C_{1-2}$ alkyl), —(CH$_2$)$_{0-2}$C(O)NR$_x$R$_x$, —(CH$_2$)$_{1-3}$(cyclopropyl), —C(O)O($C_{1-2}$ alkyl), —C(O)NR$_x$($C_{1-3}$ alkyl), —CR$_x$=CH$_2$, —CH=CH($C_{3-6}$ cycloalkyl), —C(O)(pyrrolidinyl), or a cyclic group selected from pyrrolidinyl, pyrazolyl, phenyl, pyridinyl, and pyrimidinyl, each substituted with zero, 1, or 2 R$_y$; and each R$_y$ is independently F, —CN, —CH$_3$, —CF$_3$, —OCH$_3$, —NHC(O)CH$_3$, —C(O)NH$_2$, —C(O)NH(CH$_3$), cyclopropyl, or morpholinyl. Also included in this embodiment are compounds in which each $R_{2a}$ is independently H, F, Cl, —CN, —NH$_2$, $C_{1-5}$ alkyl, —CF$_3$, —CH$_2$OH, —OCH$_3$, —CH$_2$OCH$_3$, —CH$_2$CH$_2$(cyclopropyl), —C(O)OCH$_3$, —C(O)N(CH$_3$)$_2$, —C(O)NH(CH$_2$CH$_2$CH$_3$), —CH=CH$_2$, —C(CH$_3$)=CH$_2$, —CH=CH(cyclopropyl), —C(O)(pyrrolidinyl), or a cyclic group selected from pyrrolidinyl, pyrazolyl, phenyl, pyridinyl, and pyrimidinyl, each substituted with zero, 1, or 2 R$_y$; and each R$_y$ is independently F, —CN, —CH$_3$, —CF$_3$, —OCH$_3$, —NHC(O)CH$_3$, —C(O)NH$_2$, —C(O)NH(CH$_3$), cyclopropyl, or morpholinyl.

One embodiment provides a compound of Formula (I) or a salt thereof, wherein $R_3$ is -$L_1$-A; and Y, $R_1$, $R_2$, $R_{2a}$, $R_{2b}$, $R_{2c}$, $R_4$, $R_5$, $L_1$, A, m, and n are defined in the first aspect. Included in this embodiment are compounds in which each $L_1$ is a bond, —(CR$_x$R$_x$)$_{1-2}$—, —(CR$_x$R$_x$)$_{1-2}$O—, —CR$_x$R$_x$C(O)—, —(CR$_x$R$_x$)$_2$NR$_x$(CR$_x$R$_x$)$_{0-1}$—, —CR$_x$R$_x$C(O)NR$_x$(CR$_x$R$_x$)$_{0-4}$—, —C(O)(CR$_x$R$_x$)$_{0-3}$—, —C(O)(CR$_x$R$_x$)$_{0-2}$NR$_x$(CR$_x$R$_x$)$_{0-2}$—, —C(O)(CR$_x$R$_x$)$_{1-2}$C(O)NR$_x$—, —C(O)(CR$_x$R$_x$)$_{0-1}$O—, —C(O)(CR$_x$R$_x$)$_{1-2}$NHS(O)$_2$—, —C(O)NR$_x$(CR$_x$R$_x$)$_{1-2}$—, or —S(O)$_2$(CR$_x$R$_x$)$_{0-2}$—. Also included in this embodiment are compounds in which $L_1$ is a bond, —(CR$_x$R$_x$)$_{1-2}$—, —CR$_x$R$_x$C(O)—, —C(O)(CR$_x$R$_x$)$_{0-1}$—, —C(O)O—, or —S(O)$_2$(CR$_x$R$_x$)$_{0-2}$—.

One embodiment provides a compound of Formula (I) or a salt thereof, wherein $R_3$ is -$L_1$-A; $L_1$ is a bond, —(CR$_x$R$_x$)$_{1-2}$—, —CR$_x$R$_x$C(O)—, —C(O)(CR$_x$R$_x$)$_{0-1}$—, —C(O)O—, or —S(O)$_2$(CR$_x$R$_x$)$_{0-2}$—; A is azetidinyl, $C_{3-6}$ cycloalkyl, dioxotetrahydrothiophenyl, oxetanyl, phenyl, piperidinyl, pyrazolyl, pyrazolidinonyl, pyrrolidinonyl, pyrrolidin-dionyl, pyrrolidinyl, tetrahydrofuranyl, tetrahydrofuranonyl, tetrahydropyranyl, or triazolyl, each substituted with zero, 1, or 2 $R_{3a}$; and Y, $R_1$, $R_2$, $R_{2a}$, $R_{2b}$, $R_{2c}$, $R_4$, $R_5$, m, and n are defined in the first aspect. Included in this embodiment are compounds in which $R_1$ is —CH(CH$_3$)$_2$. Also included in this embodiment are compounds in which Y is

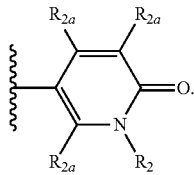

One embodiment provides a compound of Formula (I) or a salt thereof, wherein $R_3$ is —CH$_2$(methyl triazolyl), —CH$_2$(trifluoromethyl phenyl), —CH$_2$(difluoromethyl, fluorophenyl), —CH$_2$(fluoro, chlorophenyl), —CH$_2$(difluorocyclopropyl), —CH$_2$CH$_2$(pyrrolidin-dionyl), —CH$_2$(oxetanyl), —CH$_2$(tetrahydropyranyl), —CH$_2$C(O)(hydroxypyrrolidinyl), —CH$_2$C(O)(pyrazolidinonyl), —CH$_2$C(O)(pyrrolidinyl), —CH$_2$(dimethyl pyrazolyl), —CH$_2$(methyl pyrazolyl), —CH$_2$(pyrazolyl), —CH$_2$(cyclopropyl), —CH$_2$(tetrahydrofuranyl), —CH$_2$(i-propyl pyrazolyl), —CH$_2$(n-propyl pyrazolyl), —CH(CH$_3$)(methyl pyrazolyl), —C(O)(aminocyclopropyl), —C(O)(hydroxypyrrolidinyl), —C(O)(methyl, hydroxypyrrolidinyl), —C(O)CH$_2$(pyrrolidinonyl), —C(O)CH$_2$(pyrrolidinyl), —C(O)O(methyl pyrrolidinyl), —S(O)$_2$CH$_2$CH$_2$(pyrrolidinyl), —CH$_2$(hydroxytetrahydropyranyl), or a cyclic group selected from cyclopentyl, cyclohexyl, oxetanyl, azetidinyl, pyrrolidinonyl, tetrahydrofuranyl, tetrahydrofuranonyl, tetrahydropyranyl, piperidinyl, and dioxotetrahydrothiophenyl, each substituted with zero, 1, or 2 $R_{3a}$; and Y, $R_1$, $R_2$, $R_{2a}$, $R_{2b}$, $R_{2c}$, $R_{3a}$, $R_4$, $R_5$, m, and n are defined in the first aspect. Included in this embodiment are compounds in which each One embodiment provides a compound of Formula (I) or a salt thereof, wherein $R_3$ is H, $C_{1-6}$ alkyl, $C_{1-6}$ fluoroalkyl, $C_{1-6}$ hydroxyalkyl, $C_{1-3}$ cyanoalkyl, —(CH$_2$)$_{0-4}$O(C$_{1-3}$ alkyl), —(CH$_2$CH$_2$O)$_{2-3}$O(C$_{1-3}$ alkyl), —CH$_2$CH$_2$NR$_x$R$_x$, —CR$_x$R$_x$C(O)OH, —(CR$_x$R$_x$)$_{0-2}$C(O)NR$_x$R$_x$, —CH$_2$C(O)NR$_x$(C$_{1-3}$ alkyl), —CH$_2$C(O)NR$_x$(C$_{1-4}$ hydroxyalkyl), —(CR$_x$R$_x$)$_{0-2}$S(O)$_2$(C$_{1-3}$ alkyl), —C(O)(C$_{1-3}$ alkyl), —C(O)(C$_{1-3}$ fluoroalkyl), —C(O)CR$_x$R$_x$NR$_x$R$_x$, —C(O)(C$_{1-6}$ hydroxyalkyl), or —NR$_x$C(O)(C$_{1-3}$ alkyl); and $R_1$, $R_2$, $R_{2a}$, $R_{2b}$, $R_{2c}$, $R_4$, $R_5$, $R_x$, m, and n are defined in the first aspect. Included in this embodiment are compounds in which each $R_{3a}$ is independently F, Cl, —OH, —NH$_2$, $C_{1-3}$ alkyl, $C_{1-2}$ fluoroalkyl, or —C(O)NR$_x$R$_x$. Also included are compounds in which each $R_{3a}$ is independently F, —OH, —CH$_3$, —CH(CH$_3$)$_2$, —CF$_3$, or —C(O)NH$_2$.

One embodiment provides a compound of Formula (I) or a salt thereof, wherein each $R_4$ is independently F, —OH, —CH$_3$, or —OCH$_3$; or two $R_4$ attached to the same carbon atom form =O; and $R_1$, $R_2$, $R_{2a}$, $R_{2b}$, $R_{2c}$, $R_3$, $R_5$, m, and n are defined in the first aspect. Included in this embodiment are compounds in which each $R_4$ is independently F, —CH$_3$, or —OCH$_3$; or two $R_4$ attached to the same carbon atom form =O.

One embodiment provides a compound of Formula (I) or a salt thereof, wherein each $R_5$ is independently F, —CN, —CH$_3$, —CF$_3$, or —OCH$_3$; and $R_1$, $R_2$, $R_{2a}$, $R_{2b}$, $R_{2c}$, $R_3$, $R_4$, m, and n are defined in the first aspect. Included in this embodiment are compounds in which each $R_5$ is independently F, —CH$_3$, or —CF$_3$. Also included in this embodiment are compounds in which $R_5$ is F and n is zero or 1.

One embodiment provides a compound of Formula (I) or a salt thereof, wherein Y is

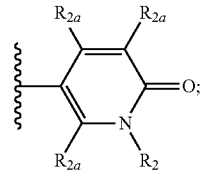

$R_1$ is —CH(CH$_3$)$_2$; $R_5$ is F; m is zero; n is zero or 1; and $R_2$, $R_{2a}$, $R_3$, and $R_4$ are defined in the first aspect. Included in this embodiment are compounds in which n is zero.

One embodiment provides a compound of Formula (I) or a salt thereof, wherein $R_1$ is H, $C_{1-4}$ alkyl or $C_{1-3}$ fluoroalkyl, or $C_{3-6}$ cycloalkyl; $R_2$ is $C_{1-4}$ alkyl, $C_{1-2}$ fluoroalkyl, $C_{1-4}$ hydroxyalkyl, —(CH$_2$)$_{1-3}$OCH$_3$, $C_{3-6}$ cycloalkyl, —CH$_2$C(O)NR$_x$R$_x$, —CH$_2$(C$_{3-6}$ cycloalkyl), —CH$_2$(phenyl), tetrahydrofuranyl, or phenyl; each $R_{2a}$ is independently H, F, Cl, —CN, —NR$_x$R$_x$, $C_{1-6}$ alkyl, $C_{1-2}$ fluoroalkyl, $C_{1-3}$ hydroxyalkyl, —(CH$_2$)$_{0-2}$O(C$_{1-2}$ alkyl), —(CH$_2$)$_{0-2}$C(O)NR$_x$R$_x$, —(CH$_2$)$_{1-3}$(cyclopropyl), —C(O)O(C$_{1-2}$ alkyl), —C(O)NR$_x$(C$_{1-3}$ alkyl), —CR$_x$=CH$_2$, —CH=CH(C$_{3-6}$ cycloalkyl), —C(O)(pyrrolidinyl), or a cyclic group selected from pyrrolidinyl, pyrazolyl, phenyl, pyridinyl, and pyrimidinyl, each substituted with zero, 1, or 2 $R_y$; each $R_y$ is independently F, Cl, —CN, $C_{1-2}$ alkyl, $C_{1-2}$ alkoxy, —NR$_x$C(O)(C$_{1-2}$ alkyl), —C(O)NR$_x$R$_x$, $C_{3-6}$ cycloalkyl, or morpholinyl; $R_3$ is (a) -L$_1$-A; or (b) H, $C_{1-6}$ alkyl, $C_{1-6}$ fluoroalkyl, $C_{1-6}$ hydroxyalkyl, $C_{1-3}$ cyanoalkyl, —(CH$_2$)$_{0-3}$O(C$_{1-2}$ alkyl), —(CH$_2$CH$_2$O)$_{2-3}$O(C$_{1-2}$ alkyl), —CH$_2$CH$_2$NR$_x$R$_x$, —CR$_x$R$_x$C(O)OH, —(CR$_x$R$_x$)$_{0-2}$C(O)NR$_x$R$_x$, —CH$_2$C(O)NR$_x$(C$_{1-2}$ alkyl), —CH$_2$C(O)NH(C$_{1-4}$ hydroxyalkyl), —(CR$_x$R$_x$)$_{1-2}$S(O)$_2$(C$_{1-2}$ alkyl), —C(O)(C$_{1-2}$ alkyl), —C(O)(C$_{1-2}$ fluoroalkyl), —C(O)CR$_x$R$_x$NR$_x$R$_x$, —C(O)(C$_{1-4}$ hydroxyalkyl), or —NR$_x$C(O)(C$_{1-2}$ alkyl); L$_1$ is a bond, —(CR$_x$R$_x$)$_{1-2}$—, —CR$_x$R$_x$C(O)—, —C(O)(CR$_x$R$_x$)$_{0-1}$—, —C(O)O—, or —S(O)$_2$(CR$_x$R$_x$)$_{0-2}$—; A is azetidinyl, $C_{3-6}$ cycloalkyl, dioxotetrahydrothiophenyl, oxetanyl, phenyl, piperidinyl, pyrazolyl, pyrazolidinonyl, pyrrolidinonyl, pyrrolidin-dionyl, pyrrolidinyl, tetrahydrofuranyl, tetrahydrofuranonyl, tetrahydropyranyl, or triazolyl, each substituted with zero, 1, or 2 $R_{3a}$; each $R_{3a}$ is independently F, Cl, —OH, —NH$_2$, $C_{1-3}$ alkyl, $C_{1-2}$ fluoroalkyl, or —C(O)NR$_x$R$_x$; each $R_4$ is independently F, —OH, —CH$_3$, or —OCH$_3$; or two $R_4$ attached to the same carbon atom form =O; each $R_5$ is independently F, —CN, —CH$_3$, —CF$_3$, or —OCH$_3$; and $R_z$ is H or —CH$_3$.

One embodiment provides a compound of Formula (I) or a salt thereof, wherein $R_1$ is —CH$_2$CH$_3$ or —CH(CH$_3$)$_2$; $R_2$ is —CH$_3$, —CH$_2$CH$_3$, —CH(CH$_3$)$_2$, —CH$_2$CH(CH$_3$)$_2$, —CH$_2$CH$_2$OH, —CH$_2$CH$_2$CH$_2$OH, —CH$_2$C(CH$_3$)$_2$OH, —CH$_2$CHF$_2$, —CH$_2$CF$_3$, —CH$_2$CH$_2$OCH$_3$, —CH$_2$(cyclopropyl), —CH$_2$(phenyl), —CH$_2$C(O)NH$_2$, tetrahydrofuranyl, or phenyl; each $R_{2a}$ is independently H, F, Cl, —CN, —NH$_2$, $C_{1-5}$ alkyl, —CF$_3$, —CH$_2$OH, —OCH$_3$, —CH$_2$OCH$_3$, —CH$_2$CH$_2$(cyclopropyl), —C(O)OCH$_3$, —C(O)N(CH$_3$)$_2$, —C(O)NH(CH$_2$CH$_2$CH$_3$), —CH=CH$_2$, —C(CH$_3$)=CH$_2$, —CH=CH(cyclopropyl), —C(O)(pyrrolidinyl), or a cyclic group selected from pyrrolidinyl, pyrazolyl, phenyl, pyridinyl, and pyrimidinyl, each substituted with zero, 1, or 2 $R_y$; each $R_y$ is independently F, —CN, —CH$_3$, —CF$_3$, —OCH$_3$, —NHC(O)CH$_3$, —C(O)NH$_2$, —C(O)NH(CH₃), cyclopropyl, or morpholinyl; $R_{2b}$ is $R_2$ or $R_{2a}$; $R_{2c}$ is $R_2$ or $R_{2a}$; provided that one of $R_{2b}$ and $R_{2c}$ is $R_2$, and the other of $R_{2b}$ and $R_{2c}$ is $R_{2a}$; $R_3$ is H, —CH₃, —CH₂CH₂CH₃, —CH(CH₃)₂, —CH₂CH₂CH₂CH₃, —CH₂CH(CH₃)₂, —CH₂CH₂CH(CH₃)₂, —CH₂CH₂CF₃, —CH₂CH₂CH₂CF₃, —CH₂CH₂CH(CF₃)₂, —CH₂CH₂OH, —CH₂CH₂CH₂OH, —C(CH₃)₂OH, —CH₂C(CH₃)₂OH, —CH₂CH₂C(CH₃)₂OH, —CH₂CH(OH)CH(CH₃)₂, —CH₂CH(OH)CH₂OH, —CH(CH₂CH₂OH)₂, —CH₂CN, —CH₂CH₂CN, —CH₂CH₂OCH₃, —CH₂CH₂CH₂OCH₃, —(CH₂CH₂O)₂₋₃OCH₃, —CH₂CH₂NH(CH₃), —C(CH₃)₂C(O)OH, —CH₂C(O)NH₂, —CH₂C(O)NH(CH₃), —CH₂C(O)N(CH₃)₂, —CH₂C(O)NH(CH₂CH₃), —CH₂C(O)NH(CH₂CH(CH₃)OH), —CH₂C(O)NH(CH₂C(CH₃)₂OH), —CH(CH₃)C(O)NH₂, —C(CH₃)₂C(O)NH₂, —CH₂CH₂C(O)NH₂, —CH₂CH₂S(O)₂CH₃, —C(O)CH₃, —C(O)CF₃, —C(O)CH₂N(CH₃)₂, —C(O)C(CH₃)₂NH₂, —C(O)CH(CH₃)NH(CH₃), —C(O)C(CH₃)₂NH(CH₃), —C(O)CH₂CH(CH₃)OH, —C(O)CH₂C(CH₃)₂OH, —C(O)C(CH₃)₂CH₂OH, —NHC(O)CH₃, —CH₂(methyl triazolyl), —CH₂(trifluoromethyl phenyl), —CH₂(difluoromethyl, fluorophenyl), —CH₂(fluoro, chlorophenyl), —CH₂(difluorocyclopropyl), —CH₂CH₂(pyrrolidin-dionyl), —CH₂(oxetanyl), —CH₂(tetrahydropyranyl), —CH₂C(O)(hydroxypyrrolidinyl), —CH₂C(O)(pyrazolidinonyl), —CH₂C(O)(pyrrolidinyl), —CH₂(dimethyl pyrazolyl), —CH₂(methyl pyrazolyl), —CH₂(pyrazolyl), —CH₂(cyclopropyl), —CH₂(tetrahydrofuranyl), —CH₂(i-propyl pyrazolyl), —CH₂(n-propyl pyrazolyl), —CH(CH₃)(methyl pyrazolyl), —C(O)(aminocyclopropyl), —C(O)(hydroxypyrrolidinyl), —C(O)(methyl, hydroxypyrrolidinyl), —C(O)CH₂(pyrrolidinonyl), —C(O)CH₂(pyrrolidinyl), —C(O)O(methyl pyrrolidinyl), —S(O)₂CH₂CH₂(pyrrolidinyl), —CH₂(hydroxytetrahydropyranyl), or a cyclic group selected from cyclopentyl, cyclohexyl, oxetanyl, azetidinyl, pyrrolidinonyl, tetrahydrofuranyl, tetrahydrofuranonyl, tetrahydropyranyl, piperidinyl, and dioxotetrahydrothiophenyl, each substituted with zero, 1, or 2 $R_{3a}$; each $R_{3a}$ is independently F, —OH, —CH₃, —CH(CH₃)₂, —CF₃, or —C(O)NH₂; $R_5$ is F; m is zero; and n is zero or 1.

One embodiment provides a compound of Formula (I) or a salt thereof, wherein said compound is selected from 5-(3-isopropyl-5-(piperidin-4-yl)-1H-indol-2-yl)-1-methylpyridin-2(1H)-on (1); 5-(3-isopropyl-5-(piperidin-4-yl)-1H-indol-2-yl)-1,3-dimethylpyridin-2(1H)-one (2); 5-(3-isopropyl-5-(piperidin-4-yl)-1H-indol-2-yl)-1,3,6-trimethylpyridin-2(1H)-one (3); 5-(3-isopropyl-5-(piperidin-4-yl)-1H-indol-2-yl)-1,6-dimethylpyridin-2(1H)-one (6); 5-(3-isopropyl-5-(piperidin-4-yl)-1H-indol-2-yl)-1,4-dimethylpyridin-2(1H)-one (8); 3-amino-5-(3-isopropyl-5-(piperidin-4-yl)-1H-indol-2-yl)-1-methylpyridin-2(1H)-one (9); 3-fluoro-5-(3-isopropyl-5-(piperidin-4-yl)-1H-indol-2-yl)-1-methylpyridin-2(1H)-one (13); 5-(3-isopropyl-5-(piperidin-4-yl)-1H-indol-2-yl)-1,3,4-trimethylpyridin-2(1H)-one (14); 1-ethyl-5-(3-isopropyl-5-(piperidin-4-yl)-1H-indol-2-yl)-3-methylpyridin-2(1H)-one (15); 1-isopropyl-5-(3-isopropyl-5-(piperidin-4-yl)-1H-indol-2-yl)pyridin-2(1H)-one (16); 3-amino-5-(3-isopropyl-5-(piperidin-4-yl)-1H-indol-2-yl)-1,4-dimethylpyridin-2(1H)-one (19); 5-(3-isopropyl-5-(piperidin-4-yl)-1H-indol-2-yl)-3-methoxy-1-methylpyridin-2(1H)-one (20); 3-chloro-5-(3-isopropyl-5-(piperidin-4-yl)-1H-indol-2-yl)-1-methylpyridin-2(1H)-one (22); 5-(3-isopropyl-5-(piperidin-4-yl)-1H-indol-2-yl)-1,6-dimethyl-2-oxo-1,2-dihydropyridine-3-carbonitrile (23); 5-(3-isopropyl-5-(piperidin-4-yl)-1H-indol-2-yl)-1,4-dimethyl-2-oxo-1,2-dihydropyridine-3-carbonitrile (24); 3-ethyl-5-(3-isopropyl-5-(piperidin-4-yl)-1H-indol-2-yl)-1,6-dimethylpyridin-2(1H)-one (25); 1-ethyl-5-(3-isopropyl-5-(piperidin-4-yl)-1H-indol-2-yl)-3,4-dimethylpyridin-2(1H)-one (26); 5-(3-isopropyl-5-(piperidin-4-yl)-1H-indol-2-yl)-3-methoxy-1,6-dimethylpyridin-2(1H)-one (28); 5-(3-isopropyl-5-(piperidin-4-yl)-1H-indol-2-yl)-3-methoxy-1,4-dimethylpyridin-2(1H)-one (29); 1-(2-hydroxyethyl)-5-(3-isopropyl-5-(piperidin-4-yl)-1H-indol-2-yl)-3-methylpyridin-2(1H)-one (30); 3-chloro-5-(3-isopropyl-5-(piperidin-4-yl)-1H-indol-2-yl)-1,4-dimethylpyridin-2(1H)-one (31); 3-chloro-1-ethyl-5-(3-isopropyl-5-(piperidin-4-yl)-1H-indol-2-yl) pyridin-2(1H)-one (32); 3-chloro-5-(3-isopropyl-5-(piperidin-4-yl)-1H-indol-2-yl)-1,6-dimethylpyridin-2(1H)-one (33); 1-(cyclopropylmethyl)-5-(3-isopropyl-5-(piperidin-4-yl)-1H-indol-2-yl)-3-methylpyridin-2(1H)-one (34); 1,3-diethyl-5-(3-isopropyl-5-(piperidin-4-yl)-1H-indol-2-yl)-6-methylpyridin-2(1H)-one (35); 1-isobutyl-5-(3-isopropyl-5-(piperidin-4-yl)-1H-indol-2-yl)-3-methylpyridin-2(1H)-one (36); methyl 5-(3-isopropyl-5-(piperidin-4-yl)-1H-indol-2-yl)-1-methyl-2-oxo-1,2-dihydropyridine-3-carboxylate (37); 1-(3-hydroxypropyl)-5-(3-isopropyl-5-(piperidin-4-yl)-1H-indol-2-yl)-3-methylpyridin-2(1H)-one (38); 5-(3-isopropyl-5-(piperidin-4-yl)-1H-indol-2-yl)-1-(2-methoxyethyl)-3-methylpyridin-2(1H)-one (39); 1-(2,2-difluoroethyl)-5-(3-isopropyl-5-(piperidin-4-yl)-1H-indol-2-yl)-3-methylpyridin-2(1H)-one (40); 5-(3-isopropyl-5-(piperidin-4-yl)-1H-indol-2-yl)-1-methyl-3-(trifluoromethyl)pyridin-2(1H)-one (41); 5-(3-isopropyl-5-(piperidin-4-yl)-1H-indol-2-yl)-3-methyl-1-(tetrahydrofuran-3-yl)pyridin-2(1H)-one (42); 1-(2-hydroxy-2-methylpropyl)-5-(3-isopropyl-5-(piperidin-4-yl)-1H-indol-2-yl)-3-methylpyridin-2(1H)-one (43); 5-(3-isopropyl-5-(piperidin-4-yl)-1H-indol-2-yl)-3-methyl-1-phenylpyridin-2(1H)-one (44); 5-(3-isopropyl-5-(piperidin-4-yl)-1H-indol-2-yl)-3-methyl-1-(2,2,2-trifluoroethyl)pyridin-2(1H)-one (45); 1-benzyl-5-(3-isopropyl-5-(piperidin-4-yl)-1H-indol-2-yl)-3-methylpyridin-2(1H)-one (46); 5-(3-isopropyl-5-(piperidin-4-yl)-1H-indol-2-yl)-1-methyl-2-oxo-1,2-dihydropyridine-3-carbonitrile (47); 1-(2-hydroxy-2-methylpropyl)-5-(3-isopropyl-5-(piperidin-4-yl)-1H-indol-2-yl)pyridin-2(1H)-one (48); 2-(5-(3-isopropyl-5-(piperidin-4-yl)-1H-indol-2-yl)-2-oxopyridin-1(2H)-yl)acetamide (49); 5-(3-isopropyl-5-(piperidin-4-yl)-1H-indol-2-yl)-1-methyl-[3,3'-bipyridin]-2(1H)-one (50); 5-(3-isopropyl-5-(piperidin-4-yl)-1H-indol-2-yl)-1-methyl-3-(prop-1-en-2-yl)pyridin-2(1H)-one (51); (E)-3-(2-cyclopropylvinyl)-5-(3-isopropyl-5-(piperidin-4-yl)-1H-indol-2-yl)-1-methylpyridin-2(1H)-one (52); 5-(3-isopropyl-5-(piperidin-4-yl)-1H-indol-2-yl)-1-methyl-3-phenylpyridin-2(1H)-one (53); 5-(3-isopropyl-5-(piperidin-4-yl)-1H-indol-2-yl)-1-methyl-3-(pyrimidin-5-yl)pyridin-2(1H)-one (54); 5-(3-isopropyl-5-(piperidin-4-yl)-1H-indol-2-yl)-1-methyl-3-(p-tolyl) pyridin-2(1H)-one (55); 3-(5-(3-isopropyl-5-(piperidin-4-yl)-1H-indol-2-yl)-1-methyl-2-oxo-1,2-dihydropyridin-3-yl)benzonitrile (56); 5-(3-isopropyl-5-(piperidin-4-yl)-1H-indol-2-yl)-2'-methoxy-1-methyl[3,3'-bipyridin]-2(1H)-one (57); 3-(5-(3-isopropyl-5-(piperidin-4-yl)-1H-indol-2-yl)-1-methyl-2-oxo-1,2-dihydropyridin-3-yl) benzamide (58); 3-(5-(3-isopropyl-5-(piperidin-4-yl)-1H-indol-2-yl)-1-methyl-2-oxo-1,2-dihydropyridin-3-yl)-N-methylbenzamide (59); N-(3-(5-(3-isopropyl-5-(piperidin-4-yl)-1H-indol-2-yl)-1-methyl-2-oxo-1,2-dihydropyridin-3-yl)phenyl)acetamide (60); 3-(3,3-dimethylbutyl)-5-(3-isopropyl-5-(piperidin-4-yl)-1H-indol-2-yl)-1-methylpyridin-2(1H)-one (61); 3-(2-cyclopropylethyl)-5-(3-isopropyl-5-(piperidin-4-yl)-1H-indol-2-yl)-1- methylpyridin-2(1H)-one (62); 5-(3-isopropyl-5-(piperidin-4-yl)-1H-indol-2-yl)-N,N,1-trimethyl-2-oxo-1,2-dihydropyridine-3-carboxamide (63); 5-(3-isopropyl-5-(piperidin-4-yl)-1H-indol-2-yl)-1-methyl-2-oxo-N-propyl-1,2-dihydropyridine-3-carboxamide (64); 5-(3-isopropyl-5-(piperidin-4-yl)-1H-indol-2-yl)-1,4-dimethyl-[3,3'-bipyridin]-2(1H)-one (65); 3-isopropyl-5-(3-isopropyl-5-(piperidin-4-yl)-1H-indol-2-yl)-1-methylpyridin-2(1H)-one (66); 3-ethyl-5-(3-isopropyl-5-(piperidin-4-yl)-1H-indol-2-yl)-1-methylpyridin-2(1H)-one (67); 1,3-diethyl-5-(3-isopropyl-5-(piperidin-4-yl)-1H-indol-2-yl)pyridin-2(1H)-one (68); -(3-isopropyl-5-(piperidin-4-yl)-1H-indol-2-yl)-1-methyl-3-(pyrrolidine-1-carbonyl) pyridin-2(1H)-one (69); 3-(hydroxymethyl)-5-(3-isopropyl-5-(piperidin-4-yl)-1H-indol-2-yl)-1-methylpyridin-2(1H)-one (70); 2-(4-(2-(1,5-dimethyl-6-oxo-1,6-dihydropyridin-3-yl)-3-isopropyl-1H-indol-5-yl) piperidin-1-yl)-N,N-dimethylacetamide (71); 5-(3-isopropyl-5-(1-((1-methyl-1H-1,2,4-triazol-3-yl)methyl)piperidin-4-yl)-1H-indol-2-yl)-1,3-dimethylpyridin-2(1H)-one (72); 5-(5-(1-(3-hydroxy-3-methylbutyl)piperidin-4-yl)-3-isopropyl-1H-indol-2-yl)-1,3,4-trimethylpyridin-2(1H)-one (73); 5-(5-(1-(3-hydroxy-3-methylbutyl)piperidin-4-yl)-3-isopropyl-1H-indol-2-yl)-1,3,6-trimethylpyridin-2(1H)-one (74); 5-(5-(1-isobutylpiperidin-4-yl)-3-isopropyl-1H-indol-2-yl)-1,3-dimethylpyridin-2(1H)-one (75); 3-(4-(2-(1,5-dimethyl-6-oxo-1,6-dihydropyridin-3-yl)-3-isopropyl-1H-indol-5-yl)piperidin-1-yl)propanenitrile (76); 5-(3-isopropyl-5-(1-(4-(trifluoromethoxy) benzyl)piperidin-4-yl)-1H-indol-2-yl)-1,3-dimethylpyridin-2(1H)-one (77); 5-(5-(1-(5-(difluoromethoxy)-2-fluorobenzyl)piperidin-4-yl)-3-isopropyl-1H-indol-2-yl)-1,3-dimethylpyridin-2(1H)-one (78); 5-(3-isopropyl-5-(1-(4,4,4-trifluorobutyl)piperidin-4-yl)-1H-indol-2-yl)-1,3-dimethylpyridin-2(1H)-one (79); 5-(5-(1-(5-chloro-2-fluorobenzyl)piperidin-4-yl)-3-isopropyl-1H-indol-2-yl)-1,3-dimethylpyridin-2(1H)-one (80); 5-(5-(1-(1,1-dioxidotetrahydrothiophen-3-yl)piperidin-4-yl)-3-isopropyl-1H-indol-2-yl)-1,3-dimethylpyridin-2(1H)-one (81); 3-(4-(2-(1,5-dimethyl-6-oxo-1,6-dihydropyridin-3-yl)-3-isopropyl-1H-indol-5-yl)piperidin-1-yl) propanamide (82); 5-(5-(1-((2,2-difluorocyclopropyl)methyl)piperidin-4-yl)-3-isopropyl-1H-indol-2-yl)-1,3-dimethylpyridin-2(1H)-one (83); 1-(2-(4-(2-(1,5-dimethyl-6-oxo-1,6-dihydropyridin-3-yl)-3-isopropyl-1H-indol-5-yl)piperidin-1-yl)ethyl)pyrrolidine-2,5-dione (84); 5-(5-(1-(3-hydroxypropyl)piperidin-4-yl)-3-isopropyl-1H-indol-2-yl)-1,3-dimethylpyridin-2(1H)-one (85); 5-(5-(1-isopentylpiperidin-4-yl)-3-isopropyl-1H-indol-2-yl)-1,3-dimethylpyridin-2(1H)-one (86); 5-(5-(1-cyclohexylpiperidin-4-yl)-3-isopropyl-1H-indol-2-yl)-1,3-dimethylpyridin-2(1H)-one (87); 5-(3-isopropyl-5-(1-(4,4,4-trifluoro-3-(trifluoromethyl)butyl)piperidin-4-yl)-1H-indol-2-yl)-1,3-dimethylpyridin-2(1H)-one (88); 5-(5-(1-isobutylpiperidin-4-yl)-3-isopropyl-1H-indol-2-yl)-1-methyl-3-phenylpyridin-2(1H)-one (89); 5-(5-(1-isopentylpiperidin-4-yl)-3-isopropyl-1H-indol-2-yl)-1-methyl-3-phenylpyridin-2(1H)-one (90); 3-chloro-5-(5-(1-isopentylpiperidin-4-yl)-3-isopropyl-1H-indol-2-yl)-1,4-dimethylpyridin-2(1H)-one (91); 3-chloro-5-(3-isopropyl-5-(1-(oxetan-3-ylmethyl)piperidin-4-yl)-1H-indol-2-yl)-1,4-dimethylpyridin-2(1H)-one (92); 3-chloro-5-(3-isopropyl-5-(1-((tetrahydro-2H-pyran-4-yl)methyl)piperidin-4-yl)-1H-indol-2-yl)-1,4-dimethylpyridin-2(1H)-one (93); 5-(3-isopropyl-5-(1-(oxetan-3-ylmethyl)piperidin-4-yl)-1H-indol-2-yl)-1-methyl-3-(pyrimidin-5-yl)pyridin-2(1H)-one (94); 3-chloro-5-(3-isopropyl-5-(1-(2-methoxyethyl)piperidin-4-yl)-1H-indol-2-yl)-1,4-dimethylpyridin-2(1H)-one (95); 2-(4-(2-(5-chloro-1,4-dimethyl-6-oxo-1,6-dihydropyridin-3-yl)-3-isopropyl-1H-indol-5-yl)piperidin-1-yl)acetonitrile (96); 3-chloro-5-(5-(1-cyclopentylpiperidin-4-yl)-3-isopropyl-1H-indol-2-yl)-1,4-dimethylpyridin-2(1H)-one (97); 3-chloro-5-(3-isopropyl-5-(1-(2-(2-(2-methoxyethoxy)ethoxy)ethyl) piperidin-4-yl)-1H-indol-2-yl)-1,4-dimethylpyridin-2(1H)-one (98); 3-chloro-5-(3-isopropyl-5-(1-(3-methoxypropyl)piperidin-4-yl)-1H-indol-2-yl)-1,4-dimethylpyridin-2(1H)-one (99); 5-(3-isopropyl-5-(1-((tetrahydro-2H-pyran-4-yl)methyl)piperidin-4-yl)-1H-indol-2-yl)-1-methyl-3-(pyrimidin-5-yl)pyridin-2(1H)-one (100); 3-chloro-5-(3-isopropyl-5-(1-(2-(2-methoxyethoxy)ethyl)piperidin-4-yl)-1H-indol-2-yl)-1,4-dimethylpyridin-2(1H)-one (101); 3-chloro-5-(3-isopropyl-5-(1-(3,3,3-trifluoropropyl) piperidin-4-yl)-1H-indol-2-yl)-1,4-dimethylpyridin-2(1H)-one (102); 5-(3-isopropyl-5-(1-(2-methoxyethyl)piperidin-4-yl)-1H-indol-2-yl)-1-methyl-3-(pyrimidin-5-yl)pyridin-2(1H)-one (103); 5-(3-isopropyl-5-(1-(4,4,4-trifluorobutyl)piperidin-4-yl)-1H-indol-2-yl)-1-methyl-3-(pyrimidin-5-yl)pyridin-2(1H)-one (104); 3-chloro-5-(3-isopropyl-5-(1-(4,4,4-trifluorobutyl)piperidin-4-yl)-1H-indol-2-yl)-1,4-dimethylpyridin-2(1H)-one (105); 3-chloro-5-(5-(1-isobutylpiperidin-4-yl)-3-isopropyl-1H-indol-2-yl)-1,4-dimethylpyridin-2(1H)-one (106); 3-chloro-5-(3-isopropyl-5-(1-(2-(methylsulfonyl)ethyl) piperidin-4-yl)-1H-indol-2-yl)-1,4-dimethylpyridin-2(1H)-one (107); 5-(3-isopropyl-5-(1-(2-(methylsulfonyl)ethyl)piperidin-4-yl)-1H-indol-2-yl)-1-methyl-3-(pyrimidin-5-yl) pyridin-2(1H)-one (108); 5-(5-(1-isobutylpiperidin-4-yl)-3-isopropyl-1H-indol-2-yl)-1-(2-methoxyethyl)-3-methylpyridin-2(1H)-one (109); 1-isobutyl-5-(3-isopropyl-5-(1-(4,4,4-trifluorobutyl)piperidin-4-yl)-1H-indol-2-yl)-3-methylpyridin-2(1H)-one (110); 1-benzyl-5-(3-isopropyl-5-(1-(4,4,4-trifluorobutyl)piperidin-4-yl)-1H-indol-2-yl)-3-methylpyridin-2(1H)-one (111); 1-isobutyl-5-(5-(1-isobutylpiperidin-4-yl)-3-isopropyl-1H-indol-2-yl)-3-methylpyridin-2(1H)-one (112); 1-benzyl-5-(5-(1-isobutylpiperidin-4-yl)-3-isopropyl-1H-indol-2-yl)-3-methylpyridin-2(1H)-one (113); 2-(4-(3-isopropyl-2-(1-methyl-6-oxo-1,6-dihydropyridin-3-yl)-1H-indol-5-yl)piperidin-1-yl)-N,N-dimethylacetamide (114); 2-(4-(2-(1,5-dimethyl-6-oxo-1,6-dihydropyridin-3-yl)-3-isopropyl-1H-indol-5-yl)piperidin-1-yl)-N-methylacetamide (117); (S)-5-(5-(1-(2-(3-hydroxypyrrolidin-1-yl)-2-oxoethyl)piperidin-4-yl)-3-isopropyl-1H-indol-2-yl)-1,3-dimethylpyridin-2(1H)-one (119); (R)-5-(5-(1-(2-(3-hydroxypyrrolidin-1-yl)-2-oxoethyl) piperidin-4-yl)-3-isopropyl-1H-indol-2-yl)-1,3-dimethylpyridin-2(1H)-one (120); 5-(3-isopropyl-5-(1-(2-oxo-2-(3-oxopyrazolidin-1-yl)ethyl)piperidin-4-yl)-1H-indol-2-yl)-1,3-dimethylpyridin-2(1H)-one (121); 5-(3-isopropyl-5-(1-(2-oxo-2-(pyrrolidin-1-yl)ethyl) piperidin-4-yl)-1H-indol-2-yl)-1,3-dimethylpyridin-2(1H)-one (122); (R)-5-(3-isopropyl-5-(1-(2-oxopyrrolidin-3-yl)piperidin-4-yl)-1H-indol-2-yl)-1,3-dimethylpyridin-2(1H)-one (123); 2-(4-(2-(1,5-dimethyl-6-oxo-1,6-dihydropyridin-3-yl)-3-isopropyl-1H-indol-5-yl) piperidin-1-yl)-N-(2-hydroxy-2-methylpropyl)acetamide (124); (R)-2-(4-(2-(1,5-dimethyl-6-oxo-1,6-dihydropyridin-3-yl)-3-isopropyl-1H-indol-5-yl) piperidin-1-yl)-N-(2-hydroxypropyl)acetamide (125); (S)-2-(4-(2-(1,5-dimethyl-6-oxo-1,6-dihydropyridin-3-yl)-3-isopropyl-1H-indol-5-yl)piperidin-1-yl)-N-(2-hydroxypropyl)acetamide (126); 5-(3-isopropyl-5-(1-(1-methyl-2-oxopyrrolidin-3-yl)piperidin-4-yl)-1H-indol-2-yl)-1,3-dimethylpyridin-2(1H)-one (127); 2-(4-(3-isopropyl-2-(5-methoxy-1-methyl-6-oxo-1,6-dihydropyridin-3-yl)-1H-indol-5-yl)piperidin-1-yl)-N,N-dimethylacetamide (128); 2-(4-(3-isopropyl-2-(5-methoxy- 1-methyl-6-oxo-1,6-dihydropyridin-3-yl)-1H-indol-5-yl)piperidin-1-yl)-N-methylacetamide (129); 2-(4-(2-(1-ethyl-5-methyl-6-oxo-1,6-dihydropyridin-3-yl)-3-isopropyl-1H-indol-5-yl)piperidin-1-yl)-N-methylacetamide (132); 2-(4-(2-(1-ethyl-5-methyl-6-oxo-1,6-dihydropyridin-3-yl)-3-isopropyl-1H-indol-5-yl)piperidin-1-yl)-N,N-dimethylacetamide (133); 2-(4-(3-isopropyl-2-(1,4,5-trimethyl-6-oxo-1,6-dihydropyridin-3-yl)-1H-indol-5-yl)piperidin-1-yl)-N,N-dimethylacetamide (134); 2-(4-(3-isopropyl-2-(1,4,5-trimethyl-6-oxo-1,6-dihydropyridin-3-yl)-1H-indol-5-yl)piperidin-1-yl)-N-methylacetamide (135); 2-(4-(2-(1-ethyl-4,5-dimethyl-6-oxo-1,6-dihydropyridin-3-yl)-3-isopropyl-1H-indol-5-yl)piperidin-1-yl)-N,N-dimethylacetamide (136); 2-(4-(2-(1-ethyl-4,5-dimethyl-6-oxo-1,6-dihydropyridin-3-yl)-3-isopropyl-1H-indol-5-yl)piperidin-1-yl)-N-methylacetamide (137); 2-(4-(3-isopropyl-2-(1,2,5-trimethyl-6-oxo-1,6-dihydropyridin-3-yl)-1H-indol-5-yl)piperidin-1-yl)-N,N-dimethylacetamide (138); 2-(4-(3-isopropyl-2-(1,2,5-trimethyl-6-oxo-1,6-dihydropyridin-3-yl)-1H-indol-5-yl)piperidin-1-yl)-N-methylacetamide (139); 2-(4-(3-isopropyl-2-(5-methoxy-1,4-dimethyl-6-oxo-1,6-dihydropyridin-3-yl)-1H-indol-5-yl)piperidin-1-yl)-N-methylacetamide (140); 2-(4-(3-isopropyl-2-(5-methoxy-1,4-dimethyl-6-oxo-1,6-dihydropyridin-3-yl)-1H-indol-5-yl)piperidin-1-yl)-N,N-dimethylacetamide (141); 2-(4-(3-isopropyl-2-(5-methoxy-1,2-dimethyl-6-oxo-1,6-dihydropyridin-3-yl)-1H-indol-5-yl)piperidin-1-yl)-N-methylacetamide (142); 2-(4-(3-isopropyl-2-(5-methoxy-1,2-dimethyl-6-oxo-1,6-dihydropyridin-3-yl)-1H-indol-5-yl)piperidin-1-yl)-N,N-dimethylacetamide (143); 2-(4-(2-(5-cyano-1,2-dimethyl-6-oxo-1,6-dihydropyridin-3-yl)-3-isopropyl-1H-indol-5-yl)piperidin-1-yl)-N-methylacetamide (144); 2-(4-(2-(5-cyano-1,2-dimethyl-6-oxo-1,6-dihydropyridin-3-yl)-3-isopropyl-1H-indol-5-yl)piperidin-1-yl)-N,N-dimethylacetamide (145); 2-(4-(2-(5-cyano-1,4-dimethyl-6-oxo-1,6-dihydropyridin-3-yl)-3-isopropyl-1H-indol-5-yl)piperidin-1-yl)-N-methylacetamide (146); 2-(4-(2-(5-cyano-1,4-dimethyl-6-oxo-1,6-dihydropyridin-3-yl)-3-isopropyl-1H-indol-5-yl)piperidin-1-yl)-N,N-dimethylacetamide (147); 2-(4-(2-(1,5-dimethyl-6-oxo-1,6-dihydropyridin-3-yl)-3-isopropyl-1H-indol-5-yl)piperidin-1-yl)-2-methylpropanoic acid (148); 5-(3-isopropyl-5-(1-(5-methyl-2-oxotetrahydrofuran-3-yl)piperidin-4-yl)-1H-indol-2-yl)-1,3-dimethylpyridin-2(1H)-one (149); 2-(4-(2-(1,5-dimethyl-6-oxo-1,6-dihydropyridin-3-yl)-3-yl)-3-isopropyl-1H-indol-5-yl)piperidin-1-yl)acetamide (150); 2-(4-(2-(1,5-dimethyl-6-oxo-1,6-dihydropyridin-3-yl)-3-isopropyl-1H-indol-5-yl)piperidin-1-yl)-2-methylpropanamide (151); 2-(4-(2-(5-chloro-1,4-dimethyl-6-oxo-1,6-dihydropyridin-3-yl)-3-isopropyl-1H-indol-5-yl)piperidin-1-yl)-N,N-dimethylacetamide (152); 2-(4-(2-(5-chloro-1,4-dimethyl-6-oxo-1,6-dihydropyridin-3-yl)-3-isopropyl-1H-indol-5-yl)piperidin-1-yl)-N-methylacetamide (153); 2-(4-(2-(5-chloro-1,4-dimethyl-6-oxo-1,6-dihydropyridin-3-yl)-3-isopropyl-1H-indol-5-yl)piperidin-1-yl)-2-methylpropanamide (154); 2-(4-(2-(5-chloro-1,4-dimethyl-6-oxo-1,6-dihydropyridin-3-yl)-3-isopropyl-1H-indol-5-yl)piperidin-1-yl)-N-ethylacetamide (155); 2-(4-(2-(5-chloro-1,4-dimethyl-6-oxo-1,6-dihydropyridin-3-yl)-3-isopropyl-1H-indol-5-yl)piperidin-1-yl)propanamide (156); 2-(4-(2-(5-chloro-1,4-dimethyl-6-oxo-1,6-dihydropyridin-3-yl)-3-ethyl-1H-indol-5-yl)piperidin-1-yl)-N,N-dimethylacetamide (157); 2-(4-(2-(5-chloro-1,4-dimethyl-6-oxo-1,6-dihydropyridin-3-yl)-4-fluoro-3-isopropyl-1H-indol-5-yl)piperidin-1-yl)-N,N-dimethylacetamide (158); 2-(4-(3-isopropyl-2-(1-(2-methoxyethyl)-5-methyl-6-oxo-1,6-dihydropyridin-3-yl)-1H-indol-5-yl)piperidin-1-yl)-N,N-dimethylacetamide (159); 2-(4-(3-isopropyl-2-(1-(2-methoxyethyl)-5-methyl-6-oxo-1,6-dihydropyridin-3-yl)-1H-indol-5-yl)piperidin-1-yl)-N-methylacetamide (160); 2-(4-(2-(1-isobutyl-5-methyl-6-oxo-1,6-dihydropyridin-3-yl)-3-isopropyl-1H-indol-5-yl)piperidin-1-yl)-N-methylacetamide (161); 2-(4-(2-(1-benzyl-5-methyl-6-oxo-1,6-dihydropyridin-3-yl)-3-isopropyl-1H-indol-5-yl)piperidin-1-yl)-N-methylacetamide (162); 2-(4-(2-(1-isobutyl-5-methyl-6-oxo-1,6-dihydropyridin-3-yl)-3-isopropyl-1H-indol-5-yl)piperidin-1-yl)-N,N-dimethylacetamide (163); 2-(4-(2-(1-benzyl-5-methyl-6-oxo-1,6-dihydropyridin-3-yl)-3-isopropyl-1H-indol-5-yl)piperidin-1-yl)-N,N-dimethylacetamide (164); 2-(4-(3-isopropyl-2-(5-methyl-6-oxo-1-(2,2,2-trifluoroethyl)-1,6-dihydropyridin-3-yl)-1H-indol-5-yl)piperidin-1-yl)-N,N-dimethylacetamide (165); 2-(4-(2-(1-(2,2-difluoroethyl)-5-methyl-6-oxo-1,6-dihydropyridin-3-yl)-3-isopropyl-1H-indol-5-yl)piperidin-1-yl)-N,N-dimethylacetamide (166); 2-(4-(2-(1-(2-hydroxyethyl)-5-methyl-6-oxo-1,6-dihydropyridin-3-yl)-3-isopropyl-1H-indol-5-yl)piperidin-1-yl)-N,N-dimethylacetamide (167); 2-(4-(2-(5-ethyl-1-methyl-6-oxo-1,6-dihydropyridin-3-yl)-3-isopropyl-1H-indol-5-yl)piperidin-1-yl)-N,N-dimethylacetamide (168); 2-(4-(3-isopropyl-2-(1-methyl-2-oxo-1,2-dihydro-[3,3'-bipyridin]-5-yl)-1H-indol-5-yl)piperidin-1-yl)-N,N-dimethylacetamide (169); 2-(4-(3-isopropyl-2-(1-methyl-6-oxo-5-phenyl-1,6-dihydropyridin-3-yl)-1H-indol-5-yl)piperidin-1-yl)-N,N-dimethylacetamide (170); 5-(3-isopropyl-5-(1-(oxetan-3-yl)piperidin-4-yl)-1H-indol-2-yl)-1,3-dimethylpyridin-2(1H)-one (171); 5-(3-isopropyl-5-(1-(2-(methylamino)ethyl)piperidin-4-yl)-1H-indol-2-yl)-1-methylpyridin-2(1H)-one (172); 5-(3-isopropyl-5-(1-propylpiperidin-4-yl)-1H-indol-2-yl)-1-methyl-3-(piperidin-1-yl) pyridin-2(1H)-one (173); 5-(5-(1-(1-acetylazetidin-3-yl)piperidin-4-yl)-3-isopropyl-1H-indol-2-yl)-3-chloro-1,4-dimethylpyridin-2(1H)-one (174); 5-(3-isopropyl-5-(1-(oxetan-3-yl)piperidin-4-yl)-1H-indol-2-yl)-1-methylpyridin-2(1H)-one (175); 5-(3-isopropyl-5-(1-(2-(methylamino)ethyl)piperidin-4-yl)-1H-indol-2-yl)-1,3-dimethylpyridin-2(1H)-one (176); 5-(3-isopropyl-5-(1-(tetrahydrofuran-3-yl)piperidin-4-yl)-1H-indol-2-yl)-1-methylpyridin-2(1H)-one (177); 5-(3-isopropyl-5-(1-(tetrahydro-2H-pyran-4-yl) piperidin-4-yl)-1H-indol-2-yl)-1,3-dimethylpyridin-2(1H)-one (178); 5-(3-isopropyl-5-(1-(oxetan-3-yl)piperidin-4-yl)-1H-indol-2-yl)-1-methylpyridin-2(1H)-one (179); 5-(3-isopropyl-5-(1-(tetrahydrofuran-3-yl)piperidin-4-yl)-1H-indol-2-yl)-1,3-dimethylpyridin-2(1H)-one (180); 5-(3-isopropyl-5-(1-methylpiperidin-4-yl)-1H-indol-2-yl)-1,3-dimethylpyridin-2(1H)-one (181); 5-(3-isopropyl-5-(1-isopropylpiperidin-4-yl)-1H-indol-2-yl)-1,3-dimethylpyridin-2(1H)-one (182); 5-(3-isopropyl-5-(1-((1-methyl-1H-pyrazol-3-yl)methyl)piperidin-4-yl)-1H-indol-2-yl)-1,3-dimethylpyridin-2(1H)-one (195); 5-(3-isopropyl-5-(1-((1-methyl-1H-pyrazol-4-yl)methyl)piperidin-4-yl)-1H-indol-2-yl)-1,3-dimethylpyridin-2(1H)-one (196); 5-(3-isopropyl-5-(1-((1-methyl-1H-pyrazol-5-yl) methyl)piperidin-4-yl)-1H-indol-2-yl)-1,3-dimethylpyridin-2(1H)-one (197); 5-(3-isopropyl-5-(1-((1-methyl-1H-1,2,4-triazol-5-yl)methyl)piperidin-4-yl)-1H-indol-2-yl)-1,3-dimethylpyridin-2(1H)-one (198); 5-(5-(1-(4,4-difluorocyclohexyl)piperidin-4-yl)-3-isopropyl-1H-indol-2-yl)-1,3-dimethylpyridin-2(1H)-one (199); 5-(5-(1-((4H-pyrazol-3-yl)methyl)piperidin-4-yl)-3-isopropyl-1H-indol-2-yl)-1,3-dimethylpyridin-2(1H)-one (200); 5-(3-isopropyl-5-(1-(tetrahydro-2H-pyran-4-yl)piperidin-4-yl)-1H-indol-2-yl)-3-methoxy-1-methylpyridin-2(1H)-one (201); 5-(3-isopropyl-5-(1-(oxetan-3-yl)piperidin-4-yl)-1H-indol-2-yl)-3-methoxy-1-methylpyridin-2(1H)-one (202);

1-ethyl-5-(3-isopropyl-5-(1-(oxetan-3-yl)piperidin-4-yl)-1H-indol-2-yl)-3-methylpyridin-2(1H)-one (204); 5-(3-isopropyl-5-(1-(tetrahydro-2H-pyran-4-yl)piperidin-4-yl)-1H-indol-2-yl)-1,3,4-trimethylpyridin-2(1H)-one (206); 5-(3-isopropyl-5-(1-(oxetan-3-yl)piperidin-4-yl)-1H-indol-2-yl)-1,3,4-trimethylpyridin-2(1H)-one (207); 1-ethyl-5-(3-isopropyl-5-(1-(tetrahydro-2H-pyran-4-yl)piperidin-4-yl)-1H-indol-2-yl)-3,4-dimethylpyridin-2(1H)-one (208); 1-ethyl-5-(3-isopropyl-5-(1-(oxetan-3-yl)piperidin-4-yl)-1H-indol-2-yl)-3,4-dimethylpyridin-2(1H)-one (209); 5-(3-isopropyl-5-(1-(tetrahydro-2H-pyran-4-yl) piperidin-4-yl)-1H-indol-2-yl)-1,3,6-trimethylpyridin-2(1H)-one (210); 5-(3-isopropyl-5-(1-(oxetan-3-yl)piperidin-4-yl)-1H-indol-2-yl)-1,3,6-trimethylpyridin-2(1H)-one (211); 5-(3-isopropyl-5-(1-isopropylpiperidin-4-yl)-1H-indol-2-yl)-1,3,4-trimethylpyridin-2(1H)-one (212); 1-ethyl-5-(3-isopropyl-5-(1-isopropylpiperidin-4-yl)-1H-indol-2-yl)-3,4-dimethylpyridin-2(1H)-one (213); 5-(3-isopropyl-5-(1-isopropylpiperidin-4-yl)-1H-indol-2-yl)-1,3,6-trimethylpyridin-2(1H)-one (214); 5-(3-isopropyl-5-(1-(oxetan-3-yl) piperidin-4-yl)-1H-indol-2-yl)-3-methoxy-1,4-dimethylpyridin-2(1H)-one (215); 5-(3-isopropyl-5-(1-(tetrahydro-2H-pyran-4-yl)piperidin-4-yl)-1H-indol-2-yl)-3-methoxy-1,4-dimethylpyridin-2(1H)-one (216); 5-(3-isopropyl-5-(1-(oxetan-3-yl)piperidin-4-yl)-1H-indol-2-yl)-3-methoxy-1,6-dimethylpyridin-2(1H)-one (217); 5-(3-isopropyl-5-(1-(tetrahydro-2H-pyran-4-yl)piperidin-4-yl)-1H-indol-2-yl)-3-methoxy-1,6-dimethylpyridin-2(1H)-one (218); 5-(3-isopropyl-5-(1-(oxetan-3-yl)piperidin-4-yl)-1H-indol-2-yl)-1,6-dimethyl-2-oxo-1,2-dihydropyridine-3-carbonitrile (219); 5-(3-isopropyl-5-(1-(tetrahydro-2H-pyran-4-yl)piperidin-4-yl)-1H-indol-2-yl)-1,6-dimethyl-2-oxo-1,2-dihydropyridine-3-carbonitrile (220); 5-(3-isopropyl-5-(1-(oxetan-3-yl)piperidin-4-yl)-1H-indol-2-yl)-1,4-dimethyl-2-oxo-1,2-dihydropyridine-3-carbonitrile (221); 5-(3-isopropyl-5-(1-(tetrahydro-2H-pyran-4-yl)piperidin-4-yl)-1H-indol-2-yl)-1,4-dimethyl-2-oxo-1,2-dihydropyridine-3-carbonitrile (222); 5-(5-(1-(cyclopropylmethyl)piperidin-4-yl)-3-isopropyl-1H-indol-2-yl)-1,3-dimethylpyridin-2(1H)-one (223); 5-(3-isopropyl-5-(1-propylpiperidin-4-yl)-1H-indol-2-yl)-1,3-dimethylpyridin-2(1H)-one (224); 5-(3-isopropyl-5-(1-((tetrahydrofuran-3-yl)methyl)piperidin-4-yl)-1H-indol-2-yl)-1,3-dimethylpyridin-2(1H)-one (225); 3-chloro-5-(3-isopropyl-5-(1-(tetrahydro-2H-pyran-4-yl)piperidin-4-yl)-1H-indol-2-yl)-1-methylpyridin-2(1H)-one (226); 3-chloro-5-(3-isopropyl-5-(1-((1-isopropyl-1H-pyrazol-4-yl)methyl)piperidin-4-yl)-1H-indol-2-yl)-1-methylpyridin-2(1H)-one (227); 5-(3-isopropyl-5-(1-(((1-propyl-1H-pyrazol-4-yl)methyl) piperidin-4-yl)-1H-indol-2-yl)-1,3-dimethylpyridin-2(1H)-one (228); N-(4-(4-(2-(1,5-dimethyl-6-oxo-1,6-dihydropyridin-3-yl)-3-isopropyl-1H-indol-5-yl)piperidin-1-yl) cyclohexyl)acetamide (229); 5-(3-isopropyl-5-(1-(4-(trifluoromethyl)cyclohexyl) piperidin-4-yl)-1H-indol-2-yl)-1,3-dimethylpyridin-2(1H)-one (230); 5-(3-isopropyl-5-(1-(4-(trifluoromethyl)cyclohexyl) piperidin-4-yl)-1H-indol-2-yl)-1,3-dimethylpyridin-2(1H)-one (231); 5-(5-(1-((1,3-dimethyl-1H-pyrazol-4-yl)methyl) piperidin-4-yl)-3-isopropyl-1H-indol-2-yl)-1,3-dimethylpyridin-2(1H)-one (232); 5-(3-isopropyl-5-(1-(4-isopropylcyclohexyl)piperidin-4-yl)-1H-indol-2-yl)-1,3-dimethylpyridin-2(1H)-one (233); 5-(3-isopropyl-5-(1-(4-isopropylcyclohexyl)piperidin-4-yl)-1H-indol-2-yl)-1,3-dimethylpyridin-2(1H)-one (234); 5-(3-isopropyl-5-(1-isopropylpiperidin-4-yl)-1H-indol-2-yl)-1-methyl-[3,3'-bipyridin]-2(1H)-one (235); 5-(5-(1-(2-hydroxyethyl) piperidin-4-yl)-3-isopropyl-1H-indol-2-yl)-1-methyl-[3,3'-bipyridin]-2(1H)-one (236); 5-(3-isopropyl-5-(1-isopropylpiperidin-4-yl)-1H-indol-2-yl)-1,4-dimethyl-[3,3'-bipyridin]-2(1H)-one (237); 3-chloro-5-(3-isopropyl-5-(1-isopropylpiperidin-4-yl)-1H-indol-2-yl)-1,4-dimethylpyridin-2(1H)-one (238); 3-chloro-5-(3-isopropyl-5-(1-(tetrahydro-2H-pyran-4-yl)piperidin-4-yl)-1H-indol-2-yl)-1,4-dimethylpyridin-2(1H)-one (241); 3-chloro-5-(3-isopropyl-5-(1-methylpiperidin-4-yl)-1H-indol-2-yl)-1,4-dimethylpyridin-2(1H)-one (240); 5-(5-(1-acetylpiperidin-4-yl)-3-isopropyl-1H-indol-2-yl)-3-chloro-1,4-dimethylpyridin-2(1H)-one (241); 3-chloro-5-(3-isopropyl-5-(1-propylpiperidin-4-yl)-1H-indol-2-yl)-1,4-dimethylpyridin-2(1H)-one (242); 3-chloro-5-(5-(1-(1,5-dihydroxypentan-3-yl)piperidin-4-yl)-3-isopropyl-1H-indol-2-yl)-1,4-dimethylpyridin-2(1H)-one (243); 5-(3-isopropyl-5-(1-isopropylpiperidin-4-yl)-1H-indol-2-yl)-1-methyl-3-(pyrimidin-5-yl)pyridin-2(1H)-one (244); 5-(3-isopropyl-5-(1-propylpiperidin-4-yl)-1H-indol-2-yl)-1-methyl-[3,3'-bipyridin]-2(1H)-one (245); 5-(3-isopropyl-5-(1-methylpiperidin-4-yl)-1H-indol-2-yl)-1-methyl-3-(pyrimidin-5-yl)pyridin-2(1H)-one (246); 5-(3-isopropyl-5-(1-methylpiperidin-4-yl)-1H-indol-2-yl)-1-methyl-[3,3'-bipyridin]-2(1H)-one (247); 3-chloro-5-(3-isopropyl-5-(1-(oxetan-3-yl)piperidin-4-yl)-1H-indol-2-yl)-1,4-dimethylpyridin-2(1H)-one (248); 5-(3-isopropyl-5-(1-propylpiperidin-4-yl)-1H-indol-2-yl)-1-methyl-3-(pyrimidin-5-yl)pyridin-2(1H)-one (249); 3-chloro-5-(3-isopropyl-5-(1-((tetrahydrofuran-2-yl)methyl)piperidin-4-yl)-1H-indol-2-yl)-1,4-dimethylpyridin-2(1H)-one (250); 5-(5-(1-butylpiperidin-4-yl)-3-isopropyl-1H-indol-2-yl)-3-chloro-1,4-dimethylpyridin-2(1H)-one (251); 3-chloro-5-(3-isopropyl-5-(1-((tetrahydrofuran-3-yl)methyl)piperidin-4-yl)-1H-indol-2-yl)-1,4-dimethylpyridin-2(1H)-one (252); 3-chloro-5-(5-(1-(2,3-dihydroxypropyl)piperidin-4-yl)-3-isopropyl-1H-indol-2-yl)-1,4-dimethylpyridin-2(1H)-one (253); 3-chloro-5-(3-isopropyl-5-(1-((tetrahydrofuran-3-yl)methyl)piperidin-4-yl)-1H-indol-2-yl)-1,4-dimethylpyridin-2(1H)-one (254-255); 5-(5-(1-isobutylpiperidin-4-yl)-3-isopropyl-1H-indol-2-yl)-1-methyl-3-(pyrimidin-5-yl)pyridin-2(1H)-one (256); 5-(3-isopropyl-5-(1-((tetrahydrofuran-3-yl)methyl)piperidin-4-yl)-1H-indol-2-yl)-1-methyl-3-(pyrimidin-5-yl)pyridin-2(1H)-one (257); 5-(4-fluoro-3-isopropyl-5-(1-propylpiperidin-4-yl)-1H-indol-2-yl)-1-methyl-3-(pyrimidin-5-yl)pyridin-2(1H)-one (258); 5-(4-fluoro-3-isopropyl-5-(1-((tetrahydrofuran-3-yl)methyl) piperidin-4-yl)-1H-indol-2-yl)-1-methyl-3-(pyrimidin-5-yl) pyridin-2(1H)-one (259); 1-ethyl-5-(3-isopropyl-5-(1-propylpiperidin-4-yl)-1H-indol-2-yl)-3-(pyrimidin-5-yl) pyridin-2(1H)-one (260); 5-(3-isopropyl-5-(1-(tetrahydro-2H-pyran-4-yl)piperidin-4-yl)-1H-indol-2-yl)-1-(2-methoxyethyl)-3-methylpyridin-2(1H)-one (261); 1-isobutyl-5-(3-isopropyl-5-(1-(tetrahydro-2H-pyran-4-yl) piperidin-4-yl)-1H-indol-2-yl)-3-methylpyridin-2(1H)-one (262); 1-benzyl-5-(3-isopropyl-5-(1-(tetrahydro-2H-pyran-4-yl)piperidin-4-yl)-1H-indol-2-yl)-3-methylpyridin-2(1H)-one (263); 1-(2-hydroxyethyl)-5-(3-isopropyl-5-(1-methylpiperidin-4-yl)-1H-indol-2-yl)-3-methylpyridin-2(1H)-one (264); 5-(3-isopropyl-5-(1-methylpiperidin-4-yl)-1H-indol-2-yl)-3-methyl-1-(2,2,2-trifluoroethyl)pyridin-2(1H)-one (265); 1-(2,2-difluoroethyl)-5-(3-isopropyl-5-(1-methylpiperidin-4-yl)-1H-indol-2-yl)-3-methylpyridin-2 (1H)-one (266); 5-(5-(1-(4-(2-hydroxypropan-2-yl) cyclohexyl)piperidin-4-yl)-3-isopropyl-1H-indol-2-yl)-1,3-dimethylpyridin-2(1H)-one (267-268); 5-(3-isopropyl-5-(1-(1-(1-methyl-1H-pyrazol-4-yl)ethyl)piperidin-4-yl)-1H-indol-2-yl)-1,3-dimethylpyridin-2(1H)-one (269); 5-(5-(1-(4-(2-hydroxypropan-2-yl)cyclohexyl)piperidin-4-yl)-3-isopropyl-1H-indol-2-yl)-1,3-dimethylpyridin-2(1H)-one (270); 5-(5-(1-(2-(dimethylamino)acetyl)piperidin-4-yl)-3-isopropyl-1H-indol-2-yl)-1,3-dimethylpyridin-2(1H)-one (271); 5-(5-(1-(1-aminocyclopropanecarbonyl)piperidin-4-yl)-3-isopropyl-1H-indol-2-yl)-1,3-dimethylpyridin-2(1H)-one (272); 5-(5-(1-(dimethylglycyl)piperidin-4-yl)-3-isopropyl-1H-indol-2-yl)-1,6-dimethyl-2-oxo-1,2-dihydropyridine-3-carbonitrile (273); 5-(5-(1-(dimethylglycyl)piperidin-4-yl)-3-isopropyl-1H-indol-2-yl)-1,4-dimethyl-2-oxo-1,2-dihydropyridine-3-carbonitrile (274); 5-(5-(1-(dimethylglycyl)piperidin-4-yl)-3-isopropyl-1H-indol-2-yl)-3-methoxy-1,6-dimethylpyridin-2(1H)-one (275); 5-(5-(1-(dimethylglycyl)piperidin-4-yl)-3-isopropyl-1H-indol-2-yl)-3-methoxy-1,4-dimethylpyridin-2(1H)-one (276); 5-(5-(1-(dimethylglycyl)piperidin-4-yl)-3-isopropyl-1H-indol-2-yl)-3-(methoxymethyl)-1-methylpyridin-2(1H)-one (277); 3-chloro-5-(5-(1-(dimethylglycyl)piperidin-4-yl)-3-isopropyl-1H-indol-2-yl)-1,4-dimethylpyridin-2(1H)-one (278); 5-(5-(1-(dimethylglycyl)piperidin-4-yl)-3-isopropyl-1H-indol-2-yl)-1,3,6-trimethylpyridin-2(1H)-one (279); 5-(5-(1-(dimethylglycyl)piperidin-4-yl)-3-isopropyl-1H-indol-2-yl)-1,3,4-trimethylpyridin-2(1H)-one (280); 5-(5-(1-(dimethylglycyl) piperidin-4-yl)-3-isopropyl-1H-indol-2-yl)-1-ethyl-3,4-dimethylpyridin-2(1H)-one (281); 5-(5-(1-(dimethylglycyl)piperidin-4-yl)-3-isopropyl-1H-indol-2-yl)-1-ethyl-3-methylpyridin-2(1H)-one (282); 1-benzyl-5-(5-(1-(dimethylglycyl)piperidin-4-yl)-3-isopropyl-1H-indol-2-yl)-3-methylpyridin-2(1H)-one (284); 5-(5-(1-(dimethylglycyl) piperidin-4-yl)-3-isopropyl-1H-indol-2-yl)-1-isobutyl-3-methylpyridin-2(1H)-one (285); 5-(5-(1-(dimethylglycyl)piperidin-4-yl)-3-isopropyl-1H-indol-2-yl)-3-methoxy-1-methylpyridin-2(1H)-one (286); 5-(5-(1-(dimethylglycyl)piperidin-4-yl)-3-isopropyl-1H-indol-2-yl)-1-(2-methoxyethyl)-3-methylpyridin-2(1H)-one (287); 5-(5-(1-((2R,4S)-4-hydroxypyrrolidine-2-carbonyl)piperidin-4-yl)-3-isopropyl-1H-indol-2-yl)-1,3-dimethylpyridin-2(1H)-one (288); 5-(5-(1-((2S,4R)-4-hydroxy-1-methylpyrrolidine-2-carbonyl)piperidin-4-yl)-3-isopropyl-1H-indol-2-yl)-1,3-dimethylpyridin-2(1H)-one (289); 5-(5-(1-((2S,4R)-4-hydroxypyrrolidine-2-carbonyl)piperidin-4-yl)-3-isopropyl-1H-indol-2-yl)-1,3-dimethylpyridin-2(1H)-one (290); 5-(5-(1-((2S,3S)-3-hydroxypyrrolidine-2-carbonyl)piperidin-4-yl)-3-isopropyl-1H-indol-2-yl)-1,3-dimethylpyridin-2(1H)-one (291); 5-(5-(1-((2R,4S)-4-hydroxypyrrolidine-2-carbonyl)piperidin-4-yl)-3-isopropyl-1H-indol-2-yl)-1,3-dimethylpyridin-2(1H)-one (292); 5-(5-(1-((2S,4R)-4-hydroxypyrrolidine-2-carbonyl)piperidin-4-yl)-3-isopropyl-1H-indol-2-yl)-1,3-dimethylpyridin-2(1H)-one (293); 5-(5-(1-(2-amino-2-methylpropanoyl)piperidin-4-yl)-3-isopropyl-1H-indol-2-yl)-1,3-dimethylpyridin-2(1H)-one (296); 5-(3-isopropyl-5-(1-(methyl-L-alanyl)piperidin-4-yl)-1H-indol-2-yl)-1,3-dimethylpyridin-2(1H)-one (297); 5-(3-isopropyl-5-(1-(2-methyl-2-(methylamino)propanoyl) piperidin-4-yl)-1H-indol-2-yl)-1,3-dimethylpyridin-2(1H)-one (298); 5-(3-isopropyl-5-(1-(methyl-D-alanyl)piperidin-4-yl)-1H-indol-2-yl)-1,3-dimethylpyridin-2(1H)-one (299); 5-(3-isopropyl-5-(1-(2-(2-oxopyrrolidin-1-yl)acetyl)piperidin-4-yl)-1H-indol-2-yl)-1,3-dimethylpyridin-2(1H)-one (300); 5-(5-(1-(dimethylglycyl)piperidin-4-yl)-3-isopropyl-1H-indol-2-yl)-1-methylpyridin-2(1H)-one (301); 3-chloro-5-(3-isopropyl-5-(1-(2,2,2-trifluoroacetyl) piperidin-4-yl)-1H-indol-2-yl)-1,4-dimethylpyridin-2(1H)-one (302); 5-(5-(1-(3-hydroxy-3-methylbutanoyl)piperidin-4-yl)-3-isopropyl-1H-indol-2-yl)-1,3-dimethylpyridin-2(1H)-one (303); 5-(5-(1-(3-hydroxy-2,2-dimethylpropanoyl)piperidin-4-yl)-3-isopropyl-1H-indol-2-yl)-1,3-dimethylpyridin-2(1H)-one (304); (S)-5-(5-(1-(3-hydroxybutanoyl) piperidin-4-yl)-3-isopropyl-1H-indol-2-yl)-1,3-dimethylpyridin-2(1H)-one (305); (R)-5-(3-isopropyl-5-(1-(2-(pyrrolidin-2-yl)acetyl)piperidin-4-yl)-1H-indol-2-yl)-1,3-dimethylpyridin-2(1H)-one (306); (S)-1-methylpyrrolidin-3-yl 4-(2-(5-chloro-1,4-dimethyl-6-oxo-1,6-dihydropyridin-3-yl)-3-isopropyl-1H-indol-5-yl)piperidine-1-carboxylate (307); 3-chloro-5-(3-isopropyl-5-(1-((2-(pyrrolidin-1-yl)ethyl)sulfonyl) piperidin-4-yl)-1H-indol-2-yl)-1,4-dimethylpyridin-2(1H)-one (308); 3-chloro-5-(5-(1-(2-hydroxy-2-methylpropyl)piperidin-4-yl)-3-isopropyl-1H-indol-2-yl)-1,4-dimethylpyridin-2(1H)-one (309); 5-(5-(1-(2-hydroxy-2-methylpropyl)piperidin-4-yl)-3-isopropyl-1H-indol-2-yl)-1,3-dimethylpyridin-2(1H)-one (310); 5-(5-(1-((3R,4S)-3-hydroxytetrahydro-2H-pyran-4-yl)piperidin-4-yl)-3-isopropyl-1H-indol-2-yl)-1,3-dimethylpyridin-2(1H)-one (313); 5-(5-(1-((3S,4S)-4-hydroxytetrahydro-2H-pyran-3-yl)piperidin-4-yl)-3-isopropyl-1H-indol-2-yl)-1,3-dimethylpyridin-2(1H)-one (314); 5-(5-(1-(2-hydroxy-2-methylpropyl)piperidin-4-yl)-3-isopropyl-1H-indol-2-yl)-1,3,4-trimethylpyridin-2(1H)-one (315); 5-(5-(1-(2-hydroxy-2-methylpropyl)piperidin-4-yl)-3-isopropyl-1H-indol-2-yl)-1,3,6-trimethylpyridin-2(1H)-one (316); 5-(5-(1-(2-hydroxy-2-methylpropyl) piperidin-4-yl)-3-isopropyl-1H-indol-2-yl)-3-methoxy-1,4-dimethylpyridin-2(1H)-one (317); 5-(5-(1-(2-hydroxy-2-methylpropyl)piperidin-4-yl)-3-isopropyl-1H-indol-2-yl)-3-methoxy-1,6-dimethylpyridin-2(1H)-one (318); 5-(5-(1-((4-hydroxytetrahydro-2H-pyran-4-yl)methyl)piperidin-4-yl)-3-isopropyl-1H-indol-2-yl)-1,3,4-trimethylpyridin-2(1H)-one (319); 5-(5-(1-((4-hydroxytetrahydro-2H-pyran-4-yl)methyl)piperidin-4-yl)-3-isopropyl-1H-indol-2-yl)-1,3,6-trimethylpyridin-2(1H)-one (320); 5-(5-(1-(2-hydroxy-2-methylpropyl)piperidin-4-yl)-3-isopropyl-1H-indol-2-yl)-1,6-dimethyl-2-oxo-1,2-dihydropyridine-3-carbonitrile (321); 5-(5-(1-(2-hydroxy-2-methylpropyl)piperidin-4-yl)-3-isopropyl-1H-indol-2-yl)-1,4-dimethyl-2-oxo-1,2-dihydropyridine-3-carbonitrile (322); 5-(5-(1-(2-hydroxy-2-methylpropyl)piperidin-4-yl)-3-isopropyl-1H-indol-2-yl)-3-(methoxymethyl)-1-methylpyridin-2(1H)-one (323); 5-(5-(1-(2-hydroxy-3-methylbutyl) piperidin-4-yl)-3-isopropyl-1H-indol-2-yl)-1,3-dimethylpyridin-2(1H)-one (324); 5-(5-(1-(2-hydroxy-3,3-dimethylbutyl)piperidin-4-yl)-3-isopropyl-1H-indol-2-yl)-1,3-dimethylpyridin-2(1H)-one (325); 5-(5-(1-(2-hydroxy-2-methylpropyl)piperidin-4-yl)-3-isopropyl-1H-indol-2-yl)-1-methyl-3-(pyrimidin-5-yl)pyridin-2(1H)-one (326); 3-chloro-5-(4-fluoro-5-(1-(2-hydroxy-2-methylpropyl)piperidin-4-yl)-3-isopropyl-1H-indol-2-yl)-1,4-dimethylpyridin-2(1H)-one (327); 5-(5-(1-(2-hydroxy-2-methylpropyl) piperidin-4-yl)-3-isopropyl-1H-indol-2-yl)-1-isobutyl-3-methylpyridin-2(1H)-one (328); 1-benzyl-5-(5-(1-(2-hydroxy-2-methylpropyl)piperidin-4-yl)-3-isopropyl-1H-indol-2-yl)-3-methylpyridin-2(1H)-one (329); 5-(3-isopropyl-5-(1-propylpiperidin-4-yl)-1H-indol-2-yl)-1-methyl-6'-morpholino-[3,3'-bipyridin]-2(1H)-one (330); 5-(3-isopropyl-5-(1-propylpiperidin-4-yl)-1H-indol-2-yl)-3-(2-methoxypyrimidin-5-yl)-1-methylpyridin-2(1H)-one (331); 5-(3-isopropyl-5-(1-propylpiperidin-4-yl)-1H-indol-2-yl)-1,5'-dimethyl-[3,3'-bipyridin]-2(1H)-one (332); 5-(3-isopropyl-5-(1-propylpiperidin-4-yl)-1H-indol-2-yl)-1,4-dimethyl-3-(1-methyl-1H-pyrazol-4-yl)pyridin-2(1H)-one (333); 5-(3-isopropyl-5-(1-propylpiperidin-4-yl)-1H-indol-2-yl)-1-methyl-3-(1-methyl-1H-pyrazol-4-yl) pyridin-2(1H)-one (334); N-(5'-(3-isopropyl-5-(1-propylpiperidin-4-yl)-1H-indol-2-yl)-1'-methyl-2'-oxo-1',2'-dihydro-[3,3'-bipyridin]-6-yl)acetamide (335); 5-(3-isopropyl-5-(1-propylpiperidin-4-yl)-1H-indol-2-yl)-1-methyl-[3,4'-bipyridin]-2(1H)-one (336); 5-(3-isopropyl-5-(1-propylpiperidin-4-yl)-1H-indol-2-yl)-1-methyl-3-(2- methylpyrimidin-5-yl)pyridin-2(1H)-one (337); 3-(2-cyclopropylpyrimidin-5-yl)-5-(3-isopropyl-5-(1-propylpiperidin-4-yl)-1H-indol-2-yl)-1-methylpyridin-2(1H)-one (338); 5-(3-isopropyl-5-(1-propylpiperidin-4-yl)-1H-indol-2-yl)-1-methyl-3-(2-(trifluoromethyl)pyrimidin-5-yl) pyridin-2 (1H)-one (339); 5-(3-isopropyl-5-(1-propylpiperidin-4-yl)-1H-indol-2-yl)-3-(3-methoxyphenyl)-1-methylpyridin-2 (1H)-one (340); 6'-fluoro-5-(3-isopropyl-5-(1-propylpiperidin-4-yl)-1H-indol-2-yl)-1-methyl-[3,3'-bipyridin]-2(1H)-one (341); 6'-fluoro-5-(3-isopropyl-5-(1-isopropylpiperidin-4-yl)-1H-indol-2-yl)-1-methyl-[3,3'-bipyridin]-2(1H)-one (342); 6'-fluoro-5-(3-isopropyl-5-(1-isopropylpiperidin-4-yl)-1H-indol-2-yl)-1,5'-dimethyl-[3,3'-bipyridin]-2(1H)-one (343); 5-(3-isopropyl-5-(1-isopropylpiperidin-4-yl)-1H-indol-2-yl)-1,2'-dimethyl-[3,3'-bipyridin]-2(1H)-one (244); 5-(3-isopropyl-5-(1-(tetrahydro-2H-pyran-4-yl)piperidin-4-yl)-1H-indol-2-yl)-3-(methoxymethyl)-1-methylpyridin-2(1H)-one (345); 5-(3-isopropyl-5-(1-(oxetan-3-yl) piperidin-4-yl)-1H-indol-2-yl)-3-(methoxymethyl)-1-methylpyridin-2(1H)-one (346); 5-(3-isopropyl-5-(1-isopropylpiperidin-4-yl)-1H-indol-2-yl)-3-(methoxymethyl)-1-methylpyridin-2(1H)-one (347); 5-(3-isopropyl-5-(1-propylpiperidin-4-yl)-1H-indol-2-yl)-3-(methoxymethyl)-1-methylpyridin-2(1H)-one (348); 5-(3-isopropyl-5-(1-(2-methoxyethyl)piperidin-4-yl)-1H-indol-2-yl)-1,6'-dimethyl-[3,3'-bipyridin]-2(1H)-one (349); 5-(3-isopropyl-5-(1-(2-methoxyethyl)piperidin-4-yl)-1H-indol-2-yl)-1-methyl-3-(1-methyl-1H-pyrazol-4-yl)pyridin-2 (1H)-one (350); 2-(4-(3-isopropyl-2-(5-(methoxymethyl)-1-methyl-6-oxo-1,6-dihydropyridin-3-yl)-1H-indol-5-yl) piperidin-1-yl)-N,N-dimethylacetamide (351); 2-(4-(3-isopropyl-2-(1-methyl-6-oxo-5-vinyl-1,6-dihydropyridin-3-yl)-1H-indol-5-yl)piperidin-1-yl)-N,N-dimethylacetamide (352); and 5-(3-isopropyl-5-(piperidin-4-yl)-1H-indol-2-yl)-3-(methoxymethyl)-1-methylpyridin-2(1H)-one (353).

One embodiment provides a compound of Formula (I) or a salt thereof, wherein said compound is selected from 5-(3-isopropyl-5-(piperidin-4-yl)-1H-indol-2-yl)-1-methylpyrazin-2(1H)-one (4); 5-(3-isopropyl-5-(piperidin-4-yl)-1H-indol-2-yl)-1,3-dimethylpyrazin-2(1H)-one (12); 2-(4-(2-(4,6-dimethyl-5-oxo-4,5-dihydropyrazin-2-yl)-3-isopropyl-1H-indol-5-yl)piperidin-1-yl)-N,N-dimethylacetamide (115); 5-(3-isopropyl-5-(1-methylpiperidin-4-yl)-1H-indol-2-yl)-1,3-dimethylpyrazin-2(1H)-one (183); 5-(3-isopropyl-5-(1-isopropylpiperidin-4-yl)-1H-indol-2-yl)-1,3-dimethylpyrazin-2(1H)-one (184); 5-(3-isopropyl-5-(1-(tetrahydro-2H-pyran-4-yl)piperidin-4-yl)-1H-indol-2-yl)-1,3-dimethylpyrazin-2(1H)-one (185); 5-(3-isopropyl-5-(1-(oxetan-3-yl) piperidin-4-yl)-1H-indol-2-yl)-1,3-dimethylpyrazin-2(1H)-one (186); 5-(3-isopropyl-5-(1-(tetrahydro-2H-pyran-3-yl)piperidin-4-yl)-1H-indol-2-yl)-1,3-dimethylpyrazin-2(1H)-one (187); 5-(3-isopropyl-5-(1-(tetrahydrofuran-3-yl)piperidin-4-yl)-1H-indol-2-yl)-1,3-dimethylpyrazin-2(1H)-one (190); 5-(5-(1-(dimethylglycyl)piperidin-4-yl)-3-isopropyl-1H-indol-2-yl)-1,3-dimethylpyrazin-2(1H)-one (295); and 5-(5-(1-(2-hydroxy-2-methylpropyl)piperidin-4-yl)-3-isopropyl-1H-indol-2-yl)-1,3-dimethylpyrazin-2(1H)-one (312).

One embodiment provides a compound of Formula (I) or a salt thereof, wherein said compound is selected from 6-(3-isopropyl-5-(piperidin-4-yl)-1H-indol-2-yl)-2-methylpyridazin-3(2H)-one (5); 6-(3-isopropyl-5-(piperidin-4-yl)-1H-indol-2-yl)-2,5-dimethylpyridazin-3(2H)-one (10); 6-(3-isopropyl-5-(piperidin-4-yl)-1H-indol-2-yl)-2,4-dimethylpyridazin-3(2H)-one (11); 6-(3-isopropyl-5-(piperidin-4-yl)-1H-indol-2-yl)-2,4,5-trimethylpyridazin-3(2H)-one (17); 2-ethyl-6-(3-isopropyl-5-(piperidin-4-yl)-1H-indol-2-yl)-4-methylpyridazin-3(2H)-one (18); 2-ethyl-6-(3-isopropyl-5-(piperidin-4-yl)-1H-indol-2-yl)-4,5-dimethylpyridazin-3(2H)-one (27); 2-(4-(2-(1,5-dimethyl-6-oxo-1,6-dihydropyridazin-3-yl)-3-isopropyl-1H-indol-5-yl) piperidin-1-yl)-N,N-dimethylacetamide (116); 2-(4-(2-(1,5-dimethyl-6-oxo-1,6-dihydropyridazin-3-yl)-3-isopropyl-1H-indol-5-yl)piperidin-1-yl)-N-methylacetamide (118); 2-(4-(3-isopropyl-2-(1,4,5-trimethyl-6-oxo-1,6-dihydropyridazin-3-yl)-1H-indol-5-yl)piperidin-1-yl)-N,N-dimethylacetamide (130); 2-(4-(3-isopropyl-2-(1,4,5-trimethyl-6-oxo-1,6-dihydropyridazin-3-yl)-1H-indol-5-yl)piperidin-1-yl)-N-methylacetamide (131); 6-(3-isopropyl-5-(1-(tetrahydro-2H-pyran-3-yl)piperidin-4-yl)-1H-indol-2-yl)-2,4-dimethylpyridazin-3(2H)-one (188); 6-(3-isopropyl-5-(1-(oxetan-3-yl)piperidin-4-yl)-1H-indol-2-yl)-2,4-dimethylpyridazin-3(2H)-one (189); 6-(3-isopropyl-5-(1-methylpiperidin-4-yl)-1H-indol-2-yl)-2,4-dimethylpyridazin-3(2H)-one (191); 6-(3-isopropyl-5-(1-isopropylpiperidin-4-yl)-1H-indol-2-yl)-2,4-dimethylpyridazin-3(2H)-one (192); 6-(3-isopropyl-5-(1-(tetrahydrofuran-3-yl)piperidin-4-yl)-1H-indol-2-yl)-2,4-dimethylpyridazin-3(2H)-one (193); 6-(3-isopropyl-5-(1-(tetrahydro-2H-pyran-4-yl) piperidin-4-yl)-1H-indol-2-yl)-2,4-dimethylpyridazin-3(2H)-one (194); 6-(3-isopropyl-5-(1-(oxetan-3-yl)piperidin-4-yl)-1H-indol-2-yl)-2,4,5-trimethylpyridazin-3(2H)-one (203); 6-(3-isopropyl-5-(1-(tetrahydro-2H-pyran-4-yl) piperidin-4-yl)-1H-indol-2-yl)-2,4,5-trimethylpyridazin-3(2H)-one (205); 6-(5-(1-(dimethylglycyl)piperidin-4-yl)-3-isopropyl-1H-indol-2-yl)-2,4,5-trimethylpyridazin-3(2H)-one (283); 6-(5-(1-(dimethylglycyl) piperidin-4-yl)-3-isopropyl-1H-indol-2-yl)-2,4-dimethylpyridazin-3(2H)-one (294); and 6-(5-(1-(2-hydroxy-2-methylpropyl)piperidin-4-yl)-3-isopropyl-1H-indol-2-yl)-2,4-dimethylpyridazin-3(2H)-one (311).

One embodiment provides a compound of Formula (I) or a salt thereof, wherein said compound is 5-(3-isopropyl-5-(piperidin-4-yl)-1H-indol-2-yl)-1,3-dimethylpyrimidine-2,4 (1H,3H)-dione (21).

The present invention may be embodied in other specific forms without departing from the spirit or essential attributes thereof. The invention encompasses all combinations of the aspects and/or embodiments of the invention noted herein. It is understood that any and all embodiments of the present invention may be taken in conjunction with any other embodiment or embodiments to describe additional embodiments. It is also to be understood that each individual element of the embodiments is meant to be combined with any and all other elements from any embodiment to describe an additional embodiment.

Definitions

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof. Embodiments identified herein as exemplary or preferred are intended to be illustrative and not limiting.

Unless specifically stated otherwise herein, references made in the singular may also include the plural. For example, "a" and "an" may refer to either one, or one or more.

As used herein, the phrase "compounds" refers to at least one compound. For example, a compound of Formula (I) includes a compound of Formula (I) and two or more compounds of Formula (I).

Unless otherwise indicated, any heteroatom with unsatisfied valences is assumed to have hydrogen atoms sufficient to satisfy the valences.

The definitions set forth herein take precedence over definitions set forth in any patent, patent application, and/or patent application publication incorporated herein by reference.

Listed below are definitions of various terms used to describe the present invention. These definitions apply to the terms as they are used throughout the specification (unless they are otherwise limited in specific instances) either individually or as part of a larger group.

Throughout the specification, groups and substituents thereof may be chosen by one skilled in the field to provide stable moieties and compounds.

In accordance with a convention used in the art,

is used in structural formulas herein to depict the bond that is the point of attachment of the moiety or substituent to the core or backbone structure.

The terms "halo" and "halogen," as used herein, refer to F, Cl, Br, and I.

The term "cyano" refers to the group —CN.
The term "amino" refers to the group —NH$_2$.
The term "oxo" refers to the group =O.

The term "alkyl" as used herein, refers to both branched and straight-chain saturated aliphatic hydrocarbon groups containing, for example, from 1 to 12 carbon atoms, from 1 to 6 carbon atoms, and from 1 to 4 carbon atoms. Examples of alkyl groups include, but are not limited to, methyl (Me), ethyl (Et), propyl (e.g., n-propyl and i-propyl), butyl (e.g., n-butyl, i-butyl, sec-butyl, and t-butyl), and pentyl (e.g., n-pentyl, isopentyl, neopentyl), n-hexyl, 2-methylpentyl, 2-ethylbutyl, 3-methylpentyl, and 4-methylpentyl. When numbers appear in a subscript after the symbol "C", the subscript defines with more specificity the number of carbon atoms that a particular group may contain. For example, "$C_{1-6}$ alkyl" denotes straight and branched chain alkyl groups with one to six carbon atoms.

The term "fluoroalkyl" as used herein is intended to include both branched and straight-chain saturated aliphatic hydrocarbon groups substituted with one or more fluorine atoms. For example, "$C_{1-4}$ fluoroalkyl" is intended to include $C_1$, $C_2$, $C_3$, and $C_4$ alkyl groups substituted with one or more fluorine atoms. Representative examples of fluoroalkyl groups include, but are not limited to, —CF$_3$ and —CH$_2$CF$_3$.

The term "chloroalkyl" as used herein is intended to include both branched and straight-chain saturated aliphatic hydrocarbon groups substituted with one or more chlorine atoms. For example, "$C_{1-4}$ chloroalkyl" is intended to include $C_1$, $C_2$, $C_3$, and $C_4$ alkyl groups substituted with one or more chlorine atoms. Representative examples of fluoroalkyl groups include, but are not limited to, —CCl$_3$ and —CH$_2$CCl$_3$.

The term "cyanoalkyl" includes both branched and straight-chain saturated alkyl groups substituted with one or more cyano groups. For example, "cyanoalkyl" includes —CH$_2$CN, —CH$_2$CH$_2$CN, and $C_{1-4}$ cyanoalkyl.

The term "aminoalkyl" includes both branched and straight-chain saturated alkyl groups substituted with one or more amino groups. For example, "aminoalkyl" includes —CH$_2$NH$_2$, —CH$_2$CH$_2$NH$_2$, and $C_{1-4}$ aminoalkyl.

The term "hydroxyalkyl" includes both branched and straight-chain saturated alkyl groups substituted with one or more hydroxyl groups. For example, "hydroxyalkyl" includes —CH$_2$OH, —CH$_2$CH$_2$OH, and $C_{1-4}$ hydroxyalkyl.

The term "hydroxy-fluoroalkyl" includes both branched and straight-chain saturated alkyl groups substituted with one or more hydroxyl groups and one or more fluorine atoms. For example, "hydroxy-fluoroalkyl" includes —CHFCH$_2$OH, —CH$_2$CHFC(CH$_3$)$_2$OH, and $C_{1-4}$ hydroxyfluoroalkyl.

The term "cycloalkyl," as used herein, refers to a group derived from a non-aromatic monocyclic or polycyclic hydrocarbon molecule by removal of one hydrogen atom from a saturated ring carbon atom. Representative examples of cycloalkyl groups include, but are not limited to, cyclopropyl, cyclopentyl, and cyclohexyl. When numbers appear in a subscript after the symbol "C", the subscript defines with more specificity the number of carbon atoms that a particular cycloalkyl group may contain. For example, "C3-C6 cycloalkyl" denotes cycloalkyl groups with three to six carbon atoms.

The term "alkoxy," as used herein, refers to an alkyl group attached to the parent molecular moiety through an oxygen atom, for example, methoxy group (—OCH$_3$). For example, "$C_{1-3}$ alkoxy" denotes alkoxy groups with one to three carbon atoms.

The terms "fluoroalkoxy" and "—O(fluoroalkyl)" represent a fluoroalkyl group as defined above attached through an oxygen linkage (—O—). For example, "$C_{1-4}$ fluoroalkoxy" is intended to include $C_1$, $C_2$, $C_3$, and $C_4$ fluoroalkoxy groups.

The term "alkoxyalkoxy," as used herein, refers to an alkoxy group attached to the parent molecular moiety through an alkoxy group, for example, methoxymethoxy group (—OCH$_2$OCH$_3$). For example, "$C_{1-4}$ alkoxyalkoxy" denotes alkoxy groups with one to four carbon atoms.

The term "benzyl," as used herein, refers to a methyl group in which one of the hydrogen atoms is replaced by a phenyl group. The phenyl ring may be unsubstituted or may contain one or more substituents as valence allows.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The compounds of Formula (I) can be provided as amorphous solids or crystalline solids. Lyophilization can be employed to provide the compounds of Formula (I) as amorphous solids.

It should further be understood that solvates (e.g., hydrates) of the compounds of Formula (I) are also within the scope of the present invention. The term "solvate" means a physical association of a compound of Formula (I) with one or more solvent molecules, whether organic or inorganic. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, isopropanolates, acetonitrile solvates, and ethyl acetate solvates. Methods of solvation are known in the art.

Various forms of prodrugs are well known in the art and are described in:

a) The *Practice of Medicinal Chemistry*, Camille G. Wermuth et al., Ch 31, (Academic Press, 1996);

b) *Design of Prodrugs*, edited by H. Bundgaard, (Elsevier, 1985);

c) *A Textbook of Drug Design and Development*, P. Krogsgaard-Larson and H. Bundgaard, eds. Ch 5, pgs 113-191 (Harwood Academic Publishers, 1991); and d) *Hydrolysis in Drug and Prodrug Metabolism*, Bernard Testa and Joachim M. Mayer, (Wiley-VCH, 2003).

In addition, compounds of Formula (I), subsequent to their preparation, can be isolated and purified to obtain a composition containing an amount by weight equal to or greater than 99% of a compound of Formula (I) ("substantially pure"), which is then used or formulated as described herein. Such "substantially pure" compounds of Formula (I) are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to act as an inhibitor to TLR7/8/9, or effective to treat or prevent autoimmune and/or inflammatory disease states, such as SLE, IBD, multiple sclerosis (MS), Sjögren's syndrome, and rheumatoid arthritis.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting its development; and/or (c) relieving the disease-state, i.e., causing regression of the disease state.

The compounds of the present invention are intended to include all isotopes of atoms occurring in the present compounds. Isotopes include those atoms having the same atomic number but different mass numbers. By way of general example and without limitation, isotopes of hydrogen include deuterium (D) and tritium (T). Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. For example, methyl (—$CH_3$) also includes deuterated methyl groups such as —$CD_3$.

Utility

The human immune system has evolved to defend the body from micro-organisms, viruses, and parasites that can cause infection, disease or death. Complex regulatory mechanisms ensure that the various cellular components of the immune system target the foreign substances or organisms, while not causing permanent or significant damage to the individual. While the initiating events are not well understood at this time, in autoimmune disease states the immune system directs its inflammatory response to target organs in the afflicted individual. Different autoimmune diseases are typically characterized by the predominate or initial target organ or tissues affected; such as the joint in the case of rheumatoid arthritis, the thyroid gland in the case of Hashimoto's thyroiditis, the central nervous system in the case of multiple sclerosis, the pancreas in the case of type I diabetes, and the bowel in the case of inflammatory bowel disease.

The compounds of the invention inhibit signaling through Toll-like receptor 7, or 8, or 9 (TLR7, TLR8, TLR9) or combinations thereof. Accordingly, compounds of Formula (I) have utility in treating conditions associated with the inhibition of signaling through one or more of TLR7, TLR8, or TLR9. Such conditions include TLR7, TLR8, or TLR9 receptor associated diseases in which cytokine levels are modulated as a consequence of intracellular signaling.

As used herein, the terms "treating" or "treatment" encompass the treatment of a disease state in a mammal, particularly in a human, and include: (a) preventing or delaying the occurrence of the disease state in a mammal, in particular, when such mammal is predisposed to the disease state but has not yet been diagnosed as having it; (b) inhibiting the disease state, i.e., arresting its development; and/or (c) achieving a full or partial reduction of the symptoms or disease state, and/or alleviating, ameliorating, lessening, or curing the disease or disorder and/or its symptoms.

In view of their activity as selective inhibitors of TLR7, TLR8, or TLR9, the compounds of Formula (I) are useful in treating TLR7, TLR8, or TLR9 family receptor associated diseases, but not limited to, inflammatory diseases such as Crohn's disease, ulcerative colitis, asthma, graft versus host disease, allograft rejection, chronic obstructive pulmonary disease; autoimmune diseases such as Graves' disease, rheumatoid arthritis, systemic lupus erythematosus, psoriasis; auto-inflammatory diseases including CAPS, TRAPS, FMF, adult onset Still's disease, systemic onset juvenile idiopathic arthritis, gout, gouty arthritis; metabolic diseases including type 2 diabetes, atherosclerosis, myocardial infarction; destructive bone disorders such as bone resorption disease, osteoarthritis, osteoporosis, multiple myeloma-related bone disorder; proliferative disorders such as acute myelogenous leukemia, chronic myelogenous leukemia; angiogenic disorders such as angiogenic disorders including solid tumors, ocular neovasculization, and infantile haemangiomas; infectious diseases such as sepsis, septic shock, and Shigellosis; neurodegenerative diseases such as Alzheimer's disease, Parkinson's disease, cerebral ischemias or neurodegenerative disease caused by traumatic injury, oncologic and viral diseases such as metastatic melanoma, Kaposi's sarcoma, multiple myeloma, and HIV infection and CMV retinitis, AIDS, respectively.

More particularly, the specific conditions or diseases that may be treated with the inventive compounds include, without limitation, pancreatitis (acute or chronic), asthma, allergies, adult respiratory distress syndrome, chronic obstructive pulmonary disease, glomerulonephritis, rheumatoid arthritis, systemic lupus erythematosus, scleroderma, chronic thyroiditis, Graves' disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, graft vs. host disease, inflammatory reaction induced by endotoxin, tuberculosis, atherosclerosis, muscle degeneration, cachexia, psoriatic arthritis, Reiter's syndrome, gout, traumatic arthritis, rubella arthritis, acute synovitis, pancreatic β-cell disease; diseases characterized by massive neutrophil infiltration; rheumatoid spondylitis, gouty arthritis and other arthritic conditions, cerebral malaria, chronic pulmonary inflammatory disease, silicosis, pulmonary sarcoidosis, bone resorption disease, allograft rejections, fever and myalgias due to infection, cachexia secondary to infection, keloid formation, scar tissue formation, ulcerative colitis, pyresis, influenza, osteoporosis, osteoarthritis, acute myelogenous leukemia, chronic myelogenous leukemia, metastatic melanoma, Kaposi's sarcoma, multiple myeloma, sepsis, septic shock, and Shigellosis; Alzheimer's disease, Parkinson's disease, cerebral ischemias or neurodegenerative disease caused by traumatic injury; angiogenic disorders including solid tumors, ocular neovasculization, and infantile haemangiomas; viral diseases including acute hepatitis infection (including hepatitis A, hepatitis B and hepatitis C), HIV infection and CMV retinitis, AIDS, ARC or malignancy, and herpes; stroke, myocardial ischemia, ischemia in stroke heart attacks, organ hypoxia, vascular hyperplasia, cardiac and renal reperfusion injury, thrombosis, cardiac hypertrophy, thrombin-induced platelet aggregation, endotoxemia and/or toxic shock syndrome, conditions associated with prostaglandin endoperoxidase syndase-2, and pemphigus vulgaris. Preferred methods of treatment are those wherein the condition is selected from Crohn's disease, ulcerative colitis, allograft rejection, rheumatoid arthritis, psoriasis, ankylosing spondylitis, psoriatic arthritis, and pemphigus vulgaris. Alternatively preferred methods of treatment are those wherein the condition is selected from ischemia reperfusion injury, including cerebral ischemia reperfusions injury arising from stroke and cardiac ischemia reperfusion injury arising from myocardial infarction. Another preferred method of treatment is one in which the condition is multiple myeloma.

In one embodiment, the compounds of Formula (I) are useful in treating cancer, including Waldenstrom's Macroglobulinemia (WM), diffuse large B cell lymphoma (DLBCL), chronic lymphocytic leukemia (CLL), cutaneous diffuse large B cell lymphoma, and primary CNS lymphoma.

In addition, the TLR7, TLR8, or TLR9 inhibitors of the present invention inhibit the expression of inducible pro-inflammatory proteins such as prostaglandin endoperoxide synthase-2 (PGHS-2), also referred to as cyclooxygenase-2 (COX-2), IL-1, IL-6, IL-18, chemokines. Accordingly, additional TLR7/8/9 associated conditions include edema, analgesia, fever and pain, such as neuromuscular pain, headache, pain caused by cancer, dental pain and arthritis pain. The inventive compounds also may be used to treat veterinary viral infections, such as lentivirus infections, including, but not limited to equine infectious anemia virus; or retrovirus infections, including feline immunodeficiency virus, bovine immunodeficiency virus, and canine immunodeficiency virus.

The present invention thus provides methods for treating such conditions, comprising administering to a subject in need thereof a therapeutically-effective amount of at least one compound of Formula (I) or a salt thereof "Therapeutically effective amount" is intended to include an amount of a compound of the present invention that is effective when administered alone or in combination to inhibit autoimmune disease or chronic inflammatory disease.

The methods of treating TLR7, TLR8, or TLR9 associated conditions may comprise administering compounds of Formula (I) alone or in combination with each other and/or other suitable therapeutic agents useful in treating such conditions. Accordingly, "therapeutically effective amount" is also intended to include an amount of the combination of compounds claimed that is effective to inhibit TLR7, TLR8, or TLR9 and/or treat diseases associated with TLR7, TLR8, or TLR9.

Exemplary of such other therapeutic agents include corticosteroids, rolipram, calphostin, cytokine-suppressive anti-inflammatory drugs (CSAIDs), Interleukin-10, glucocorticoids, salicylates, nitric oxide, and other immunosuppressants; nuclear translocation inhibitors, such as deoxyspergualin (DSG); non-steroidal anti-inflammatory drugs (NSAIDs) such as ibuprofen, celecoxib and rofecoxib; steroids such as prednisone or dexamethasone; antiviral agents such as abacavir; antiproliferative agents such as methotrexate, leflunomide, FK506 (tacrolimus, PROGRAF®); anti-malarials such as hydroxychloroquine; cytotoxic drugs such as azathiprine and cyclophosphamide; TNF-α inhibitors such as tenidap, anti-TNF antibodies or soluble TNF receptor, and rapamycin (sirolimus or RAPAMUNE®) or derivatives thereof.

The above other therapeutic agents, when employed in combination with the compounds of the present invention, may be used, for example, in those amounts indicated in the *Physicians' Desk Reference* (PDR) or as otherwise determined by one of ordinary skill in the art. In the methods of the present invention, such other therapeutic agent(s) may be administered prior to, simultaneously with, or following the administration of the inventive compounds. The present invention also provides pharmaceutical compositions capable of treating TLR7/8/9 receptor-associated conditions, including IL-1 family receptor-mediated diseases as described above.

The inventive compositions may contain other therapeutic agents as described above and may be formulated, for example, by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulation.

Accordingly, the present invention further includes compositions comprising one or more compounds of Formula (I) and a pharmaceutically acceptable carrier.

A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include without limitation the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences,* 17th Edition (1985), which is incorporated herein by reference in its entirety.

Compounds in accordance with Formula (I) can be administered by any means suitable for the condition to be treated, which can depend on the need for site-specific treatment or quantity of Formula (I) compound to be delivered.

Also embraced within this invention is a class of pharmaceutical compositions comprising a compound of Formula (I) and one or more non-toxic, pharmaceutically-acceptable carriers and/or diluents and/or adjuvants (collectively referred to herein as "carrier" materials) and, if desired, other active ingredients. The compounds of Formula (I) may be administered by any suitable route, preferably in the form of a pharmaceutical composition adapted to such a route, and in a dose effective for the treatment intended. The compounds and compositions of the present invention may, for example, be administered orally, mucosally, or parentally including intravascularly, intravenously, intraperitoneally, subcutaneously, intramuscularly, and intrasternally in dosage unit formulations containing conventional pharmaceutically acceptable carriers, adjuvants, and vehicles. For example, the pharmaceutical carrier may contain a mixture of mannitol or lactose and microcrystalline cellulose. The mixture may contain additional components such as a lubricating agent, e.g. magnesium stearate and a disintegrating agent such as crospovidone. The carrier mixture may be filled into a gelatin capsule or compressed as a tablet. The pharmaceutical composition may be administered as an oral dosage form or an infusion, for example.

For oral administration, the pharmaceutical composition may be in the form of, for example, a tablet, capsule, liquid capsule, suspension, or liquid. The pharmaceutical composition is preferably made in the form of a dosage unit containing a particular amount of the active ingredient. For example, the pharmaceutical composition may be provided as a tablet or capsule comprising an amount of active ingredient in the range of from about 0.1 to 1000 mg, preferably from about 0.25 to 250 mg, and more preferably from about 0.5 to 100 mg. A suitable daily dose for a human or other mammal may vary widely depending on the condition of the patient and other factors, but, can be determined using routine methods.

Any pharmaceutical composition contemplated herein can, for example, be delivered orally via any acceptable and suitable oral preparations. Exemplary oral preparations, include, but are not limited to, for example, tablets, troches, lozenges, aqueous and oily suspensions, dispersible powders or granules, emulsions, hard and soft capsules, liquid capsules, syrups, and elixirs. Pharmaceutical compositions intended for oral administration can be prepared according to any methods known in the art for manufacturing pharmaceutical compositions intended for oral administration. In order to provide pharmaceutically palatable preparations, a pharmaceutical composition in accordance with the invention can contain at least one agent selected from sweetening agents, flavoring agents, coloring agents, demulcents, antioxidants, and preserving agents.

A tablet can, for example, be prepared by admixing at least one compound of Formula (I) with at least one non-toxic pharmaceutically acceptable excipient suitable for the manufacture of tablets. Exemplary excipients include, but are not limited to, for example, inert diluents, such as, for example, calcium carbonate, sodium carbonate, lactose, calcium phosphate, and sodium phosphate; granulating and disintegrating agents, such as, for example, microcrystalline cellulose, sodium crosscarmellose, corn starch, and alginic acid; binding agents, such as, for example, starch, gelatin, polyvinyl-pyrrolidone, and acacia; and lubricating agents, such as, for example, magnesium stearate, stearic acid, and talc. Additionally, a tablet can either be uncoated, or coated by known techniques to either mask the bad taste of an unpleasant tasting drug, or delay disintegration and absorption of the active ingredient in the gastrointestinal tract thereby sustaining the effects of the active ingredient for a longer period. Exemplary water soluble taste masking materials, include, but are not limited to, hydroxypropyl-methylcellulose and hydroxypropyl-cellulose. Exemplary time delay materials, include, but are not limited to, ethyl cellulose and cellulose acetate butyrate.

Hard gelatin capsules can, for example, be prepared by mixing at least one compound of Formula (I) with at least one inert solid diluent, such as, for example, calcium carbonate; calcium phosphate; and kaolin.

Soft gelatin capsules can, for example, be prepared by mixing at least one compound of Formula (I) with at least one water soluble carrier, such as, for example, polyethylene glycol; and at least one oil medium, such as, for example, peanut oil, liquid paraffin, and olive oil.

An aqueous suspension can be prepared, for example, by admixing at least one compound of Formula (I) with at least one excipient suitable for the manufacture of an aqueous suspension. Exemplary excipients suitable for the manufacture of an aqueous suspension, include, but are not limited to, for example, suspending agents, such as, for example, sodium carboxymethylcellulose, methylcellulose, hydroxypropylmethyl-cellulose, sodium alginate, alginic acid, polyvinyl-pyrrolidone, gum tragacanth, and gum acacia; dispersing or wetting agents, such as, for example, a naturally-occurring phosphatide, e.g., lecithin; condensation products of alkylene oxide with fatty acids, such as, for example, polyoxyethylene stearate; condensation products of ethylene oxide with long chain aliphatic alcohols, such as, for example heptadecaethylene-oxycetanol; condensation products of ethylene oxide with partial esters derived from fatty acids and hexitol, such as, for example, polyoxyethylene sorbitol monooleate; and condensation products of ethylene oxide with partial esters derived from fatty acids and hexitol anhydrides, such as, for example, polyethylene sorbitan monooleate. An aqueous suspension can also contain at least one preservative, such as, for example, ethyl and n-propyl p-hydroxybenzoate; at least one coloring agent; at least one flavoring agent; and/or at least one sweetening agent, including but not limited to, for example, sucrose, saccharin, and aspartame.

Oily suspensions can, for example, be prepared by suspending at least one compound of Formula (I) in either a vegetable oil, such as, for example, arachis oil; olive oil; sesame oil; and coconut oil; or in mineral oil, such as, for example, liquid paraffin. An oily suspension can also contain at least one thickening agent, such as, for example, beeswax; hard paraffin; and cetyl alcohol. In order to provide a palatable oily suspension, at least one of the sweetening agents already described hereinabove, and/or at least one flavoring agent can be added to the oily suspension. An oily suspension can further contain at least one preservative, including, but not limited to, for example, an anti-oxidant, such as, for example, butylated hydroxyanisol, and alpha-tocopherol.

Dispersible powders and granules can, for example, be prepared by admixing at least one compound of Formula (I) with at least one dispersing and/or wetting agent; at least one suspending agent; and/or at least one preservative. Suitable dispersing agents, wetting agents, and suspending agents are as already described above. Exemplary preservatives include, but are not limited to, for example, anti-oxidants, e.g., ascorbic acid. In addition, dispersible powders and granules can also contain at least one excipient, including, but not limited to, for example, sweetening agents; flavoring agents; and coloring agents.

An emulsion of at least one compound of Formula (I) thereof can, for example, be prepared as an oil-in-water emulsion. The oily phase of the emulsions comprising compounds of Formula (I) may be constituted from known ingredients in a known manner. The oil phase can be provided by, but is not limited to, for example, a vegetable oil, such as, for example, olive oil and arachis oil; a mineral oil, such as, for example, liquid paraffin; and mixtures thereof. While the phase may comprise merely an emulsifier, it may comprise a mixture of at least one emulsifier with a fat or an oil or with both a fat and an oil. Suitable emulsifying agents include, but are not limited to, for example, naturally-occurring phosphatides, e.g., soy bean lecithin; esters or partial esters derived from fatty acids and hexitol anhydrides, such as, for example, sorbitan monooleate; and condensation products of partial esters with ethylene oxide, such as, for example, polyoxyethylene sorbitan monooleate. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. An emulsion can also contain a sweetening agent, a flavoring agent, a preservative, and/or an antioxidant. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The compounds of Formula (I) can, for example, also be delivered intravenously, subcutaneously, and/or intramuscularly via any pharmaceutically acceptable and suitable injectable form. Exemplary injectable forms include, but are not limited to, for example, sterile aqueous solutions comprising acceptable vehicles and solvents, such as, for example, water, Ringer's solution, and isotonic sodium chloride solution; sterile oil-in-water microemulsions; and aqueous or oleaginous suspensions.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e. Captisol), cosolvent solubilization (i.e. propylene glycol) or micellar solubilization (i.e. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

A sterile injectable oil-in-water microemulsion can, for example, be prepared by 1) dissolving at least one compound of Formula (I) in an oily phase, such as, for example, a mixture of soybean oil and lecithin; 2) combining the Formula (I) containing oil phase with a water and glycerol mixture; and 3) processing the combination to form a microemulsion.

A sterile aqueous or oleaginous suspension can be prepared in accordance with methods already known in the art. For example, a sterile aqueous solution or suspension can be prepared with a non-toxic parenterally-acceptable diluent or solvent, such as, for example, 1,3-butane diol; and a sterile oleaginous suspension can be prepared with a sterile non-toxic acceptable solvent or suspending medium, such as, for example, sterile fixed oils, e.g., synthetic mono- or diglycerides; and fatty acids, such as, for example, oleic acid.

Pharmaceutically acceptable carriers, adjuvants, and vehicles that may be used in the pharmaceutical compositions of this invention include, but are not limited to, ion exchangers, alumina, aluminum stearate, lecithin, self-emulsifying drug delivery systems (SEDDS) such as d-alpha-tocopherol polyethyleneglycol 1000 succinate, surfactants used in pharmaceutical dosage forms such as Tweens, polyethoxylated castor oil such as CREMOPHOR surfactant (BASF), or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as alpha-, beta-, and gamma-cyclodextrin, or chemically modified derivatives such as hydroxyalkylcyclodextrins, including 2- and 3-hydroxypropyl-cyclodextrins, or other solubilized derivatives may also be advantageously used to enhance delivery of compounds of the formulae described herein.

The pharmaceutically active compounds of this invention can be processed in accordance with conventional methods of pharmacy to produce medicinal agents for administration to patients, including humans and other mammals. The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

The amounts of compounds that are administered and the dosage regimen for treating a disease condition with the compounds and/or compositions of this invention depends on a variety of factors, including the age, weight, sex, the medical condition of the subject, the type of disease, the severity of the disease, the route and frequency of administration, and the particular compound employed. Thus, the dosage regimen may vary widely, but can be determined routinely using standard methods. A daily dose of about 0.001 to 100 mg/kg body weight, preferably between about 0.0025 and about 50 mg/kg body weight and most preferably between about 0.005 to 10 mg/kg body weight, may be appropriate. The daily dose can be administered in one to four doses per day. Other dosing schedules include one dose per week and one dose per two day cycle.

For therapeutic purposes, the active compounds of this invention are ordinarily combined with one or more adjuvants appropriate to the indicated route of administration. If administered orally, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

Pharmaceutical compositions of this invention comprise at least one compound of Formula (I) and optionally an additional agent selected from any pharmaceutically acceptable carrier, adjuvant, and vehicle. Alternate compositions of this invention comprise a compound of the Formula (I) described herein, or a prodrug thereof, and a pharmaceutically acceptable carrier, adjuvant, or vehicle.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of a cardiovascular and/or inflammatory disorder (as defined previously). In another embodiment, the package insert states that the pharmaceutical composition can be used in combination (as defined previously) with a second therapeutic agent to treat cardiovascular and/or inflammatory disorder. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Methods of Preparation

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety by reference.

The compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Third Edition, Wiley and Sons, 1999).

Compounds of Formula (I) may be prepared by reference to the methods illustrated in the following Scheme. As shown therein the end product is a compound having the same structural formula as Formula (I). It will be understood that any compound of Formula (I) may be produced by the schemes by the suitable selection of reagents with appropriate substitution. Solvents, temperatures, pressures, and other reaction conditions may readily be selected by one of ordinary skill in the art. Starting materials are commercially available or readily prepared by one of ordinary skill in the art. Constituents of compounds are as defined herein or elsewhere in the specification.

As shown in Scheme 1, compounds of Formula I may be produced, starting with the substituted 5-haloindoles (2). 2 can be prepared from the 3-formyl indoles (via reduction) or from the 3-H indoles, via alkylation. Transition metal catalyzed cross coupling of 2 and boronate 3 followed by olefin reduction and bromination affords 4, which can then be converted to the boronic ester 5. Transition metal catalyzed cross coupling of 5 with aryl halide 6 followed by Boc deprotection yields 7. Alkylation of 7 leads to the production of the compounds of Formula I.

SCHEME 1

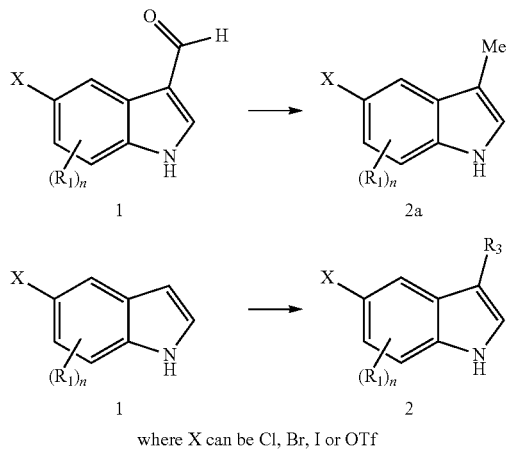

where X can be Cl, Br, I or OTf

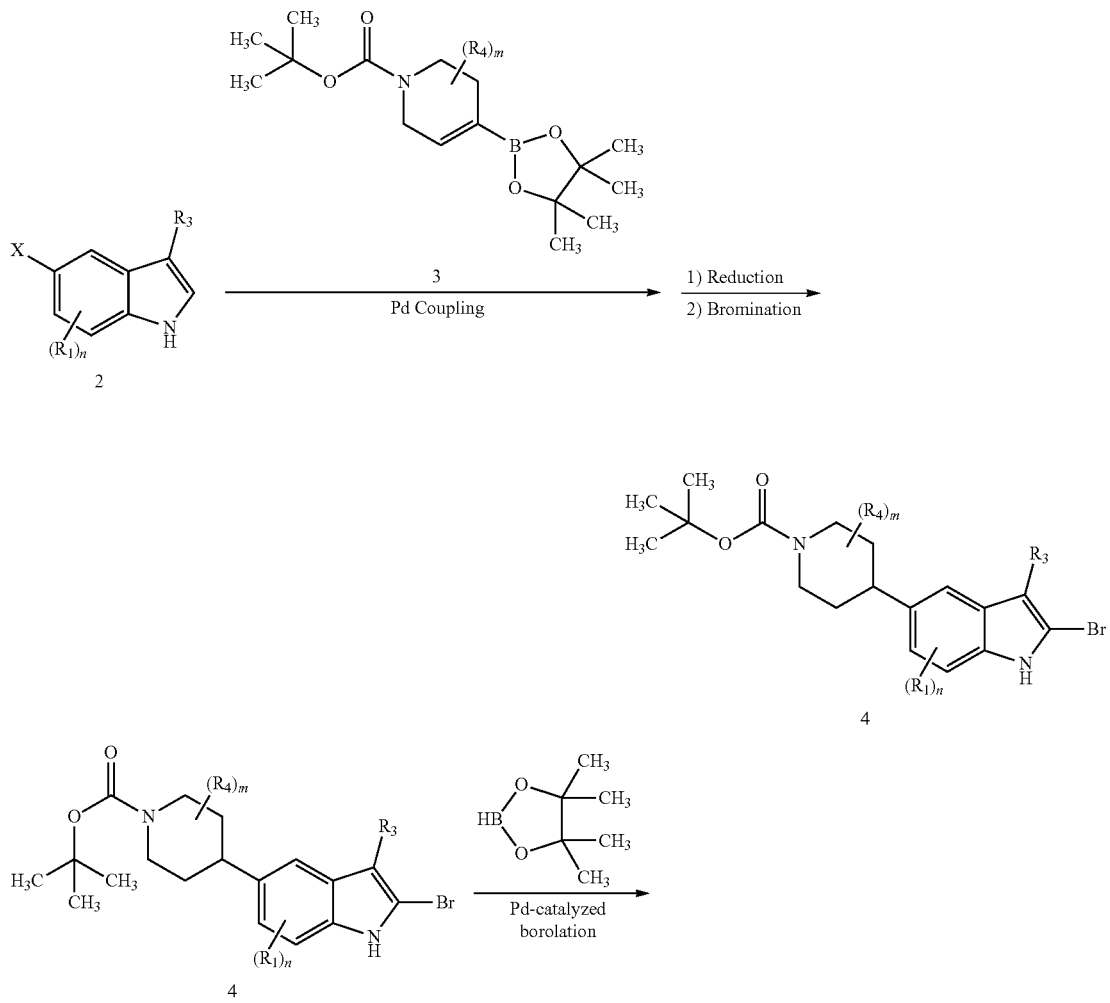

-continued

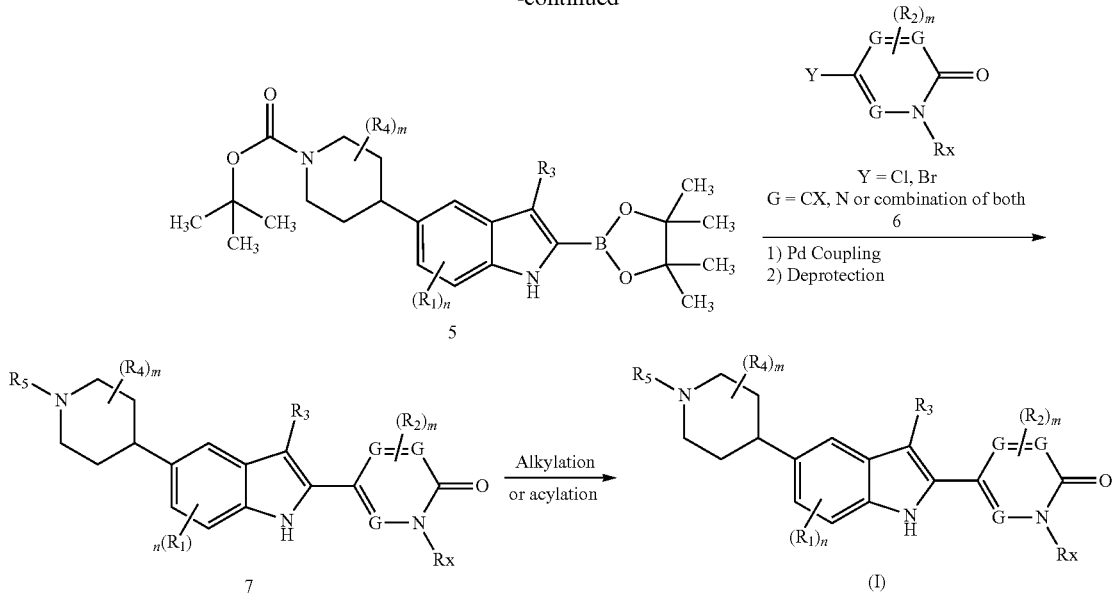

Abbreviations

Ac acetyl
ACN acetonitrile
anhyd. anhydrous
aq. aqueous
$BH_3DMS$ boron dimethylsulfide
Bn benzyl
Bu butyl
Boc tert-butoxycarbonyl
CV Column Volumes
DBU 1,8-diazabicyclo[5.4.0]undec-7-ene
DCE dichloroethane
DCM dichloromethane
DMF dimethylformamide
DMSO dimethylsulfoxide
EtOAc ethyl acetate
Et ethyl
EtOH ethanol
$Et_3N$ triethylamine
H or $H_2$ hydrogen
h, hr or hrs hour(s)
hex hexane
i iso
IPA isopropyl alcohol
HCl hydrochloric acid
HPLC high pressure liquid chromatography
LC liquid chromatography
M molar
mM millimolar
Me methyl
MeOH methanol
MHz megahertz
min. minute(s)
mins minute(s)
$M^{+1}$ $(M+H)^+$
MS mass spectrometry
n or N normal
NBS n-bromosuccinimide
nm nanometer
nM nanomolar Pd/C palladium on carbon
$PdCl_2$(dppf) [1,1'-bis(diphenylphosphino)ferrocene]dichloropalladium(II)
Ph phenyl
Pr propyl
PSI pounds per square inch
Ret Time retention time
sat. saturated
SFC supercritical fluid chromatography
T3P propane phosphonic anhydride
TEA triethylamine
TFA trifluoroacetic acid
THF tetrahydrofuran
TsCl 4-toluenesulfonyl chloride
XPhos G2 Precatalyst chloro(2-dicyclohexylphosphino-2',4',6'-triisopropyl-1,1'-biphenyl)[2-(2'-amino-1,1'-biphenyl)]palladium(II)

Analytical and Preparative HPLC Conditions:

QC-ACN-AA-XB: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm.

QC-ACN-TFA-XB: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm.

Method A1: L3 Acquity: Column: (LCMS) UPLC BEH C18, 2.1×50 mm, 1.7 μm particles; Mobile Phase: (A) water; (B) acetonitrile; Buffer: 0.05% TFA; Gradient Range: 2%-98% B (0 to 1 min) 98% B (to 1.5 min) 98%-2% B (to 1.6 min); Gradient Time: 1.6 min; Flow Rate: 0.8 mL/min; Analysis Time: 2.2 min; Detection: Detector 1: UV at 220 nm; Detector 2: MS (ESI$^+$).

Method B1: L2 Aquity (4); Column: (LCMS) UPLC BEH C18, 2.1×50 mm, 1.7 μm particles; Mobile Phase: (A)

water; (B) acetonitrile; Buffer: 0.05% TFA; Gradient Range: 2%-98% B (0 to 1 min) 98% B (to 1.5 min) 98%-2% B (to 1.5 min); Gradient Time: 1.8 min; Flow Rate: 0.8 mL/min; Analysis Time: 2.2 min; Detection: Detector 1: UV at 220 nm; Detector 2: MS (ESI+).

Method C1 SCP: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate. Temperature: 50° C.; Gradient: 0-100% B over 3 minutes, then a 0.75-minute hold at 100% B; Flow: 1.11 mL/min; Detection: UV at 220 nm.

Method D1 SCP: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.11 mL/min; Detection: UV at 220 nm.

Method D2 SCP: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 10-50% B over 20 minutes, then a 5-minute hold at 100% B; Flow: 20 mL/min. Detection: UV at 220 nm.

Method D3 SCP: Column: XBridge C18, 19×200 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: 6-46% B over 20 minutes, then a 4-minute hold at 100% B; Flow: 20 mL/min. Detection: UV at 220 nm.

Method E1 iPAC: Column: Waters Xbridge C18 4.6×50 mm 5 um particles; Mobile Phase A: 5:95 acetonitrile:water with 10 mM ammonium acetate; Mobile Phase B: 95:5 acetonitrile:water with 10 mM ammonium acetate. Temperature: 50° C.; Gradient: 0-100% B over 1 minute; Flow: 4 mL/min; Detection: UV at 220 nm.

Method F1 iPAC: Column: Waters Acquity BEH C18 2.1× 50 mm 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 2.20 minutes; Flow: 0.800 mL/min; Detection: UV at 220 nm.

Waters Acquity SDS: Run Time: 2.20 min; Comment: Generic gradient; Solvent Selection A: A1; Solvent Selection B: B1; Low Pressure Limit: 0 psi; High Pressure Limit: 15000 psi; Solvent Name A: 100% H₂O w/0.05% TFA; Solvent Name B: 100% ACN w/0.05% TFA.

(A): Column-Ascentis Express C18 (50×2.1 mm-2.7 μm) Mphase A: 10 mM NH₄COOH in water: ACN (98:02); Mphase B: 10 mM NH₄COOH in water: ACN (02:98), Gradient: 0-100% B over 3 minutes, Flow=1 mL/min.

(B): Waters Acquity BEH C18 (2.1×50 mm) 1.7 micron; Buffer: 5 mM ammonium acetate pH 5 adjusted with HCOOH, Solvent A: Buffer:ACN (95:5), Solvent B: Buffer:ACN (5:95), Method:% B: 0 min-5%: 1.1 min-95%: 1.7 min-95%, Flow: 0.8 mL/min.

(C): Column-Ascentis Express C18 (50×2.1 mm-2.7 μm) Mobile phase A: 0.1% HCOOH in water; Mobile phase B: ACN. Temperature: 50° C.; Gradient: 0-100% B over 3 minutes; Flow rate: 1.0 mL/min.

(D): Kinetex XB-C18 (75×3 mm) 2.6 micron; Solvent A: 10 mM ammonium formate in water: acetonitrile (98:02); Mobile Phase B: 10 mM ammonium formate in water: acetonitrile (02:98); Temperature: 50° C.; Gradient: 0-100% B over 3 minutes; Flow rate: 1.1 mL/min; Detection: UV at 220 nm.

(E): Column: Ascentis Express C18 (50×2.1) mm, 2.7 μm; Mobile Phase A: 5:95 acetonitrile: water with 10 mM NH₄OAc; Mobile Phase B: 95:5 acetonitrile: water with 10 mM NH₄OAc; Temperature: 50° C.; Gradient: 0-100% B over 3 minutes; Flow: 1.1 mL/min.

(F): Column: Ascentis Express C18 (50×2.1) mm, 2.7 μm; Mobile Phase A: 5:95 acetonitrile: water with 0.1% TFA; Mobile Phase B: 95:5 acetonitrile: water with 0.1% TFA; Temperature: 50° C.; Gradient: 0-100% B over 3 minutes; Flow: 1.1 mL/min.

(G): Column: Waters Acquity UPLC BEH C18 (2.1×50 mm), 1.7 micron; Solvent A=100% water with 0.05% TFA; Solvent B=100% acetonitrile with 0.05% TFA; gradient=2-98% B over 1 minute, then a 0.5-minute hold at 98% B; Flow rate: 0.8 mL/min; Detection: UV at 220 nm.

Template 1: tert-butyl 4-(2-bromo-3-isopropyl-1H-indol-5-yl)piperidine-1-carboxylate

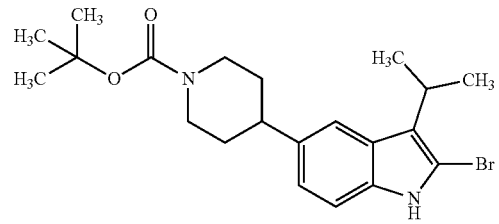

(T-1)

Intermediate T-1A: 5-bromo-3-isopropyl-1H-indole

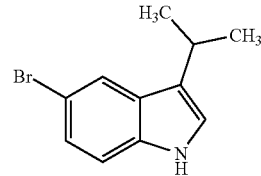

(T-1A)

A 250 mL round bottom flask was charged with triethylsilane (8.90 g, 77 mmol), trichloroacetic acid (6.25 g, 38.3 mmol) and toluene (50 mL). The solution was heated to 70° C., then a solution of 5-bromo-1H-indole (5.0 g, 25.5 mmol) and acetone (2.247 mL, 30.6 mmol) in toluene (30 mL) was added drop wise via an addition funnel. The resulting brown solution was heated at 70° C. for 1.5 h. The solution was cooled to 10° C., quenched with 10% sodium bicarbonate and diluted with diethyl ether. The organic layer was separated, dried, and concentrated under vacuum to afford crude compound. The crude was purified using silica gel chromatography eluting with 5% ethyl acetate in hexanes to afford 5-bromo-3-isopropyl-1H-indole (5.5 g, 23.10 mmol 95% yield) as an oil. LC retention time 1.42 min [D]. MS (E−) m/z: 238.2 (M+H). ¹H NMR (400 MHz, DMSO-d₆) δ 10.96 (br s, 1H), 7.70 (d, J=2.0 Hz, 1H), 7.31 (d, J=8.6 Hz, 1H), 7.18 (d, J=2.0 Hz, 1H), 7.15 (t, J=2.1 Hz, 1H), 3.12 (dtd, J=13.8, 6.8, 0.7 Hz, 1H), 1.29 (d, J=6.8 Hz, 6H).

Intermediate T-1B: tert-butyl 4-(3-isopropyl-1H-indol-5-yl)-5,6-dihydropyridine-1(2H)-carboxylate

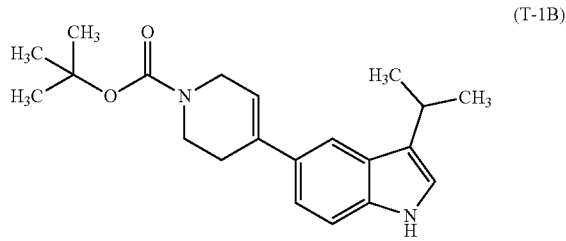

(T-1B)

To a mixture of 5-bromo-3-isopropyl-1H-indole (5.5 g, 23.10 mmol), tert-butyl 4-(4,4,5,5-tetramethyl-1,3,2-dioxaborolan-2-yl)-5,6-dihydropyridine-1(2H)-carboxylate (7.50 g, 24.25 mmol) in a 250 mL round bottom flask were added THF (50 mL) followed by aqueous solution of potassium phosphate, dibasic (12.07 g, 69.3 mmol, 20 mL). The resulting reaction mixture was degassed for 10 minutes with nitrogen gas, then $PdCl_2(dppf)$-$CH_2Cl_2$ adduct, (0.472 g, 0.577 mmol) was added. The mixture was degassed again for 5 min. The resulting reaction mixture was heated at 75° C. for 18 hours. The reaction mixture was diluted with ethyl acetate (100 mL), poured into a separate funnel and was washed with water (2×50 mL), brine (50 mL), dried over sodium sulfate, and concentrated to afford crude product. The crude material was purified using silica gel chromatography, eluting with 15% ethyl acetate in hexane. The fractions were collected and concentrated to afford tert-butyl 4-(3-isopropyl-1H-indol-5-yl)-5,6-dihydropyridine-1(2H)-carboxylate (6.5 g, 83% yield) as an oil. LCMS retention time 1.21 min [B]. MS (E−) m/z: 339 (M−H). $^1$H NMR (400 MHz, CHLOROFORM-d) 7.94 (br. s., 1H), 7.67-7.61 (m, 1H), 7.33 (dd, 0.5 Hz, 1H), 7.27 (dd, J=8.6, 1.7 Hz, 1H), 6.98 (dd, J=2.3, 0.7 Hz, 1H), 6.02 (br. s., 1H), 4.12 (d, J=2.0 Hz, 2H), 3.70 (t, J=5.7 Hz, 2H), 3.24 (sptd, J=6.8, 0.7 Hz, 1H), 2.66 (br. s., 2H), 1.53 (s, 9H), 1.39 (d, J=6.8 Hz, 6H).

Intermediate T-1C: tert-butyl 4-(3-isopropyl-1H-indol-5-yl)piperidine-1-carboxylate

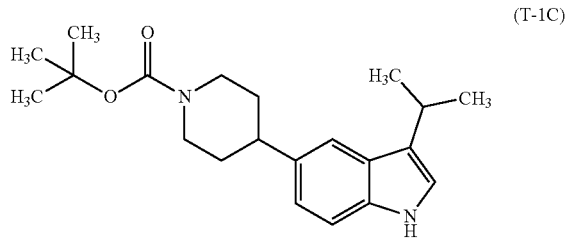 [SMILES: CC(C)c1c[nH]c2ccc(C3=CCN(C(=O)OC(C)(C)C)CC3)cc12]

(T-1C)

To a solution of tert-butyl 4-(3-isopropyl-1H-indol-5-yl)-5,6-dihydropyridine-1(2H)-carboxylate (7.9 g, 23.20 mmol) in ethyl acetate (150 mL), under a nitrogen atmosphere, was added palladium on carbon (0.617 g, 0.580 mmol). The vessel was pimp/purged three times with nitrogen gas then evacuated. Hydrogen gas was introduced via a balloon and the mixture was stirred at room temperature for 5 hours. The suspension was filtered through celite and the filtrate was concentrated to afford crude compound. The crude residue was purified by ISCO using a 40 g silica column, eluting with 15% ethyl acetate in hexane. The combined fractions were collected and concentrated to afford tert-butyl 4(3-isopropyl-1H-indol-5-yl)piperidine-1-carboxylate (6.5 g, 82% yield) as a white solid. LCMS retention time 2.48 min [C]. MS (E−) m/z: 341 (M−H). $^1$H NMR (400 MHz, CHLOROFORM-d) δ 7.88 (br. s., 1H), 7.48 (s, 1H), 7.31 (d, J=8.3 Hz, 1H), 7.06 (dd, J=8.3, 1.6 Hz, 1H), 6.97 (d, J=1.8 Hz, 1H), 4.29 (br. s., 2H), 3.22 (sptd, J=6.8, 0.5 Hz, 1H), 2.86 (t, J=12.3 Hz, 2H), 2.77 (tt, J=12.1, 3.7 Hz, 1H), 1.91 (d, J=13.0 Hz, 2H), 1.73 (qd, J=12.8, 4.6 Hz, 2H), 1.52 (s, 9H), 1.38 (d, J=7.0 Hz, 6H).

Template 1: tert-butyl 4-(2-bromo-3-isopropyl-1H-indol-5-yl)piperidine-1-carboxylate

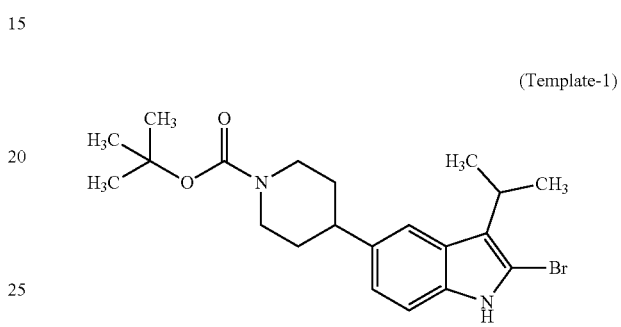

(Template-1)

To a solution of tert-butyl 4(3-isopropyl-1H-indol-5-yl) piperidine-1-carboxylate (6.3 g, 18.40 mmol) in DCE (60 mL) was added NBS (3.27 g, 18.40 mmol) dissolved in DCE (50 mL) drop wise via an addition funnel over 10 min at 0° C. The resulting brown solution was stirred at room temperature for 20 min. The reaction was quenched with sodium sulfite solution (15 mL). The volatiles were removed and the residue was taken up in DCM (50 mL) and the aqueous layer was separated. The organic layer was dried over $Na_2SO_4$ and concentrated to afford crude compound. The crude material was purified by ISCO using 40 g silica column. The compound eluted in 15% ethyl acetate in petroleum ether, the fractions were collected and concentrated to afford tert-butyl 4-(2-bromo-3-isopropyl-1H-indol-5-yl)piperidine-1-carboxylate (6.4 g, 83% yield) as a white solid. LCMS retention time 2.58 min [H]. MS (E−) m/z: 367.2 (M−H). $^1$H NMR (400 MHz, CHLOROFORM-d) δ 7.88 (br. s., 1H), 7.48 (s, 1H), 7.31 (d, J=8.3 Hz, 1H), 7.06 (dd, J=8.3, 1.6 Hz, 1H), 6.97 (d, J=1.8 Hz, 1H), 4.29 (br. s., 2H), 3.22 (sptd, J=6.8, 0.5 Hz, 1H), 2.86 (t, J=12.3 Hz, 2H), 2.77 (tt, J=12.1, 3.7 Hz, 1H), 1.91 (d, J=13.0 Hz, 2H), 1.73 (qd, J=12.8, 4.6 Hz, 2H), 1.52 (s, 9H), 1.38 (d, J=7.0 Hz, 6H).

Template 2: tert-butyl 4-(3-isopropyl-2-(4,4,5,5-tetramethyl-1,3,2-dioxaborolan-2-yl)-1H-indol-5-yl)piperidine-1-carboxylate

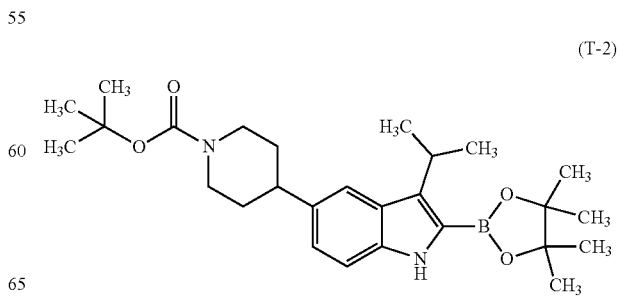

(T-2)

To a mixture of tert-butyl 4-(2-bromo-3-isopropyl-1H-indol-5-yl)piperidine-1-carboxylate (1.0 g, 2.373 mmol), 2-dicyclohexyphosphino-2',6'-dimethoxybiphenyl (0.117 g, 0.285 mmol) and bis(benzonitrile)palladium(II)chloride (0.027 g, 0.071 mmol) in a 50 mL reaction tube was added dioxane (10 mL). The resulting reaction mixture was degassed for 10 min and then pinacolborane (0.456 g, 3.56 mmol) was added followed by dropwise addition of TEA (0.992 mL, 7.12 mmol). The solution was again degassed for 5 min. The resulting reaction mixture was heated at 85° C. for 3 h. The reaction mixture was concentrated and the crude residue was dissolved in ethyl acetate (100 mL), poured into a separatory funnel and was washed thoroughly with water (2×250 mL). The organic layer was dried over $Na_2SO_4$, filtered and the filtrate was concentrated under vacuum to afford the crude product. The residue was taken up in DCM (3 mL). The crude was purified by combiflash system by eluting with 12% EtOAc/Pet ether. Following concentration of the fractions, the product was isolated as a white gummy product (0.75 g, 67.5% yield). LCMS retention time 4.27 min [H]. MS (E−) m/z: 467.3 (M−H). $^1$H NMR (400 MHz, DMSO-$d_6$) δ 10.65 (s, 1H), 7.50 (s, 1H), 7.29 (d, J=8.4 Hz, 1H), 6.99 (dd, J=8.5, 1.3 Hz, 1H), 4.09 (br d, J=11.1 Hz, 2H), 3.71-3.61 (m, 1H), 2.91-2.66 (m, 3H), 1.77 (br d, J=11.7 Hz, 2H), 1.59-1.46 (m, 2H), 1.43 (s, 9H), 1.36 (d, J=7.1 Hz, 6H), 1.32 (s, 12H).

Template 3: tert-butyl 5-(1-(tert-butoxycarbonyl)piperidin-4-yl)-3-isopropyl-1H-indole-1-carboxylate

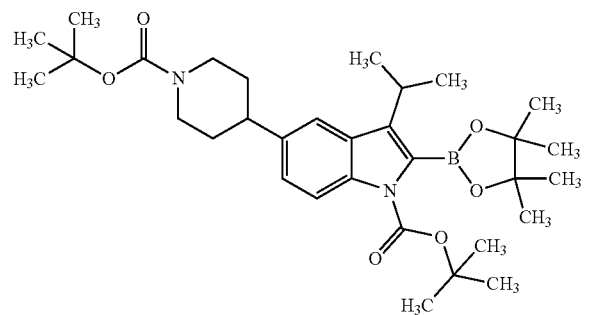

(T-3)

Tert-butyl 4-(3-isopropyl-1H-indol-5-yl)piperidine-1-carboxylate (328 mg, 0.958 mmol) (T-1C) was dissolved in THF (7662 μl) in a 50 mL recovery flask containing a Teflon-covered stir bar. Di-tert-butyl dicarbonate (298 μl, 1.245 mmol) was added to the flask, followed by 4-dimethylaminopyridine (11.70 mg, 0.096 mmol). The flask was capped and stirred at room temperature for 16 h. Excess solvent was evaporated from the reaction mixture under reduced pressure. The residue was taken up in DCM (~3 mL) and purified by flash chromatography on a 24 g $SiO_2$ column, eluting with 0%-50% gradient using EtOAc and hexanes, on an ISCO Rf instrument to afford tert-butyl 5-(1-(tert-butoxycarbonyl)piperidin-4-yl)-3-isopropyl-1H-indole-1-carboxylate (313.7 mg, 0.702 mmol, 73.3% yield) as a colorless foam. LCMS of product; mass ion observed corresponds to (product−2×tBu)=331.3, 1.51 min). $^1$H NMR (400 MHz, CHLOROFORM-d) δ 8.05 (d, J=6.2 Hz, 1H), 7.39 (d, J=1.6 Hz, 1H), 7.33 (br. s., 1H), 7.17 (dd, J=8.6, 1.7 Hz, 1H), 4.29 (br. s., 2H), 3.13 (sptd, J=6.8, 0.9 Hz, 1H), 2.86 (t, J=12.3 Hz, 2H), 2.77 (tt, J=12.0, 3.5 Hz, 1H), 1.90 (d, J=12.7 Hz, 2H), 1.80-1.70 (m, 2H), 1.68 (s, 9H), 1.52 (s, 9H), 1.36 (d, J=7.0 Hz, 6H).

Tert-butyl 5-(1-(tert-butoxycarbonyl)piperidin-4-yl)-3-isopropyl-1H-indole-1-carboxylate (100 mg, 0.226 mmol) and 2-isopropoxy-4,4,5,5-tetramethyl-1,3,2-dioxaborolane (73.8 μl, 0.362 mmol) were dissolved in THF (1808 μl) in a 2-dram vial containing a Teflon-covered stir bar. The vial was cooled to −20° C. (dry ice/NMP bath) under an $N_2$ atmosphere. Lithium diisopropylamide (169 μl, 0.339 mmol) was added dropwise to the vial (via a syringe through the septum cap) over ~15 min. The reaction mixture was stirred at −20° C. for 1 h, then allowed to slowly warm to 10° C. The reaction was quenched by addition of 1 M $KHSO_4$ (2 mL), and the resulting mixture was extracted with EtOAc (3×2 mL). The combined organic exacts were dried over $Na_2SO_4$, and filtered. Excess solvent was evaporated off under an $N_2$ stream. The residue was taken up in DCM (2.5 mL) and purified by flash chromatography on a 4 g $SiO_2$ column, eluting with 0%-50% gradient using EtOAc and hexanes, on an ISCO Rf instrument to afford tert-butyl 5-(1-(tert-butoxycarbonyl)piperidin-4-yl)-3-isopropyl-2-(4,4,5,5-tetramethyl-1,3,2-dioxaborolan-2-yl)-1H-indole-1-carboxylate (112.9 mg, 0.189 mmol, 83% yield) as a colorless foam, m/z, (observed M−2tBu+H$^+$=457.2, M+H$^+$= 569.3). A mass ion corresponding to the starting material was not observed. $^1$H NMR (400 MHz, CHLOROFORM-d) δ 7.79 (d, J=8.6 Hz, 1H), 7.42 (d, J=1.5 Hz, 1H), 7.09 (dd, J=8.6, 1.6 Hz, 1H), 4.28 (br. s., 2H), 3.20 (spt, J=7.1 Hz, 1H), 2.85 (t, J=12.2 Hz, 2H), 2.74 (tt, J=12.1, 3.5 Hz, 1H), 1.89 (d, J=12.7 Hz, 2H), 1.75-1.69 (m, 2H), 1.68 (s, 9H), 1.51 (s, 9H), 1.44 (s, 12H), 1.42 (d, J=7.1 Hz, 6H).

Fragment 1:
5-bromo-1,3-dimethylpyridin-2(1H)-one

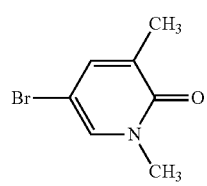

(F-1)

To a mixture containing 5-bromo-3-methylpyridin-2(1H)-one (1.3 g, 6.91 mmol) and $K_2CO_3$ (2.87 g, 20.74 mmol) in DMF (20 mL) was added dropwise MeI (0.865 mL, 13.83 mmol). The reaction mixture was stirred for 16 h and diluted with ethyl acetate (150 mL). The mixture was filtered through a pad of celite to remove the solids and the filtrate was washed with aqueous 10% LiCl solution (3×30 mL). The aqueous washes were combined and back extracted with additional ethyl acetate (2×25 mL). The organic extracts were combined and washed with saturated aqueous NaCl solution (50 mL), dried ($Na_2SO_4$), filtered and concentrated to afford a mixture of O-methylated (minor) and N-methylated (major) products. The crude product was dissolved in a small amount of DCM and charged to a 24 g ISCO silica gel column which was eluted over a 15 min gradient with 10%-100% hexanes/ethyl acetate to afford 5-bromo-1,3-dimethylpyridin-2(1H)-one (1 g, 4.95 mmol, 71.6% yield). LCMS MH$^+$: 202. HPLC Ret. Time 0.64 min. Method:

Method B1. ¹H NMR: (400 MHz, CHLOROFORM-d) δ 7.32 (d, J=2.6 Hz, 1H), 7.30-7.25 (J=2.6 Hz, 1H), 3.55 (s, 3H), 2.17 (s, 3H).

Fragment 2:
5-bromo-1-isobutyl-3-methylpyridin-2(1H)-one

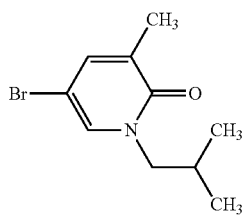

(F2)

To a 20 mL vial with a pressure relief septum containing 5-bromo-3-methylpyridin-2(1H)-one (250 mg, 1.330 mmol) were added DMF (2.659 mL), potassium carbonate (184 mg, 1.330 mmol) and 1-bromo-2-methylpropane (182 mg, 1.330 mmol). The vial was sealed. The reaction mixture was stirred at 65° C. for 4 hours, and then at room temperature overnight. The contents of the vial were diluted with brine (20 mL) and extracted with ethyl acetate (3×25 mL). The combined organic extracts were washed with water (10 mL), dried over sodium sulfate, filtered and concentrated to yield an oil. The oil was purified on an Isco silica gel column (24 g) eluting with 100% hexane to 100% ethyl acetate over 15 minutes. Like fractions were combined and concentrated under vacuum to afford 5-bromo-1-isobutyl-3-methylpyridin-2(1H)-one (175 mg, 0.717 mmol, 53.9% yield). LCMS MH⁺: 244. HPLC Ret. Time 0.85 min. Method: Method B1.

Fragment 3:
5-Bromo-3-methyl-1-phenylpyridin-2(1H)-one

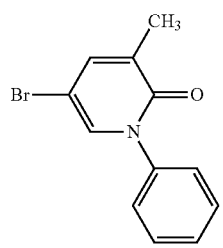

(F3)

To a dried nitrogen flushed 50 mL round bottom flask containing 3 Å molecular sieves (100 mg) were added 5-bromo-3-methylpyridin-2(1H)-one (100 mg, 0.532 mmol), phenylboronic acid (46.3 mg, 0.380 mmol), copper (II) acetate (207 mg, 1.140 mmol), pyridine (92 µl, 1.140 mmol), and pyridine-N-oxide (108 mg, 1.140 mmol) in DCM (5427 µl). Air (passed over drying agent) was bubbled into the solution for 15 minutes. The flask was sealed and the reaction mixture was stirred at room temperature for 3 days. The solution was filtered, washed with brine (2×10 mL), dried over sodium sulfate, filtered and concentrated under vacuum. The resulting solid was purified on an Isco silica gel column (12 g, 100% hexanes-100% EtOAc). Fractions were combined and concentrated under vacuum to afford 5-bromo-3-methyl-1-phenylpyridin-2(1H)-one (10 mg, 0.038 mmol, 9.97% yield). LCMS MH⁺: 266. HPLC Ret. Time 0.83 min. Method B1.

Fragment 4:
5-Bromo-1,3,4-trimethylpyridin-2(1H)-one

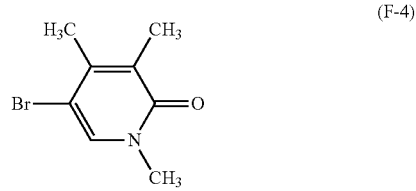

(F-4)

To a mixture of 5-bromo-3,4-dimethylpyridin-2-amine (0.6 g, 2.98 mmol) in concentrated H₂SO₄ (2 mL) and water (15 mL) was added a solution of sodium nitrite (0.309 g, 4.48 mmol) in water (1.5 mL) at 0° C. The mixture was allowed to equilibrate to room temperature and stirred for 1 h. The precipitate was filtered and washed with water and dried to afford 5-bromo-3,4-dimethylpyridin-2-ol (400 mg, 1.980 mmol, 66.3% yield). m/z (203, M+H).

To a mixture containing 5-bromo-3,4-dimethylpyridin-2-ol (500 mg, 2.475 mmol) and K₂CO₃ (684 mg, 4.95 mmol) in DMF (5 mL) was added MeI (0.309 mL, 4.95 mmol). The reaction mixture was stirred for 20 h. The reaction mixture was diluted with ethyl acetate (100 mL) and the solids were filtered through a pad of celite. The filtrate was washed with aqueous 10% LiCl solution (3×20 mL). The aqueous washes were combined and back extracted with ethyl acetate (2×25 mL). The organic extracts were combined and washed with saturated aqueous NaCl solution (50 mL), dried (Na₂SO₄), filtered and concentrated to afford a mixture of O-methylated (minor) and N-methylated products. The crude product was dissolved in a small amount of DCM and charged to a 12 g ISCO silica gel column which was eluted over a 15 min gradient with 10%-100% hexanes/ethyl acetate to afford 5-bromo-1,3,4-trimethylpyridin-2(1H)-one (430 mg, 1.990 mmol, 80% yield), m/z (218, M+H). LCMS MH⁺: 218. HPLC Ret. Time 0.70 min. Method B1. ¹H NMR: (400 MHz, CHLOROFORM-d) δ 7.39 (s, 1H), 3.54 (s, 3H), 2.29 (s, 3H), 2.21 (s, 3H).

Fragment 5:
5-bromo-3-chloro-1,6-dimethylpyridin-2(1H)-one

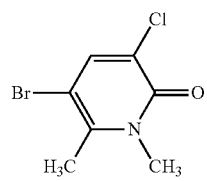

(F-5)

A solution containing 5-bromo-6-methylpyridin-2-ol (1 g, 5.32 mmol) and NCS (0.852 g, 6.38 mmol) in THF (20 mL) was heated at 60° C. for 2 h. Additional NCS (~100 mg) was added and the reaction mixture was heated for an additional 1 h, cooled to room temperature and concentrated to dryness. The residue was re-suspended in diethyl ether/hexanes (20 mL, 9/1), stirred and sonicated for 1 h. The solids were collected and rinsed with additional ether/hexanes mixture (20 mL, 9/1). The filtrate was re-concentrated ~½ volume to afford second crop of 5-bromo-3-chloro-6-methylpyridin-2-ol (1 g total), m/z (224, M+H). The product was contaminated with ~10% of a bis chlorinated material, m/z (268, M+H).

To a mixture containing crude 5-bromo-3-chloro-6-methylpyridin-2-ol (1.5 g, 6.74 mmol) and $K_2CO_3$ (1.9 g, 13.49 mmol) in DMF (10 mL) was added MeI (0.843 mL, 13.49 mmol). The reaction mixture was stirred for 20 h and diluted with ethyl acetate (100 mL). The resulting solids were filtered through a plug of celite. The filtrate was washed with aqueous 10% LiCl solution (2×30 mL) and saturated aqueous NaCl solution (10 mL). The aqueous washes were combined and extracted with ethyl acetate (50 mL) and the ethyl acetate layer washed again with 10% LiCl aqueous solution (1×20 mL) and saturated aqueous NaCl solution (10 mL). The organic extracts were combined, dried ($Na_2SO_4$), filtered and concentrated. The crude product was dissolved in a small amount of DCM and charged to an ISCO silica gel 40 g column which was eluted over a 15 min gradient with 5%-100% hexanes/ethyl acetate to afford impure 5-bromo-3-chloro-1,6-dimethylpyridin-2(1H)-one (800 mg). LCMS $MH^+$: 238. HPLC Ret. Time 0.72 min. Method B1. $^1H$ NMR (400 MHz, CHLOROFORM-d) δ 7.65 (s, 1H), 3.68-3.66 (s, 3H), 2.53 (s, 3H).

Fragment 6:
5-bromo-3-chloro-1-methylpyridin-2(1H)-one

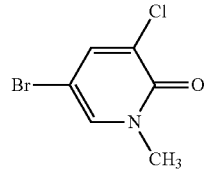

(F-6)

5-bromo-3-chloropyridin-2(1H)-one (400 mg, 1.919 mmol) was stirred with iodomethane (350 μl, 2.303 mmol) and potassium carbonate (530 mg, 3.84 mmol) in DMF (6397 μl) in a 20 mL scintillation vial at room temperature for 3 h. The reaction mixture was partitioned between 1:1 water and ethyl acetate (~20 mL total volume). The organic phase was extracted with brine (2×10 mL), then dried over sodium sulfate and filtered. Excess solvent was evaporated from the filtered organic phase to yield 5-bromo-3-chloro-1-methylpyridin-2(1H)-one (458.7 mg, 1.856 mmol, 97% yield, 90% purity) as a white solid. LCMS $MH^+$: 223.8. HPLC Ret. Time 0.64 min. Method B1. $^1H$ NMR (400 MHz, CHLOROFORM-d) δ 7.61 (d, J=2.6 Hz, 1H), 7.41 (d, J=2.6 Hz, 1H), 3.61 (s, 3H).

| Fragment | Structure | Name | CAS number |
|---|---|---|---|
| F-7 | 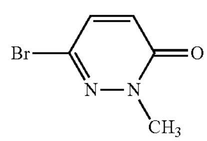 | 6-bromo-2-methylpyridazin-3(2H)-one | 10071-38-2 |
| F-8 | 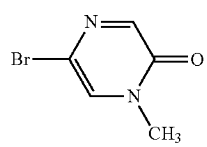 | 5-bromo-1-methylpyrazin-2(1H)-one | 1243288-53-0 |
| F-9 | 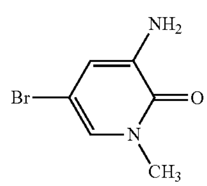 | 3-amino-5-bromo-1-methylpyridin-2(1H)-one | 910543-72-5 |
| F-10 | 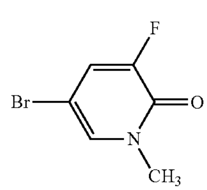 | 5-bromo-3-fluoro-1-methylpyridin-2(1H)-one | 1352152-46-5 |
| F-11 | 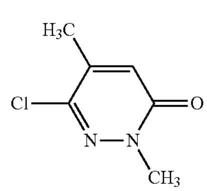 | 6-chloro-2,5-dimethylpyridazin-3(2H)-one | 1114563-59-5 |

-continued

| Fragment | Name | CAS number |
|---|---|---|
| F-12 | 6-chloro-2,4-dimethylpyridazin-3(2H)-one | 1114563-58-4 |
| F-13 | 5-bromo-1,3-dimethylpyrimidine-2,4(1H,3H)-dione | 7033-39-8 |
| F-14 | 5-bromo-1-isopropylpyridin-2(1H)-one | 851087-08-6 |
| F-15 | 5-bromo-1-methylpyridin-2(1H)-one | 81971-39-3 |
| F-16 | 3-amino-5-bromo-1,4-dimethylpyridin-2(1H)-one | 1446237-41-7 |
| F-17 | 5-bromo-1-methyl-3-(trifluoromethyl)pyridin-2(1H)-one | 214342-73-1 |
| F-18 | 5-bromo-1-(2-hydroxy-2-methylpropyl)pyridin-2(1H)-one | 1193335-01-1 |
| F-19 | 2-(5-bromo-2-oxopyridin-1(2H)-yl)acetamide | 924712-35-6 |

Fragment 20:
5-chloro-1,3-dimethylpyrazin-2(1H)-one

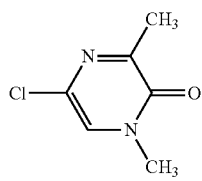
(F-20)

A solution containing 3,5-dichloro-1-methylpyrazin-2 (1H)-one (300 mg, 1.676 mmol) (CAS 87486-33-7), tetramethyltin (0.256 mL, 1.844 mmol) and tetrakis(triphenylphosphine)palladium(0) (48.4 mg, 0.042 mmol) in DMF (2 mL) in a Biotage microwave vial was sealed with a Teflon-lined septa cap. The vial was evacuated under vacuum and back-filled with nitrogen gas, using a needle from a vacuum manifold. The procedure repeated and the nitrogen line removed. The vial was heated in a Biotage microwave at 150° C. for 20 min. The reaction mixture was cooled to room temperature and diluted with ethyl acetate (50 mL) and washed with aqueous 10% NaF solution (2×10 mL) and saturated aqueous NaCl solution (1×10 mL), dried ($Na_2SO_4$), filtered and concentrated. The crude product was dissolved in a small amount of DCM and charged to a 10 g ISCO silica gel column, placed on a Teledyne ISCO system and eluted over a 20 min gradient using 0%-100% hexanes/ethyl acetate eluent to afford 5-chloro-1,3-dimethylpyrazin-2(1H)-one (170 mg, 1.072 mmol, 64.0% yield). LCMS $MH^+$: 159.0. HPLC Ret. Time 0.52 min. Method B1. $^1H$ NMR (400 MHz, CHLOROFORM-d) δ 7.13 (bm, 1H), 3.52 (s, 3H), 2.48 (d, J=0.6 Hz, 3H).

Fragment 21:
6-Chloro-2,4,5-trimethylpyridazin-3(2H)-one

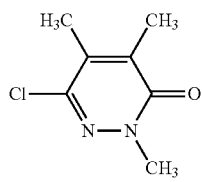
(F-21)

3,6-dichloro-4,5-dimethylpyridazine (1 g, 5.65 mmol) was suspended in water (10 mL) and powdered KOH (1.585 g, 28.2 mmol) was added. The mixture was heated at 120° C. for 2 h in a sealed pressure vessel, cooled to room temperature and acidified to pH 5 with concentrated aqueous HCl. The resulting solids were filtered and washed with water (~5 mL) and dried to afford pure 6-chloro-4,5-dimethylpyridazin-3-ol (700 mg, 4.41 mmol, 78% yield), m/z (159, M+H).

To a mixture containing 6-chloro-4,5-dimethylpyridazin-3-ol (100 mg, 0.631 mmol) and $K_2CO_3$ (349 mg, 2.52 mmol) in DMF (1 mL) was added MeI (0.079 mL, 1.261 mmol). The mixture was stirred for 2 h, diluted with water (10 mL) and extracted with ethyl acetate (4×15 mL). The extracts were combined and washed with 10% LiCl (1×10 mL) and saturated aqueous NaCl solution (10 mL), dried, filtered and concentrated. The crude material was dissolved in a small amount of DCM and charged to an ISCO silica gel 12 g column, which was eluted over a 10 min gradient with 5%-100% hexanes/ethyl acetate to afford 6-chloro-2,4,5-trimethylpyridazin-3(2H)-one (100 mg, 0.579 mmol, 92% yield), m/z (173, M+H). LCMS $MH^+$: 173. HPLC Ret. Time 0.68 min. Method B1. $^1H$ NMR (400 MHz, CHLOROFORM-d) δ 3.76 (s, 3H), 2.27 (d, J=0.7 Hz, 3H), 2.24 (d, J=0.7 Hz, 3H).

Fragment 22:
6-Chloro-2-ethyl-4,5-dimethylpyridazin-3(2H)-one

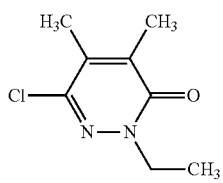
(F-22)

To a solution containing 6-chloro-4,5-dimethylpyridazin-3-ol (100 mg, 0.631 mmol) (see fragment 16) and iodoethane (0.051 mL, 0.631 mmol) in DMF (2.5 mL) was added $K_2CO_3$ (349 mg, 2.52 mmol). The reaction mixture was stirred for 20 h, diluted with ethyl acetate (50 mL) and washed with water (1×20 mL) and aqueous 10% LiCl solution (2×10 mL). The aqueous fractions were washed, combined and back extracted with ethyl acetate (20 mL). The organic extracts were combined and washed with saturated aqueous NaCl solution, dried ($Na_2SO_4$), filtered and concentrated. The crude product was dissolved in a small amount of DCM and charged to an ISCO silica gel 120 g ISCO Column which was eluted over a 15 min gradient with 5%-100% hexanes/ethyl acetate to afford 6-chloro-2-ethyl-4,5-dimethylpyridazin-3(2H)-one (105 mg, 0.563 mmol, 89% yield). LCMS $MH^+$: 187. HPLC Ret. Time 0.77 min. Method B1. $^1H$ NMR (400 MHz, CHLOROFORM-d) δ 4.18 (q, J=7.1 Hz, 2H), 2.27 (s, 3H), 2.23 (s, 3H), 1.42-1.35 (t, 7.1 Hz, 3H).

Fragment 23:
6-Chloro-2-ethyl-4-methylpyridazin-3(2H)-one

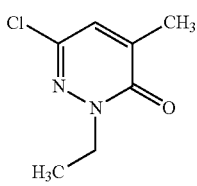
(F-23)

To a mixture containing 6-chloro-4-methylpyridazin-3 (2H)-one (250 mg, 1.729 mmol) and $K_2CO_3$ (598 mg, 4.32 mmol) in DMF (2.5 mL) was added ethyl iodide (0.210 mL, 2.59 mmol). The reaction mixture was stirred at room temperature for 22 h. The reaction mixture was diluted with water (25 mL) and extracted with ethyl acetate (3×40 mL). The combined extracts were washed with 10% LiCl (2×20 mL) and saturated aqueous NaCl solution (1×20 mL), dried ($Na_2SO_4$), filtered and concentrated to afford crude product.

The crude product was dissolved in a small amount of DCM and charged to an ISCO silica gel 12 g ISCO column which was eluted over a 10 min gradient with 0%-100% hexanes/ethyl acetate to afford 6-chloro-2-ethyl-4-methylpyridazin-3(2H)-one (250 mg, 1.448 mmol, 84% yield), m/z (173, M+H). LCMS MH+: 173. HPLC Ret. Time 0.70 min. Method B1. $^1$H NMR (400 MHz, CHLOROFORM-d) δ 7.06 (q, J=1.2 Hz, 1H), 4.17 (q, J=7.2 Hz, 2H), 2.21 (d, J=1.2 Hz, 3H), 1.37 (t, J=7.2 Hz, 3H).

Fragment 24:
5-Bromo-3-methoxy-6-methylpyridin-2(1H)-one

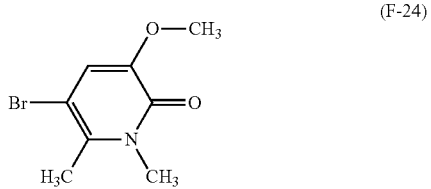

(F-24)

A solution containing 5-bromo-3-methoxy-6-methylpyridin-2-amine (1 g, 4.61 mmol) in sulfuric acid (2 mL, 37.5 mmol) and 4 mL water was cooled in an ice bath. A solution of sodium nitrite (0.636 g, 9.21 mmol) in water (1 mL) was added dropwise and the ice bath was removed. The reaction mixture was stirred at room temperature for 1 h. Water (25 mL) was added and the mixture was cooled in an ice bath and stirred for 20 min. The resulting solids were filtered, washed with water and dried to afford 5-bromo-3-methoxy-6-methylpyridin-2-ol (700 mg, 3.21 mmol, 69.7% yield), m/z (220, M+H).

To a solution containing 5-bromo-3-methoxy-6-methylpyridin-2-ol (700 mg, 3.21 mmol) in DMF (7.5 mL) was added $K_2CO_3$ (887 mg, 6.42 mmol) followed by the addition of MeI (0.401 mL, 6.42 mmol). The mixture was stirred for 2 h, diluted with ethyl acetate (100 mL) and the solids filtered through a pad of celite. The filtrate was washed with aqueous 10% LiCl solution (3×25 mL), saturated aqueous NaCl solution (25 m), dried ($Na_2SO_4$), filtered and concentrated. The crude product was dissolved in a small amount of DCM and charged to a 24 g ISCO silica gel column, which was eluted over a 15 min gradient with 5%-100% DCM/EtOAc to afford 5-bromo-3-methoxy-1,6-dimethylpyridin-2(1H)-one (525 mg, 2.262 mmol, 70.5% yield). LCMS MH+: 233.9. HPLC Ret. Time 0.65 min. Method B1. $^1$H NMR (400 MHz, CHLOROFORM-d) δ 6.74 (s, 1H), 3.82 (s, 3H), 3.64 (s, 3H), 2.48 (s, 3H).

Fragment 25:
5-Bromo-3-methoxy-1,4-dimethylpyridin-2(1H)-one

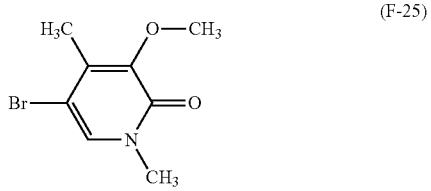

(F-25)

To a mixture of 5-bromo-3-methoxy-4-methylpyridin-2-amine (0.45 g, 2.073 mmol) in concentrated $H_2SO_4$ (1 mL) and water (3 mL) was added a solution of sodium nitrite (0.215 g, 3.11 mmol) in water (1 mL) at 0° C. The mixture was allowed to come to room temperature and stirred for 1 h. Ice cold water (10 mL) was added and the precipitate was filtered and washed with ice water and dried to afford 5-bromo-3-methoxy-4-methylpyridin-2-ol (250 mg, 1.147 mmol, 55.3% yield).

To a mixture containing 5-bromo-3-methoxy-4-methylpyridin-2-ol (250 mg, 1.147 mmol) and $K_2CO_3$ (396 mg, 2.87 mmol) in DMF (2.5 mL) was added MeI (0.143 mL, 2.293 mmol). The reaction mixture was stirred for 20 h and diluted with ethyl acetate (50 mL). The solids were filtered through a pad of celite and the filtrate washed with aqueous 10% LiCl solution (3×10 mL) and saturated aqueous NaCl solution (10 mL), dried ($Na_2SO_4$), filtered and concentrated to afford crude product. The crude product was dissolved in a small amount of DCM and charged to a 12 g ISCO silica gel column, which was eluted over a 10 min gradient with 5%-100% hexanes/ethyl acetate to afford 5-bromo-3-methoxy-1,4-dimethylpyridin-2(1H)-one (218 mg, 0.939 mmol, 82% yield). LCMS MH+: 233.9. HPLC Ret. Time 0.67 min. Method B1. $^1$H NMR (400 MHz, DMSO-$d_6$) δ 7.88 (s, 1H), 3.75 (s, 2H), 3.43 (s, 3H), 2.15 (s, 3H).

Fragment 26: 5-Chloro-1-methyl-3-(1-methyl-1H-pyrazol-4-yl)pyridin-2(1H)-one

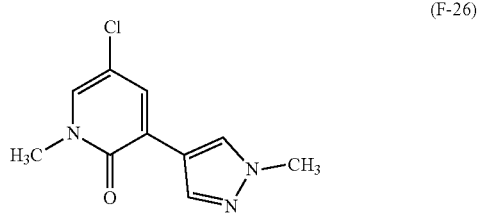

(F-26)

3-bromo-5-chloropyridin-2(1H)-one (Combi-Blocks, CAS: 137628-16-1, 170 mg, 0.816 mmol) was stirred with iodomethane (149 μl, 0.979 mmol) and potassium carbonate (564 mg, 4.08 mmol) in DMF (2719 μl) in a 20 mL vial for 2 h at room temperature. The reaction mixture was partitioned between water and ethyl acetate (4 mL total volume). The aqueous phase was extracted with ethyl acetate (2×1.5 mL). The combined organic phases were extracted with brine (2×10 mL). Excess solvent was evaporated from the combined organic phases to afford 3-bromo-5-chloro-1-methylpyridin-2(1H)-one (151.8 mg, 0.662 mmol, 81% yield) as a pale yellow solid. M+H+=221.9, 223.9. $^1$H NMR (400 MHz, CHLOROFORM-d) δ 7.75 (d, J=2.7 Hz, 1H), 7.38 (d, J=2.7 Hz, 1H), 3.62 (s, 3H).

1-methyl-4-(4,4,5,5-tetramethyl-1,3,2-dioxaborolan-2-yl)-1H-pyrazole (31.1 mg, 0.149 mmol) and 3-bromo-5-chloro-1-methylpyridin-2(1H)-one (35 mg, 0.157 mmol) were weighed into a 1-dram vial. THF (1049 μl) was added to the vial, followed by 2 M aqueous tripotassium phosphate (236 μl, 0.472 mmol). The reaction mixture was degassed by bubbling nitrogen through the solution for 2 min. 2nd generation XPhos precatalyst (4.95 mg, 6.29 μmol) were added to the reaction mixture. The reaction mixture was placed under a nitrogen atmosphere and stirred at 60° C. for 3 h. The reaction mixture was cooled to room temperature and the aqueous phase was removed, and excess solvent was evaporated from the organic phase. The residue was taken up in DCM (3 mL) and purified by flash chromatography on a 4 g silica column, eluting with dichloromethane and methanol on an ISCO Rf instrument to afford 5-chloro-1-methyl-3-(1-methyl-1H-pyrazol-4-yl)pyridin-2(1H)-one (30.8 mg, 0.131 mmol, 83% yield) as a pale yellow solid. LCMS MH+: 224.0. HPLC Ret. Time 0.63 min. Method B1. $^1$H NMR (400 MHz, CHLOROFORM-d) δ 8.36 (s, 1H), 7.89-7.83 (m, 1H), 7.57 (d, J=2.7 Hz, 1H), 7.26 (d, J=2.8 Hz, 1H), 3.94 (s, 3H), 3.60 (s, 3H).

Fragment 27: 5-Chloro-1,4-dimethyl-3-(1-methyl-1H-pyrazol-4-yl)pyridin-2(1H)-one

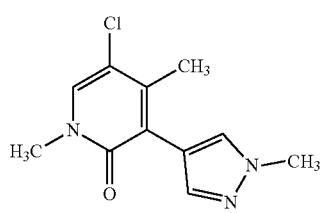

(F-27)

3-bromo-5-chloro-4-methylpyridin-2-ol (Combi-Blocks, CAS: 1199773-45-9, 170 mg, 0.764 mmol) was stirred with iodomethane (140 µl, 0.917 mmol) and potassium carbonate (528 mg, 3.82 mmol) in DMF (2547 µl) in a 20 mL vial at room temperature for 40 min. The reaction mixture was partitioned between water and ethyl acetate (4 mL total volume), and the aqueous phase was extracted with ethyl acetate (2×1.5 mL). The combined organic phases were extracted with brine (2×10 mL). Excess solvent was evaporated from the combined organic phases to afford 3-bromo-5-chloro-1,4-dimethylpyridin-2(1H)-one (217.2 mg, 0.735 mmol, 96% yield) as a pale yellow solid. m/z (237.9, 239.9, M+H). $^1$H NMR: (400 MHz, METHANOL-$d_4$) δ 7.89 (s, 1H), 3.61 (s, 3H), 2.50 (s, 3H).

1-Methyl-4-(4,4,5,5-tetramethyl-1,3,2-dioxaborolan-2-yl)-1H-pyrazole (31.7 mg, 0.152 mmol) and 3-bromo-5-chloro-1,4-dimethylpyridin-2(1H)-one (30 mg, 0.127 mmol) were weighed into a 1-dram vial. THF (846 µl) was added to the vial, followed by 2 M aqueous tripotassium phosphate (190 µl, 0.381 mmol). The reaction mixture was degassed by bubbling nitrogen through the solution for 2 min. 2nd Generation XPhos precatalyst (3.99 mg, 5.07 µmol) was added to the reaction mixture. The reaction mixture was placed under a nitrogen atmosphere and stirred at 60° C. for 20 h. The aqueous phase was removed, and excess solvent was evaporated from the organic phase. The residue was taken up in DCM (3 mL) and purified by flash chromatography on a 4 g silica column, eluting with ethyl acetate and hexanes on an Isco Rf instrument. The product did not elute, so the column was then eluted with 1-15% MeOH in dichloromethane. Excess solvent was evaporated from the product-containing fractions to afford 5-chloro-1,4-dimethyl-3-(1-methyl-1H-pyrazol-4-yl)pyridin-2(1H)-one (12.8 mg, 0.053 mmol, 41.6% yield) as a white solid. LCMS MH$^+$: 238.0. HPLC Ret. Time 0.64 min. Method B1. $^1$H NMR (400 MHz, CHLOROFORM-d) δ 7.85 (s, 1H), 7.62 (s, 1H), 7.33 (s, 1H), 3.96 (s, 3H), 3.56 (s, 3H), 2.39 (s, 3H).

Fragment 28:
5-Bromo-3-chloro-1-ethylpyridin-2(1H)-one

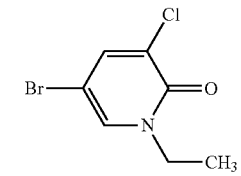

(F-28)

5-bromo-3-chloropyridin-2(1H)-one (150 mg, 0.720 mmol) was stirred with iodoethane (69.4 µl, 0.864 mmol) and potassium carbonate (497 mg, 3.60 mmol) in DMF (2399 µl) in a 20 mL vial containing a Teflon-coated stir bar at room temperature for 19 h. The reaction mixture was partitioned between water and ethyl acetate (8 mL total volume). The aqueous phase was extracted with ethyl acetate (2×2 mL). The combined organic phases were then dried (Na$_2$SO$_4$), filtered and concentrated to afford 5-bromo-3-chloro-1-ethylpyridin-2(1H)-one (113.3 mg, 0.383 mmol, 53.3% yield) as a white solid. LCMS MH$^+$: 237.9. HPLC Ret. Time 0.72 min. Method B1.

Fragment 29:
5-Bromo-3-chloro-1,4-dimethylpyridin-2(1H)-one

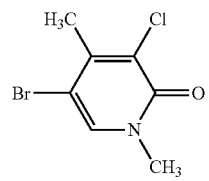

(F-29)

5-bromo-4-methylpyridin-2-ol (1.00 g, 5.32 mmol) and N-chlorosuccinimide (0.473 mL, 5.85 mmol) were suspended in DCM (21.27 mL) in a 40 mL scintillation vial. The reaction mixture was stirred at room temperature for 3 h, then at 40° C. for 17 h. The reaction mixture was heated to 50° C. for 30 min, then allowed to cool to room temperature. The reaction mixture was washed with water (2×10 mL) and then brine (1×5 mL). The yellow solid began to crash out of the organic solution after the second aqueous wash. Excess solvent was evaporated from the organic phase. The resulting residue was taken up in DMF (15 mL) in a 40 mL scintillation vial. Potassium carbonate (1.470 g, 10.64 mmol) and iodomethane (1.200 mL, 7.89 mmol) were added to the vial, and the resulting reaction mixture was stirred at room temperature for 2 h. The reaction mixture was partitioned between water and ethyl acetate, total volume~30 mL. The phases were separated, and the aqueous phase was extracted with ethyl acetate (2×10 mL). The combined organic phases were dried over sodium sulfate, filtered, and excess solvent was evaporated off. The residue was taken up in DCM/MeOH and dried onto silica, then purified by flash chromatography on a 24 g silica column, eluting with ethyl acetate and hexanes on an ISCO Rf instrument. The product-containing fractions were pooled and solvent was evaporated off to yield 5-bromo-3-chloro-1,4-dimethylpyridin-2(1H)-one (1.0025 g, 4.03 mmol, 76% yield) as a yellow-orange solid. LCMS MH$^+$: 237.8. HPLC Ret. Time 0.70 min. Method B1. $^1$H NMR (400 MHz, CHLOROFORM-d) δ 7.46 (s, 1H), 3.60 (s, 3H), 2.46 (s, 3H).

Fragment 30: 5-Bromo-1-(2-hydroxy-2-methylpropyl)-3-methylpyridin-2(1H)-one

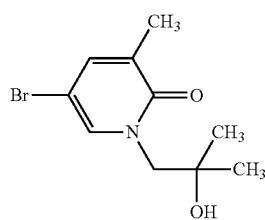

(F-30)

To a 20 mL vial fitted with a Teflon lined septum were added 5-bromo-3-methylpyridin-2(1H)-one (100 mg, 0.532 mmol), DMF (1064 μL), potassium carbonate (73.5 mg, 0.532 mmol), and 2,2-dimethyloxirane (38.3 mg, 0.532 mmol). The vial was sealed. The reaction mixture was stirred at 65° C. for 3 h. The reaction mixture was cooled to room temperature and stirred for 20 h. The mixture was diluted with water (10 mL) and extracted with ethyl acetate (3×5 mL). Organic layers are combined, concentrated and purified by ISCO (12 g silica, 100% hexanes-100% ethyl acetate). Like fractions were combined and concentrated under vacuum to afford 5-bromo-1-(2-hydroxy-2-methylpropyl)-3-methylpyridin-2(1H)-one (101 mg, 0.369 mmol, 69.4% yield). LC MS at t=peak #1, 0.67 min. (m$^{+1}$=260) showed one major product that was consistent with Fragment 30. LCMS MH$^+$: 260. HPLC Ret. Time 0.67 min. Method B1.

Fragment 31A

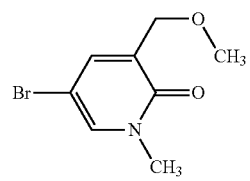

(F-31)

To a mixture of 5-bromo-1,3-dimethylpyridin-2(1H)-one (300 mg, 1.485 mmol) (F1) and NBS (264 mg, 1.485 mmol) in CCl$_4$ (20 mL) was added AIBN (24.38 mg, 0.148 mmol). The reaction mixture was heated at 90° C. for 1 hour and then cooled to room temperature. The reaction mixture was diluted with dichloromethane and washed with saturated NaHCO$_3$. The organic layer was dried with MgSO$_4$, filtered and concentrated to afford 5-bromo-3-(bromomethyl)-1-methylpyridin-2(1H)-one (420 mg, 1.4 mmol, 100% yield). $^1$H NMR (400 MHz, CHLOROFORM-d) δ 7.58 (d, J=2.6 Hz, 1H), 7.46 (d, J=2.6 Hz, 1H), 4.43 (s, 2H), 3.59 (s, 3H).

To a mixture of MeOH (0.079 mL, 1.950 mmol) in THF (5 mL) was added sodium hydride (90 mg, 2.250 mmol). After stirring 30 minutes, 5-bromo-3-(bromomethyl)-1-methylpyridin-2(1H)-one (421 mg, 1.5 mmol) was added. The reaction mixture was stirred at room temperature for 3 hours. The reaction was quenched with water. The reaction mixture was diluted with ethyl acetate and washed with saturated NaCl. The organic layer was dried with MgSO$_4$, filtered and concentrated. The crude material was purified on a silica gel cartridge (24 g) using an ethyl acetate/hexane gradient (0-100% ethyl acetate over 12.5 min) to afford 5-bromo-3-(methoxymethyl)-1-methylpyridin-2(1H)-one (160 mg, 0.689 mmol, 46.0% yield). LCMS MH$^+$: 217.9. HPLC Ret. Time 0.64 min. Method Acquity. $^1$H NMR (400 MHz, CHLOROFORM-d) δ 7.50 (dt, J=2.8, 1.3 Hz, 1H), 7.38 (d, J=2.6 Hz, 1H), 4.44-4.36 (m, 2H), 3.55 (s, 3H), 3.49 (s, 3H).

The following fragments were prepared according to the general procedures for the above fragments, using the indicated starting materials and synthetic methods. The HPLC method was Method B1.

TABLE 1

| Frag. No. | Structure | Starting material | Synthetic Method | Mol. Weight | LCMS MH$^+$ | Ret Time (min) |
|---|---|---|---|---|---|---|
| F31B | 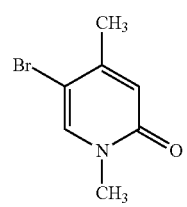 | 5-bromo-6-methylpyridin-2(1H)-one | 1 | 202.0 | 203.9 | 0.62 |
| F32 | 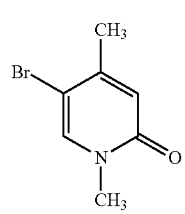 | 5-bromo-4-methylpyridin-2(1H)-one | 1 | 202.0 | 203.9 | 0.61 |

TABLE 1-continued

| Frag. No. | Structure | Starting material | Synthetic Method | Mol. Weight | LCMS MH+ | Ret Time (min) |
|---|---|---|---|---|---|---|
| F33 | 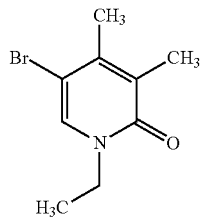 | 5-bromo-3,4-dimethylpyridin-2-ol | 1 | 229.0 | 230.0 | 0.76 |
| F34 | 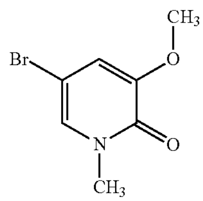 | 5-bromo-3-methoxypyridine-2-ol | 1 | 218.0 | 219.9 | 0.57 |
| F35 | 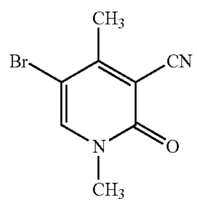 | 5-bromo-4-methyl-2-oxo-1,2-dihydropyridine-3-carbonitrile | 1 | 227.0 | 228.7 | 0.63 |
| F36 | 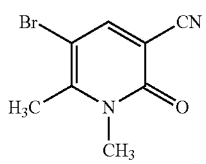 | 5-bromo-2-hydroxy-6-methylnicotinonitrile | 1 | 227.0 | 228.9 | 0.62 |
| F37 | 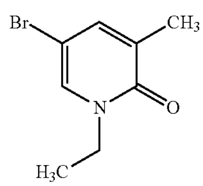 | 5-bromo-3-methylpyridin-2(1H)-one | 1 | 216.0 | 217.9 | 0.73 |
| F38 | 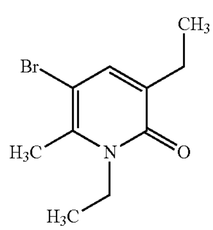 | 5-bromo-3-ethyl-6-methylpyridin-2-ol | 1 | 244.1 | 246.0 | 0.87 |
| F39 | 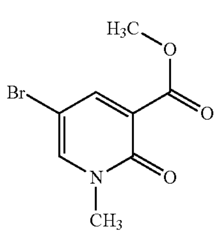 | ethyl 5-bromo-2-oxo-1,2-dihydropyridine-3-carboxylate | 1 | 245.0 | 245.9 | 0.59 |

TABLE 1-continued

| Frag. No. | Structure | Starting material | Synthetic Method | Mol. Weight | LCMS MH+ | Ret Time (min) |
|---|---|---|---|---|---|---|
| F40 | 5-bromo-3-methyl-1-(2-methoxyethyl)pyridin-2(1H)-one | 5-bromo-3-methylpyridin-2(1H)-one | 2 | 246.1 | 248 | 0.70 |
| F41 | 1-benzyl-5-bromo-3-methylpyridin-2(1H)-one | 5-bromo-3-methylpyridin-2(1H)-one | 2 | 278.1 | 280 | 0.87 |
| F42 | 5-bromo-1-(cyclopropylmethyl)-3-methylpyridin-2(1H)-one | 5-bromo-3-methylpyridin-2(1H)-one | 2 | 242.1 | 244 | 0.80 |
| F43 | 5-bromo-1-(2-hydroxyethyl)-3-methylpyridin-2(1H)-one | 5-bromo-3-methylpyridin-2(1H)-one | 2 | 232.1 | 234 | 0.57 |
| F44 | 5-bromo-1-(2,2-difluoroethyl)-3-methylpyridin-2(1H)-one | 5-bromo-3-methylpyridin-2(1H)-one | 2 | 252.1 | 254 | 0.74 |
| F45 | 5-bromo-3-methyl-1-(2,2,2-trifluoroethyl)pyridin-2(1H)-one | 5-bromo-3-methylpyridin-2(1H)-one | 2 | 270.0 | 271.9 | 0.80 |

TABLE 1-continued

| Frag. No. | Structure | Starting material | Synthetic Method | Mol. Weight | LCMS MH+ | Ret Time (min) |
|---|---|---|---|---|---|---|
| F46 | (structure) | 5-bromo-3-methylpyridin-2(1H)-one | 2 | 258.1 | 260 | 0.96 |
| F47 | (structure) | 5-bromo-3-methylpyridin-2(1H)-one | 2 | 246.1 | 248 | 0.61 |
| F48 | (structure) | 5-bromo-3-cyanopyridin-2(1H)-one | 1 | 211.9 | 212.7 | 0.55 |
| F49 | (structure) | 5-bromo-3-ethyl-6-methylpyridin-2-ol | 1 | 229.01 | 230.0 | 0.80 |

Example 1

5-(3-isopropyl-5-(piperidin-4-yl)-1H-indol-2-yl)-1-methylpyridin-2(1H)-one

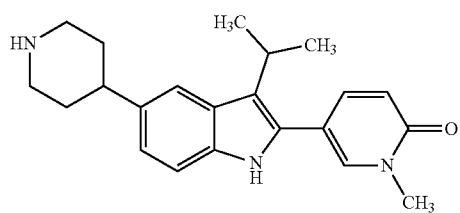

(1)

To a mixture containing 5-bromo-1-methylpyridin-2(1H)-one (15.05 mg, 0.080 mmol), tert-butyl 4-(3-isopropyl-2-(4,4,5,5-tetramethyl-1,3,2-dioxaborolan-2-yl)-1H-indol-5-yl)piperidine-1-carboxylate (25 mg, 0.053 mmol), and Xphos Pd G2 (2.100 mg, 2.67 μmol) in a screw cap vial was added THF (1 mL) followed by an aqueous solution of tripotassium phosphate (100 μL, 0.300 mmol). The vial was fitted with a Teflon lined septum cap. The vial was evacuated under vacuum (via a needle from a nitrogen/vacuum manifold line) and backfilled with nitrogen gas. The evacuation procedure was repeated three times. The needle was removed and the vial was heated at 65° C. for 18 h. The reaction mixture was concentrated to dryness and treated with TFA (1 mL) for 30 min to facilitate the removal of the tert-butyloxycarbonyl group. The reaction mixture was re-concentrated to dryness and re-dissolved in DMF (2 mL). The sample was filtered through an Acrodisc, 13 mm, 0.45 micron nylon membrane syringe filter and was purified via preparative LC/MS with using condition Method D2 to afford 5-(3-isopropyl-5-(piperidin-4-yl)-1H-indol-2-yl)-1-methylpyridin-2(1H)-one (12 mg, 0.034 mmol, 64.3% yield). LCMS MH+: 350. HPLC Ret. Time 0.58 min. Method B1. $^1$H NMR (500 MHz, DMSO-$d_6$) δ 10.84 (s, 1H), 7.81 (d, J=2.1 Hz, 1H), 7.53 (dd, J=9.3, 2.3 Hz, 1H), 7.47 (s, 1H), 7.23 (d, J=8.2 Hz, 1H), 6.94 (d, J=8.3 Hz, 1H), 6.52 (d, J=9.3 Hz, 1H), 3.52 (s, 3H), 3.19-3.09 (m, 2H), 2.77-2.66 (m, 2H), 1.84 (m, 3H), 1.80-1.75 (m, 2H), 1.72-1.59 (m, 2H), 1.39 (d, J=7.0 Hz, 6H).

Example 2

5-(3-isopropyl-5-(piperidin-4-yl)-1H-indol-2-yl)-1,3-dimethylpyridin-2(1H)-one

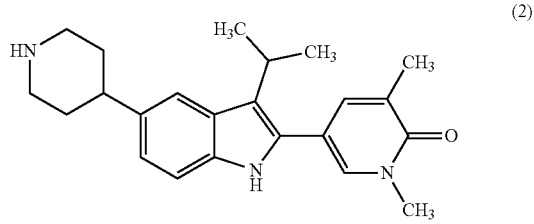 [SMILES: Cc1cc(-c2[nH]c3ccc(C4CCNCC4)cc3c2C(C)C)cn(C)c1=O]

(2)

Intermediate 2A: tert-butyl 4-(2-(1,5-dimethyl-6-oxo-1,6-dihydropyridin-3-yl)-3-isopropyl-1H-indol-5-yl)piperidine-1-carboxylate

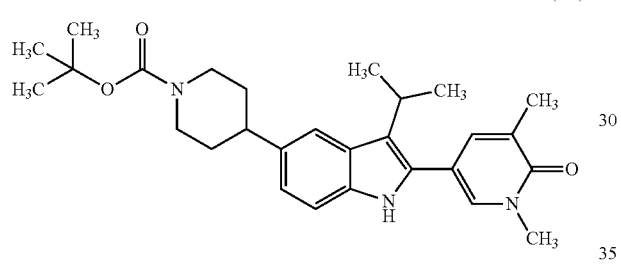

(2A)

To a mixture containing tert-butyl 4-(3-isopropyl-2-(4,4,5,5-tetramethyl-1,3,2-dioxaborolan-2-yl)-1H-indol-5-yl)piperidine-1-carboxylate (2434 mg, 5.20 mmol), 5-bromo-1,3-dimethylpyridin-2(1H)-one (1000 mg, 4.95 mmol), and Xphos Pd G2 (97 mg, 0.124 mmol) in a screw cap vial was added THF (25 mL) followed by an aqueous solution of potassium phosphate, tribasic (4.95 mL, 14.85 mmol). The vial was fitted with a Teflon lined septum cap. The vial was evacuated under vacuum (via a needle from a nitrogen/vacuum manifold line) and backfilled with nitrogen gas. The evacuation procedure was repeated three times. The needle was removed and the vial was heated at 65° C. for 2 h. The reaction mixture was cooled to room temperature, diluted with ethyl acetate (50 mL) and washed with saturated aqueous NaCl solution (10 mL), dried (Na$_2$SO$_4$), filtered and concentrated to afford crude material. The crude product was dissolved in a small amount of DCM and charged to a 40 g ISCO silica gel column, which was eluted over a 15 min gradient with 5%-100% hexanes/ethyl acetate to afford tert-butyl 4-(2-(1,5-dimethyl-6-oxo-1,6-dihydropyridin-3-yl)-3-isopropyl-1H-indol-5-yl) piperidine-1-carboxylate, 2.1 g (90% yield) m/e (464, M$^{+1}$).

Example 2

The purified tert-butyl 4-(2-(1,5-dimethyl-6-oxo-1,6-dihydropyridin-3-yl)-3-isopropyl-1H-indol-5-yl)piperidine-1-carboxylate was dissolved in DCM (10 mL) and treated with TFA (10 mL). The reaction mixture was stirred for 30 min and concentrated to dryness. The residue was treated with saturated aqueous ammonium hydroxide (20 mL) and stirred for 30 min. The resulting fine suspension was filtered and rinsed with additional ammonium hydroxide and dried to afford 5-(3-isopropyl-5-(piperidin-4-yl)-1H-indol-2-yl)-1,3-dimethylpyridin-2(1H)-one (1.55 g, 4.26 mmol, 86% yield) as a yellow solid. LCMS MH$^+$: 364. HPLC Ret. Time 0.63 min. Method B1. $^1$H NMR (400 MHz, DMSO-d$_6$) δ 10.80 (s, 1H), 7.66 (d, J=2.3 Hz, 1H), 7.48 (s, 1H), 7.44 (dd, J=2.3, 1.1 Hz, 1H), 7.23 (d, J=8.3 Hz, 1H), 6.94 (dd, J=8.4, 1.5 Hz, 1H), 3.91 (s, 1H), 3.54 (s, 3H), 3.21-3.10 (m, 3H), 2.77-2.65 (m, 3H), 1.84 (s, 3H), 1.82-1.62 (m, 4H), 1.41 (s, 3H), 1.39 (s, 3H).

Example 3

5-(3-isopropyl-5-(piperidin-4-yl)-1H-indol-2-yl)-1,3,6-trimethylpyridin-2(1H)-one

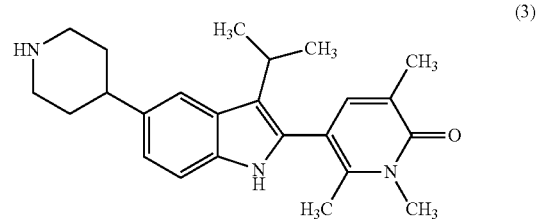 [SMILES: Cc1cc(-c2[nH]c3ccc(C4CCNCC4)cc3c2C(C)C)c(C)n(C)c1=O]

(3)

Intermediate 3A: tert-butyl 4-(2-(5-chloro-1,2-dimethyl-6-oxo-1,6-dihydropyridin-3-yl)-3-isopropyl-1H-indol-5-yl)piperidine-1-carboxylate

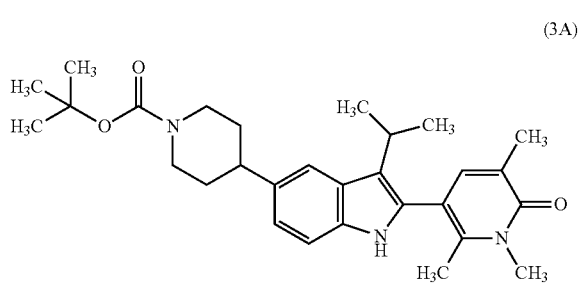 [SMILES: Cc1cc(-c2[nH]c3ccc(C4CCN(C(=O)OC(C)(C)C)CC4)cc3c2C(C)C)c(C)n(C)c1=O]

(3A)

To a mixture containing tert-butyl 4-(3-isopropyl-2-(4,4,5,5-tetramethyl-1,3,2-dioxaborolan-2-yl)-1H-indol-5-yl)piperidine-1-carboxylate (1.0 g, 2.135 mmol), 5-bromo-3-chloro-1,6-dimethylpyridin-2(1H)-one (0.606 g, 2.56 mmol), and Pd(dppf)Cl$_2$ (0.078 g, 0.107 mmol) in a screw cap vial was added THF (10 mL) followed by the addition of 3 M aqueous solution of potassium phosphate, tribasic (2.135 mL, 6.40 mmol). The vial was fitted with a Teflon lined septum cap. The vial was evacuated under vacuum (via a needle from a nitrogen/vacuum manifold line) and backfilled with nitrogen gas. The procedure was repeated three times. The needle was removed and the vial was heated at 65° C. for 20 h. The reaction mixture was cooled to room temperature, diluted with ethyl acetate (10 mL) and washed with saturated aqueous NaCl solution (5 mL), dried (Na$_2$SO$_4$), filtered and concentrated to afford crude material. The crude product was dissolved in a small amount of DCM and charged to a 80 g ISCO column which was eluted over a 20 min gradient with 5%-100% hexanes/ethyl acetate to afford tert-butyl 4-(2-(5-chloro-1,2-dimethyl-6-oxo-1,6-dihydropyridin-3-yl)-3-isopropyl-1H-indol-5-yl) piperidine-1-carboxylate, m/z (448.2, M+H), which was contaminated with dimer, m/z (804, M+H), 700 mg.

Example 3

To a mixture containing crude tert-butyl 4-(2-(5-chloro-1,2-dimethyl-6-oxo-1,6-dihydropyridin-3-yl)-3-isopropyl-1H-indol-5-yl)piperidine-1-carboxylate (25 mg, 0.050 mmol), bis(triphenylphosphine)palladium(II) dichloride (1.762 mg, 2.510 μmol), and lithium chloride (4.26 mg, 0.100 mmol) in a screw cap vial was added DMF (0.5 mL) followed by the addition of tetramethyltin (0.014 mL, 0.100 mmol). The vial was fitted with a Teflon lined septum cap and the system was evacuated under vacuum (via a needle from a nitrogen/vacuum manifold line) and backfilled with nitrogen gas. The procedure was repeated three times. The needle was removed and the vial was heated at 100° C. for 6 h. Additional Pd catalyst (~1 mg) and tetramethyl tin (20 μL) were added and the reaction mixture was heated for an additional 18 h. The reaction mixture was cooled to room temperature, diluted with ethyl acetate (5 mL) and washed with 10% aqueous LiCl solution (3×2 mL), dried ($Na_2SO_4$), filtered and concentrated.

The crude tert-butyl 4-(3-isopropyl-2-(1,2,5-trimethyl-6-oxo-1,6-dihydropyridin-3-yl)-1H-indol-5-yl)piperidine-1-carboxylate was suspended in DCM/TFA (1/1) (1 mL) for 30 min to facilitate the removal of the tert-butyloxycarbonyl group. The reaction mixture was concentrated and the crude material was purified via preparative HPLC/MS. Fractions containing the product were combined and dried via centrifugal evaporation to afford TFA salt. The material was free based by suspending the salt in concentrated ammonium hydroxide (1 mL) and stirring for 20 min. The solids were filtered and dried to afford 5-(3-isopropyl-5-(piperidin-4-yl)-1H-indol-2-yl)-1,3,6-trimethylpyridin-2(1H)-one (5 mg, 0.013 mmol, 25% yield). LCMS MH$^+$: 378. HPLC Ret. Time 0.63 min. Method B1. $^1$H NMR (400 MHz, METHANOL-$d_4$) δ 7.56-7.52 (m, 1H), 7.34 (s, 1H), 7.26 (d, J=8.3 Hz, 1H), 7.03 (dd, J=8.4, 1.3 Hz, 1H), 3.69 (s, 3H), 3.23-3.15 (m, 2H), 3.01-2.90 (m, 1H), 2.85-2.70 (m, 3H), 2.31 (s, 3H), 2.16 (s, 3H), 1.95-1.87 (m, 2H), 1.85-1.71 (m, 2H), 1.44-1.33 (m, 6H).

The following examples were prepared according to the general procedures for Examples 1 and 2 using the indicated fragment.

TABLE 2

| Ex. No. | Structure | Fragment | LCMS MH$^+$ | Ret Time (min) | HPLC Method |
|---|---|---|---|---|---|
| 4 | 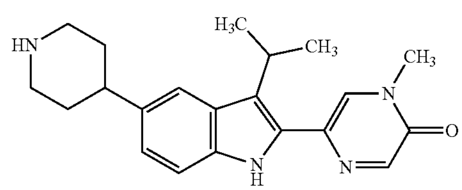 [SMILES: CC(C)c1c(-c2cn(C)c(=O)cn2)[nH]c2ccc(C3CCNCC3)cc12] | F-8 | 351.1 | 1 | QC-ACN-TFA-XB |
| 5 | 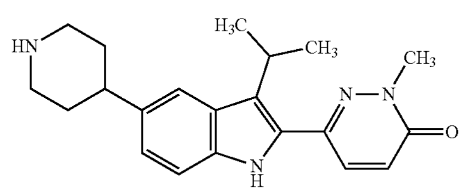 | F-7 | 351.2 | 1.2 | QC-ACN-AA-XB |
| 6 | 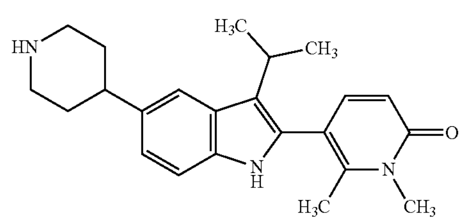 [SMILES: Cc1c(-c2[nH]c3ccc(C4CCNCC4)cc3c2C(C)C)ccc(=O)n1C] | F-31B | 364.1 | 0.60 | Method B1 |
| 8 | 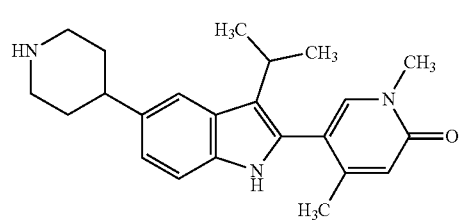 | F-32 | 364.2 | 0.99 | QC-ACN-AA-XB |

TABLE 2-continued

| Ex. No. | Structure | Fragment | LCMS MH+ | Ret Time (min) | HPLC Method |
|---|---|---|---|---|---|
| 9 | 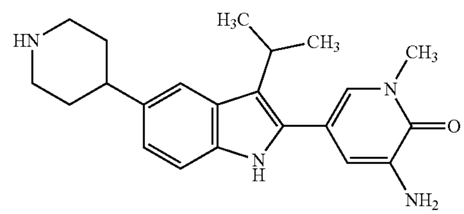 [SMILES: CC(C)c1c(-c2cc(N)c(=O)n(C)c2)[nH]c2ccc(C3CCNCC3)cc12] | F-9 | 365.2 | 1.07 | QC-ACN-AA-XB |
| 10 | 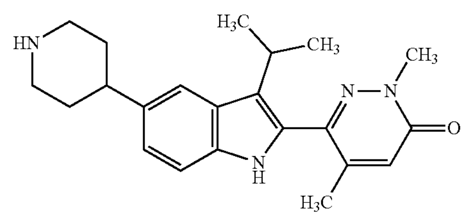 | F-11 | 364.9 | 1.01 | QC-ACN-AA-XB |
| 11 | 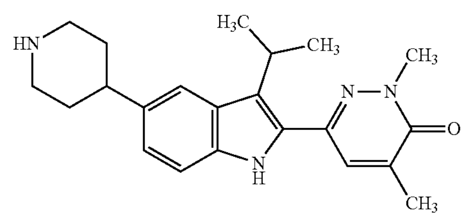 [SMILES: Cc1cc(-c2[nH]c3ccc(C4CCNCC4)cc3c2C(C)C)nn(C)c1=O] | F-12 | 365.3 | 0.65 | Method B1 |
| 12 | 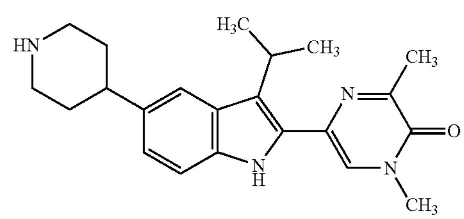 | F-20 | 365.3 | 0.62 | Method B1 |
| 13 | 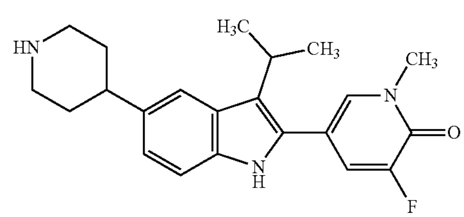 [SMILES: CC(C)c1c(-c2cc(F)c(=O)n(C)c2)[nH]c2ccc(C3CCNCC3)cc12] | F-10 | 368.2 | 0.96 | QC-ACN-AA-XB |
| 14 | 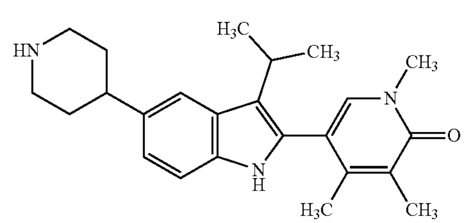 [SMILES: Cc1c(-c2[nH]c3ccc(C4CCNCC4)cc3c2C(C)C)cn(C)c(=O)c1C] | F-4 | 378.3 | 0.65 | Method B1 |
| 15 | 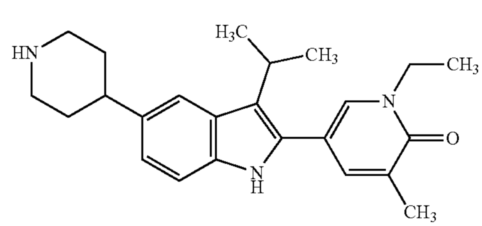 [SMILES: CCn1cc(-c2[nH]c3ccc(C4CCNCC4)cc3c2C(C)C)cc(C)c1=O] | F-37 | 378.2 | 1.16 | QC-ACN-AA-XB |

TABLE 2-continued
| Ex. No. | Structure | Fragment | LCMS MH+ | Ret Time (min) | HPLC Method |
|---|---|---|---|---|---|
| 16 | 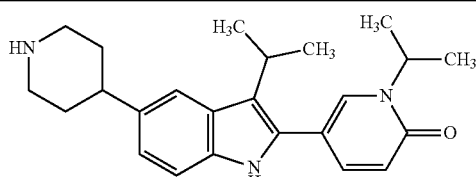 | F-14 | 378.1 | 1.12 | QC-ACN-TFA-XB1 |
| 17 | 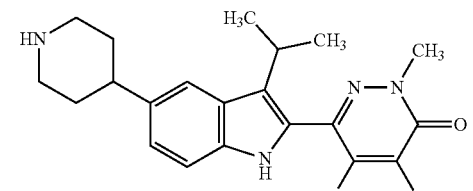 | F-21 | 379.3 | 1.05 | QC-ACN-AA-XB |
| 18 | 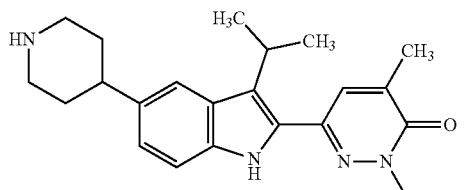 | F-23 | 379 | 1.36 | QC-ACN-AA-XB |
| 19 | 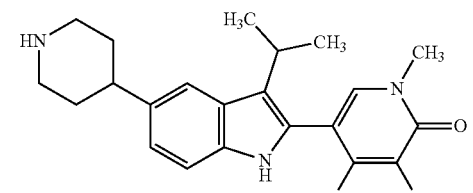 | F-16 | 379.3 | 0.91 | QC-ACN-AA-XB |
| 20 | 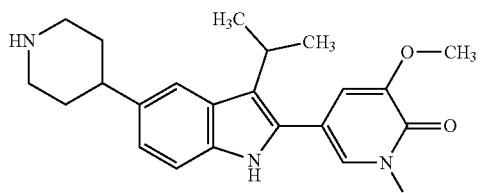 | F-34 | 380.3 | 0.59 | Method B1 |
| 21 | 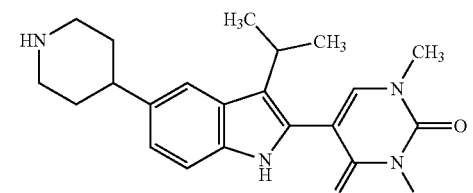 | F-13 | 381.3 | 1.27 | QC-ACN-AA-XB |
| 22 | 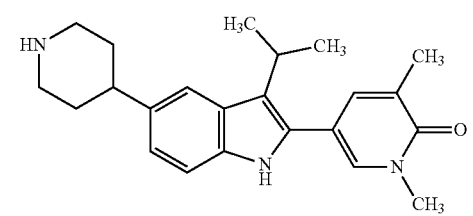 | F-6 | 384.3 | 1.14 | QC-ACN-TFA-XB |

TABLE 2-continued

| Ex. No. | Structure | Fragment | LCMS MH+ | Ret Time (min) | HPLC Method |
|---|---|---|---|---|---|
| 23 | 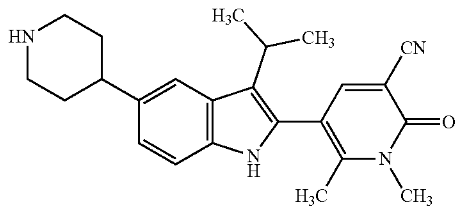 [SMILES: Cc1c(-c2[nH]c3ccc(C4CCNCC4)cc3c2C(C)C)cc(C#N)c(=O)n1C] | F-36 | 389.2 | 0.64 | Method B1 |
| 24 | 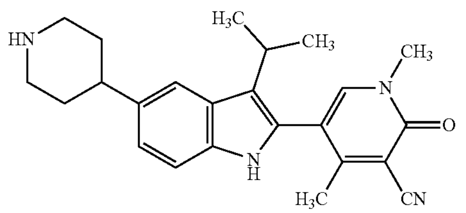 | F-35 | 389.2 | 0.64 | Method B1 |
| 25 | 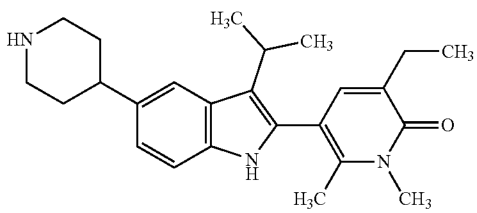 [SMILES: CCc1cc(-c2[nH]c3ccc(C4CCNCC4)cc3c2C(C)C)c(C)n(C)c1=O] | F-49 | 392.1 | 0.71 | Method B1 |
| 26 | 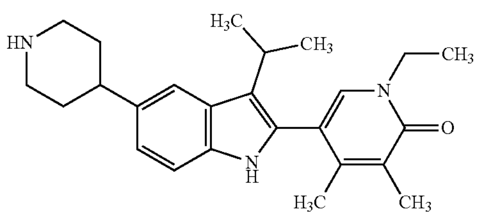 [SMILES: CCn1nc(-c2[nH]c3ccc(C4CCNCC4)cc3c2C(C)C)c(C)c(C)c1=O] | F-33 | 392.4 | 0.68 | Method B1 |
| 27 | 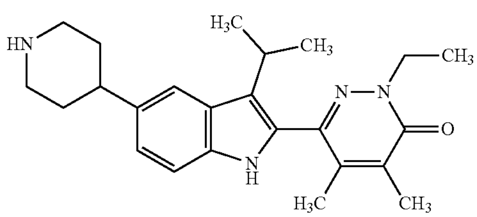 | F-22 | 393.2 | 1.23 | Method B1 |
| 28 | 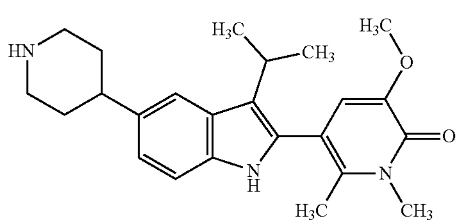 [SMILES: COc1cc(-c2[nH]c3ccc(C4CCNCC4)cc3c2C(C)C)c(C)n(C)c1=O] | F-24 | 394.2 | 0.61 | Method B1 |
| 29 | 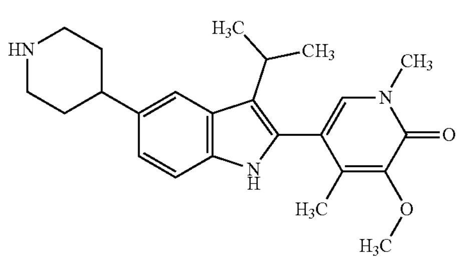 [SMILES: COc1c(C)c(-c2[nH]c3ccc(C4CCNCC4)cc3c2C(C)C)cn(C)c1=O] | F-25 | 394.1 | 0.63 | Method B1 |

TABLE 2-continued

| Ex. No. | Structure | Fragment | LCMS MH+ | Ret Time (min) | HPLC Method |
|---|---|---|---|---|---|
| 30 | 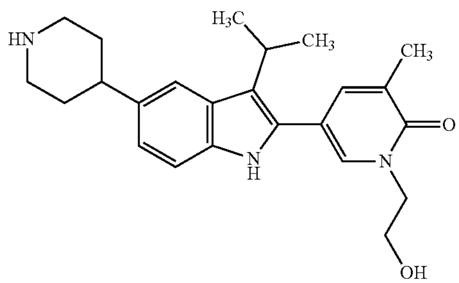 [SMILES: Cc1cc(-c2[nH]c3ccc(C4CCNCC4)cc3c2C(C)C)cn(CCO)c1=O] | F-43 | 394.2 | 1.05 | QC-ACN-AA-XB |
| 31 | 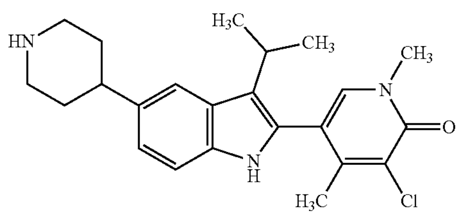 [SMILES: Cc1c(-c2[nH]c3ccc(C4CCNCC4)cc3c2C(C)C)cn(C)c(=O)c1Cl] | F-29 | 398.2 | 1.19 | QC-ACN-TFA-XB |
| 32 | 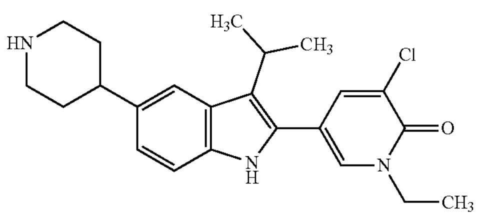 [SMILES: CCn1cc(-c2[nH]c3ccc(C4CCNCC4)cc3c2C(C)C)cc(Cl)c1=O] | F-28 | 398.2 | 1.39 | QC-ACN-TFA-XB |
| 33 | 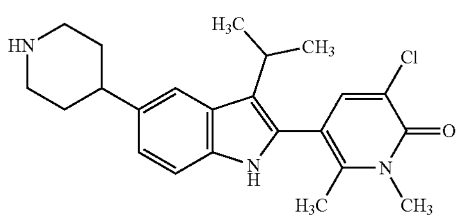 | F-5 | 398.1 | 0.66 | Method B1 |
| 34 | 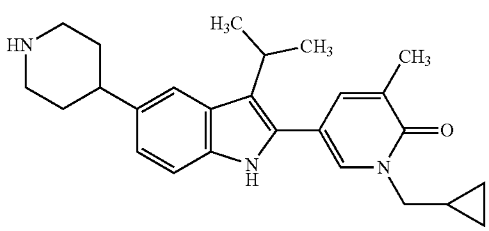 [SMILES: Cc1cc(-c2[nH]c3ccc(C4CCNCC4)cc3c2C(C)C)cn(CC2CC2)c1=O] | F-42 | 404 | 1.33 | QC-ACN-AA-XB |
| 35 | 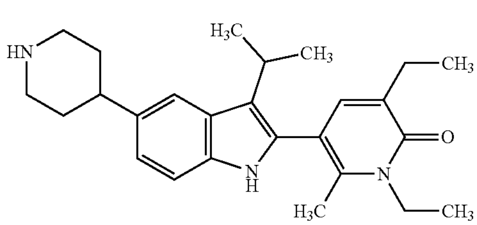 [SMILES: CCc1cc(-c2[nH]c3ccc(C4CCNCC4)cc3c2C(C)C)c(C)n(CC)c1=O] | F-38 | 406.3 | 0.73 | Method B1 |

TABLE 2-continued

| Ex. No. | Structure | Fragment | LCMS MH+ | Ret Time (min) | HPLC Method |
|---|---|---|---|---|---|
| 36 | 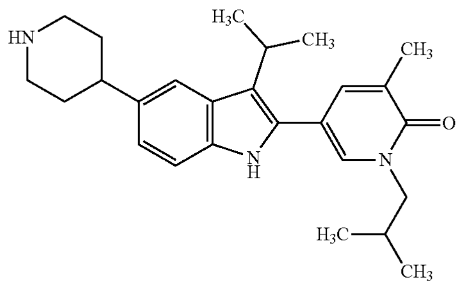 [SMILES: Cc1cc(-c2[nH]c3ccc(C4CCNCC4)cc3c2C(C)C)cn(CC(C)C)c1=O] | F-2 | 406 | 1.34 | QC-ACN-TFA-XB |
| 37 | 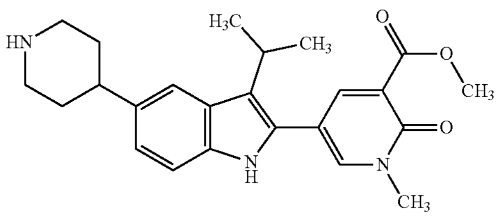 [SMILES: COC(=O)c1cc(-c2[nH]c3ccc(C4CCNCC4)cc3c2C(C)C)cn(C)c1=O] | F-39 | 408 | 1.19 | QC-ACN-TFA-XB |
| 38 | 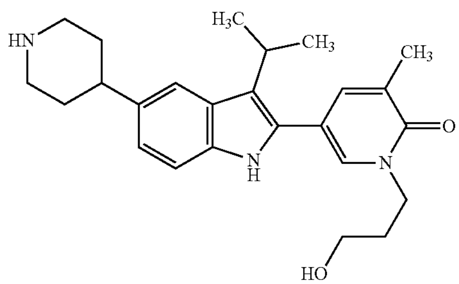 [SMILES: Cc1cc(-c2[nH]c3ccc(C4CCNCC4)cc3c2C(C)C)cn(CCCO)c1=O] | F-47 | 408.2 | 1.05 | QC-ACN-AA-XB |
| 39 | 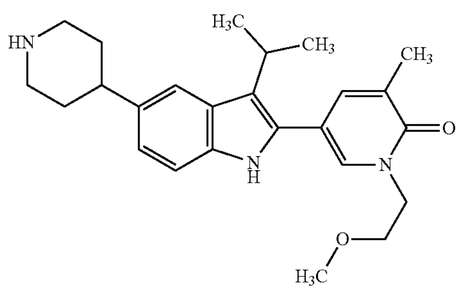 [SMILES: COCCn1cc(-c2[nH]c3ccc(C4CCNCC4)cc3c2C(C)C)cc(C)c1=O] | F-40 | 408.1 | 1.27 | QC-ACN-TFA-XB |
| 40 | 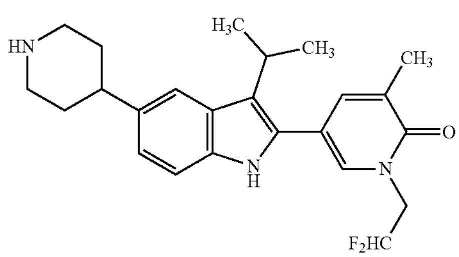 [SMILES: Cc1cc(-c2[nH]c3ccc(C4CCNCC4)cc3c2C(C)C)cn(CC(F)F)c1=O] | F-44 | 414.3 | 1.28 | QC-ACN-AA-XB |
| 41 | 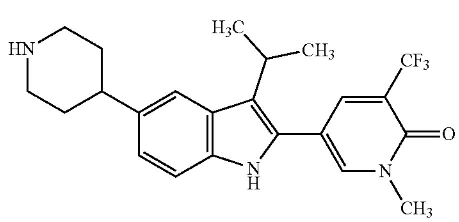 [SMILES: CC(C)c1c(-c2cc(C(F)(F)F)c(=O)n(C)c2)[nH]c2ccc(C3CCNCC3)cc12] | F-17 | 417.3 | 0.71 | Method B1 |

TABLE 2-continued

| Ex. No. | Structure | Fragment | LCMS MH+ | Ret Time (min) | HPLC Method |
|---|---|---|---|---|---|
| 42 | 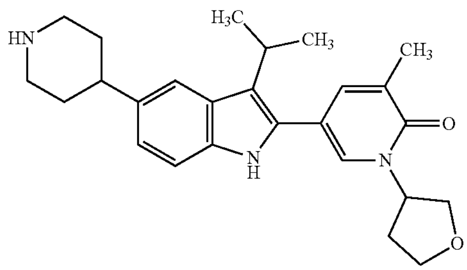 [SMILES: Cc1cc(-c2[nH]c3ccc(C4CCNCC4)cc3c2C(C)C)cn(C2CCOC2)c1=O] | F-46 | 420.3 | 1.36 | QC-ACN-AA-XB |
| 43 | 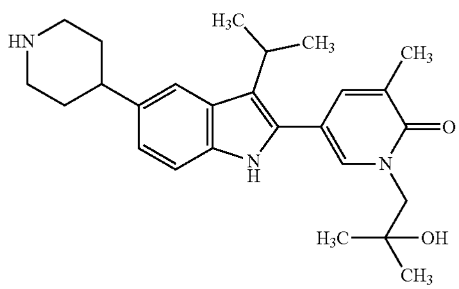 [SMILES: Cc1cc(-c2[nH]c3ccc(C4CCNCC4)cc3c2C(C)C)cn(CC(C)(C)O)c1=O] | F-30 | 422 | 1.39 | QC-ACN-AA-XB |
| 44 | 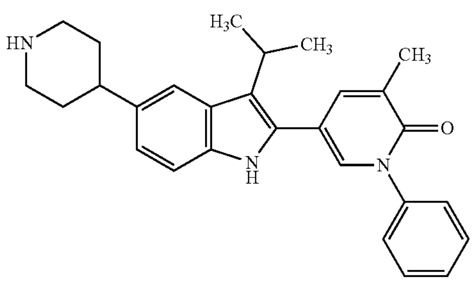 [SMILES: Cc1cc(-c2[nH]c3ccc(C4CCNCC4)cc3c2C(C)C)cn(-c2ccccc2)c1=O] | F-3 | 426.2 | 1.46 | QC-ACN-TFA-XB |
| 45 | 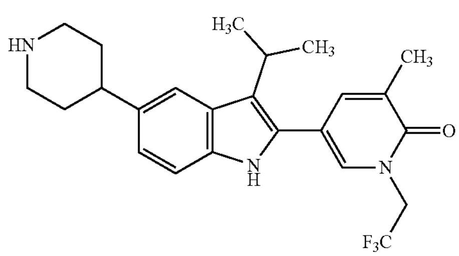 [SMILES: Cc1cc(-c2[nH]c3ccc(C4CCNCC4)cc3c2C(C)C)cn(CC(F)(F)F)c1=O] | F-45 | 432.2 | 1.54 | QC-ACN-AA-XB |
| 46 | 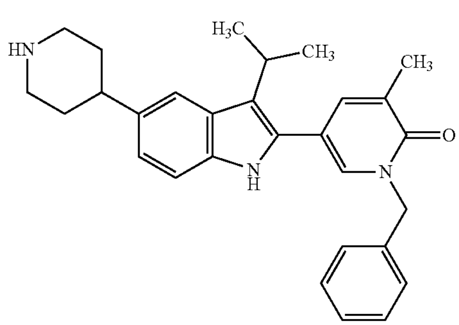 [SMILES: Cc1cc(-c2[nH]c3ccc(C4CCNCC4)cc3c2C(C)C)cn(Cc2ccccc2)c1=O] | F-41 | 440 | 1.46 | QC-ACN-AA-XB |

TABLE 2-continued

| Ex. No. | Structure | Fragment | LCMS MH+ | Ret Time (min) | HPLC Method |
|---|---|---|---|---|---|
| 47 | 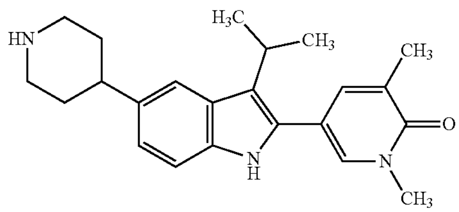 | F-48 | 375.3 | 0.63 | Method B1 |
| 48 | 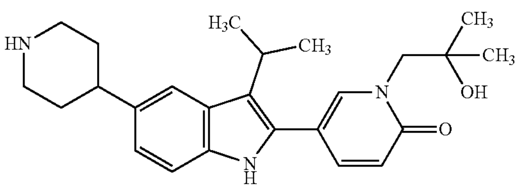 [SMILES: CC(C)c1c(-c2ccc(=O)n(CC(C)(C)O)c2)[nH]c2ccc(C3CCNCC3)cc12] | F-18 | 408.3 | 1.29 | QC-ACN-AA-XB |
| 49 | 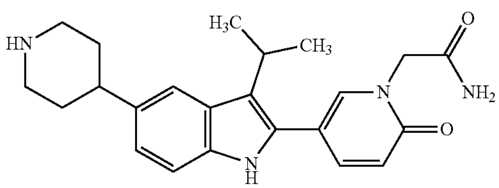 [SMILES: CC(C)c1c(-c2ccc(=O)n(CC(N)=O)c2)[nH]c2ccc(C3CCNCC3)cc12] | F-19 | 392.9 | 0.74 | QC-ACN-AA-XB |

Example 50

5-(3-isopropyl-5-(piperidin-4-yl)-1H-indol-2-yl)-1-methyl-[3,3'-bipyridin]-2(1H)-one

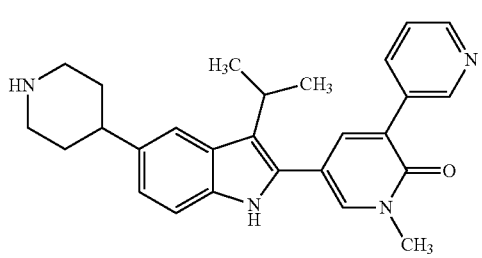

(50)

tert-Butyl 5-(1-(tert-butoxycarbonyl)piperidin-4-yl)-2-(5-chloro-1-methyl-6-oxo-1,6-dihydropyridin-3-yl)-3-isopropyl-1H-indole-1-carboxylate (30 mg, 0.051 mmol) and 3-(4,4,5,5-tetramethyl-1,3,2-dioxaborolan-2-yl)pyridine (21.06 mg, 0.103 mmol) were weighed into a 1-dram vial. THF (0.514 mL) was added to the vial, followed by aqueous tripotassium phosphate (2 M, 0.103 mL, 0.205 mmol). The reaction mixture was degassed by bubbling nitrogen through the solution for 2 min. Second generation XPhos precatalyst (1.212 mg, 1.541 µmol) was added and the reaction mixture was placed under a nitrogen atmosphere and stirred at 65° C. for 3 h. The reaction mixture was cooled to room temperature. The reaction mixture was partitioned between water and ethyl acetate (~2 mL each), separated, and the aqueous phase was extracted with ethyl acetate (2×2 mL). Excess solvent was evaporated from the organic phase. The resulting residue was Boc-deprotected with 2:1 trifluoroacetic acid/dichloromethane (1.2 mL, 0.051 mmol), stirring for 45 min at room temperature. Toluene (~0.1 mL) was added, and excess solvent was evaporated from the reaction. The crude material was purified via preparative LC/MS. Fractions containing the product were combined and dried via centrifugal evaporation to afford 5-(3-isopropyl-5-(piperidin-4-yl)-1H-indol-2-yl)-1-methyl-[3,3'-bipyridin]-2(1H)-one (9.4 mg, 0.021 mmol, 40% yield, 94% purity). LCMS MH+: 427.3. HPLC Ret. Time 1.01 min. Method QC-ACN-TFA-XB. $^1$H NMR (500 MHz, DMSO-$d_6$) δ 11.00 (s, 1H), 9.08 (br. s., 1H), 8.42 (d, J=8.2 Hz, 2H), 7.94 (s, 1H), 7.90 (d, J=2.4 Hz, 1H), 7.66 (dd, J=7.8, 5.0 Hz, 1H), 7.53 (s, 1H), 7.31 (d, J=8.2 Hz, 1H), 6.98 (d, J=8.5 Hz, 1H), 3.59-3.49 (m, 3H), 3.40 (d, J=11.9 Hz, 2H), 3.24 (dt, J=14.0, 6.9 Hz, 1H), 3.09-2.98 (m, 2H), 2.96-2.89 (m, 1H), 2.01-1.93 (m, 2H), 1.93-1.81 (m, 2H), 1.43 (d, J=7.0 Hz, 6H).

The following examples were prepared according to the general procedure for Example 50 using the indicated starting material.

TABLE 3

| Ex. No. | Structure | Starting coupling partner | LCMS MH+ | Ret Time (min) | HPLC Method |
|---|---|---|---|---|---|
| 51 | 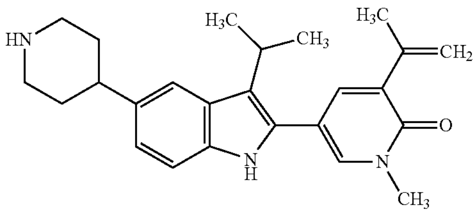 [SMILES: C=C(C)c1cc(-c2[nH]c3ccc(C4CCNCC4)cc3c2C(C)C)cn(C)c1=O] | 4,4,5,5-tetramethyl-2-(prop-1-en-2-yl)-1,3,2-dioxaborolane | 390.3 | 1.31 | QC-ACN-TFA-XB |
| 52 | 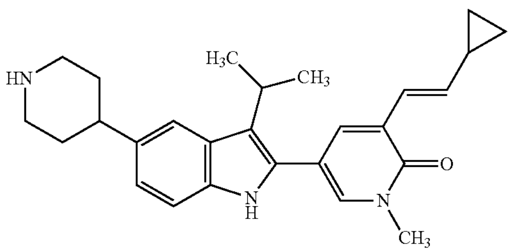 [SMILES: CC(C)c1c(-c2cc(/C=C/C3CC3)c(=O)n(C)c2)[nH]c2ccc(C3CCNCC3)cc12] | (E)-2-(2-cyclopropylvinyl)-4,4,5,5-tetramethyl-1,3,2-dioxaborolane | 416.3 | 1.47 | QC-ACN-TFA-XB |
| 53 | 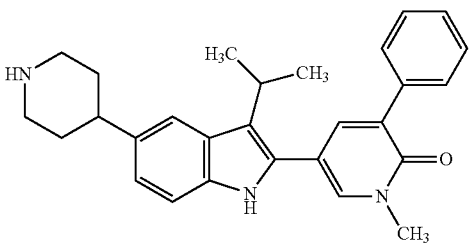 [SMILES: CC(C)c1c(-c2cc(-c3ccccc3)c(=O)n(C)c2)[nH]c2ccc(C3CCNCC3)cc12] | phenylboronic acid | 426.0 | 1.45 | QC-ACN-TFA-XB |
| 54 | 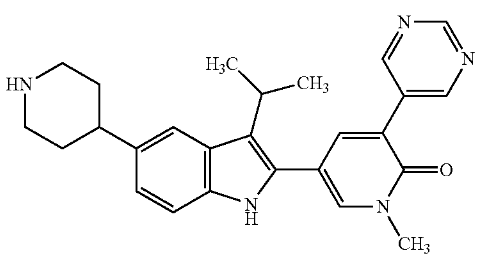 [SMILES: CC(C)c1c(-c2cc(-c3cncnc3)c(=O)n(C)c2)[nH]c2ccc(C3CCNCC3)cc12] | pyrimidin-5-yl boronic acid | 428.0 | 1.38 | QC-ACN-TFA-XB |
| 55 | 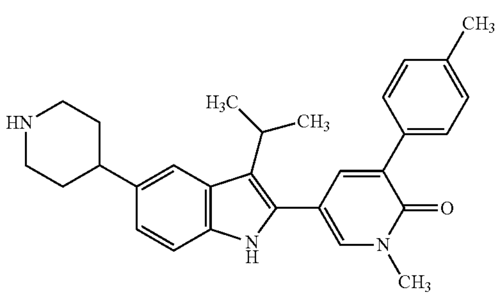 [SMILES: Cc1ccc(-c2cc(-c3[nH]c4ccc(C5CCNCC5)cc4c3C(C)C)cn(C)c2=O)cc1] | p-tolylboronic acid | 440.3 | 1.51 | QC-ACN-TFA-XB |
| 56 | 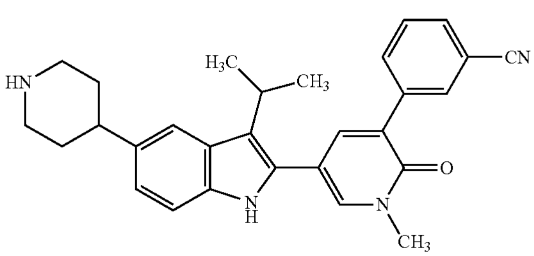 [SMILES: CC(C)c1c(-c2cc(-c3cccc(C#N)c3)c(=O)n(C)c2)[nH]c2ccc(C3CCNCC3)cc12] | (3-cyanophenyl) boronic acid | 451.2 | 1.34 | QC-ACN-TFA-XB |

TABLE 3-continued

| Ex. No. | Structure | Starting coupling partner | LCMS MH+ | Ret Time (min) | HPLC Method |
|---|---|---|---|---|---|
| 57 | 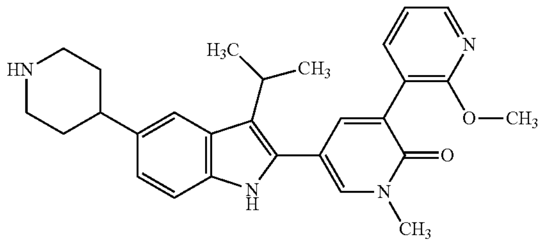 [SMILES: COc1ncccc1-c1cc(-c2[nH]c3ccc(C4CCNCC4)cc3c2C(C)C)cn(C)c1=O] | (2-methoxypyridin-3-yl)boronic acid | 456.9 | 1.28 | QC-ACN-TFA-XB |
| 58 | 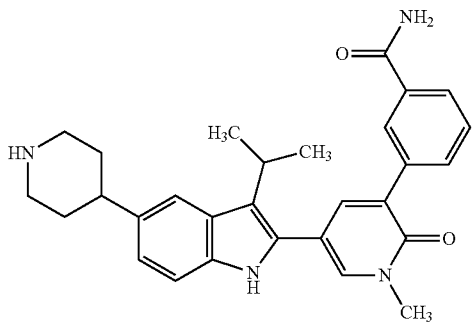 [SMILES: CC(C)c1c(-c2cc(-c3cccc(C(N)=O)c3)c(=O)n(C)c2)[nH]c2ccc(C3CCNCC3)cc12] | (3-carbamoylphenyl)boronic acid | 469.4 | 1.06 | QC-ACN-TFA-XB |
| 59 | 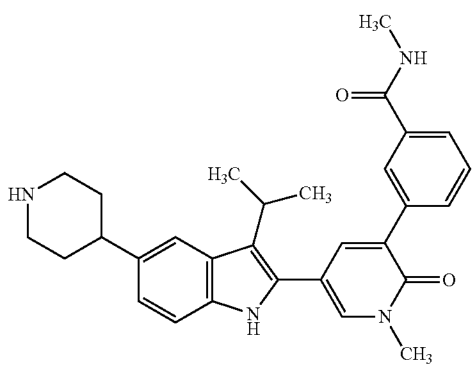 [SMILES: CNC(=O)c1cccc(-c2cc(-c3[nH]c4ccc(C5CCNCC5)cc4c3C(C)C)cn(C)c2=O)c1] | (3-(methylcarbamoyl)phenyl)boronic acid | 482.9 | 1.21 | QC-ACN-TFA-XB |
| 60 | 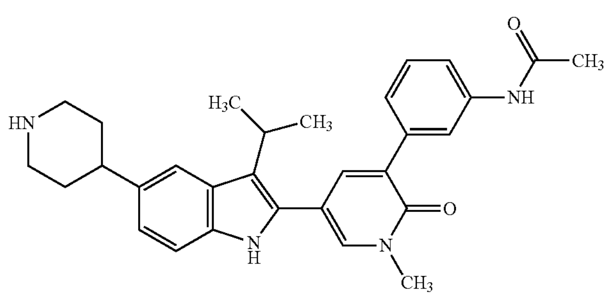 [SMILES: CC(=O)Nc1cccc(-c2cc(-c3[nH]c4ccc(C5CCNCC5)cc4c3C(C)C)cn(C)c2=O)c1] | (3-acetamidophenyl)boronic acid | 483.0 | 1.29 | QC-ACN-TFA-XB |
| 61 | 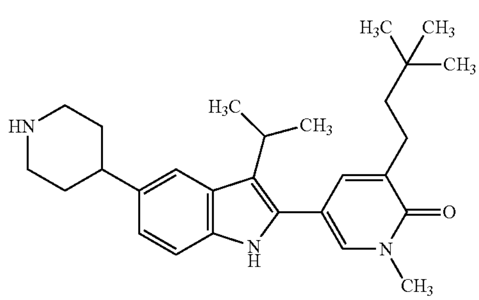 [SMILES: CC(C)c1c(-c2cc(CCC(C)(C)C)c(=O)n(C)c2)[nH]c2ccc(C3CCNCC3)cc12] | (E)-(3,3-dimethylbut-1-en-1-yl)boronic acid | 434.1 | 1.75 | QC-ACN-TFA-XB |

TABLE 3-continued

| Ex. No. | Structure | Starting coupling partner | LCMS MH+ | Ret Time (min) | HPLC Method |
|---|---|---|---|---|---|
| 62 | 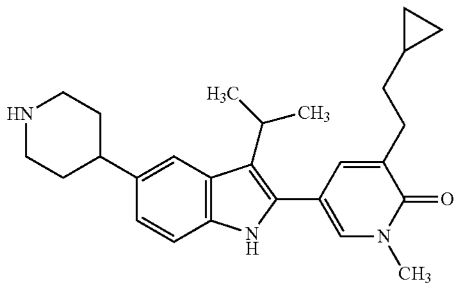 [SMILES: CC(C)c1c(-c2cc(CCC3CC3)c(=O)n(C)c2)[nH]c2ccc(C3CCNCC3)cc12] | (E)-2-(2-cyclopropylvinyl)-4,4,5,5-tetramethyl-1,3,2-dioxaborolane | 418 | 1.3 | QC-ACN-TFA-XB |
| 63 | 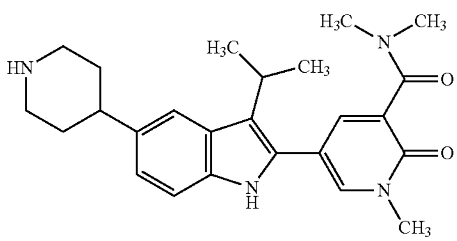 [SMILES: CC(C)c1c(-c2cc(C(=O)N(C)C)c(=O)n(C)c2)[nH]c2ccc(C3CCNCC3)cc12] | Prepared as in example 70 | 421 | 1.12 | QC-ACN-AA-XB |
| 64 | 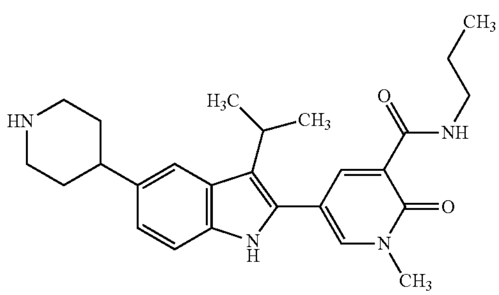 [SMILES: CCCNC(=O)c1cc(-c2[nH]c3ccc(C4CCNCC4)cc3c2C(C)C)cn(C)c1=O] | Prepared as in example 70 | 435.2 | 1.4 | QC-ACN-AA-XB |

Example 65

5-(3-isopropyl-5-(piperidin-4-yl)-1H-indol-2-yl)-1,4-dimethyl-[3,3'-bipyridin]-2(1H)-one (65)

Intermediate 65A: tert-butyl 4-(2-(5-chloro-1,4-dimethyl-6-oxo-1,6-dihydropyridin-3-yl)-3-isopropyl-1H-indol-5-yl)piperidine-1-carboxylate (65A)

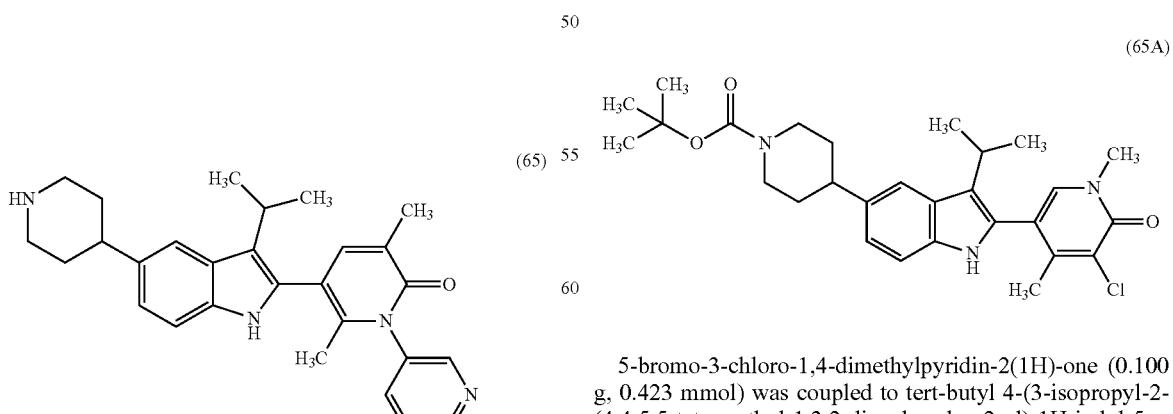

5-bromo-3-chloro-1,4-dimethylpyridin-2(1H)-one (0.100 g, 0.423 mmol) was coupled to tert-butyl 4-(3-isopropyl-2-(4,4,5,5-tetramethyl-1,3,2-dioxaborolan-2-yl)-1H-indol-5-yl)piperidine-1-carboxylate (0.172 g, 0.368 mmol) as described above for Intermediate 2A to afford tert-butyl 4-(2-(5-chloro-1,4-dimethyl-6-oxo-1,6-dihydropyridin-3-yl)-3-isopropyl-1H-indol-5-yl)piperidine-1-carboxylate (149.3 mg, 0.285 mmol, 77% yield) as a pale yellow solid. LCMS MH+: 498.2. HPLC Ret. Time 1.12 min QC-ACN-TFA-XB. $^1$H NMR (400 MHz, CHLOROFORM-d) δ 9.03 (s, 1H), 7.60 (s, 1H), 7.43 (d, J=8.3 Hz, 1H), 7.18 (s, 1H), 7.12 (dd, J=8.4, 1.5 Hz, 1H), 4.38-4.22 (m, 2H), 3.60 (s, 3H), 2.96 (quin, J=7.1 Hz, 1H), 2.87 (t, J=12.2 Hz, 2H), 2.79 (tt, J=12.1, 3.2 Hz, 1H), 2.17 (s, 3H), 1.93 (d, J=12.5 Hz, 2H), 1.75 (qd, J=12.6, 4.0 Hz, 2H), 1.52 (s, 9H), 1.39 (d, J=7.0 Hz, 6H).

Example 65 tert-Butyl 4-(2-(5-chloro-1,4-dimethyl-6-oxo-1,6-dihydropyridin-3-yl)-3-isopropyl-1H-indol-5-yl)piperidine-1-carboxylate (134.3 mg, 0.270 mmol) was coupled to pyridin-3-ylboronic acid (66.3 mg, 0.539 mmol). Next, tert-butyl 4-(2-(1,4-dimethyl-2-oxo-1,2-dihydro-[3,3'-bipyridin]-5-yl)-3-isopropyl-1H-indol-5-yl)piperidine-1-carboxylate (16.2 mg, 0.030 mmol) was deprotected as described above for Example 50 to afford 5-(3-isopropyl-5-(piperidin-4-yl)-1H-indol-2-yl)-1,4-dimethyl-[3,3'-bipyridin]-2(1H)-one (12.0 mg, 0.026 mmol, 85% yield for the deprotection, 94% purity). LCMS MH+: 441.3. HPLC Ret. Time 0.78 min. QC-ACN-TFA-XB. $^1$H NMR (500 MHz, DMSO-$d_6$) δ 10.81 (s, 1H), 8.53 (br. s., 1H), 8.44 (br. s., 1H), 7.74 (s, 1H), 7.70 (d, J=7.7 Hz, 1H), 7.48 (br. s., 1H), 7.47 (d, J=7.7 Hz, 1H), 7.24 (d, J=8.3 Hz, 1H), 6.96 (d, J=8.2 Hz, 1H), 3.52 (br. s., 3H), 3.17 (s, 2H), 3.03-2.94 (m, 1H), 2.72 (br. s., 3H), 1.79 (s, 6H), 1.71 (br. s., 2H), 1.34 (br. s., 6H).

Example 66

3-isopropyl-5-(3-isopropyl-5-(piperidin-4-yl)-1H-indol-2-yl)-1-methylpyridin-2(1H)-one

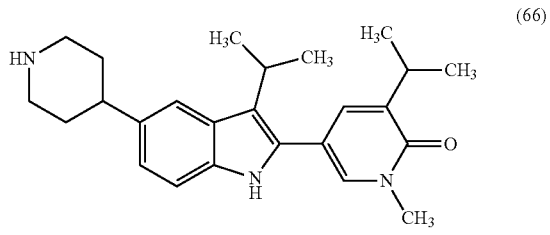 [SMILES: CC(C)c1cc(-c2[nH]c3ccc(C4CCNCC4)cc3c2C(C)C)cn(C)c1=O]

(66)

Intermediate 66A: tert-butyl 5-(1-(tert-butoxycarbonyl)piperidin-4-yl)-2-(5-chloro-1-methyl-6-oxo-1,6-dihydropyridin-3-yl)-3-isopropyl-1H-indole-1-carboxylate

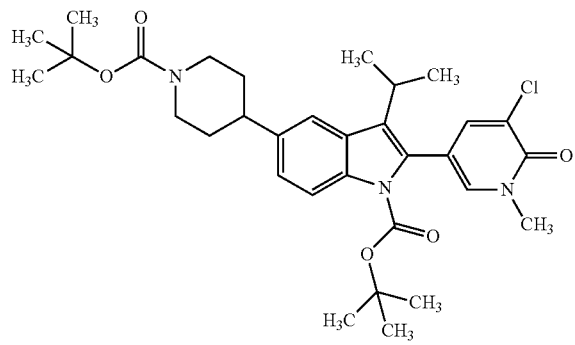

(66A)

5-Bromo-3-chloro-1-methylpyridin-2(1H)-one (0.390 g, 1.754 mmol) and tert-butyl 5-(1-(tert-butoxycarbonyl)piperidin-4-yl)-3-isopropyl-2-(4,4,5,5-tetramethyl-1,3,2-dioxaborolan-2-yl)-1H-indole-1-carboxylate (0.950 g, 1.671 mmol) were weighed into a 40 mL scintillation vial containing a Teflon-coated stir bar and equipped a pressure-release cap. THF (8.35 mL) was added to the vial, followed by tripotassium phosphate (2.506 mL, 5.01 mmol). The reaction mixture was degassed by bubbling $N_2$ through the solution for 5 min. 2nd generation XPhos precatalyst (0.039 g, 0.050 mmol) was added to the reaction mixture. The reaction mixture was placed under an $N_2$ atmosphere and stirred at 65° C. for 20 h. The reaction mixture was cooled to room temperature, diluted with ethyl acetate (20 mL) and the organic layer was isolated, dried ($Na_2SO_4$), filtered and concentrated. The residue was taken up in DCM (~5 mL) and purified by flash chromatography on a 24 g silica column, eluting with 20-100% gradient using ethyl acetate and hexanes to afford tert-butyl 5-(1-(tert-butoxycarbonyl)piperidin-4-yl)-2-(5-chloro-1-methyl-6-oxo-1,6-dihydropyridin-3-yl)-3-isopropyl-1H-indole-1-carboxylate (915.5 mg, 1.254 mmol, 75% yield) as a yellow-orange solid. $^1$H NMR indicted impurities. $^1$H NMR (400 MHz, CHLOROFORM-d) δ 8.18 (d, J=8.7 Hz, 1H), 7.54 (d, J=1.3 Hz, 1H), 7.48 (d, J=2.3 Hz, 1H), 7.22 (dd, J=8.7, 1.7 Hz, 1H), 7.18 (d, J=2.3 Hz, 1H), 4.29 (br. s., 2H), 3.69 (s, 3H), 2.99 (spt, J=7.1 Hz, 1H), 2.87 (t, J=12.0 Hz, 2H), 2.78 (tt, J=12.0, 3.4 Hz, 1H), 1.90 (d, J=12.3 Hz, 2H), 1.72 (qd, J=12.7, 3.8 Hz, 2H), 1.52 (s, 9H), 1.38 (d, J=7.1 Hz, 6H), 1.26 (s, 9H).

Intermediate 66B: tert-butyl 5-(1-(tert-butoxycarbonyl)piperidin-4-yl)-3-isopropyl-2-(1-methyl-6-oxo-5-(prop-1-en-2-yl)-1,6-dihydropyridin-3-yl)-1H-indole-1-carboxylate

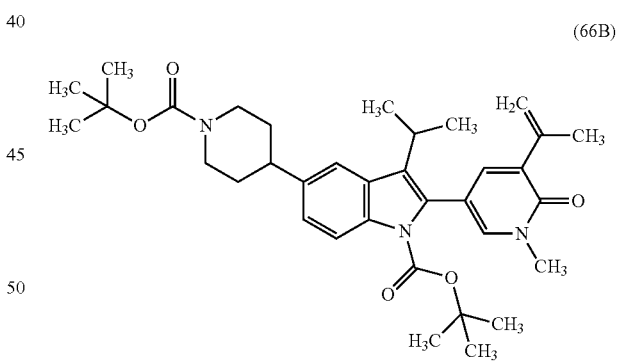

(66B)

Tert-butyl 5-(1-(tert-butoxycarbonyl)piperidin-4-yl)-2-(5-chloro-1-methyl-6-oxo-1,6-dihydropyridin-3-yl)-3-isopropyl-1H-indole-1-carboxylate (50 mg, 0.086 mmol) and 4,4,5,5-tetramethyl-2-(prop-1-en-2-yl)-1,3,2-dioxaborolane (31.6 mg, 0.188 mmol) were weighed into a 1-dram vial containing a Teflon-coated stir bar and equipped a pressure-release cap. THF (856 µl) was added to the vial, followed by aqueous 2 M tripotassium phosphate (128 µl, 0.257 mmol). The reaction mixture was degassed by vacuum-purge with nitrogen (3×). Second generation XPhos precatalyst (2.020 mg, 2.57 µmol) was added to the reaction mixture. The reaction mixture was placed under a nitrogen atmosphere and stirred at 65° C. for 17 h. The reaction mixture was cooled to room temperature. The aqueous phase was removed, and excess solvent was evaporated from the organic phase. The resulting residue was taken up in DCM (3 mL) and purified by flash chromatography on a 4 g silica column, eluting with ethyl acetate and hexanes to afford tert-butyl 5-(1-(tert-butoxycarbonyl)piperidin-4-yl)-3-isopropyl-2-(1-methyl-6-oxo-5-(prop-1-en-2-yl)-1,6-dihydropyridin-3-yl)-1H-indole-1-carboxylate (38.0 mg, 0.058 mmol, 67.7% yield) as a clear, pale yellow glass. m/z (590.1, M+H). $^1$H NMR (400 MHz, CHLOROFORM-d) δ 8.19 (d, J=8.7 Hz, 1H), 7.56-7.53 (m, 1H), 7.28 (d, J=2.4 Hz, 1H), 7.23-7.19 (m, 2H), 5.87 (d, J=1.7 Hz, 1H), 5.30-5.27 (m, 1H), 4.30 (d, J=8.7 Hz, 2H), 3.64 (s, 3H), 3.02 (spt, J=7.1 Hz, 1H), 2.86 (t, J=12.3 Hz, 2H), 2.78 (tt, J=12.1, 3.4 Hz, 1H), 2.15-2.12 (m, 3H), 1.90 (d, J=12.2 Hz, 2H), 1.72 (qd, J=12.7, 3.5 Hz, 2H), 1.52 (s, 9H), 1.41 (s, 9H), 1.38 (d, J=7.1 Hz, 6H).

Example 66

Tert-butyl 5-(1-(tert-butoxycarbonyl)piperidin-4-yl)-3-isopropyl-2-(1-methyl-6-oxo-5-(prop-1-en-2-yl)-1,6-dihydropyridin-3-yl)-1H-indole-1-carboxylate (19 mg, 0.032 mmol) was dissolved in MeOH (0.322 mL) and transferred into the vial containing the 5% Pd on carbon (20 mg, 0.032 mmol) under a nitrogen atmosphere. The suspension was stirred and kept under a nitrogen atmosphere while triethylsilane (0.051 mL, 0.322 mmol) was added dropwise via syringe over ~5 min. The reaction mixture was stirred at room temperature for 30 min. The reaction mixture was filtered through celite, flushing with MeOH. Excess solvent was evaporated from the reaction mixture to yield a pale yellow oil.

The intermediate oil was Boc-deprotected with 2:1 trifluoroacetic acid/dichloromethane (1.2 mL, 0.032 mmol) for 40 min. Toluene (~0.2 mL) was added, and excess solvent was evaporated from the reaction mixture. The resulting residue was taken up in DMF (1.5 mL) and purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 10-50% B over 20 minutes, then a 5-minute hold at 100% B; Flow: 20 mL/min. Fractions containing the product were combined and dried via centrifugal evaporation to afford 3-isopropyl-5-(3-isopropyl-5-(piperidin-4-yl)-1H-indol-2-yl)-1-methylpyridin-2 (1H)-one (4.5 mg, 10.9 μmol, 34% yield, 95% purity). LCMS MH$^+$: 392.3. HPLC Ret. Time 1.29 min. Method QC-ACN-TFA-XB. $^1$H NMR (500 MHz, DMSO-d$_6$) δ 10.86 (br. s., 1H), 7.67 (br. s., 1H), 7.48 (br. s., 1H), 7.34 (br. s., 1H), 7.25 (d, J=8.0 Hz, 1H), 6.95 (d, J=7.7 Hz, 1H), 3.17 (br. s., 2H), 3.12-3.03 (m, 1H), 2.75 (d, J=11.6 Hz, 3H), 1.83 (br. s., 6H), 1.75 (d, J=13.9 Hz, 3H), 1.40 (d, J=6.6 Hz, 6H), 1.16 (d, J=6.6 Hz, 6H).

Example 67

3-ethyl-5-(3-isopropyl-5-(piperidin-4-yl)-1H-indol-2-yl)-1-methylpyridin-2(1H)-one

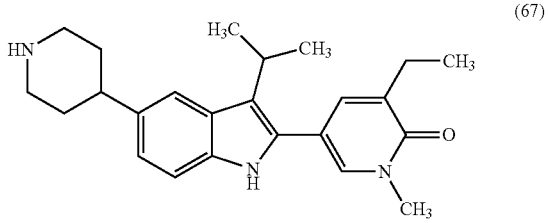 [SMILES: CCc1cc(-c2[nH]c3ccc(C4CCNCC4)cc3c2C(C)C)cn(C)c1=O]

(67)

Intermediate 67A: tert-butyl 5-(1-(tert-butoxycarbonyl)piperidin-4-yl)-3-isopropyl-2-(1-methyl-6-oxo-5-vinyl-1,6-dihydropyridin-3-yl)-1H-indole-1-carboxylate

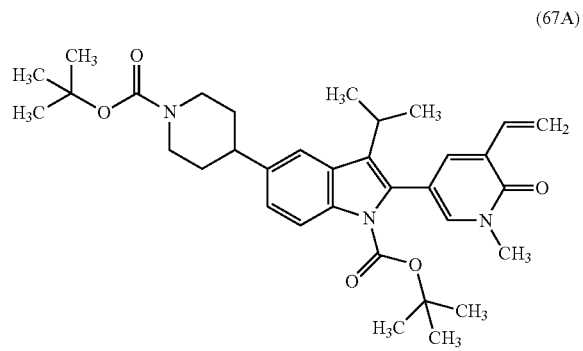 [SMILES: C=Cc1cc(-c2c(C(C)C)c3cc(C4CCN(C(=O)OC(C)(C)C)CC4)ccc3n2C(=O)OC(C)(C)C)cn(C)c1=O]

(67A)

Intermediate 67A was prepared according to the general procedure for Intermediate 66B substituting 4,4,5,5-tetramethyl-2-vinyl-1,3,2-dioxaborolane for 4,4,5,5-tetramethyl-2-(prop-1-en-2-yl)-1,3,2-dioxaborolane. tert-butyl 5-(1-(tert-butoxycarbonyl)piperidin-4-yl)-3-isopropyl-2-(1-methyl-6-oxo-5-vinyl-1,6-dihydropyridin-3-yl)-1H-indole-1-carboxylate (85.3 mg, 0.126 mmol, 72% yield, 85% purity) was obtained as a clear, pale yellow oil. LCMS MH$^+$: 576.3. HPLC Ret. Time 1.24 min. Method B1. $^1$H NMR (400 MHz, CHLOROFORM-d) δ 8.19 (d, J=8.7 Hz, 1H), 7.54 (d, J=1.5 Hz, 1H), 7.38 (d, J=2.3 Hz, 1H), 7.24-7.19 (m, 2H), 6.89 (dd, J=17.7, 11.4 Hz, 1H), 6.06 (dd, J=17.7, 1.5 Hz, 1H), 5.39 (dd, J=11.2, 1.3 Hz, 1H), 4.35-4.26 (m, 2H), 3.65 (s, 3H), 3.00 (dquin, J=14.2, 7.1 Hz, 1H), 2.86 (t, J=12.2 Hz, 2H), 2.81-2.74 (m, 1H), 1.90 (d, J=12.3 Hz, 2H), 1.71 (qd, J=12.5, 3.5 Hz, 2H), 1.51 (s, 9H), 1.40 (s, 9H), 1.38 (d, J=7.2 Hz, 6H).

Example 67

5% Pd on carbon (30 mg, 0.148 mmol) was weighed into a 2-dram vial. tert-butyl 5-(1-(tert-butoxycarbonyl)piperidin-4-yl)-3-isopropyl-2-(1-methyl-6-oxo-5-vinyl-1,6-dihydropyridin-3-yl)-1H-indole-1-carboxylate (85.3 mg, 0.148 mmol) was dissolved in MeOH (1.482 mL) and transferred into the vial containing the Pd on C while under a nitrogen atmosphere. Ammonium formate (74.7 mg, 1.185 mmol) was added to the reaction mixture. The vial was placed under a nitrogen atmosphere. The reaction mixture was stirred at 60° C. for 2 h. The reaction mixture was filtered through celite, flushing with MeOH. Excess solvent was evaporated from the reaction mixture.

The resulting residue was partitioned between DCM and water (1:1, 5 mL total volume), the phases were separated, and the aqueous phase was extracted with DCM (2×1 mL). Excess solvent was evaporated from the combined organic phases. The resulting residue was taken up in DCM and purified by flash chromatography on a 4 g silica column, eluting with ethyl acetate and hexanes to afford tert-butyl 5-(1-(tert-butoxycarbonyl)piperidin-4-yl)-2-(5-ethyl-1-methyl-6-oxo-1,6-dihydropyridin-3-yl)-3-isopropyl-1H-indole-1-carboxylate (50.4 mg, 0.079 mmol, 53.0% yield) as a white solid. This was Boc-deprotected by reacting with 2:1 trifluoroacetic acid/dichloromethane (1.2 mL, 0.044 mmol) in a 1-dram vial for 50 min. Toluene (~0.15 mL) was added, and excess solvent was then evaporated from the reaction. DMF (~1.5 mL) was added to the resulting residue, and the crude material was purified via preparative LC/MS. Fractions containing the product were combined and dried via centrifugal evaporation to afford 3-ethyl-5-(3-isopropyl-5-(piperidin-4-yl)-1H-indol-2-yl)-1-methylpyridin-2(1H)-one (4.0 mg, 10.6 μmol, 24% yield, 100% purity). LCMS MH⁺: 378.1. HPLC Ret. Time 1.15 min. Method QC-ACN-TFA-XB. ¹H NMR (500 MHz, DMSO-d₆) δ 10.81 (s, 1H), 7.65 (s, 1H), 7.47 (s, 1H), 7.37 (br. s., 1H), 7.24 (d, J=8.2 Hz, 1H), 6.94 (d, J=8.2 Hz, 1H), 3.53 (s, 2H), 3.47 (br. s., 1H), 3.20-3.08 (m, 3H), 2.71 (d, J=10.7 Hz, 3H), 1.82 (br. s., 3H), 1.78 (br. s., 2H), 1.67 (d, J=12.2 Hz, 2H), 1.39 (d, J=6.7 Hz, 6H), 1.14 (t, J=7.5 Hz, 3H).

Example 68

1,3-diethyl-5-(3-isopropyl-5-(piperidin-4-yl)-1H-indol-2-yl)pyridin-2(1H)-one

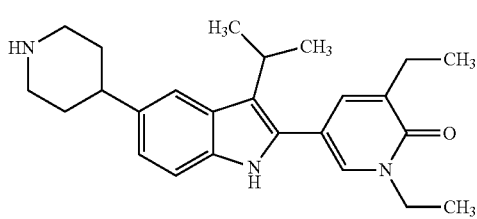

(68)

Intermediate 68A: tert-butyl 5-(1-(tert-butoxycarbonyl)piperidin-4-yl)-2-(5-chloro-1-ethyl-6-oxo-1,6-dihydropyridin-3-yl)-3-isopropyl-1H-indole-1-carboxylate

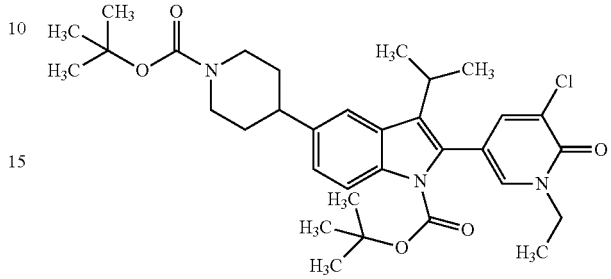

(68A)

5-bromo-3-chloro-1-ethylpyridin-2(1H)-one (F-28) 0.058 g, 0.246 mmol) was coupled to tert-butyl 5-(1-(tert-butoxycarbonyl)piperidin-4-yl)-3-isopropyl-2-(4,4,5,5-tetramethyl-1,3,2-dioxaborolan-2-yl)-1H-indole-1-carboxylate (0.140 g, 0.246 mmol) as described above for Example 2. Obtained tert-butyl 5-(1-(tert-butoxycarbonyl)piperidin-4-yl)-2-(5-chloro-1-ethyl-6-oxo-1,6-dihydropyridin-3-yl)-3-isopropyl-1H-indole-1-carboxylate (120.6 mg, 0.192 mmol, 78% yield) as a yellow foam. LCMS MH⁺: 598.2. HPLC Ret. Time 1.24 min. Method B1. ¹H NMR (400 MHz, CHLOROFORM-d) δ 8.21 (s, 1H), 8.19 (s, 1H), 7.61 (d, J=2.6 Hz, 1H), 7.54 (d, J=1.6 Hz, 1H), 7.48 (d, J=2.3 Hz, 1H), 7.39 (d, J=2.6 Hz, 1H), 7.23 (dd, J=8.7, 1.7 Hz, 1H), 7.18 (d, J=2.3 Hz, 1H), 4.30 (d, J=9.7 Hz, 2H), 4.14 (quin, J=6.9 Hz, 1H), 4.05 (q, J=7.2 Hz, 1H), 2.99 (quin, J=7.2 Hz, 1H), 2.87 (t, J=12.3 Hz, 2H), 2.79 (tt, J=12.1, 3.4 Hz, 1H), 1.91 (d, J=12.3 Hz, 2H), 1.72 (qd, J=12.3, 3.8 Hz, 2H), 1.54-1.51 (m, 9H), 1.45 (s, 9H), 1.43-1.40 (m, 2H), 1.39 (d, J=7.1 Hz, 6H).

Intermediate 68B: tert-butyl 5-(1-(tert-butoxycarbonyl)piperidin-4-yl)-2-(1-ethyl-6-oxo-5-vinyl-1,6-dihydropyridin-3-yl)-3-isopropyl-1H-indole-1-carboxylate

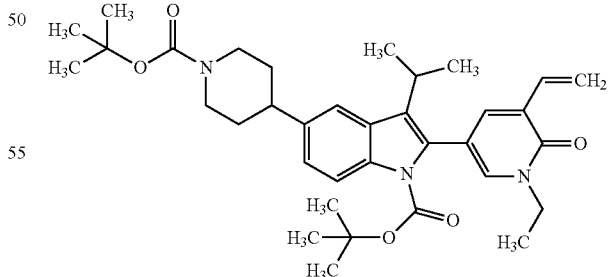

(68B)

tert-Butyl 5-(1-(tert-butoxycarbonyl)piperidin-4-yl)-2-(5-chloro-1-ethyl-6-oxo-1,6-dihydropyridin-3-yl)-3-isopropyl-1H-indole-1-carboxylate (45 mg, 0.075 mmol) was coupled to 4,4,5,5-tetramethyl-2-vinyl-1,3,2-dioxaborolane (31.9 μl, 0.188 mmol) as according to the general procedure for Intermediate 66B. Obtained tert-butyl 5-(1-(tert-butoxycarbonyl) piperidin-4-yl)-2-(1-ethyl-6-oxo-5-vinyl-1,6-dihydropyridin-3-yl)-3-isopropyl-1H-indole-1-carboxylate (43.6 mg, 0.055 mmol, 73.7% yield) as a pale yellow oil. LCMS MH⁺: 590.3. HPLC Ret. Time 1.26 min. Method B1.

Example 68 tert-Butyl 5-(1-(tert-butoxycarbonyl)piperidin-4-yl)-2-(1-ethyl-6-oxo-5-vinyl-1,6-dihydropyridin-3-yl)-3-isopropyl-1H-indole-1-carboxylate (26 mg, 0.044 mmol) was reduced and deprotected according to the general procedure for Example 66. Obtained 1,3-diethyl-5-(3-isopropyl-5-(piperidin-4-yl)-1H-indol-2-yl)pyridin-2(1H)-one (4.0 mg, 9.81 μmol, 22% yield, 96% purity). LCMS MH⁺: 392.1. HPLC Ret. Time 1.34 min. QC-ACN-TFA-XB. ¹H NMR (500 MHz, DMSO-d₆) δ 10.84 (s, 1H), 7.71-7.60 (m, 1H), 7.48 (s, 1H), 7.36 (s, 1H), 7.25 (d, J=8.2 Hz, 1H), 6.95 (d, J=8.4 Hz, 1H), 4.02 (q, J=6.9 Hz, 2H), 3.15 (dd, J=14.4, 7.2 Hz, 2H), 2.70 (br. s., 2H), 1.84 (br. s., 4H), 1.76 (br. s., 2H), 1.68 (br. s., 2H), 1.41 (d, J=7.0 Hz, 6H), 1.28 (t, J=7.1 Hz, 3H), 1.15 (t, J=7.4 Hz, 3H).

Example 69

5-(3-isopropyl-5-(piperidin-4-yl)-1H-indol-2-yl)-1-methyl-3-(pyrrolidine-1-carbonyl) pyridin-2(1H)-one

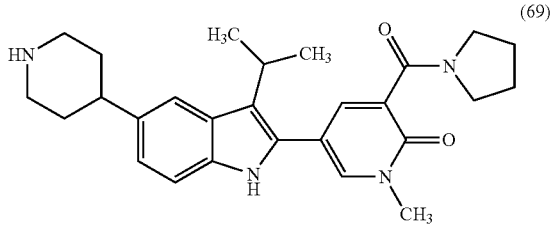 [SMILES: CC(C)c1c(-c2cc(C(=O)N3CCCC3)c(=O)n(C)c2)[nH]c2ccc(C3CCNCC3)cc12]

(69)

Intermediate 69A: Methyl 5-(5-(1-(tert-butoxycarbonyl)piperidin-4-yl)-3-isopropyl-1H-indol-2-yl)-1-methyl-2-oxo-1,2-dihydropyridine-3-carboxylate

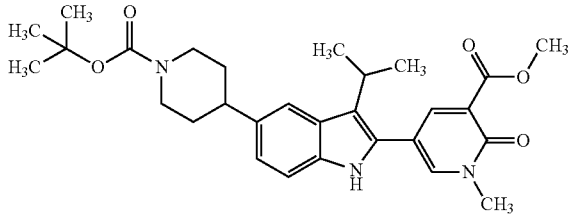

(69A)

Methyl 5-bromo-1-methyl-2-oxo-1,2-dihydropyridine-3-carboxylate (111 mg, 0.451 mmol) and tert-butyl 4-(3-isopropyl-2-(4,4,5,5-tetramethyl-1,3,2-dioxaborolan-2-yl)-1H-indol-5-yl)piperidine-1-carboxylate (176 mg, 0.376 mmol) were coupled according to the general procedure for Example 1. Obtained methyl 5-(5-(1-(tert-butoxycarbonyl)piperidin-4-yl)-3-isopropyl-1H-indol-2-yl)-1-methyl-2-oxo-1,2-dihydropyridine-3-carboxylate (141.1 mg, 0.250 mmol, 66.6% yield) as an orange solid. LCMS MH⁺: 508.3. HPLC Ret. Time 1.04 min. Method B1. ¹H NMR (400 MHz, CHLOROFORM-d) δ 8.38 (s, 1H), 8.24 (d, J=2.7 Hz, 1H), 7.63 (d, J=2.7 Hz, 1H), 7.59 (s, 1H), 7.36 (d, J=8.4 Hz, 1H), 7.09 (dd, J=8.4, 1.6 Hz, 1H), 4.38-4.22 (m, 2H), 3.88 (s, 3H), 3.67 (s, 3H), 3.14 (spt, J=7.0 Hz, 1H), 2.87 (t, J=12.3 Hz, 2H), 2.77 (tt, J=12.1, 3.4 Hz, 1H), 1.96-1.87 (m, 2H), 1.73 (qd, J=12.6, 3.8 Hz, 2H), 1.52 (s, 9H), 1.47 (d, J=7.1 Hz, 6H).

Intermediate 69B: 5-(5-(1-(tert-butoxycarbonyl)piperidin-4-yl)-3-isopropyl-1H-indol-2-yl)-1-methyl-2-oxo-1,2-dihydropyridine-3-carboxylic acid

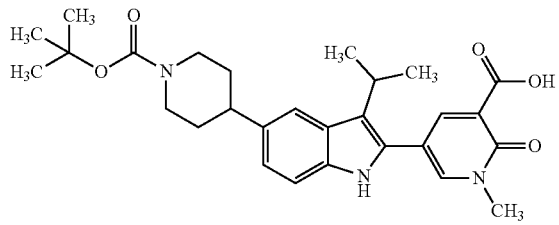

(69B)

Methyl 5-(5-(1-(tert-butoxycarbonyl)piperidin-4-yl)-3-isopropyl-1H-indol-2-yl)-1-methyl-2-oxo-1,2-dihydropyridine-3-carboxylate (50 mg, 0.098 mmol) was suspended in MeOH (1 mL) in a 1-dram vial. Sodium hydroxide (0.197 mL, 0.197 mmol) was added to the vial, and the vial was capped. The reaction mixture was stirred at 65° C. for 1.5 h. Water (0.5 mL), 1N aqueous HCl (210 μL), ethyl acetate (1.5 mL) and brine solution (0.5 mL) were added to the reaction mixture, resulting in dissolution of the solid and formation of 2 layers (a colorless aqueous layer and a yellow organic layer). The phases were separated, and the aqueous layer was extracted with ethyl acetate (2×2 mL). The combined organic extracts were dried over sodium sulfate, then filtered, and excess solvent was evaporated off to afford 5-(5-(1-(tert-butoxycarbonyl)piperidin-4-yl)-3-isopropyl-1H-indol-2-yl)-1-methyl-2-oxo-1,2-dihydropyridine-3-carboxylic acid (50.3 mg, 0.097 mmol, 98% yield) as a yellow solid. LCMS MH⁺: 494.4. HPLC Ret. Time 1.06 min. Method B1.

Example 69

PyBOP (19.45 mg, 0.037 mmol), DIEA (10.88 μl, 0.062 mmol), and 5-(5-(1-(tert-butoxycarbonyl)piperidin-4-yl)-3-isopropyl-1H-indol-2-yl)-1-methyl-2-oxo-1,2-dihydropyridine-3-carboxylic acid (12.3 mg, 0.025 mmol) were combined in DMF (500 μL) in a 1-dram vial and stirred for 10 min. Pyrrolidine (5.20 μl, 0.062 mmol) was then added to the reaction mixture. The reaction mixture was stirred at room temperature for 2 h. The reaction mixture was partitioned between water and ethyl acetate (3 mL total volume), separated, and the aqueous phase was extracted with additional ethyl acetate (2×1 mL). Excess solvent was evaporated from the combined organic extracts. The resulting residue was deprotected with 2:1 trifluoroacetic acid/dichloromethane (1.2 mL, 0.025 mmol) for 45 min. Excess solvent was evaporated from the reaction mixture. The crude material was dissolved in DMF (1.5 mL) and purified via preparative LC/MS with the following conditions: Column: XBridge C18, 19×200 mm, 5-im particles; Mobile Phase A:

5:95 acetonitrile:water with 10-mM ammonium acetate; Mobile Phase B: 95:5 acetonitrile:water with 10-mM ammonium acetate; Gradient: 5-45% B over 20 minutes, then a 5-minute hold at 100% B; Flow: 20 mL/min. Fractions containing the product were combined and dried via centrifugal evaporation. The material was further purified via preparative LC/MS with the following conditions: Column: XBridge C18, 19×200 mm, 5-im particles; Mobile Phase A: 5:95 acetonitrile:water with 0.1% trifluoroacetic acid; Mobile Phase B: 95:5 acetonitrile:water with 0.1% trifluoroacetic acid; Gradient: 7-47% B over 25 minutes, then a 5-minute hold at 100% B; Flow: 20 mL/min. Fractions containing the product were combined and dried via centrifugal evaporation to afford 5-(3-isopropyl-5-(piperidin-4-yl)-1H-indol-2-yl)-1-methyl-3-(pyrrolidine-1-carbonyl)pyridin-2(1H)-one (7.5 mg, 66% yield, 99% purity). LCMS MH$^+$: 447.2. HPLC Ret. Time 1.13 min. Method QC-ACN-TFA-XB. $^1$H NMR (500 MHz, DMSO-d$_6$) δ 10.76 (s, 1H), 7.71 (s, 1H), 7.37 (d, J=2.0 Hz, 1H), 7.31 (s, 1H), 7.09 (d, J=4.5 Hz, 1H), 6.77 (d, J=8.2 Hz, 1H), 3.39 (br. s., 3H), 3.26-3.15 (m, 3H), 3.14-3.09 (m, 2H), 3.01-2.91 (m, 1H), 2.88-2.78 (m, 2H), 2.70 (s, 2H), 1.82-1.73 (m, 2H), 1.69-1.57 (m, 7H), 1.20 (d, J=7.0 Hz, 6H).

Example 70

3-(hydroxymethyl)-5-(3-isopropyl-5-(piperidin-4-yl)-1H-indol-2-yl)-1-methylpyridin-2(1H)-one

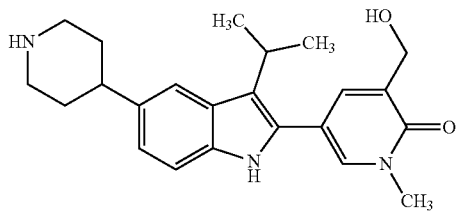

(70)

Intermediate 70A:
5-bromo-3-(hydroxymethyl)pyridin-2(1H)-one

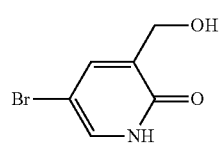

(70A)

Methyl 5-bromo-2-oxo-1,2-dihydropyridine-3-carboxylate (Combi-Blocks, CAS: 120034-05-1, 0.100 g, 0.431 mmol) was dissolved in THF (4.31 mL) and added dropwise to a 0° C. solution of lithium aluminum hydride (0.082 g, 2.155 mmol) in THF (4.31 mL). The reaction mixture was stirred at 0° C. for 30 min, then allowed to warm to room temperature and stirred for 2.5 h. Saturated aqueous NH$_4$Cl solution (8 mL) was slowly added to the reaction mixture, followed by ethyl acetate (8 mL). The phases were separated, the aqueous phase was extracted with additional ethyl acetate (2×10 mL). The combined organic phases were dried over sodium sulfate and filtered, and excess solvent was evaporated off to afford 5-bromo-3-(hydroxymethyl)pyridin-2(1H)-one (34.1 mg, 0.159 mmol, 36.8% yield) as a white solid. LCMS MH$^+$: 203.9. HPLC Ret. Time 0.47 min. Method B1. $^1$H NMR (400 MHz, METHANOL-d$_4$) δ 7.67 (dt, J=2.7, 1.4 Hz, 1H), 7.51 (d, J=2.7 Hz, 1H), 4.49 (s, 2H).

Intermediate 70B: 5-bromo-3-(hydroxymethyl)-1-methylpyridin-2(1H)-one

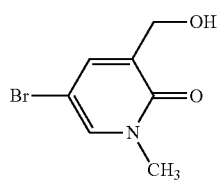

(F-50)

5-bromo-3-(hydroxymethyl)pyridin-2(1H)-one (34.1 mg, 0.167 mmol) was stirred with iodomethane (30.5 µl, 0.201 mmol) and potassium carbonate (115 mg, 0.836 mmol) in DMF (557 µl) in a 2-dram vial containing a Teflon-coated stir bar at room temperature for 1 h. Additional DMF (1.0 mL) was added to the reaction mixture. The reaction mixture was stirred at room temperature for 19 h. The reaction mixture was partitioned between water and ethyl acetate (~4 mL total volume), and the aqueous phase was extracted with ethyl acetate (3×2.5 mL). The combined organic phases were extracted with brine (2×2 mL), then dried over sodium sulfate and filtered. Excess solvent was evaporated from the filtered organic phase to afford 5-bromo-3-(hydroxymethyl)-1-methylpyridin-2(1H)-one (17.7 mg, 0.073 mmol, 43.7% yield) as a clear, pale yellow oil. LCMS MH$^+$: 217.9. HPLC Ret. Time 0.51 min. Method B1. $^1$H NMR (400 MHz, CHLOROFORM-d) δ 7.42 (s, 2H), 4.57 (d, J=6.2 Hz, 2H), 3.56 (s, 3H), 3.41 (t, J=6.4 Hz, 1H).

Example 70

5-bromo-3-(hydroxymethyl)-1-methylpyridin-2(1H)-one was coupled to tert-butyl 4-(3-isopropyl-2-(4,4,5,5-tetramethyl-1,3,2-dioxaborolan-2-yl)-1H-indol-5-yl)piperidine-1-carboxylate and deprotected according to the general procedure for Example 1 to afford 3-(hydroxymethyl)-5-(3-isopropyl-5-(piperidin-4-yl)-1H-indol-2-yl)-1-methylpyridin-2(1H)-one (21.9 mg, 70% yield, 98% purity). LCMS MH$^+$: 380.4. HPLC Ret. Time 0.82 min. Method QC-ACN-TFA-XB. $^1$H NMR (500 MHz, DMSO-d$_6$) δ 10.71 (s, 1H), 7.51 (s, 1H), 7.40 (br. s., 1H), 7.31 (s, 1H), 7.09 (d, J=8.2 Hz, 1H), 6.78 (d, J=8.2 Hz, 1H), 4.21 (s, 2H), 3.55 (br. s., 4H), 3.36 (s, 2H), 3.11 (d, J=10.3 Hz, 1H), 2.99 (quin, J=6.9 Hz, 1H), 2.72 (d, J=11.2 Hz, 2H), 2.64 (br. s., 1H), 1.75-1.68 (m, 2H), 1.67-1.56 (m, 2H), 1.20 (d, J=6.9 Hz, 6H).

Example 71

2-(4-(2-(1,5-dimethyl-6-oxo-1,6-dihydropyridin-3-yl)-3-isopropyl-1H-indol-5-yl) piperidin-1-yl)-N,N-dimethylacetamide (71)

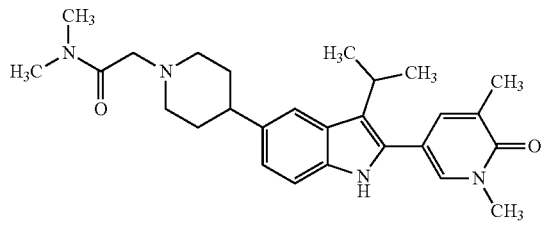

Method A: A mixture containing 5-(3-isopropyl-5-(piperidin-4-yl)-1H-indol-2-yl)-1,3-dimethylpyridin-2(1H)-one (75 mg, 0.206 mmol), 2-chloro-N,N-dimethylacetamide (0.027 mL, 0.258 mmol) and K₂CO₃ (86 mg, 0.619 mmol) was suspended in DMF (0.5 mL). The reaction mixture was stirred at room temperature for 4 h. The reaction mixture was treated with water (4 mL) and stirred for 30 min. The resulting solids were filtered and rinsed with water and diethylether, and dried to afford 2-(4-(2-(1,5-dimethyl-6-oxo-1,6-dihydropyridin-3-yl)-3-isopropyl-1H-indol-5-yl)piperidin-1-yl)-N,N-dimethylacetamide (70 mg, 0.148 mmol, 71.8% yield), as a white solid. m/e (449, M$^{+1}$). LCMS MH$^+$: 449.5. HPLC Ret. Time 0.64 min. Method B1. $^1$H NMR (400 MHz, DMSO-d$_6$) δ 10.77 (s, 1H), 7.65 (d, J=2.2 Hz, 1H), 7.48 (s, 1H), 7.45-7.40 (m, 1H), 7.22 (d, J=8.3 Hz, 1H), 6.96 (dd, J=8.4, 1.4 Hz, 1H), 3.54 (s, 3H), 3.21-3.11 (m, 3H), 3.08 (s, 3H), 2.95 (d, J=11.1 Hz, 2H), 2.83 (s, 3H), 2.23-2.12 (m, 2H), 2.09 (s, 3H), 1.84-1.63 (m, 4H), 1.40 (d, J=7.0 Hz, 6H).

The following examples were prepared according to the general procedure for Example 71 using the indicated starting material.

TABLE 4

| Ex. No. | Structure | Starting material | LCMS MH$^+$ | Ret Time (min) | HPLC Method |
|---|---|---|---|---|---|
| 72 | 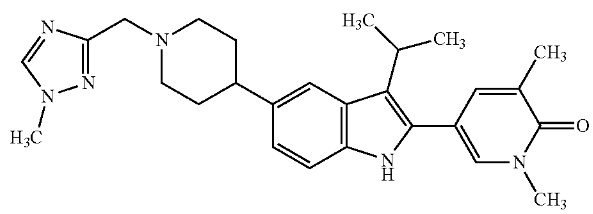 [SMILES: Cc1cc(-c2[nH]c3ccc(C4CCN(Cc5ncn(C)n5)CC4)cc3c2C(C)C)cn(C)c1=O] | Ex-2 | 459.4 | 0.63 | Method B1 |
| 73 | 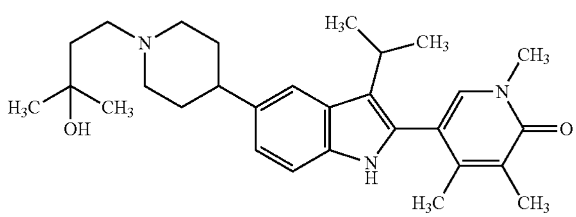 [SMILES: Cc1c(-c2[nH]c3ccc(C4CCN(CCC(C)(C)O)CC4)cc3c2C(C)C)cn(C)c(=O)c1C] | Ex-14 | 464 | 1.33 | QC-ACN-AA-XB |
| 74 | 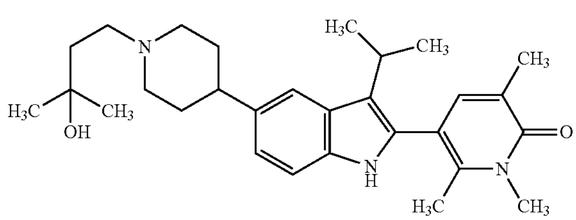 [SMILES: Cc1cc(-c2[nH]c3ccc(C4CCN(CCC(C)(C)O)CC4)cc3c2C(C)C)c(C)n(C)c1=O] | Ex-3 | 464 | 1.27 | QC-ACN-AA-XB |
| 75 | 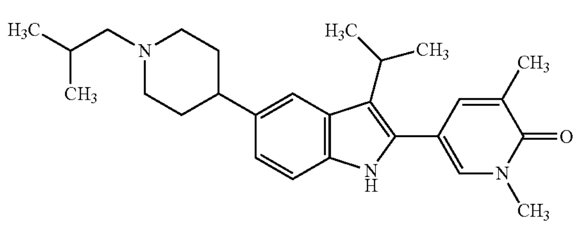 [SMILES: Cc1cc(-c2[nH]c3ccc(C4CCN(CC(C)C)CC4)cc3c2C(C)C)cn(C)c1=O] | Ex-2 | 420 | 1.33 | QC-ACN-TFA-XB |

TABLE 4-continued

| Ex. No. | Structure | Starting material | LCMS MH+ | Ret Time (min) | HPLC Method |
|---|---|---|---|---|---|
| 76 | 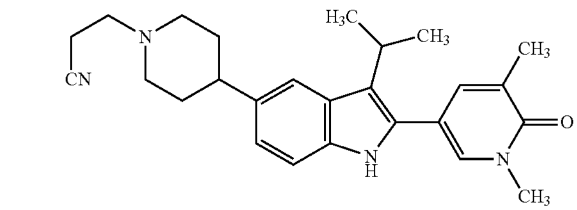 [SMILES: Cc1cc(-c2[nH]c3ccc(C4CCN(CCC#N)CC4)cc3c2C(C)C)cn(C)c1=O] | Ex-2 | 417 | 1.67 | QC-ACN-AA-XB |
| 77 | 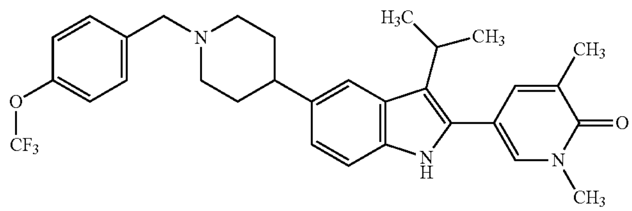 [SMILES: Cc1cc(-c2[nH]c3ccc(C4CCN(Cc5ccc(OC(F)(F)F)cc5)CC4)cc3c2C(C)C)cn(C)c1=O] | Ex-2 | 538 | 2.35 | QC-ACN-AA-XB |
| 78 | 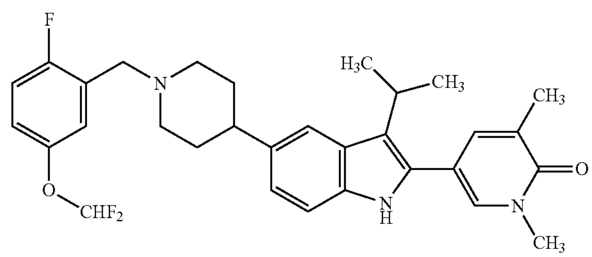 [SMILES: Cc1cc(-c2[nH]c3ccc(C4CCN(Cc5cc(OC(F)F)ccc5F)CC4)cc3c2C(C)C)cn(C)c1=O] | Ex-2 | 538 | 2.28 | QC-ACN-AA-XB |
| 79 | 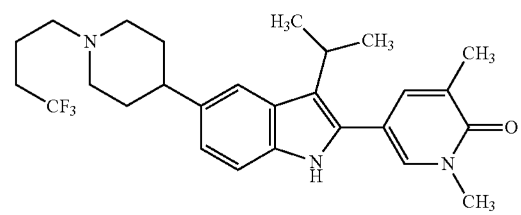 [SMILES: Cc1cc(-c2[nH]c3ccc(C4CCN(CCCC(F)(F)F)CC4)cc3c2C(C)C)cn(C)c1=O] | Ex-2 | 474 | 1.69 | QC-ACN-AA-XB |
| 80 | 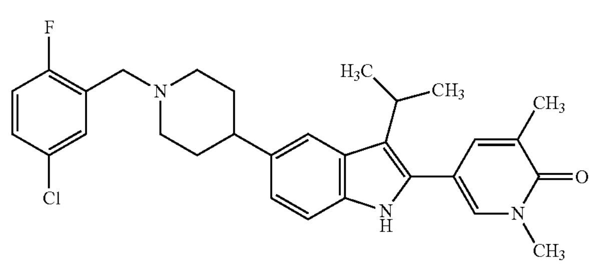 [SMILES: Cc1cc(-c2[nH]c3ccc(C4CCN(Cc5cc(Cl)ccc5F)CC4)cc3c2C(C)C)cn(C)c1=O] | Ex-2 | 506 | 2.49 | QC-ACN-AA-XB |
| 81 | 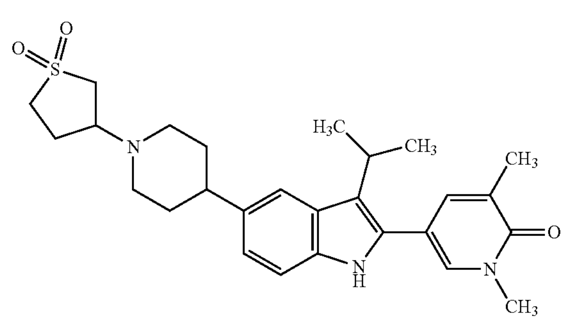 [SMILES: Cc1cc(-c2[nH]c3ccc(C4CCN(C5CCS(=O)(=O)C5)CC4)cc3c2C(C)C)cn(C)c1=O] | Ex-2 | 482 | 1.51 | QC-ACN-AA-XB |

TABLE 4-continued

| Ex. No. | Structure | Starting material | LCMS MH+ | Ret Time (min) | HPLC Method |
|---|---|---|---|---|---|
| 82 | 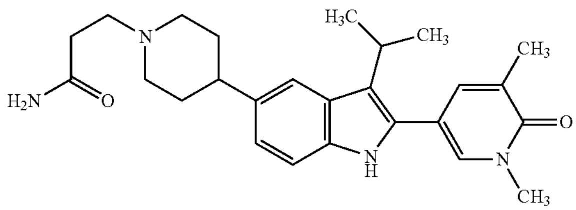 [SMILES: Cc1cc(-c2[nH]c3ccc(C4CCN(CCC(N)=O)CC4)cc3c2C(C)C)cn(C)c1=O] | Ex-2 | 435 | 1.05 | QC-ACN-AA-XB |
| 83 | 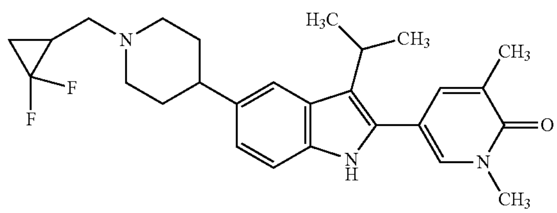 [SMILES: Cc1cc(-c2[nH]c3ccc(C4CCN(CC5CC5(F)F)CC4)cc3c2C(C)C)cn(C)c1=O] | Ex-2 | 454 | 1.31 | QC-ACN-TFA-XB |
| 84 | 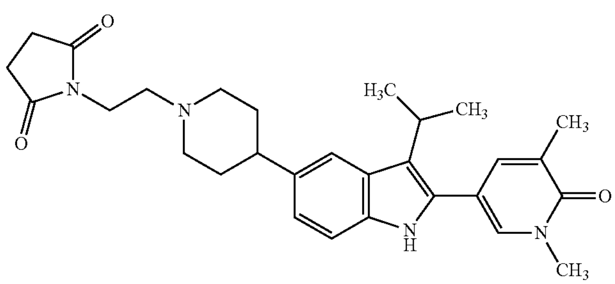 [SMILES: Cc1cc(-c2[nH]c3ccc(C4CCN(CCN5C(=O)CCC5=O)CC4)cc3c2C(C)C)cn(C)c1=O] | Ex-2 | 489 | 1.14 | QC-ACN-TFA-XB |
| 85 | 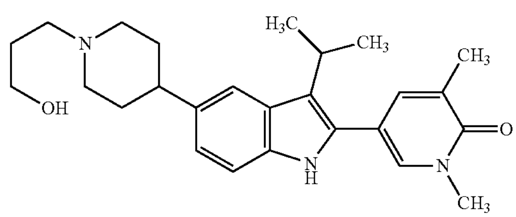 | Ex-2 | 422 | 1.09 | QC-ACN-AA-XB |
| 86 | 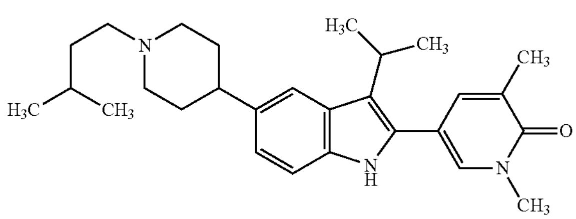 [SMILES: Cc1cc(-c2[nH]c3ccc(C4CCN(CCC(C)C)CC4)cc3c2C(C)C)cn(C)c1=O] | Ex-2 | 434 | 1.6 | QC-ACN-TFA-XB |
| 87 | 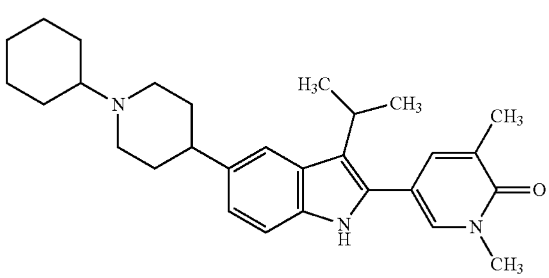 [SMILES: Cc1cc(-c2[nH]c3ccc(C4CCN(C5CCCCC5)CC4)cc3c2C(C)C)cn(C)c1=O] | Ex-2 | 446 | 1.47 | QC-ACN-TFA-XB |

TABLE 4-continued

| Ex. No. | Structure | Starting material | LCMS MH+ | Ret Time (min) | HPLC Method |
|---|---|---|---|---|---|
| 88 | 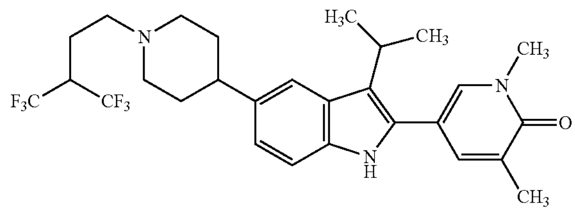 [SMILES: Cc1cc(-c2[nH]c3ccc(C4CCN(CCC(C(F)(F)F)C(F)(F)F)CC4)cc3c2C(C)C)cn(C)c1=O] | Ex-2 | 542 | 2.47 | QC-ACN-AA-XB |
| 89 | 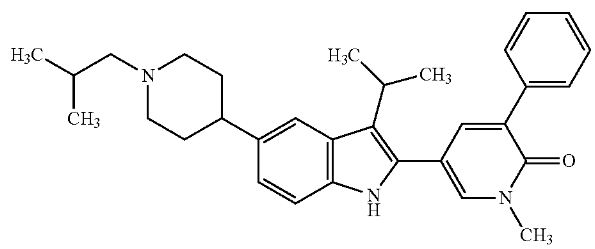 [SMILES: CC(C)CN1CCC(c2ccc3[nH]c(-c4cc(-c5ccccc5)c(=O)n(C)c4)c(C(C)C)c3c2)CC1] | Ex-50 | 483 | 1.06 | QC-ACN-TFA-XB |
| 90 | 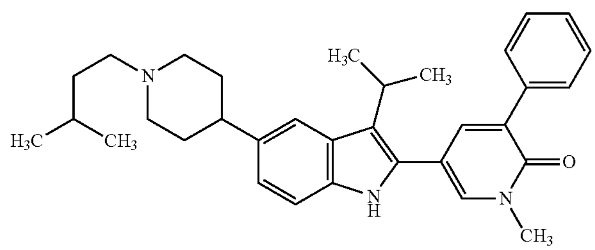 [SMILES: CC(C)CCN1CCC(c2ccc3[nH]c(-c4cc(-c5ccccc5)c(=O)n(C)c4)c(C(C)C)c3c2)CC1] | Ex-50 | 497 | 1.27 | QC-ACN-TFA-XB |
| 91 | 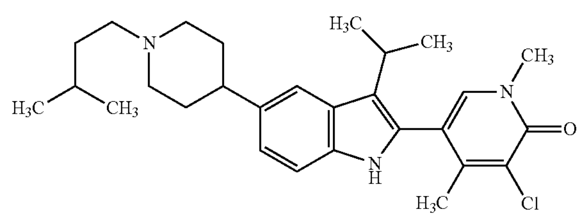 [SMILES: Cc1c(-c2[nH]c3ccc(C4CCN(CCC(C)C)CC4)cc3c2C(C)C)cn(C)c(=O)c1Cl] | Ex-31 | 468 | 1.63 | QC-ACN-AA-XB |
| 92 | 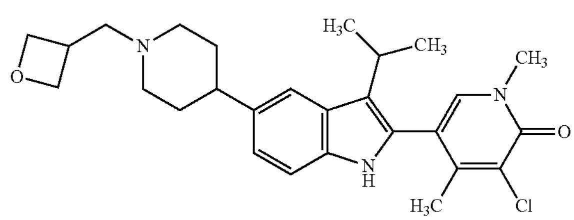 [SMILES: Cc1c(-c2[nH]c3ccc(C4CCN(CC5COC5)CC4)cc3c2C(C)C)cn(C)c(=O)c1Cl] | Ex-31 | 468 | 1.32 | QC-ACN-AA-XB |
| 93 | 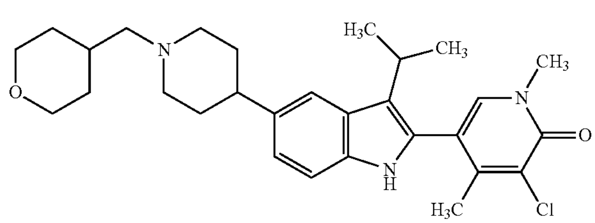 [SMILES: Cc1c(-c2[nH]c3ccc(C4CCN(CC5CCOCC5)CC4)cc3c2C(C)C)cn(C)c(=O)c1Cl] | Ex-31 | 496 | 1.32 | QC-ACN-TFA-XB |

TABLE 4-continued
| Ex. No. | Structure | Starting material | LCMS MH+ | Ret Time (min) | HPLC Method |
|---|---|---|---|---|---|
| 94 | 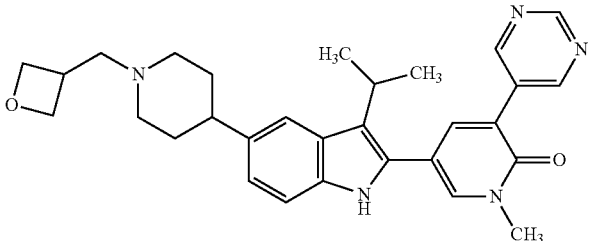 | Ex-54 | 498 | 1.32 | QC-ACN-AA-XB |
| 95 | 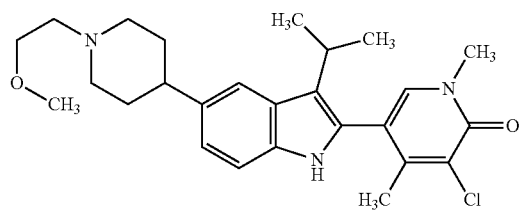 [SMILES: COCCN1CCC(c2ccc3[nH]c(-c4cn(C)c(=O)c(Cl)c4C)c(C(C)C)c3c2)CC1] | Ex-31 | 456 | 1.42 | QC-ACN-AA-XB |
| 96 | 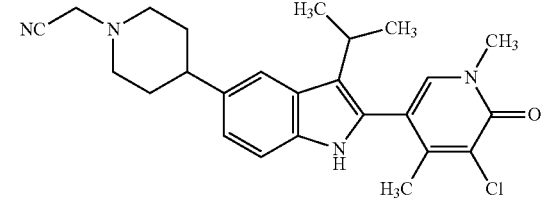 [SMILES: Cc1c(-c2[nH]c3ccc(C4CCN(CC#N)CC4)cc3c2C(C)C)cn(C)c(=O)c1Cl] | Ex-31 | 437 | 1.89 | QC-ACN-AA-XB |
| 97 | 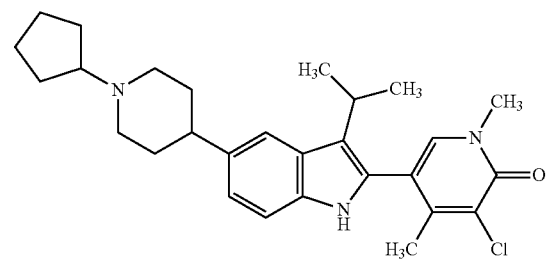 [SMILES: Cc1c(-c2[nH]c3ccc(C4CCN(C5CCCC5)CC4)cc3c2C(C)C)cn(C)c(=O)c1Cl] | Ex-31 | 466 | 1.48 | QC-ACN-AA-XB |
| 98 | 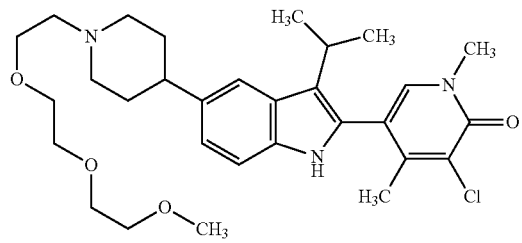 [SMILES: COCCOCCOCCN1CCC(c2ccc3[nH]c(-c4cn(C)c(=O)c(Cl)c4C)c(C(C)C)c3c2)CC1] | Ex-31 | 544 | 1.5 | QC-ACN-AA-XB |
| 99 | 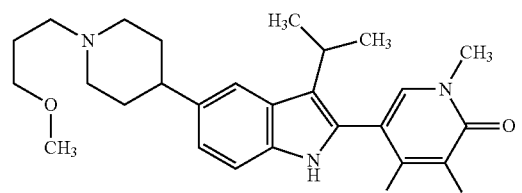 | Ex-31 | 470 | 1.32 | QC-ACN-AA-XB |

TABLE 4-continued

| Ex. No. | Structure | Starting material | LCMS MH+ | Ret Time (min) | HPLC Method |
|---|---|---|---|---|---|
| 100 | 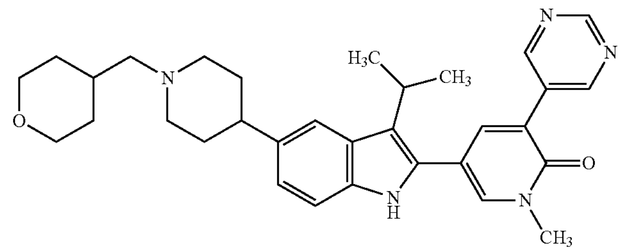 [SMILES: CC(C)c1c(-c2cc(-c3cncnc3)c(=O)n(C)c2)[nH]c2ccc(C3CCN(CC4CCOCC4)CC3)cc12] | Ex-54 | 526 | 1.16 | QC-ACN-TFA-XB |
| 101 | 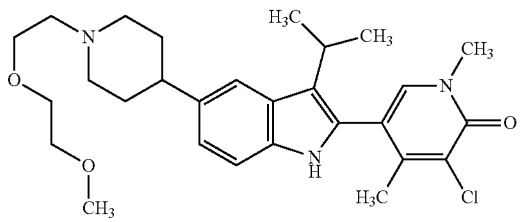 [SMILES: COCCOCCN1CCC(c2ccc3[nH]c(-c4cn(C)c(=O)c(Cl)c4C)c(C(C)C)c3c2)CC1] | Ex-31 | 500 | 1.46 | QC-ACN-AA-XB |
| 102 | 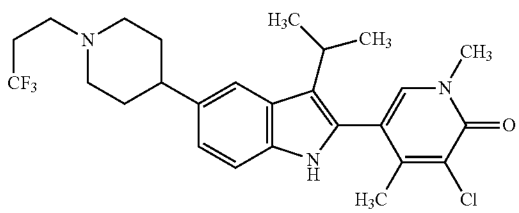 [SMILES: Cc1c(-c2[nH]c3ccc(C4CCN(CCC(F)(F)F)CC4)cc3c2C(C)C)cn(C)c(=O)c1Cl] | Ex-31 | 494 | 2.04 | QC-ACN-AA-XB |
| 103 | 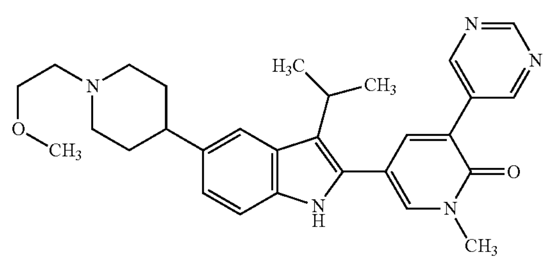 [SMILES: COCCN1CCC(c2ccc3[nH]c(-c4cc(-c5cncnc5)c(=O)n(C)c4)c(C(C)C)c3c2)CC1] | Ex-54 | 486 | 1.23 | QC-ACN-TFA-XB |
| 104 | 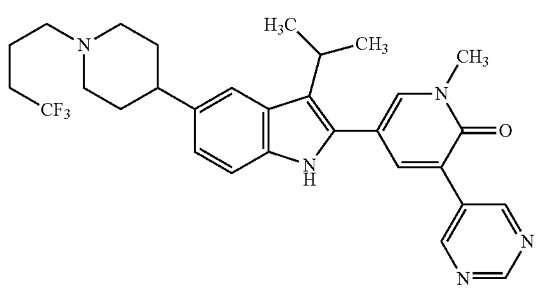 [SMILES: CC(C)c1c(-c2cc(-c3cncnc3)c(=O)n(C)c2)[nH]c2ccc(C3CCN(CCCC(F)(F)F)CC3)cc12] | Ex-54 | 538 | 1.46 | QC-ACN-AA-XB |
| 105 | 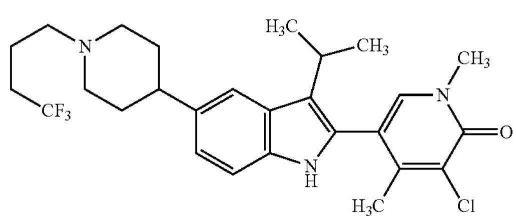 [SMILES: Cc1c(-c2[nH]c3ccc(C4CCN(CCCC(F)(F)F)CC4)cc3c2C(C)C)cn(C)c(=O)c1Cl] | 508.02 | 508 | 1.97 | QC-ACN-AA-XB |

TABLE 4-continued

| Ex. No. | Structure | Starting material | LCMS MH+ | Ret Time (min) | HPLC Method |
|---|---|---|---|---|---|
| 106 | 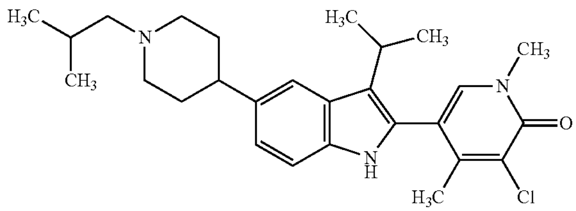 [SMILES: Cc1c(-c2[nH]c3ccc(C4CCN(CC(C)C)CC4)cc3c2C(C)C)cn(C)c(=O)c1Cl] | Ex-31 | 454 | 1.59 | QC-ACN-AA-XB |
| 107 | 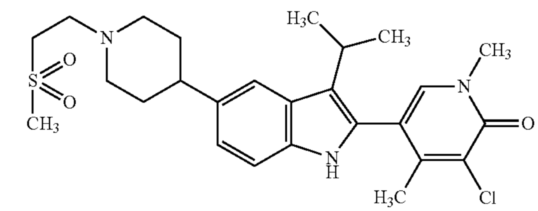 [SMILES: Cc1c(-c2[nH]c3ccc(C4CCN(CCS(C)(=O)=O)CC4)cc3c2C(C)C)cn(C)c(=O)c1Cl] | Ex-31 | 504 | 1.55 | QC-ACN-AA-XB |
| 108 | 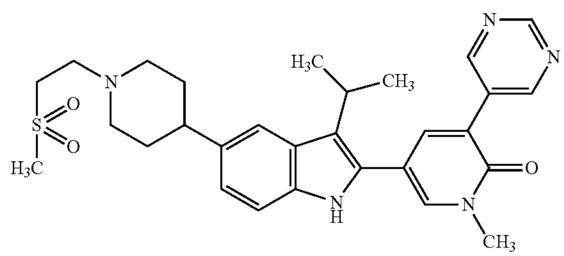 [SMILES: CC(C)c1c(-c2cc(-c3cncnc3)c(=O)n(C)c2)[nH]c2ccc(C3CCN(CCS(C)(=O)=O)CC3)cc12] | Ex-54 | 535 | 1.0 | QC-ACN-TFA-XB |
| 109 | 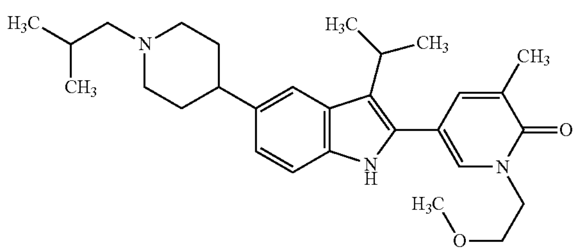 [SMILES: COCCn1cc(-c2[nH]c3ccc(C4CCN(CC(C)C)CC4)cc3c2C(C)C)cc(C)c1=O] | Ex-39 | 464 | 1.65 | QC-ACN-AA-XB |
| 110 | 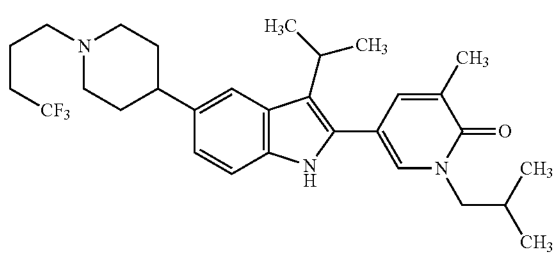 [SMILES: Cc1cc(-c2[nH]c3ccc(C4CCN(CCCC(F)(F)F)CC4)cc3c2C(C)C)cn(CC(C)C)c1=O] | Ex-36 | 516 | 1.99 | QC-ACN-AA-XB |
| 111 | 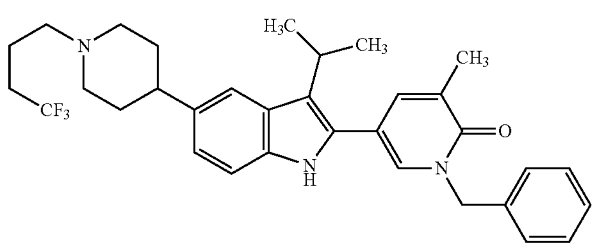 [SMILES: Cc1cc(-c2[nH]c3ccc(C4CCN(CCCC(F)(F)F)CC4)cc3c2C(C)C)cn(Cc2ccccc2)c1=O] | Ex-46 | 550 | 2.02 | QC-ACN-AA-XB |

TABLE 4-continued

| Ex. No. | Structure | Starting material | LCMS MH+ | Ret Time (min) | HPLC Method |
|---|---|---|---|---|---|
| 112 | 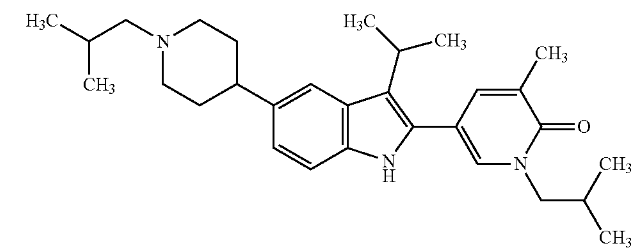 [SMILES: Cc1cc(-c2[nH]c3ccc(C4CCN(CC(C)C)CC4)cc3c2C(C)C)cn(CC(C)C)c1=O] | Ex-36 | 462 | 1.77 | QC-ACN-AA-XB |
| 113 | 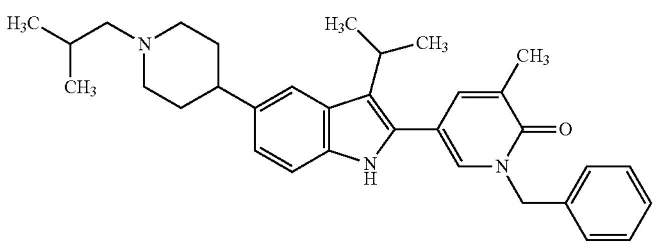 [SMILES: Cc1cc(-c2[nH]c3ccc(C4CCN(CC(C)C)CC4)cc3c2C(C)C)cn(Cc2ccccc2)c1=O] | Ex-46 | 496.2 | 1.82 | QC-ACN-AA-XB |
| 114 | 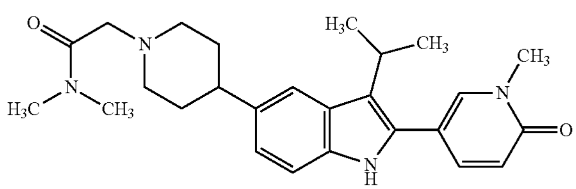 [SMILES: CC(C)c1c(-c2ccc(=O)n(C)c2)[nH]c2ccc(C3CCN(CC(=O)N(C)C)CC3)cc12] | Ex-1 | 435.1 | 1.13 | QC-ACN-AA-XB |
| 115 | 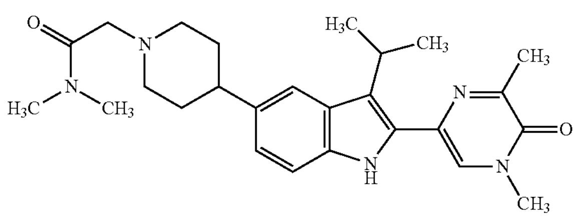 | Ex-12 | 450.2 | 1.26 | QC-ACN-AA-XB |
| 116 | 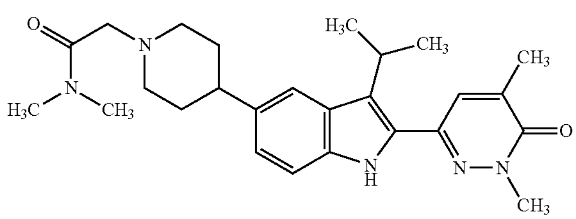 [SMILES: Cc1nc(-c2[nH]c3ccc(C4CCN(CC(=O)N(C)C)CC4)cc3c2C(C)C)cn(C)c1=O] | Ex-11 | 450 | 1.21 | QC-ACN-AA-XB |
| 117 | 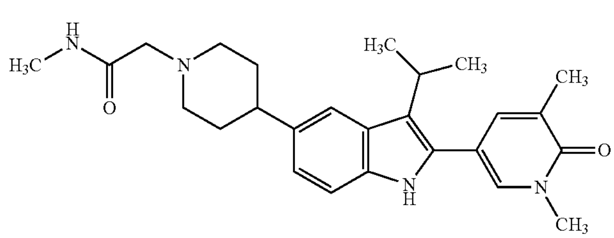 [SMILES: CNC(=O)CN1CCC(c2ccc3[nH]c(-c4cc(C)c(=O)n(C)n4)c(C(C)C)c3c2)CC1] | Ex-2 | 435.3 | 0.63 | Method B1 |

TABLE 4-continued

| Ex. No. | Structure | Starting material | LCMS MH+ | Ret Time (min) | HPLC Method |
|---|---|---|---|---|---|
| 118 | 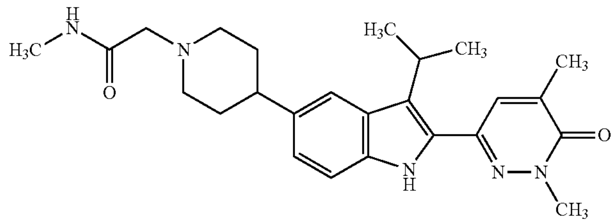 | Ex-11 | 436.3 | 0.65 | Method B1 |
| 119 | 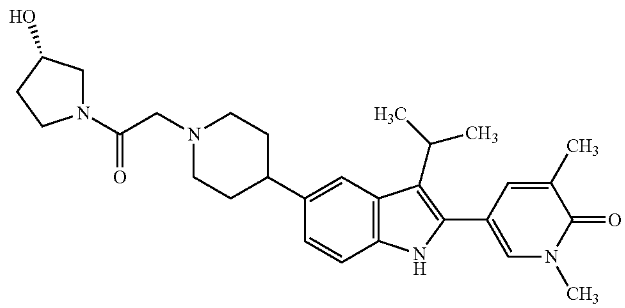 [SMILES: Cc1cc(-c2[nH]c3ccc(C4CCN(CC(=O)N5CC[C@H](O)C5)CC4)cc3c2C(C)C)cn(C)c1=O] | Ex-2 | 491.4 | 1.07 | QC-ACN-TFA-XB |
| 120 | 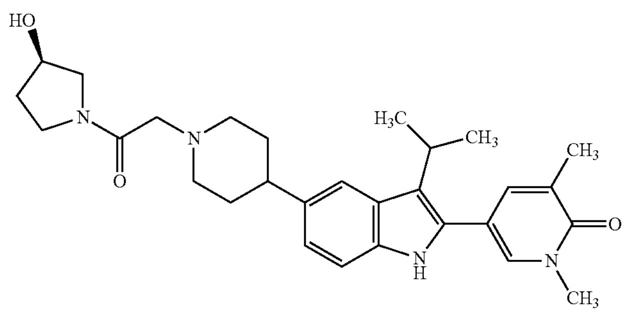 [SMILES: Cc1cc(-c2[nH]c3ccc(C4CCN(CC(=O)N5CC[C@@H](O)C5)CC4)cc3c2C(C)C)cn(C)c1=O] | Ex-2 | 491.4 | 0.62 | Method B1 |
| 121 | 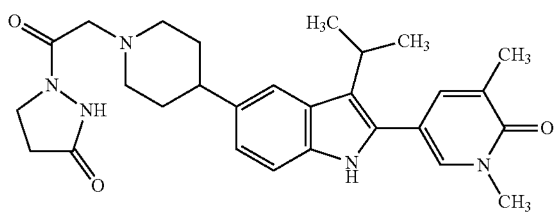 [SMILES: Cc1cc(-c2[nH]c3ccc(C4CCN(CC(=O)N5CCC(=O)N5)CC4)cc3c2C(C)C)cn(C)c1=O] | Ex-2 | 490 | 1.15 | QC-ACN-AA-XB |
| 122 | 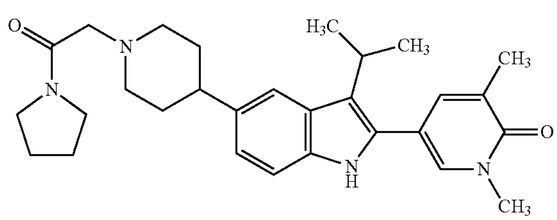 [SMILES: Cc1cc(-c2[nH]c3ccc(C4CCN(CC(=O)N5CCCC5)CC4)cc3c2C(C)C)cn(C)c1=O] | Ex-2 | 475.3 | 1.18 | QC-ACN-TFA-XB |
| 123 | 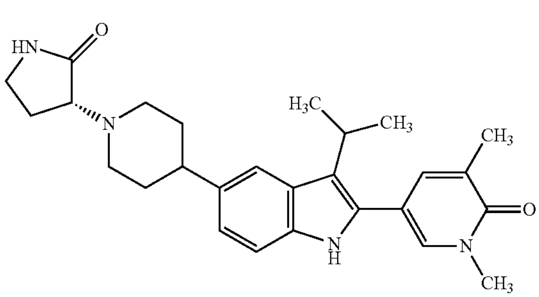 [SMILES: Cc1cc(-c2[nH]c3ccc(C4CCN([C@@H]5CCNC5=O)CC4)cc3c2C(C)C)cn(C)c1=O] | Ex-2 | 447.3 | 0.62 | Method B1 |

TABLE 4-continued

| Ex. No. | Structure | Starting material | LCMS MH+ | Ret Time (min) | HPLC Method |
|---|---|---|---|---|---|
| 124 | 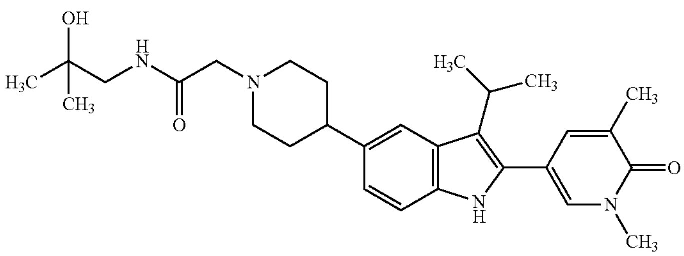 [SMILES: Cc1cc(-c2[nH]c3ccc(C4CCN(CC(=O)NCC(C)(C)O)CC4)cc3c2C(C)C)cn(C)c1=O] | Ex-2 | 493 | 1.05 | QC-ACN-TFA-XB |
| 125 | 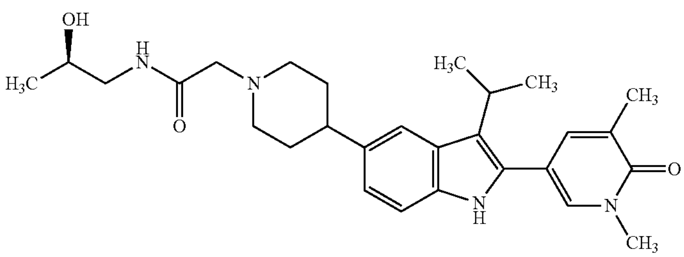 [SMILES: Cc1cc(-c2[nH]c3ccc(C4CCN(CC(=O)NC[C@@H](C)O)CC4)cc3c2C(C)C)cn(C)c1=O] | Ex-2 | 479.3 | 1.06 | QC-ACN-TFA-XB |
| 126 | 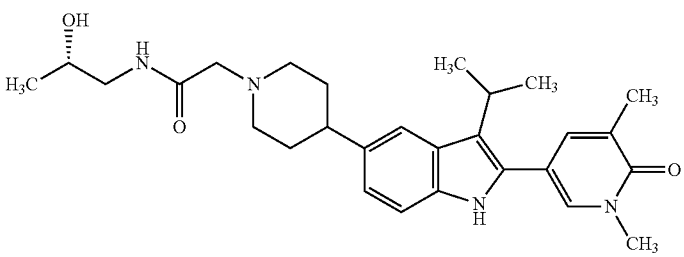 [SMILES: Cc1cc(-c2[nH]c3ccc(C4CCN(CC(=O)NC[C@H](C)O)CC4)cc3c2C(C)C)cn(C)c1=O] | Ex-2 | 479 | 1 | QC-ACN-TFA-XB |
| 127 | 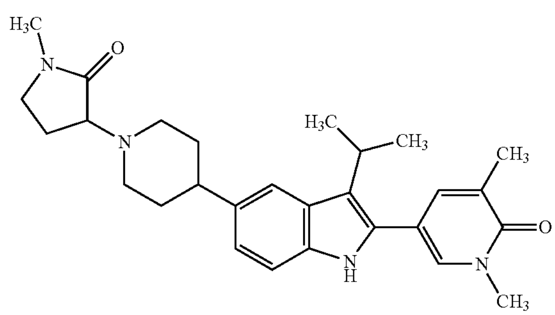 [SMILES: Cc1cc(-c2[nH]c3ccc(C4CCN(C5CCN(C)C5=O)CC4)cc3c2C(C)C)cn(C)c1=O] | Ex-2 | 461.2 | 1.11 | QC-ACN-TFA-XB |
| 128 | 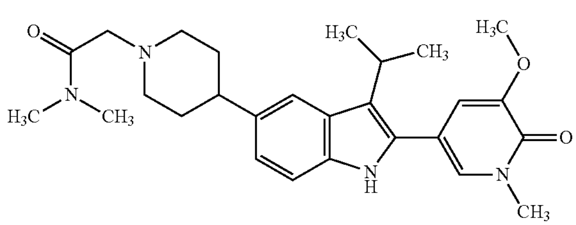 [SMILES: COc1cc(-c2[nH]c3ccc(C4CCN(CC(=O)N(C)C)CC4)cc3c2C(C)C)cn(C)c1=O] | Ex-20 | 465.3 | 0.61 | Method B1 |
| 129 | 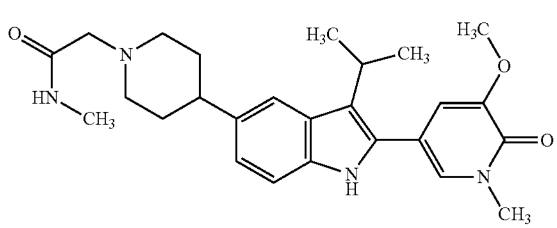 [SMILES: CNC(=O)CN1CCC(c2ccc3[nH]c(-c4cc(OC)c(=O)n(C)c4)c(C(C)C)c3c2)CC1] | Ex-20 | 451.3 | 0.59 | Method B1 |

TABLE 4-continued

| Ex. No. | Structure | Starting material | LCMS MH+ | Ret Time (min) | HPLC Method |
|---|---|---|---|---|---|
| 130 | 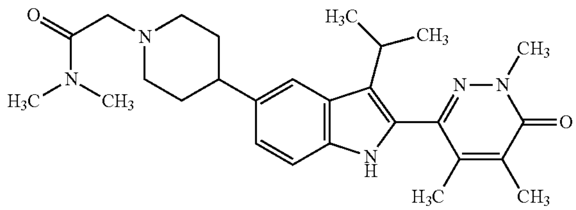 | Ex-17 | 464.3 | 0.67 | Method B1 |
| 131 | 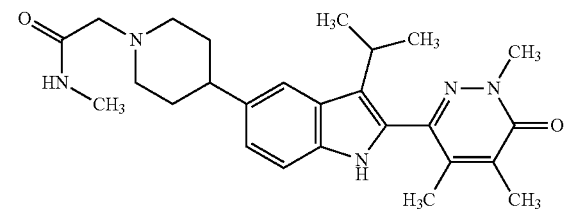 [SMILES: CNC(=O)CN1CCC(c2ccc3[nH]c(-c4nn(C)c(=O)c(C)c4C)c(C(C)C)c3c2)CC1] | Ex-17 | 450.3 | 0.65- | QC-ACN-TFA-XB |
| 132 | 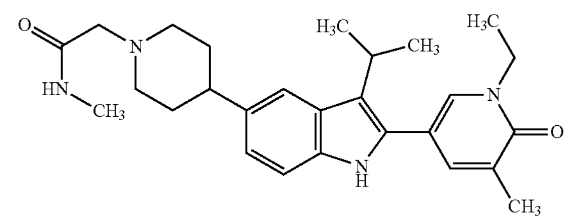 [SMILES: CCn1cc(-c2[nH]c3ccc(C4CCN(CC(=O)NC)CC4)cc3c2C(C)C)cc(C)c1=O] | Ex-15 | 449 | 1.72 | Method B1 |
| 133 | 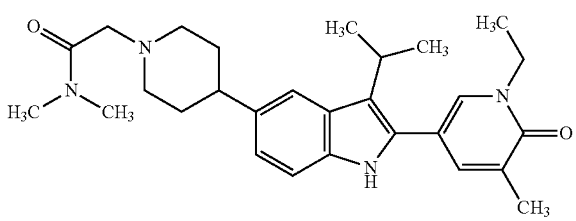 [SMILES: CCn1cc(-c2[nH]c3ccc(C4CCN(CC(=O)N(C)C)CC4)cc3c2C(C)C)cc(C)c1=O] | Ex-15 | 463.4 | 1.47 | Method B1 |
| 134 | 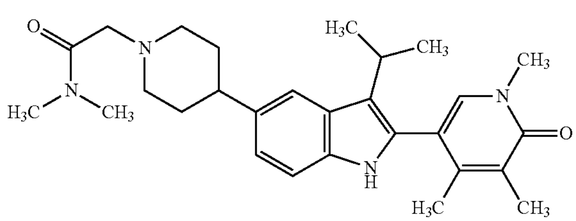 | Ex-14 | 463.3 | 0.67 | Method B1 |
| 135 | 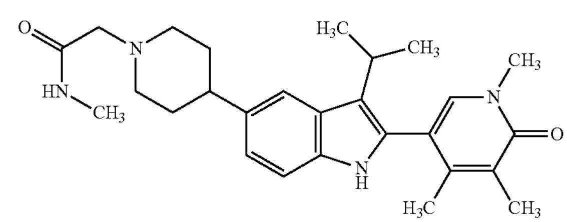 [SMILES: CNC(=O)CN1CCC(c2ccc3[nH]c(-c4cn(C)c(=O)c(C)c4C)c(C(C)C)c3c2)CC1] | Ex-14 | 449.3 | 0.64 | Method B1 |
| 136 | 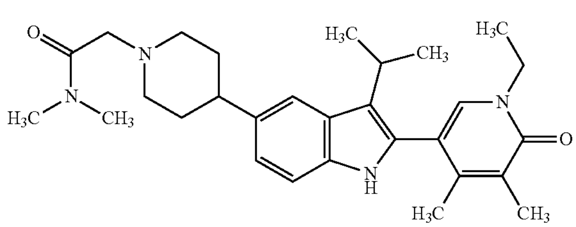 [SMILES: CCn1cc(-c2[nH]c3ccc(C4CCN(CC(=O)N(C)C)CC4)cc3c2C(C)C)c(C)c(C)c1=O] | Ex-26 | 477.3 | 0.70 | Method B1 |

TABLE 4-continued

| Ex. No. | Structure | Starting material | LCMS MH+ | Ret Time (min) | HPLC Method |
|---|---|---|---|---|---|
| 137 | 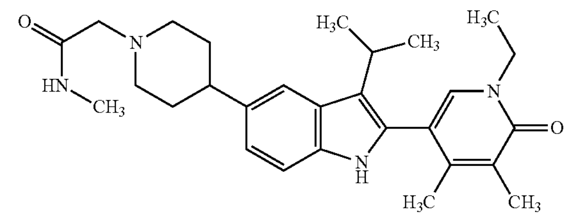 [SMILES: CCn1cc(-c2[nH]c3ccc(C4CCN(CC(=O)NC)CC4)cc3c2C(C)C)c(C)c(C)c1=O] | Ex-26 | 463.3 | 0.68 | Method B1 |
| 138 | 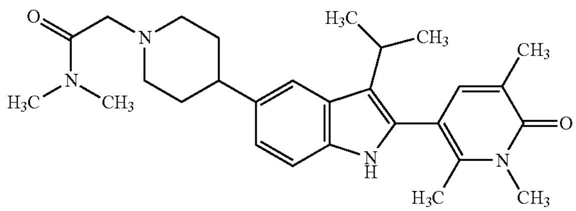 | Ex-3 | 463.3 | 0.67 | Method B1 |
| 139 | 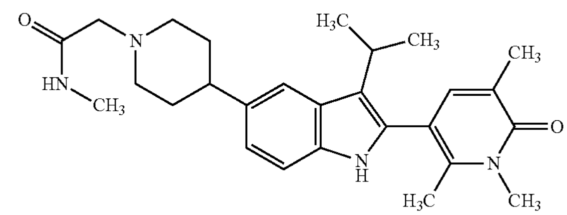 | Ex-3 | 449.3 | 0.65 | Method B1 |
| 140 | 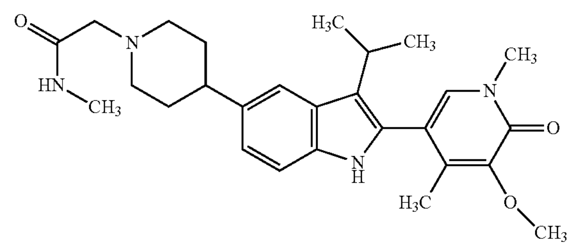 [SMILES: CNC(=O)CN1CCC(c2ccc3[nH]c(-c4cn(C)c(=O)c(OC)c4C)c(C(C)C)c3c2)CC1] | Ex-29 | 465.3 | 0.63 | Method B1 |
| 141 | 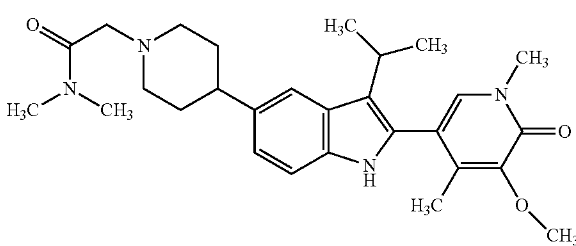 [SMILES: COc1c(C)c(-c2[nH]c3ccc(C4CCN(CC(=O)N(C)C)CC4)cc3c2C(C)C)cn(C)c1=O] | Ex-29 | 479.3 | 0.64 | Method B1 |
| 142 | 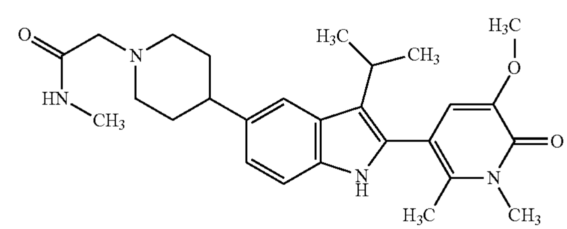 [SMILES: CNC(=O)CN1CCC(c2ccc3[nH]c(-c4cc(OC)c(=O)n(C)c4C)c(C(C)C)c3c2)CC1] | Ex-28 | 465.2 | 0.62 | Method B1 |

TABLE 4-continued

| Ex. No. | Structure | Starting material | LCMS MH+ | Ret Time (min) | HPLC Method |
|---|---|---|---|---|---|
| 143 | 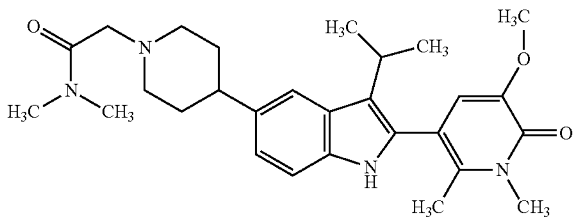 [SMILES: COc1cc(-c2[nH]c3ccc(C4CCN(CC(=O)N(C)C)CC4)cc3c2C(C)C)c(C)n(C)c1=O] | Ex-28 | 479.2 | 0.64 | Method B1 |
| 144 | 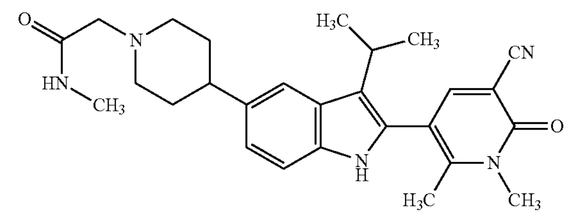 [SMILES: CNC(=O)CN1CCC(c2ccc3[nH]c(-c4cc(C#N)c(=O)n(C)c4C)c(C(C)C)c3c2)CC1] | Ex-23 | 460.3 | 0.64 | Method B1 |
| 145 | 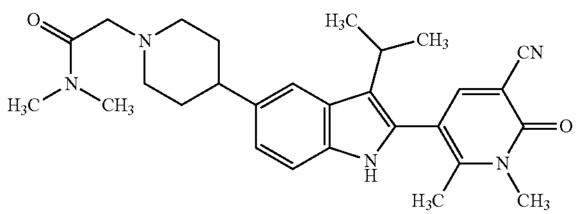 | Ex-23 | 474.3 | 0.65 | Method B1 |
| 146 | 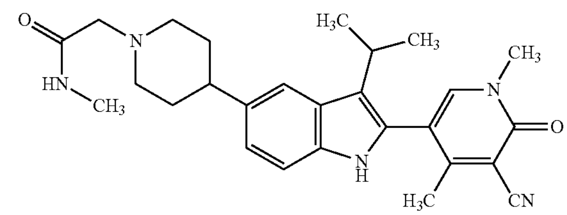 | Ex-24 | 460.3 | 0.64 | Method B1 |
| 147 | 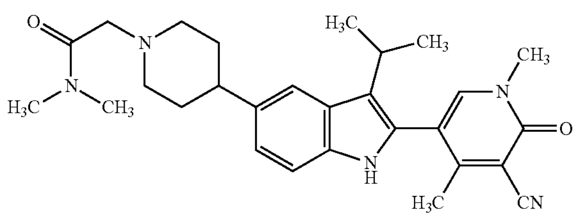 [SMILES: Cc1c(-c2[nH]c3ccc(C4CCN(CC(=O)N(C)C)CC4)cc3c2C(C)C)cn(C)c(=O)c1C#N] | Ex-24 | 474.3 | 0.66 | Method B1 |
| 148 | 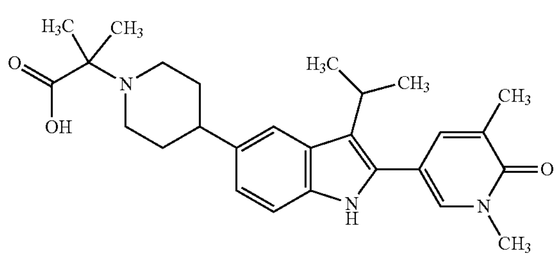 [SMILES: Cc1cc(-c2[nH]c3ccc(C4CCN(C(C)(C)C(=O)O)CC4)cc3c2C(C)C)cn(C)c1=O] | Ex-2 | 450.3 | 1.05 | QC-ACN-AA-XB |

TABLE 4-continued
| Ex. No. | Structure | Starting material | LCMS MH+ | Ret Time (min) | HPLC Method |
|---|---|---|---|---|---|
| 149 | 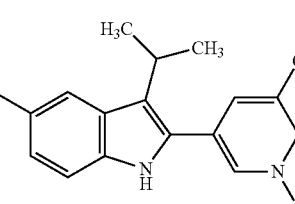 | Ex-2 | 462 | 1.75 | QC-ACN-AA-XB |
| 150 | 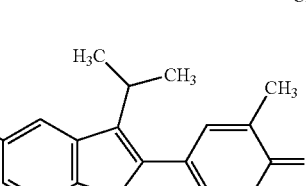 | Ex-2 | 421.3 | 1.35 | QC-ACN-AA-XB |
| 151 | 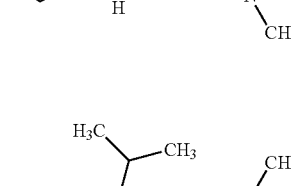 | Ex-2 | 449 | 1.62 | QC-ACN-AA-XB |
| 152 | 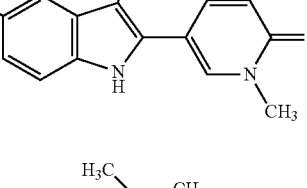 | Ex-31 | 483.3 | 1.24 | QC-ACN-TFA-XB |
| 153 | 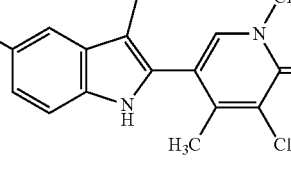 | Ex-31 | 469 | 1.25 | QC-ACN-TFA-XB |
| 154 | 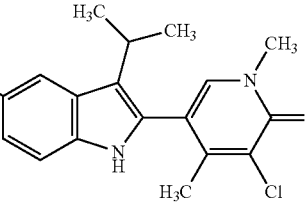 | Ex-31 | 483.4 | 1.76 | QC-ACN-AA-XB |

TABLE 4-continued

| Ex. No. | Structure | Starting material | LCMS MH+ | Ret Time (min) | HPLC Method |
|---|---|---|---|---|---|
| 155 | 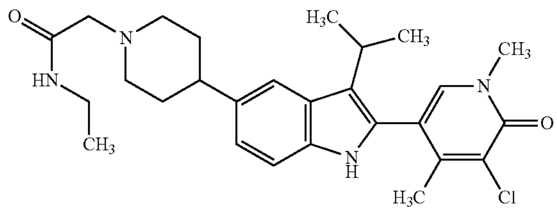 [SMILES: CCNC(=O)CN1CCC(c2ccc3[nH]c(-c4cn(C)c(=O)c(Cl)c4C)c(C(C)C)c3c2)CC1] | Ex-31 | 483 | 1.36 | QC-ACN-TFA-XB |
| 156 | 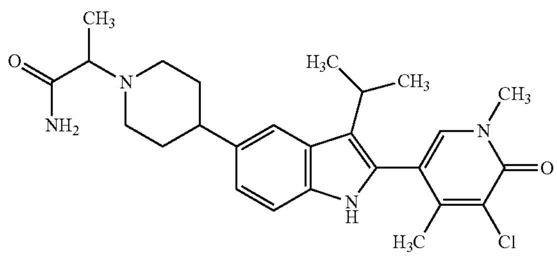 [SMILES: Cc1c(-c2[nH]c3ccc(C4CCN(C(C)C(N)=O)CC4)cc3c2C(C)C)cn(C)c(=O)c1Cl] | Ex-31 | 469 | 1.64 | QC-ACN-AA-XB |
| 157 | 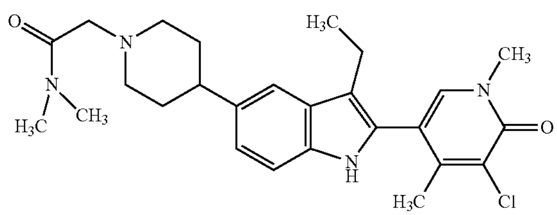 [SMILES: CCc1c(-c2cn(C)c(=O)c(Cl)c2C)[nH]c2ccc(C3CCN(CC(=O)N(C)C)CC3)cc12] | Ex-31 | 469 | 1.18 | QC-ACN-AA-XB |
| 158 | 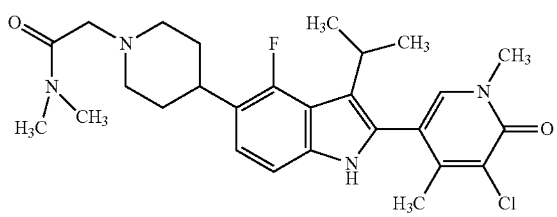 [SMILES: Cc1c(-c2[nH]c3ccc(C4CCN(CC(=O)N(C)C)CC4)c(F)c3c2C(C)C)cn(C)c(=O)c1Cl] | Ex-31 | 501 | 1.39 | QC-ACN-AA-XB |
| 159 | 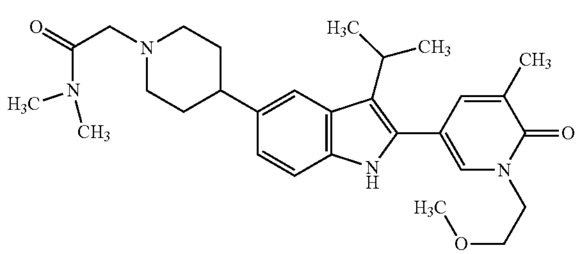 [SMILES: COCCn1cc(-c2[nH]c3ccc(C4CCN(CC(=O)N(C)C)CC4)cc3c2C(C)C)cc(C)c1=O] | Ex-39 | 493.4 | 1.46 | QC-ACN-AA-XB |
| 160 | 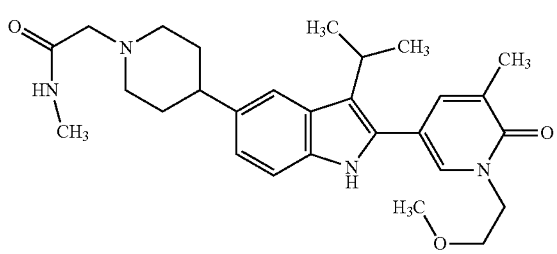 [SMILES: CNC(=O)CN1CCC(c2ccc3[nH]c(-c4cc(C)c(=O)n(CCOC)c4)c(C(C)C)c3c2)CC1] | Ex-39 | 479.1 | 1.28 | QC-ACN-TFA-XB |

TABLE 4-continued

| Ex. No. | Structure | Starting material | LCMS MH+ | Ret Time (min) | HPLC Method |
|---|---|---|---|---|---|
| 161 | 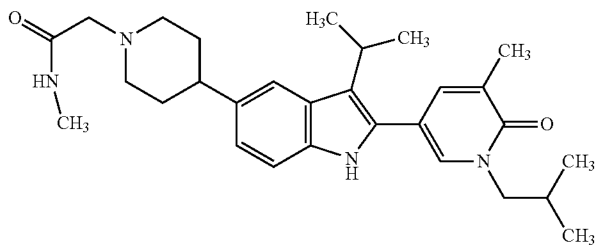 [SMILES: CNC(=O)CN1CCC(c2ccc3[nH]c(-c4cc(C)c(=O)n(CC(C)C)c4)c(C(C)C)c3c2)CC1] | Ex-36 | 477.5 | 1.75 | QC-ACN-AA-XB |
| 162 | 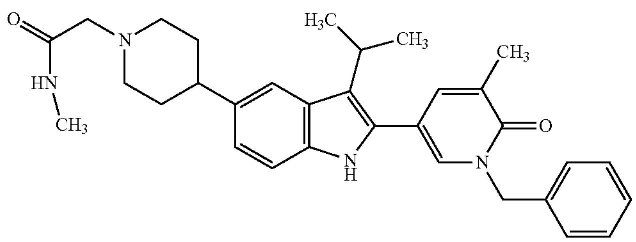 [SMILES: CNC(=O)CN1CCC(c2ccc3[nH]c(-c4cc(C)c(=O)n(Cc5ccccc5)c4)c(C(C)C)c3c2)CC1] | Ex-46 | 511.5 | 1.8 | QC-ACN-AA-XB |
| 163 | 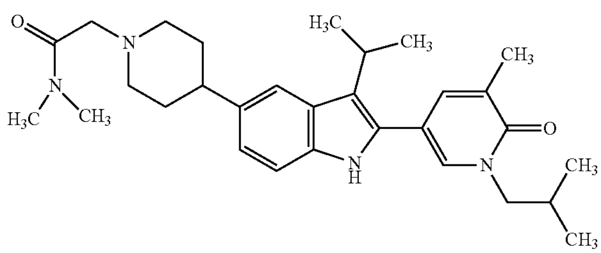 [SMILES: Cc1cc(-c2[nH]c3ccc(C4CCN(CC(=O)N(C)C)CC4)cc3c2C(C)C)cn(CC(C)C)c1=O] | Ex-36 | 491.5 | 1.55 | QC-ACN-AA-XB |
| 164 | 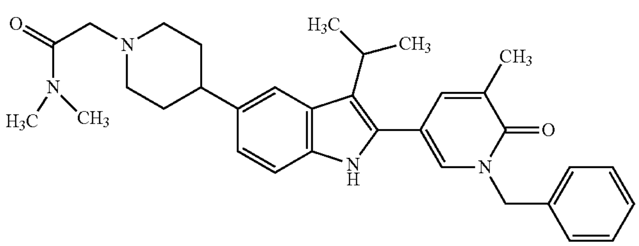 [SMILES: Cc1cc(-c2[nH]c3ccc(C4CCN(CC(=O)N(C)C)CC4)cc3c2C(C)C)cn(Cc2ccccc2)c1=O] | Ex-46 | 525 | 1.45 | QC-ACN-TFA-XB |
| 165 | 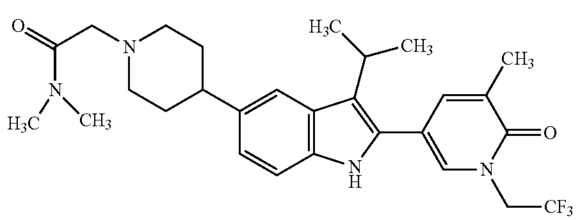 [SMILES: Cc1cc(-c2[nH]c3ccc(C4CCN(CC(=O)N(C)C)CC4)cc3c2C(C)C)cn(CC(F)(F)F)c1=O] | Ex-45 | 517.1 | 1.47 | QC-ACN-AA-XB |
| 166 | 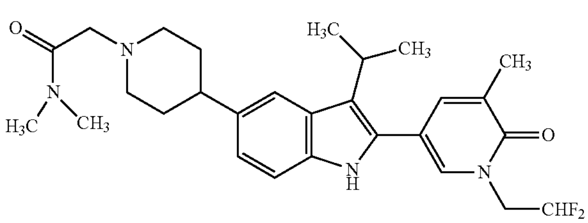 [SMILES: Cc1cc(-c2[nH]c3ccc(C4CCN(CC(=O)N(C)C)CC4)cc3c2C(C)C)cn(CC(F)F)c1=O] | Ex-40 | 499.2 | 1.33 | QC-ACN-TFA-XB |

TABLE 4-continued

| Ex. No. | Structure | Starting material | LCMS MH+ | Ret Time (min) | HPLC Method |
|---|---|---|---|---|---|
| 167 | 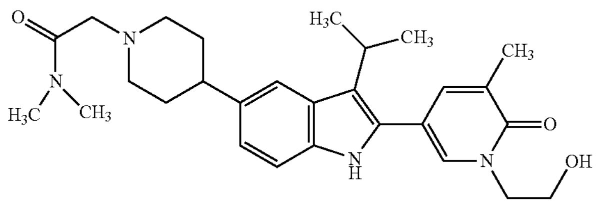 [SMILES: Cc1cc(-c2[nH]c3ccc(C4CCN(CC(=O)N(C)C)CC4)cc3c2C(C)C)cn(CCO)c1=O] | Ex-30 | 479.1 | 1.06 | QC-ACN-TFA-XB |
| 168 | 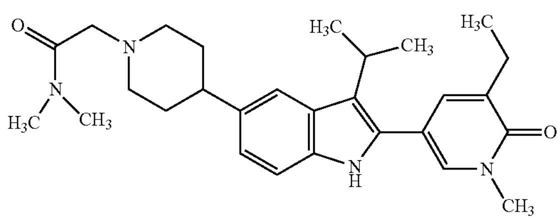 [SMILES: CCc1cc(-c2[nH]c3ccc(C4CCN(CC(=O)N(C)C)CC4)cc3c2C(C)C)cn(C)c1=O] | Ex-67 | 463.12 | 1.37 | QC-ACN-TFA-XB |
| 169 | 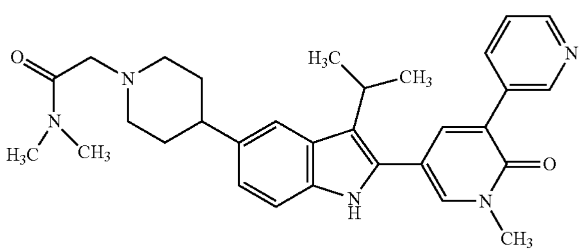 [SMILES: CC(C)c1c(-c2cc(-c3cccnc3)c(=O)n(C)c2)[nH]c2ccc(C3CCN(CC(=O)N(C)C)CC3)cc12] | Ex-50 | 512 | 1.4 | QC-ACN-AA-XB |
| 170 | 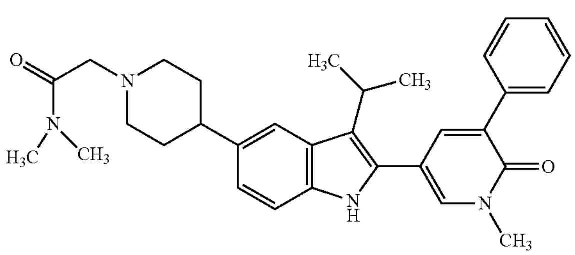 [SMILES: CC(C)c1c(-c2cc(-c3ccccc3)c(=O)n(C)c2)[nH]c2ccc(C3CCN(CC(=O)N(C)C)CC3)cc12] | Ex-53 | 511 | 1.87 | QC-ACN-AA-XB |

Example 171

5-(3-isopropyl-5-(1-(oxetan-3-yl)piperidin-4-yl)-1H-indol-2-yl)-1,3-dimethylpyridin-2(1H)-one

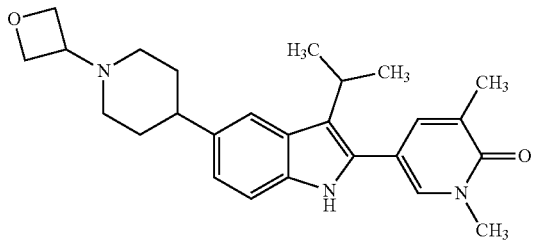

(171)

General Method 1: A mixture containing 5-(3-isopropyl-5-(piperidin-4-yl)-1H-indol-2-yl)-1,3-dimethylpyridin-2(1H)-one (100 mg, 0.275 mmol), oxetan-3-one (99 mg, 1.376 mmol) and sodium triacetoxyborohydride (233 mg, 1.100 mmol) was suspended in DMF (1 mL) followed by the addition of acetic acid (0.025 mL, 0.437 mmol). The reaction mixture was stirred for 20 h. The reaction mixture was treated with concentrated aqueous ammonium hydroxide (7 mL) and the resulting solids were stirred and sonicated periodically for 30 min. The resulting suspension was filtered, rinsed with additional ammonium hydroxide and dried to afford 5-(3-isopropyl-5-(1-(oxetan-3-yl)piperidin-4-yl)-1H-indol-2-yl)-1,3-dimethylpyridin-2(1H)-one (55 mg, 0.125 mmol, 45.3% yield), ~95% pure. m/z (420, $M^{+1}$). LCMS $MH^+$: 420.2. HPLC Ret. Time 0.61 min. Method B. $^1$H NMR (400 MHz, METHANOL-$d_4$) δ 7.63 (d, J=2.3 Hz, 1H), 7.58 (s, 2H), 7.28 (d, J=8.3 Hz, 1H), 7.03 (dd, J=8.4, 1.5 Hz, 1H), 4.77-4.71 (m, 2H), 4.71-4.66 (m, 2H), 3.68 (s, 3H), 3.58 (quin, J=6.5 Hz, 1H), 3.26-3.19 (m, 1H), 2.96 (d, J=11.4 Hz, 2H), 2.65 (td, J=10.4, 5.3 Hz, 1H), 2.22 (s, 3H), 2.10-2.01 (m, 2H), 1.97-1.86 (m, 4H), 1.48 (d, J=7.0 Hz, 6H).

Example 172

5-(3-isopropyl-5-(1-(2-(methylamino)ethyl)piperidin-4-yl)-1H-indol-2-yl)-1-methylpyridin-2(1H)-one

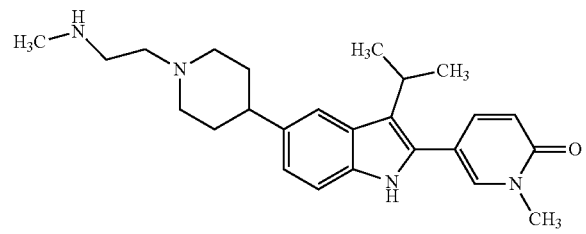

(172)

General Method 2: To a solution containing 5-(3-isopropyl-5-(piperidin-4-yl)-1H-indol-2-yl)-1-methylpyridin-2(1H)-one, HCl (30 mg, 0.078 mmol), Example 1, and tert-butyl methyl(2-oxoethyl)carbamate (26.9 mg, 0.155 mmol) in THF (1 mL) was added TEA (10.83 µl, 0.078 mmol) followed by the addition of sodium triacetoxyborohydride (65.9 mg, 0.311 mmol) and a drop of acetic acid. The reaction mixture was stirred for 20 h, diluted with ethyl acetate (5 mL) and washed with aqueous 1N NaOH (2×2 mL) and saturated aqueous NaCl solution (1×1 mL), filtered through a plug of $Na_2SO_4$ and concentrated. The residue was dissolved in DCM (1 mL) and treated with TFA (0.5 mL). The reaction mixture was concentrated. The sample was dissolved in DMF (2 mL), filtered through an Acrodisc, 13 mm, 0.45 micron nylon membrane syringe filter. The crude material was purified via preparative LC/MS. Fractions containing the product were combined and dried via centrifugal evaporation to afford 5-(3-isopropyl-5-(1-(2-(methylamino)ethyl)piperidin-4-yl)-1H-indol-2-yl)-1-methylpyridin-2(1H)-one (18.5 mg, 0.046 mmol, 58.5% yield). LCMS $MH^+$: 407. HPLC Ret. Time 0.79 min. Method B. $^1$H NMR (500 MHz, DMSO-$d_6$) δ 10.83 (s, 1H), 7.81 (d, J=2.1 Hz, 1H), 7.54 (dd, J=9.3, 2.3 Hz, 1H), 7.50-7.45 (m, 1H), 7.26-7.21 (m, 1H), 6.99-6.94 (m, 1H), 6.56-6.49 (m, 1H), 3.20-3.10 (m, 1H), 2.98 (br d, J=10.9 Hz, 2H), 2.77-2.72 (m, 2H), 2.55 (s, 3H), 2.47 (br t, J=6.2 Hz, 2H), 2.40 (s, 3H), 2.06 (br t, J=10.5 Hz, 2H), 1.87 (s, 1H), 1.81-1.67 (m, 4H), 1.40 (d, J=7.0 Hz, 6H).

Example 173

5-(3-isopropyl-5-(1-propylpiperidin-4-yl)-1H-indol-2-yl)-1-methyl-3-(piperidin-1-yl) pyridin-2(1H)-one

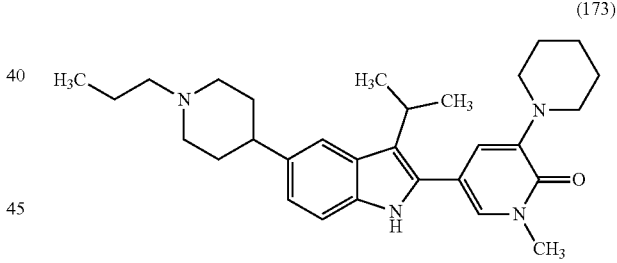

(173)

A mixture of tert-butyl 5-(1-(tert-butoxycarbonyl)piperidin-4-yl)-2-(5-chloro-1-methyl-6-oxo-1,6-dihydropyridin-3-yl)-3-isopropyl-1H-indole-1-carboxylate (20 mg, 0.034 mmol), piperidine (10.15 µl, 0.103 mmol), Xantphos (2.97 mg, 5.14 µmol), $Pd_2(dba)_3$ (2.351 mg, 2.57 µmol), and $Cs_2CO_3$ (44.6 mg, 0.137 mmol) in dioxane (1.0 mL) was purged with nitrogen for 2 min. and then stirred at 130° C. The reaction mixture was cooled to room temperature and checked by LCMS. The product m/z (633.3, M+H) was observed. The reaction mixture was partitioned between water and ethyl acetate (1:1, 3 mL total volume), and the phases were separated. The aqueous phase was extracted with ethyl acetate (2×1 mL), and excess solvent was evaporated from the combined organic phases. The resulting residue was Boc-deprotected with 2:1 trifluoroacetic acid/dichloromethane (1.2 mL, 0.034 mmol), stirring at room temperature for 30 min. Toluene (~150 µL) was added to the reaction mixture, and concentrated to dryness. The residue was taken up in DMF (~1.8 mL) and purified by preparative LCMS to afford 5-(3-isopropyl-5-(piperidin-4-yl)-1H-indol-2-yl)-1-methyl-3-(piperidin-1-yl) pyridin-2(1H)-one, TFA (12.3 mg, 0.011 mmol, 32.9% yield) as a greenish oil. DMF (225 μl) was added to 5-(3-isopropyl-5-(piperidin-4-yl)-1H-indol-2-yl)-1-methyl-3-(piperidin-1-yl)pyridin-2(1H)-one, TFA (12.3 mg, 0.023 mmol) in a 1-dram vial, followed by DIEA (9.82 μl, 0.056 mmol) and propionaldehyde (16.38 μl, 0.225 mmol). The reaction mixture was stirred at room temperature for 5 min, then acetic acid (7.73 μl, 0.135 mmol) and sodium triacetoxyborohydride (47.7 mg, 0.225 mmol) were added. The reaction mixture was stirred at room temperature for 2 h, diluted with MeOH (1 mL) and subjected to HPLC purification to afford 5-(3-isopropyl-5-(1-propylpiperidin-4-yl)-1H-indol-2-yl)-1-methyl-3-(piperidin-1-yl)pyridin-2(1H)-one, (0.7 mg, 7%). LCMS MH$^+$: 475. HPLC Ret. Time 1.76 min. Method QC-ACN-AA-XB.

The following examples were prepared according to the general procedures for Examples 171-173, using the indicated starting material.

TABLE 5

| Ex. No. | Structure | Starting Material | LCMS MH$^+$ | Ret Time (min) | HPLC Method |
|---|---|---|---|---|---|
| 174 | 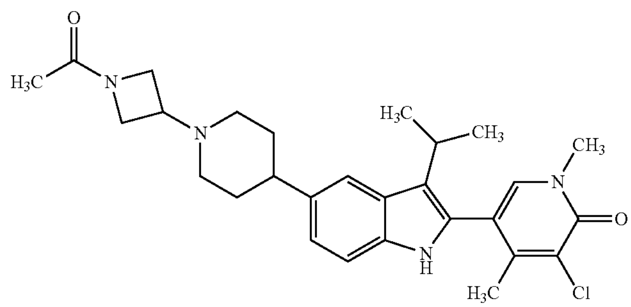 [SMILES: CC(=O)N1CC(N2CCC(c3ccc4[nH]c(-c5cn(C)c(=O)c(Cl)c5C)c(C(C)C)c4c3)CC2)C1] | Ex-31 | 495 | 1.64 | QC-ACN-AA-XB |
| 175 | 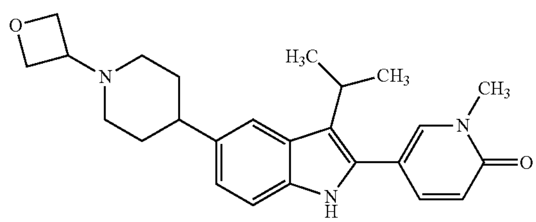 [SMILES: CC(C)c1c(-c2ccc(=O)n(C)c2)[nH]c2ccc(C3CCN(C4COC4)CC3)cc12] | Ex-1 | 406 | 1.44 | QC-ACN-AA-XB |
| 176 | 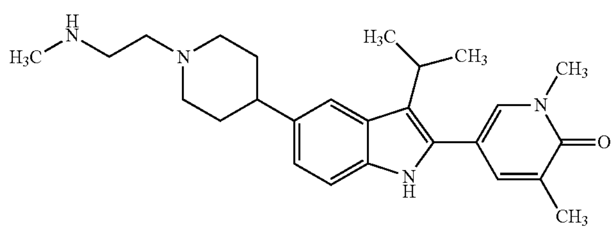 [SMILES: CNCCN1CCC(c2ccc3[nH]c(-c4cc(C)c(=O)n(C)c4)c(C(C)C)c3c2)CC1] | Ex-2 | 421 | 1.26 | QC-ACN-AA-XB |
| 177 | 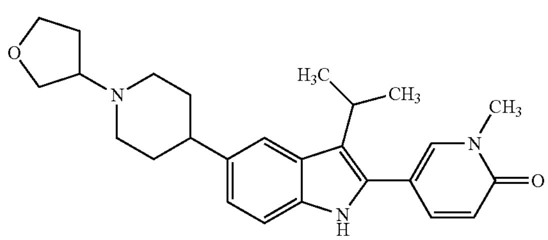 [SMILES: CC(C)c1c(-c2ccc(=O)n(C)c2)[nH]c2ccc(C3CCN(C4CCOC4)CC3)cc12] | Ex-1 | 420 | 1.28 | QC-ACN-AA-XB |
| 178 | 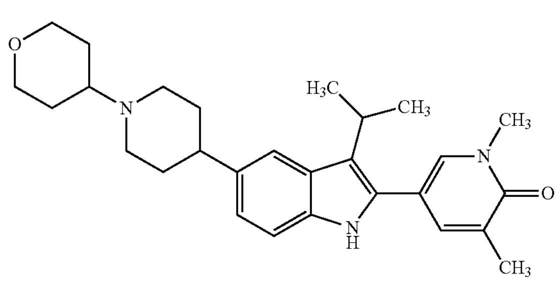 | Ex-2 | 448 | 1.3 | QC-ACN-AA-XB |

TABLE 5-continued

| Ex. No. | Structure | Starting Material | LCMS MH+ | Ret Time (min) | HPLC Method |
|---|---|---|---|---|---|
| 179 | 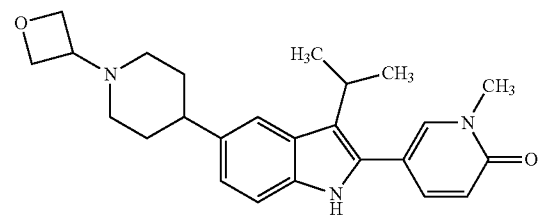 [SMILES: CC(C)c1c(-c2ccc(=O)n(C)c2)[nH]c2ccc(C3CCN(C4COC4)CC3)cc12] | Ex-1 | 434 | 1.17 | QC-ACN-AA-XB |
| 180 | 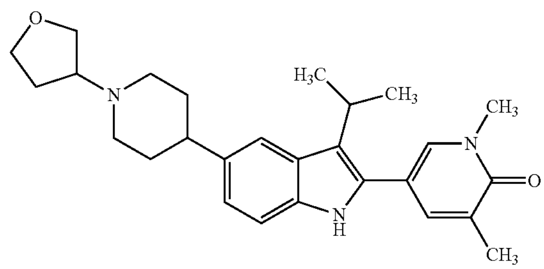 [SMILES: Cc1cc(-c2[nH]c3ccc(C4CCN(C5CCOC5)CC4)cc3c2C(C)C)cn(C)c1=O] | Ex-2 | 434 | 1.42 | QC-ACN-AA-XB |
| 181 | 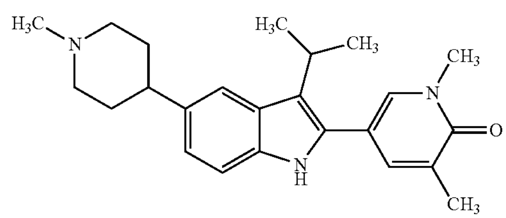 [SMILES: Cc1cc(-c2[nH]c3ccc(C4CCN(C)CC4)cc3c2C(C)C)cn(C)c1=O] | Ex-2 | 378 | 1.11 | QC-ACN-AA-XB |
| 182 | 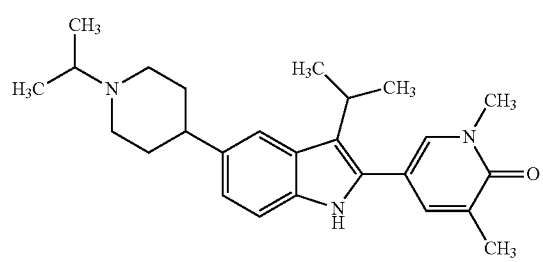 [SMILES: Cc1cc(-c2[nH]c3ccc(C4CCN(C(C)C)CC4)cc3c2C(C)C)cn(C)c1=O] | Ex-2 | 406 | 1.37 | QC-ACN-AA-XB |
| 183 | 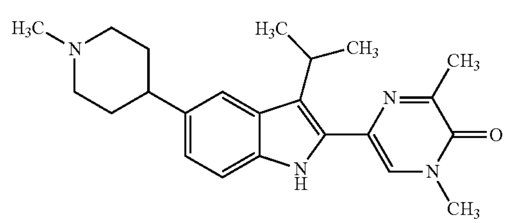 [SMILES: Cc1nc(-c2[nH]c3ccc(C4CCN(C)CC4)cc3c2C(C)C)cn(C)c1=O] | Ex-12 | 379 | 1.1 | QC-ACN-TFA-XB |
| 184 | 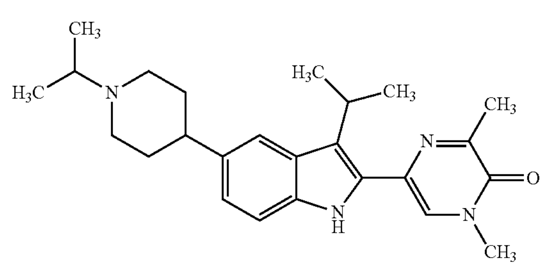 [SMILES: Cc1nc(-c2[nH]c3ccc(C4CCN(C(C)C)CC4)cc3c2C(C)C)cn(C)c1=O] | Ex-12 | 407 | 1.25 | QC-ACN-TFA-XB |

TABLE 5-continued

| Ex. No. | Structure | Starting Material | LCMS MH+ | Ret Time (min) | HPLC Method |
|---|---|---|---|---|---|
| 185 | 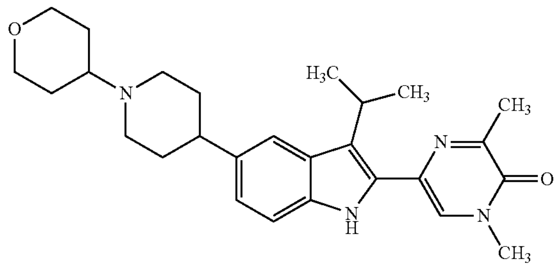 | Ex-12 | 449 | 1.24 | QC-ACN-AA-XB |
| 186 | 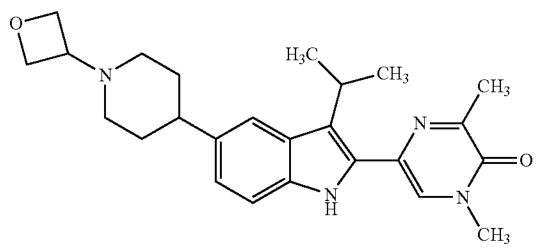 [SMILES: Cc1nc(-c2[nH]c3ccc(C4CCN(C5COC5)CC4)cc3c2C(C)C)cn(C)c1=O] | Ex-12 | 421 | 1.57 | QC-ACN-AA-XB |
| 187 | 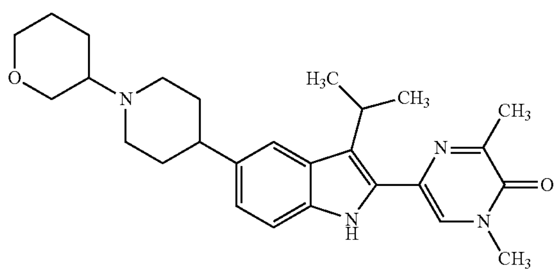 [SMILES: Cc1nc(-c2[nH]c3ccc(C4CCN(C5CCCOC5)CC4)cc3c2C(C)C)cn(C)c1=O] | Ex-12 | 449 | 1.22 | QC-ACN-TFA-XB |
| 188 | 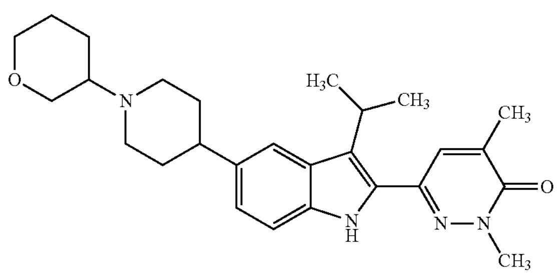 [SMILES: Cc1cc(-c2[nH]c3ccc(C4CCN(C5CCCOC5)CC4)cc3c2C(C)C)nn(C)c1=O] | Ex-11 | 449 | 1.53 | QC-ACN-AA-XB |
| 189 | 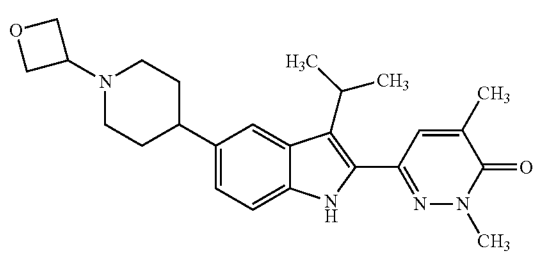 [SMILES: Cc1cc(-c2[nH]c3ccc(C4CCN(C5COC5)CC4)cc3c2C(C)C)nn(C)c1=O] | Ex-11 | 421 | 1.65 | QC-ACN-AA-XB |

TABLE 5-continued

| Ex. No. | Structure | Starting Material | LCMS MH+ | Ret Time (min) | HPLC Method |
|---|---|---|---|---|---|
| 190 | 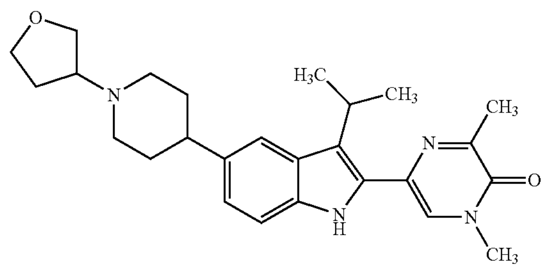 [SMILES: Cc1nc(-c2[nH]c3ccc(C4CCN(C5CCOC5)CC4)cc3c2C(C)C)cn(C)c1=O] | Ex-12 | 435 | 1.07 | QC-ACN-TFA-XB |
| 191 | 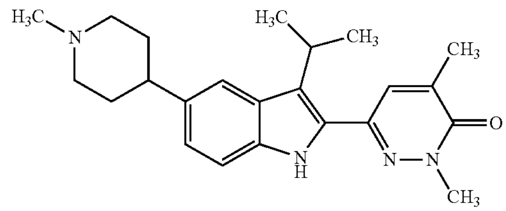 | Ex-11 | 379 | 1.15 | QC-ACN-AA-XB |
| 192 | 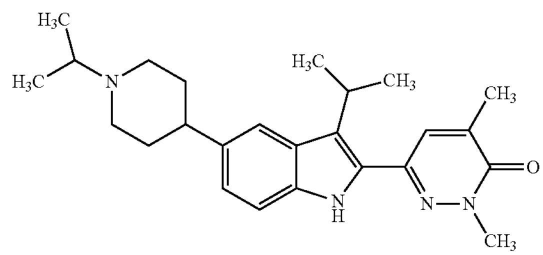 [SMILES: Cc1cc(-c2[nH]c3ccc(C4CCN(C(C)C)CC4)cc3c2C(C)C)nn(C)c1=O] | Ex-11 | 407 | 1.25 | QC-ACN-TFA-XB |
| 193 | 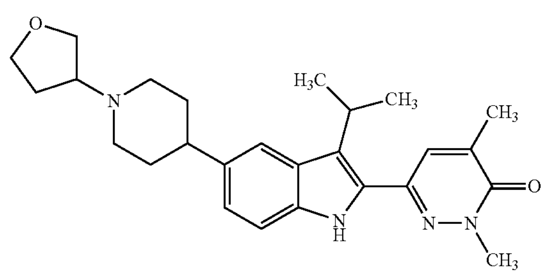 [SMILES: Cc1cc(-c2[nH]c3ccc(C4CCN(C5CCOC5)CC4)cc3c2C(C)C)nn(C)c1=O] | Ex-11 | 435 | 1.53 | QC-ACN-AA-XB |
| 194 | 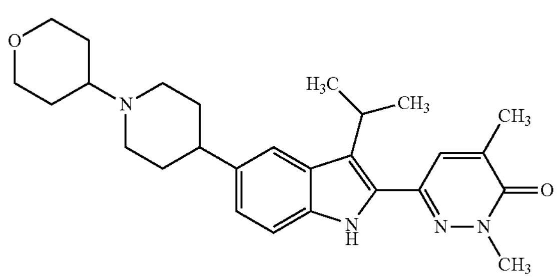 | Ex-11 | 897 | 1.18 | QC-ACN-TFA-XB |
| 195 | 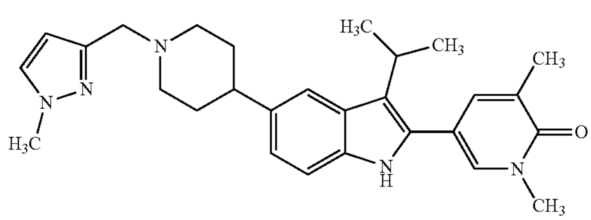 [SMILES: Cc1cc(-c2[nH]c3ccc(C4CCN(Cc5cnn(C)c5)CC4)cc3c2C(C)C)cn(C)c1=O] | Ex-2 | 458 | 1.3 | QC-ACN-AA-XB |

TABLE 5-continued

| Ex. No. | Structure | Starting Material | LCMS MH+ | Ret Time (min) | HPLC Method |
|---|---|---|---|---|---|
| 196 | 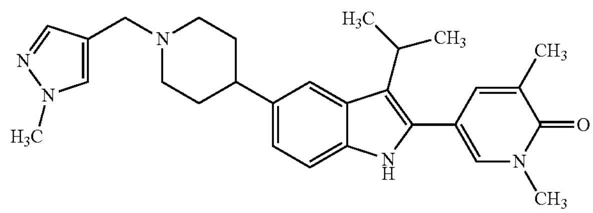 | Ex-2 | 458 | 1.22 | QC-ACN-AA-XB |
| 197 | 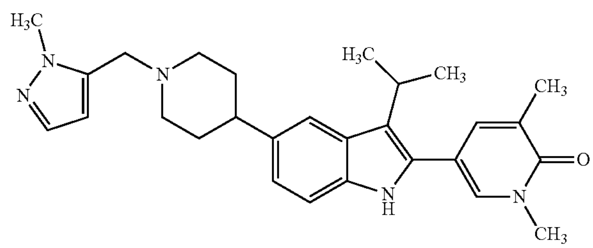 [SMILES: Cc1cc(-c2[nH]c3ccc(C4CCN(Cc5ncnn5C)CC4)cc3c2C(C)C)cn(C)c1=O] | Ex-2 | 458 | 1.76 | QC-ACN-AA-XB |
| 198 | 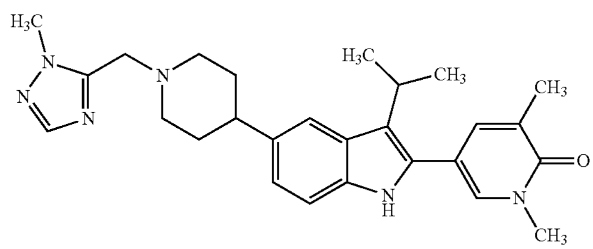 | Ex-2 | 459 | 1.52 | QC-ACN-AA-XB |
| 199 | 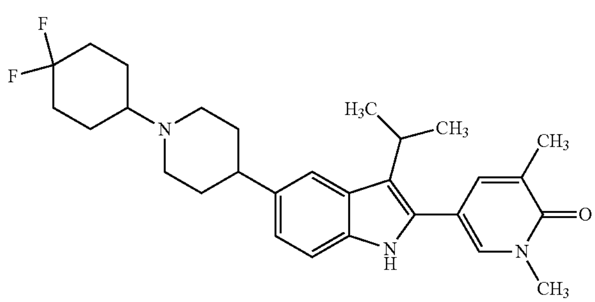 [SMILES: Cc1cc(-c2[nH]c3ccc(C4CCN(C5CCC(F)(F)CC5)CC4)cc3c2C(C)C)cn(C)c1=O] | Ex-2 | 482.4 | 0.73 | Method B1 |
| 200 | 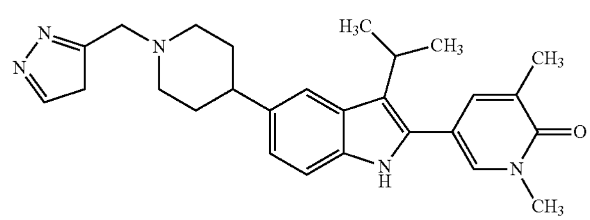 [SMILES: Cc1cc(-c2[nH]c3ccc(C4CCN(CC5=NN=CC5)CC4)cc3c2C(C)C)cn(C)c1=O] | Ex-2 | 444 | 1.1 | QC-ACN-TFA-XB |
| 201 | 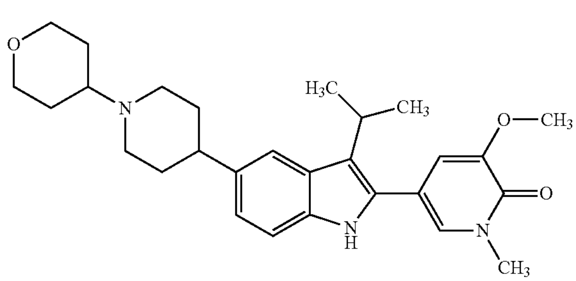 [SMILES: COc1cc(-c2[nH]c3ccc(C4CCN(C5CCOCC5)CC4)cc3c2C(C)C)cn(C)c1=O] | Ex-20 | 464.3 | 0.62 | Method B1 |

TABLE 5-continued
| Ex. No. | Structure | Starting Material | LCMS MH+ | Ret Time (min) | HPLC Method |
|---|---|---|---|---|---|
| 202 | 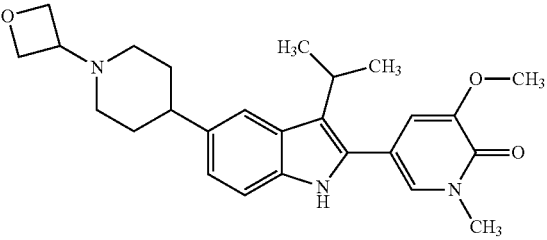 | Ex-20 | 436.3 | 0.59 | Method B1 |
| 203 | 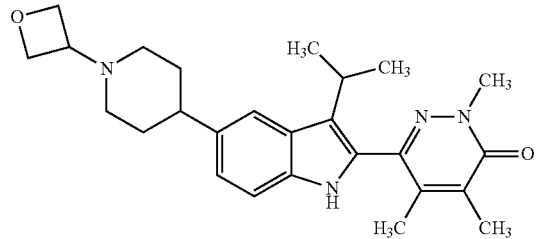 | Ex-17 | 435.3 | 0.65 | Method B1 |
| 204 | 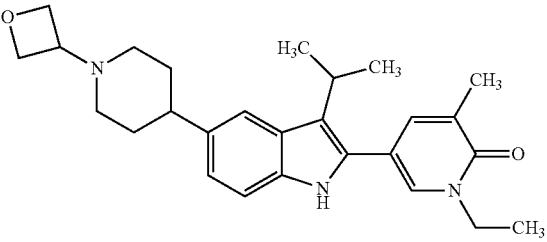 [SMILES: CCn1cc(-c2[nH]c3ccc(C4CCN(C5COC5)CC4)cc3c2C(C)C)cc(C)c1=O] | Ex-15 | 434 | 1.77 | QC-ACN-AA-XB |
| 205 | 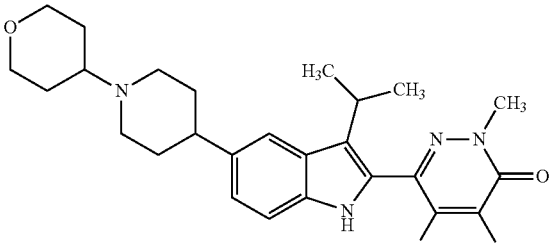 | Ex-17 | 463 | 1.45 | QC-ACN-AA-XB |
| 206 | 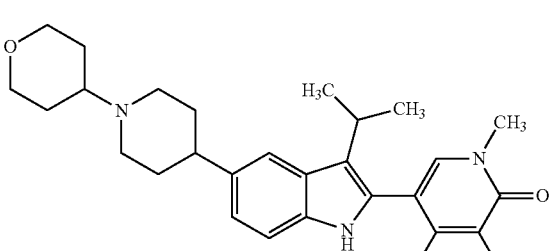 | Ex-14 | 462 | 1.2 | QC-ACN-AA-XB |
| 207 | 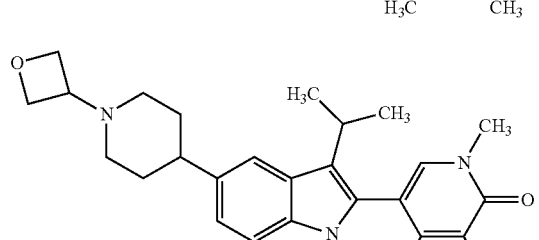 | Ex-14 | 434 | 1.33 | QC-ACN-TFA-XB |

TABLE 5-continued

| Ex. No. | Structure | Starting Material | LCMS MH+ | Ret Time (min) | HPLC Method |
|---|---|---|---|---|---|
| 208 | 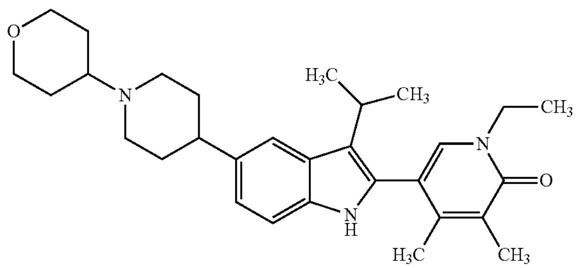 [SMILES: CCn1cc(-c2[nH]c3ccc(C4CCN(C5CCOCC5)CC4)cc3c2C(C)C)c(C)c(C)c1=O] | Ex-26 | 476 | 1.36 | QC-ACN-AA-XB |
| 209 | 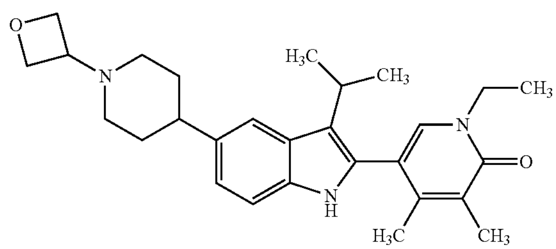 | Ex-26 | 448 | 1.75 | QC-ACN-AA-XB |
| 210 | 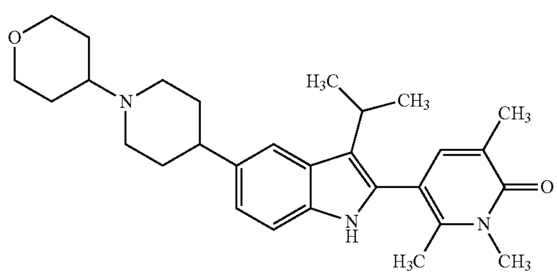 | Ex-3 | 462 | 1.21 | QC-ACN-TFA-XB |
| 211 | 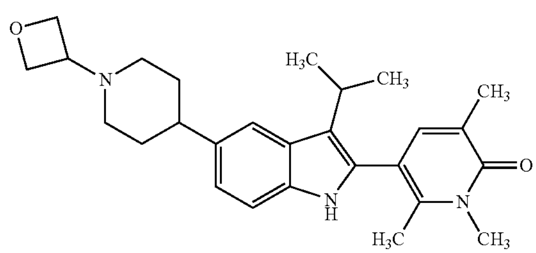 [SMILES: Cc1cc(-c2[nH]c3ccc(C4CCN(C5COC5)CC4)cc3c2C(C)C)c(C)n(C)c1=O] | Ex-3 | 434 | 1.58 | QC-ACN-AA-XB |
| 212 | 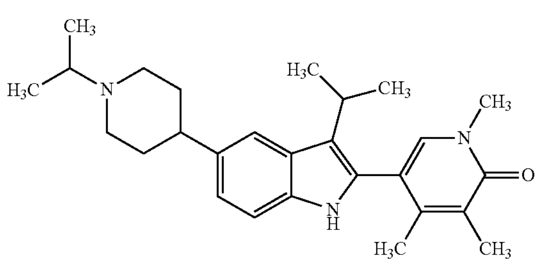 | Ex-14 | 420.1 | 0.69 | Method B1 |

TABLE 5-continued

| Ex. No. | Structure | Starting Material | LCMS MH+ | Ret Time (min) | HPLC Method |
|---|---|---|---|---|---|
| 213 | 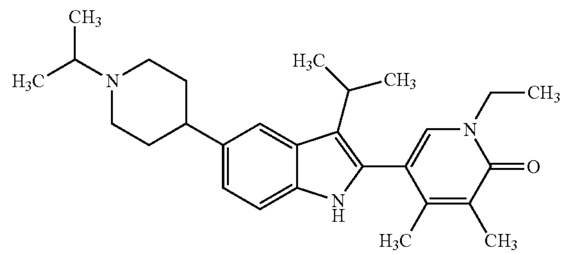 [SMILES: CCn1cc(-c2[nH]c3ccc(C4CCN(C(C)C)CC4)cc3c2C(C)C)c(C)c(C)c1=O] | Ex-26 | 434.3 | 0.73 | Method B1 |
| 214 | 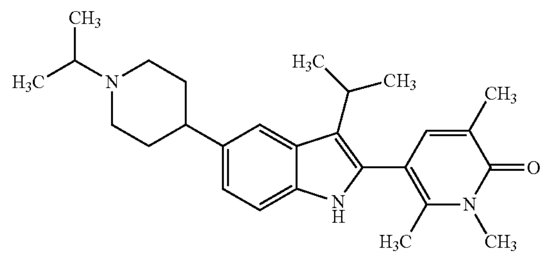 [SMILES: Cc1cc(-c2[nH]c3ccc(C4CCN(C(C)C)CC4)cc3c2C(C)C)c(C)n(C)c1=O] | Ex-3 | 420.3 | 0.70 | Method B1 |
| 215 | 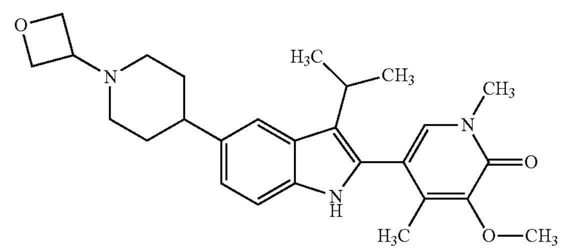 [SMILES: COc1c(C)c(-c2[nH]c3ccc(C4CCN(C5COC5)CC4)cc3c2C(C)C)cn(C)c1=O] | Ex-29 | 450.3 | 0.62 | Method B1 |
| 216 | 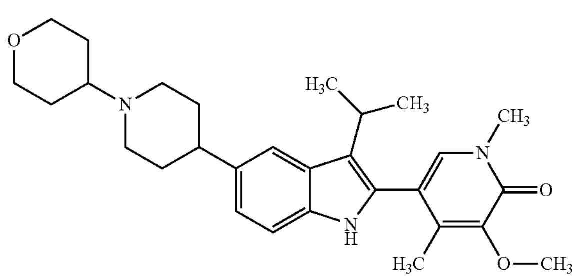 [SMILES: COc1c(C)c(-c2[nH]c3ccc(C4CCN(C5CCOCC5)CC4)cc3c2C(C)C)cn(C)c1=O] | Ex-29 | 478.3 | 0.66 | Method B1 |
| 217 | 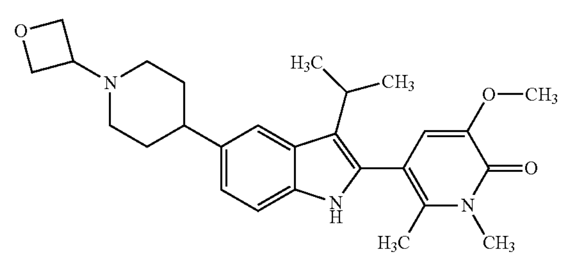 [SMILES: COc1cc(-c2[nH]c3ccc(C4CCN(C5COC5)CC4)cc3c2C(C)C)c(C)n(C)c1=O] | Ex-28 | 450.2 | 0.62 | Method B1 |
| 218 | 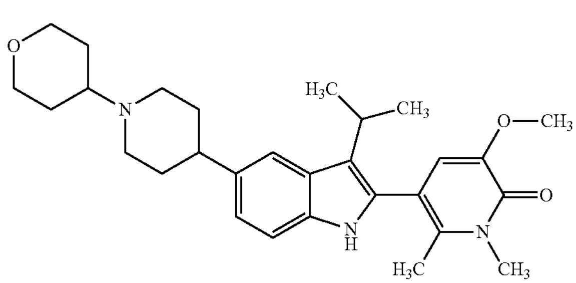 [SMILES: COc1cc(-c2[nH]c3ccc(C4CCN(C5CCOCC5)CC4)cc3c2C(C)C)c(C)n(C)c1=O] | Ex-28 | 478.2 | 0.65 | Method B1 |

TABLE 5-continued

| Ex. No. | Structure | Starting Material | LCMS MH+ | Ret Time (min) | HPLC Method |
|---|---|---|---|---|---|
| 219 | 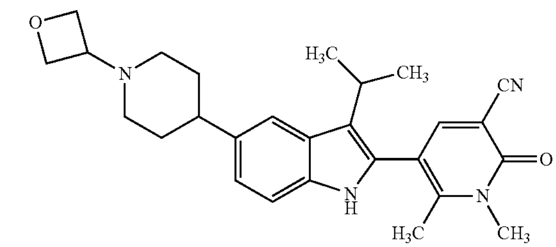 [SMILES: Cc1c(-c2[nH]c3ccc(C4CCN(C5COC5)CC4)cc3c2C(C)C)cc(C#N)c(=O)n1C] | Ex-23 | 445.0 | 0.63 | Method B1 |
| 220 | 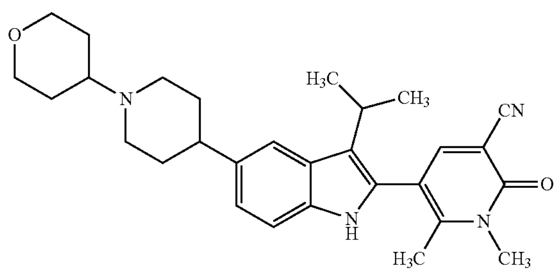 [SMILES: Cc1c(-c2[nH]c3ccc(C4CCN(C5CCOCC5)CC4)cc3c2C(C)C)cc(C#N)c(=O)n1C] | Ex-23 | 473.1 | 0.67 | Method B1 |
| 221 | 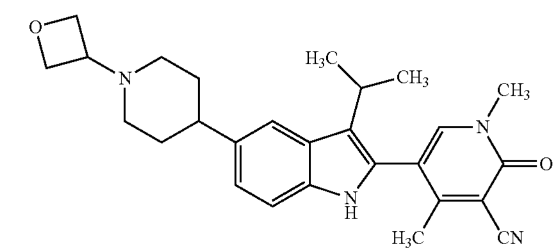 [SMILES: Cc1c(-c2[nH]c3ccc(C4CCN(C5COC5)CC4)cc3c2C(C)C)cn(C)c(=O)c1C#N] | Ex-24 | 445.1 | 0.63 | Method B1 |
| 222 | 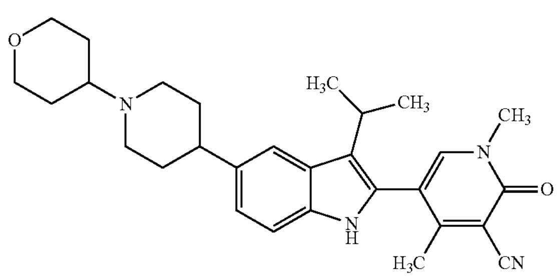 [SMILES: Cc1c(-c2[nH]c3ccc(C4CCN(C5CCOCC5)CC4)cc3c2C(C)C)cn(C)c(=O)c1C#N] | Ex-24 | 473.1 | 0.67 | Method B1 |
| 223 | 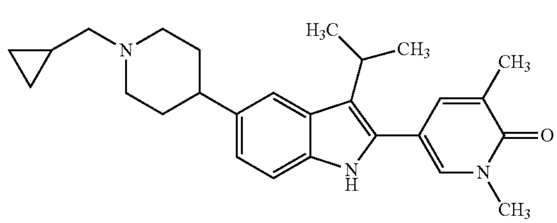 [SMILES: Cc1cc(-c2[nH]c3ccc(C4CCN(CC5CC5)CC4)cc3c2C(C)C)cn(C)c1=O] | Ex-2 | 418.3 | 1.25 | QC-ACN-TFA-XB |
| 224 | 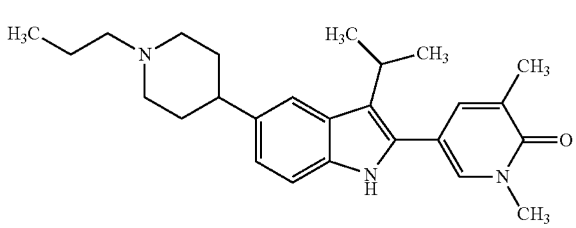 [SMILES: CCCN1CCC(c2ccc3[nH]c(-c4cc(C)c(=O)n(C)c4)c(C(C)C)c3c2)CC1] | Ex-2 | 406 | 1.3 | QC-ACN-AA-XB |

TABLE 5-continued

| Ex. No. | Structure | Starting Material | LCMS MH+ | Ret Time (min) | HPLC Method |
|---|---|---|---|---|---|
| 225 | 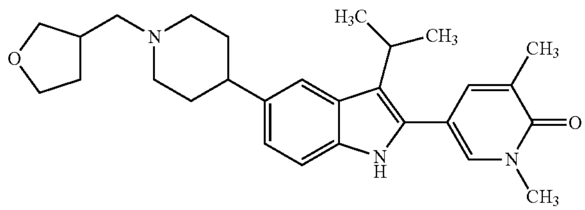 [SMILES: Cc1cc(-c2[nH]c3ccc(C4CCN(CC5CCOC5)CC4)cc3c2C(C)C)cn(C)c1=O] | Ex-2 | 448 | 1.34 | QC-ACN-AA-XB |
| 226 | 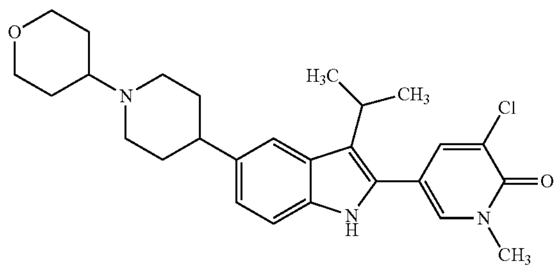 [SMILES: CC(C)c1c(-c2cc(Cl)c(=O)n(C)c2)[nH]c2ccc(C3CCN(C4CCOCC4)CC3)cc12] | Ex-22 | 468 | 1.19 | QC-ACN-TFA-XB |
| 227 | 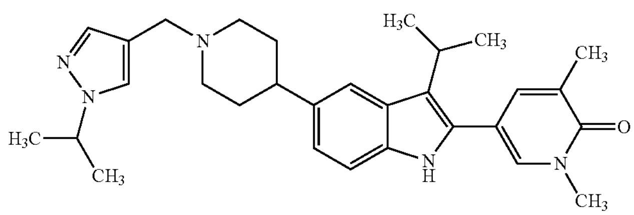 [SMILES: Cc1cc(-c2[nH]c3ccc(C4CCN(Cc5cnn(C(C)C)c5)CC4)cc3c2C(C)C)cn(C)c1=O] | Ex-2 | 486 | 1.4 | QC-ACN-AA-XB |
| 228 | 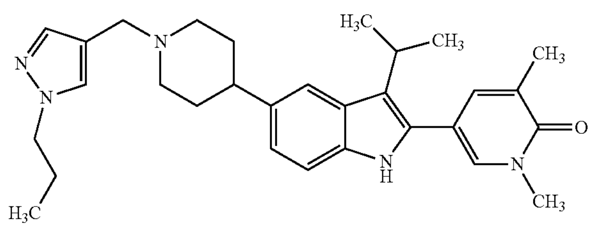 [SMILES: CCCn1cc(CN2CCC(c3ccc4[nH]c(-c5cc(C)c(=O)n(C)c5)c(C(C)C)c4c3)CC2)cn1] | Ex-2 | 486 | 1.45 | QC-ACN-AA-XB |
| 229 | 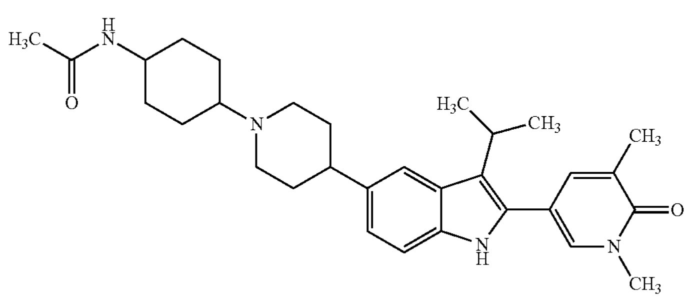 [SMILES: CC(=O)NC1CCC(N2CCC(c3ccc4[nH]c(-c5cc(C)c(=O)n(C)c5)c(C(C)C)c4c3)CC2)CC1] | Ex-2 | 503 | 1.15 | QC-ACN-TFA-XB |
| 230 | 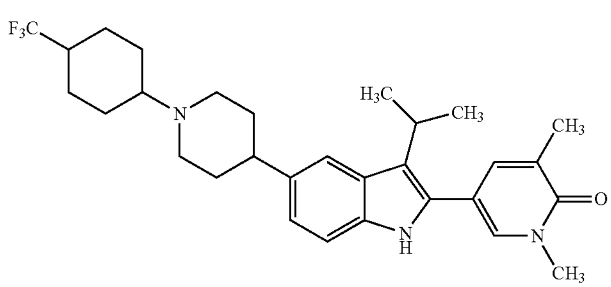 [SMILES: Cc1cc(-c2[nH]c3ccc(C4CCN(C5CCC(C(F)(F)F)CC5)CC4)cc3c2C(C)C)cn(C)c1=O] | Ex-2 | 514 | 1.8 | QC-ACN-AA-XB |

TABLE 5-continued

| Ex. No. | Structure | Starting Material | LCMS MH+ | Ret Time (min) | HPLC Method |
|---|---|---|---|---|---|
| 231 | 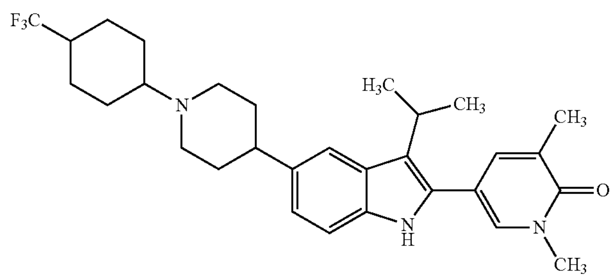 [SMILES: Cc1cc(-c2[nH]c3ccc(C4CCN(C5CCC(C(F)(F)F)CC5)CC4)cc3c2C(C)C)cn(C)c1=O] | Ex-2 | 514 | 1.56 | QC-ACN-TFA-XB |
| 232 | 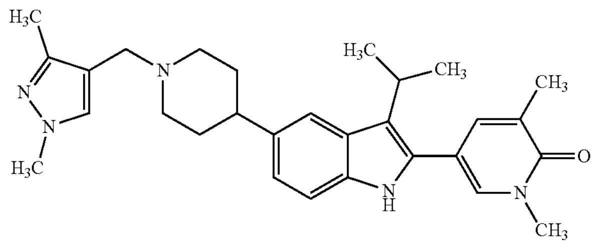 | Ex-2 | 472 | 1.31 | QC-ACN-AA-XB |
| 233 | 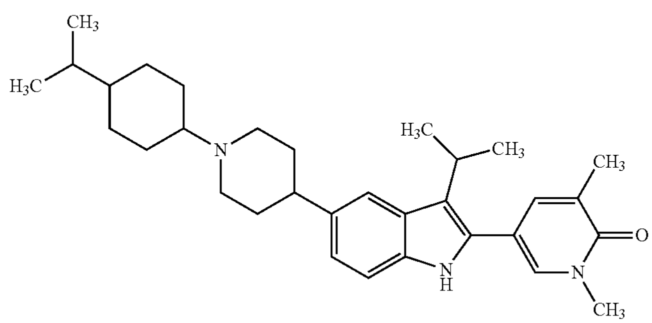 [SMILES: Cc1cc(-c2[nH]c3ccc(C4CCN(C5CCC(C(C)C)CC5)CC4)cc3c2C(C)C)cn(C)c1=O] | Ex-2 | 488 | 1.78 | QC-ACN-TFA-XB |
| 234 | 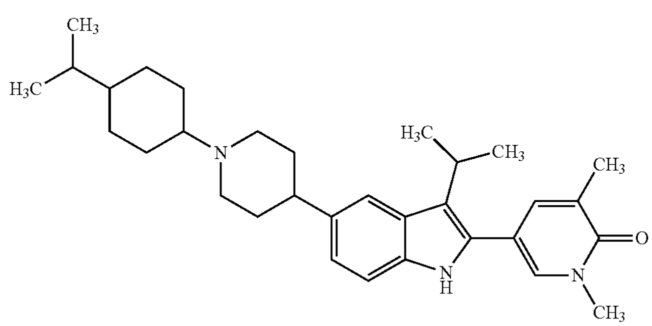 [SMILES: Cc1cc(-c2[nH]c3ccc(C4CCN(C5CCC(C(C)C)CC5)CC4)cc3c2C(C)C)cn(C)c1=O] | Ex-2 | 488 | 1.98 | QC-ACN-AA-XB |
| 235 | 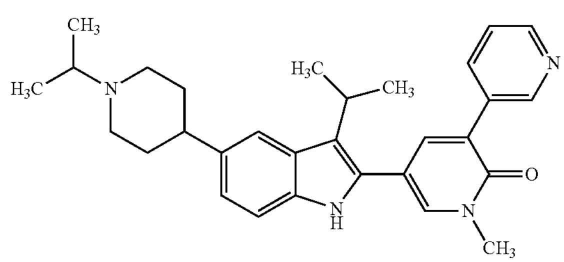 [SMILES: CC(C)c1c(-c2cc(-c3cccnc3)c(=O)n(C)c2)[nH]c2ccc(C3CCN(C(C)C)CC3)cc12] | Ex-50 | 469 | 1.11 | QC-ACN-TFA-XB |

TABLE 5-continued

| Ex. No. | Structure | Starting Material | LCMS MH+ | Ret Time (min) | HPLC Method |
|---|---|---|---|---|---|
| 236 | 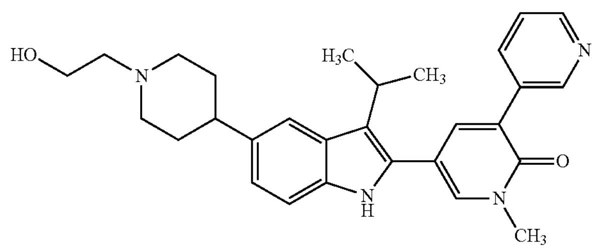 [SMILES: CC(C)c1c(-c2cc(-c3cccnc3)c(=O)n(C)c2)[nH]c2ccc(C3CCN(CCO)CC3)cc12] | Ex-50 | 471 | 0.97 | QC-ACN-TFA-XB |
| 237 | 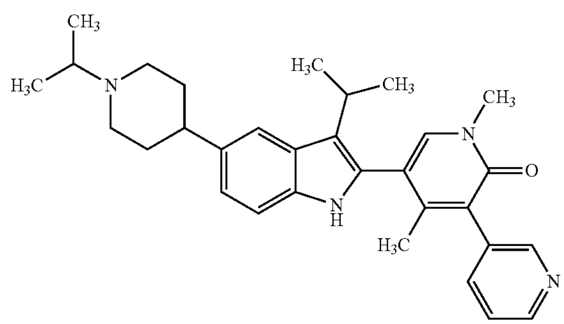 [SMILES: Cc1c(-c2[nH]c3ccc(C4CCN(C(C)C)CC4)cc3c2C(C)C)cn(C)c(=O)c1-c1cccnc1] | Ex-50 | 483 | 1.21 | QC-ACN-AA-XB |
| 238 | 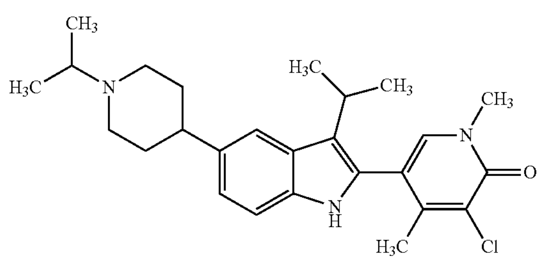 | Ex-31 | 440 | 1.31 | QC-ACN-AA-XB |
| 239 | 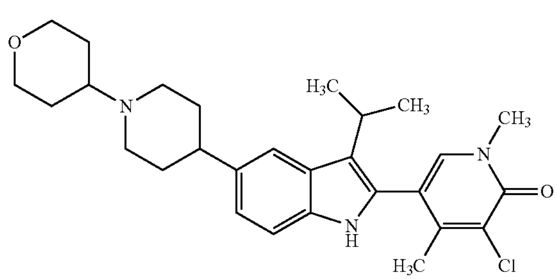 [SMILES: Cc1c(-c2[nH]c3ccc(C4CCN(C5CCOCC5)CC4)cc3c2C(C)C)cn(C)c(=O)c1Cl] | Ex-31 | 482 | 1.26 | QC-ACN-TFA-XB |
| 240 | 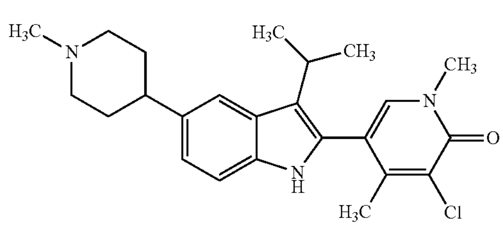 [SMILES: Cc1c(-c2[nH]c3ccc(C4CCN(C)CC4)cc3c2C(C)C)cn(C)c(=O)c1Cl] | Ex-31 | 412 | 1.19 | QC-ACN-TFA-XB |

TABLE 5-continued

| Ex. No. | Structure | Starting Material | LCMS MH+ | Ret Time (min) | HPLC Method |
|---|---|---|---|---|---|
| 241 | 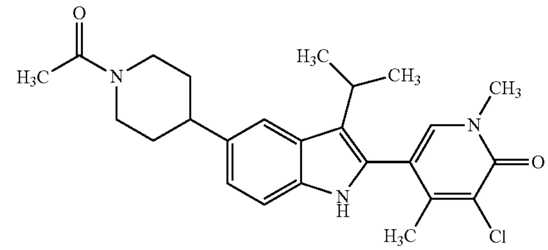 | Ex-31 | 523.3 | 1.2 | QC-ACN-AA-XB |
| 242 | 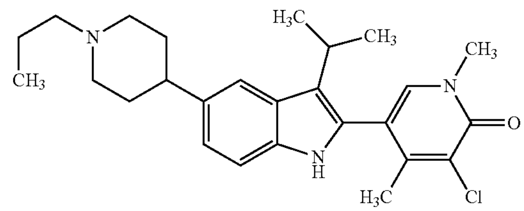 [SMILES: CCCN1CCC(c2ccc3[nH]c(-c4cn(C)c(=O)c(Cl)c4C)c(C(C)C)c3c2)CC1] | Ex-31 | 440 | 1.48 | QC-ACN-AA-XB |
| 243 | 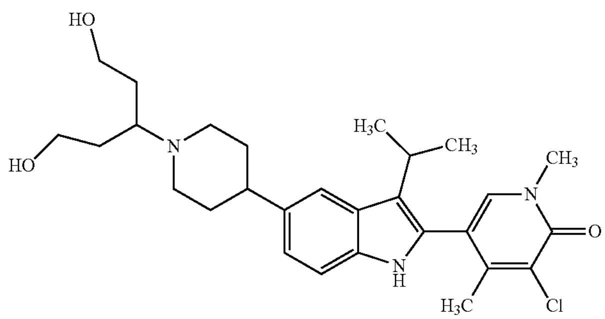 [SMILES: Cc1c(-c2[nH]c3ccc(C4CCN(C(CCO)CCO)CC4)cc3c2C(C)C)cn(C)c(=O)c1Cl] | Ex-31 | 500.4 | 1.25 | QC-ACN-AA-XB |
| 244 | 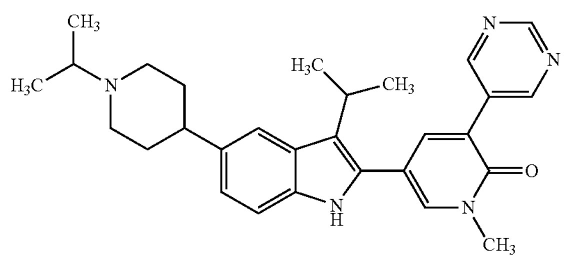 [SMILES: CC(C)c1c(-c2cc(-c3cncnc3)c(=O)n(C)c2)[nH]c2ccc(C3CCN(C(C)C)CC3)cc12] | Ex-54 | 470 | 1.16 | QC-ACN-TFA-XB |
| 245 | 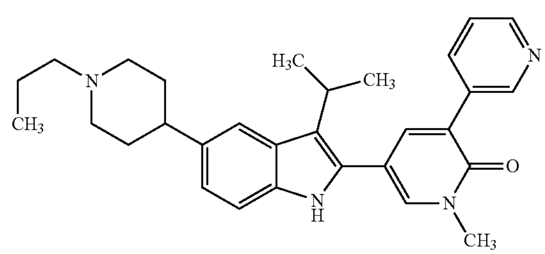 [SMILES: CCCN1CCC(c2ccc3[nH]c(-c4cc(-c5cccnc5)c(=O)n(C)c4)c(C(C)C)c3c2)CC1] | Ex-50 | 469 | 1.28 | QC-ACN-AA-XB |
| 246 | 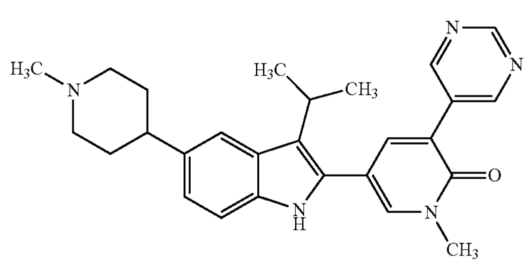 [SMILES: CC(C)c1c(-c2cc(-c3cncnc3)c(=O)n(C)c2)[nH]c2ccc(C3CCN(C)CC3)cc12] | Ex-54 | 442 | 1.14 | QC-ACN-AA-XB |

TABLE 5-continued
| Ex. No. | Structure | Starting Material | LCMS MH+ | Ret Time (min) | HPLC Method |
|---|---|---|---|---|---|
| 247 | 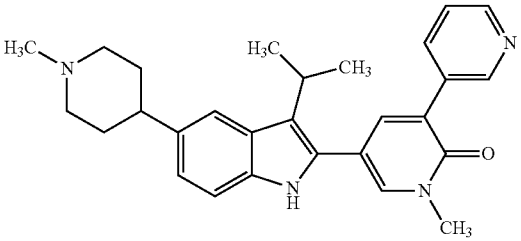 [SMILES: CC(C)c1c(-c2cc(-c3cccnc3)c(=O)n(C)c2)[nH]c2ccc(C3CCN(C)CC3)cc12] | Ex-50 | 441 | 0.85 | QC-ACN-TFA-XB |
| 248 | 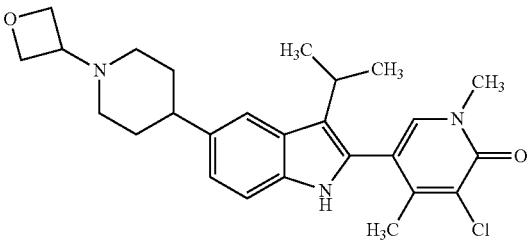 [SMILES: Cc1c(-c2[nH]c3ccc(C4CCN(C5COC5)CC4)cc3c2C(C)C)cn(C)c(=O)c1Cl] | Ex-31 | 454 | 1.75 | QC-ACN-AA-XB |
| 249 | 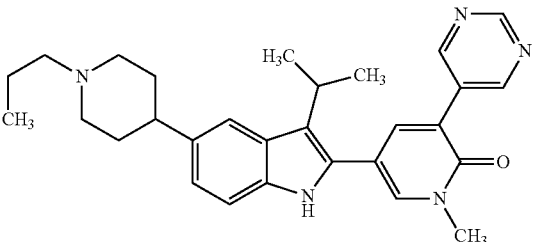 | Ex-54 | 470 | 1.17 | QC-ACN-AA-XB |
| 250 | 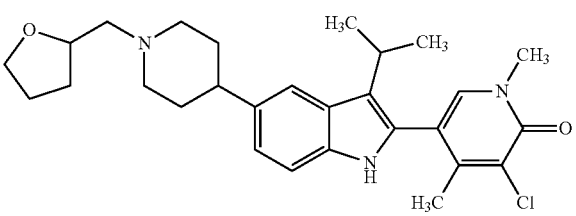 [SMILES: Cc1c(-c2[nH]c3ccc(C4CCN(CC5CCCO5)CC4)cc3c2C(C)C)cn(C)c(=O)c1Cl] | Ex-31 | 482 | 1.4 | QC-ACN-AA-XB |
| 251 | 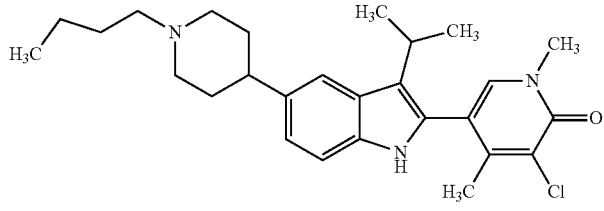 [SMILES: CCCCN1CCC(c2ccc3[nH]c(-c4cn(C)c(=O)c(Cl)c4C)c(C(C)C)c3c2)CC1] | Ex-31 | 454 | 1.51 | QC-ACN-TFA-XB |
| 252 | 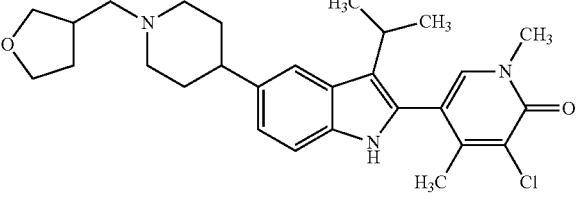 | Ex-31 | 482 | 1.26 | QC-ACN-TFA-XB |

TABLE 5-continued

| Ex. No. | Structure | Starting Material | LCMS MH+ | Ret Time (min) | HPLC Method |
|---|---|---|---|---|---|
| 253 | 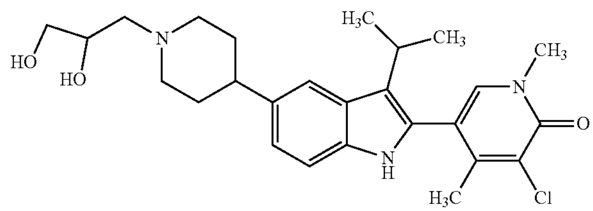 [SMILES: Cc1c(-c2[nH]c3ccc(C4CCN(CC(O)CO)CC4)cc3c2C(C)C)cn(C)c(=O)c1Cl] | Ex-31 | 472 | 1.25 | QC-ACN-TFA-XB |
| 254 | Isomer 1 | Ex-31 | 482.3 | 0.73 | QC-ACN-TFA-XB |
| 255 | Isomer 2 | Ex-31 | 482.3 | 0.73 | QC-ACN-TFA-XB |
| 256 | 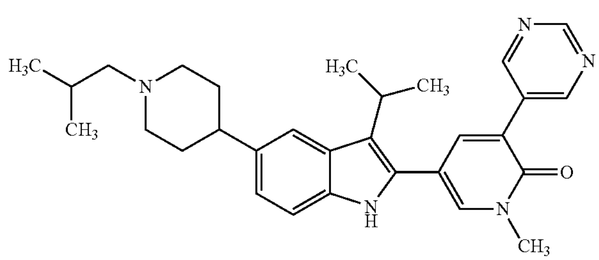 [SMILES: CC(C)CN1CCC(c2ccc3[nH]c(-c4cc(-c5cncnc5)c(=O)n(C)c4)c(C(C)C)c3c2)CC1] | Ex-54 | 484 | 1.26 | QC-ACN-AA-XB |
| 257 | 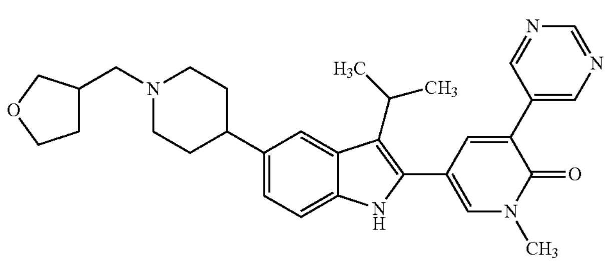 [SMILES: CC(C)c1c(-c2cc(-c3cncnc3)c(=O)n(C)c2)[nH]c2ccc(C3CCN(CC4CCOC4)CC3)cc12] | Ex-54 | 512 | 1.17 | QC-ACN-AA-XB |
| 258 | 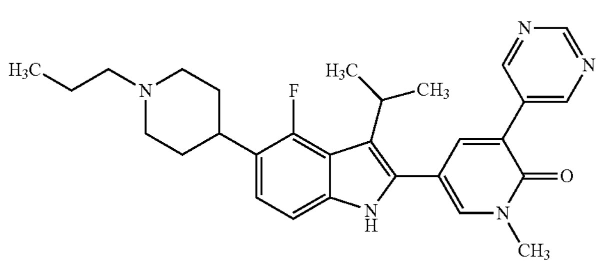 [SMILES: CCCN1CCC(c2ccc3[nH]c(-c4cc(-c5cncnc5)c(=O)n(C)c4)c(C(C)C)c3c2F)CC1] | Ex-54 | 489 | 1.28 | QC-ACN-AA-XB |

TABLE 5-continued
| Ex. No. | Structure | Starting Material | LCMS MH+ | Ret Time (min) | HPLC Method |
|---|---|---|---|---|---|
| 259 | 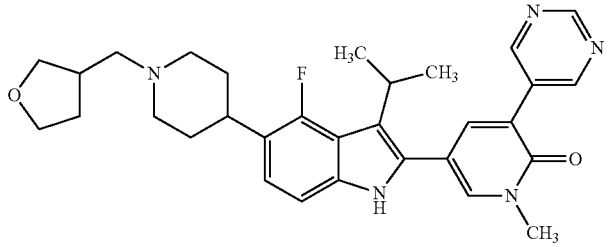 [SMILES: CC(C)c1c(-c2cc(-c3cncnc3)c(=O)n(C)c2)[nH]c2ccc(C3CCN(CC4CCOC4)CC3)c(F)c12] | Ex-54 | 531 | 1.21 | QC-ACN-AA-XB |
| 260 | 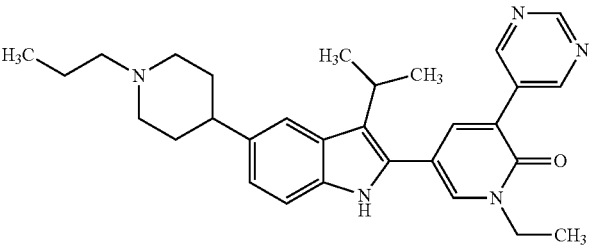 [SMILES: CCCN1CCC(c2ccc3[nH]c(-c4cc(-c5cncnc5)c(=O)n(CC)c4)c(C(C)C)c3c2)CC1] | Ex-54 | 485 | 1.22 | QC-ACN-AA-XB |
| 261 | 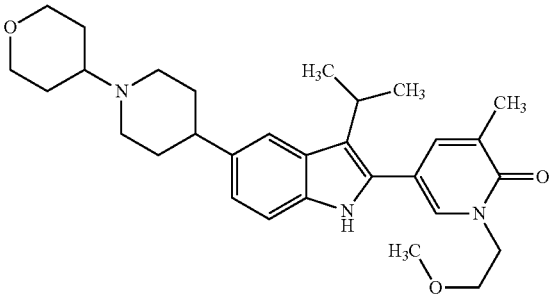 [SMILES: COCCn1cc(-c2[nH]c3ccc(C4CCN(C5CCOCC5)CC4)cc3c2C(C)C)cc(C)c1=O] | Ex-39 | 492.5 | 1.29 | QC-ACN-AA-XB |
| 262 | 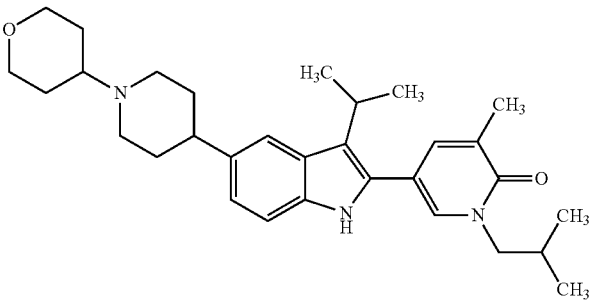 [SMILES: Cc1cc(-c2[nH]c3ccc(C4CCN(C5CCOCC5)CC4)cc3c2C(C)C)cn(CC(C)C)c1=O] | Ex-36 | 490.1 | 1.54 | QC-ACN-AA-XB |
| 263 | 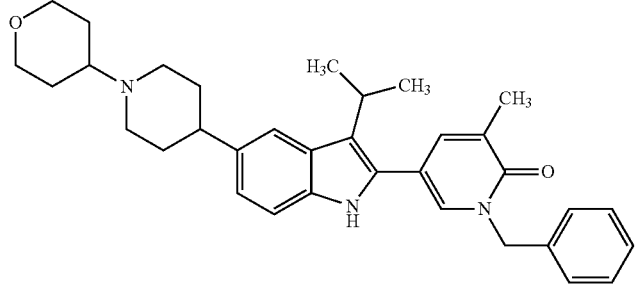 [SMILES: Cc1cc(-c2[nH]c3ccc(C4CCN(C5CCOCC5)CC4)cc3c2C(C)C)cn(Cc2ccccc2)c1=O] | Ex-46 | 524 | 1.66 | QC-ACN-AA-XB |

TABLE 5-continued

| Ex. No. | Structure | Starting Material | LCMS MH+ | Ret Time (min) | HPLC Method |
|---|---|---|---|---|---|
| 264 | 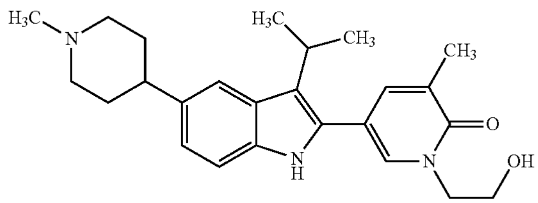 [SMILES: Cc1cc(-c2[nH]c3ccc(C4CCN(C)CC4)cc3c2C(C)C)cn(CCO)c1=O] | Ex-30 | 408 | 1.05 | QC-ACN-TFA-XB |
| 265 | 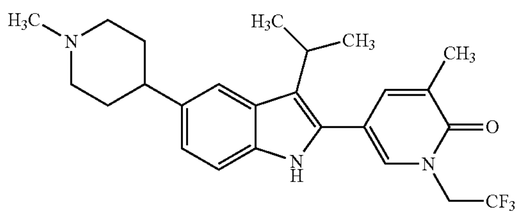 [SMILES: Cc1cc(-c2[nH]c3ccc(C4CCN(C)CC4)cc3c2C(C)C)cn(CC(F)(F)F)c1=O] | Ex-45 | 446 | 1.39 | QC-ACN-AA-XB |
| 266 | 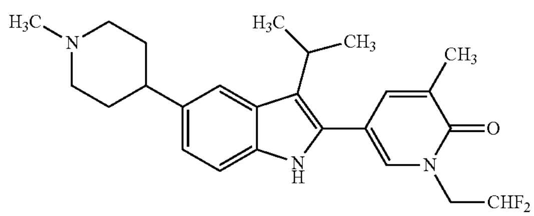 [SMILES: Cc1cc(-c2[nH]c3ccc(C4CCN(C)CC4)cc3c2C(C)C)cn(CC(F)F)c1=O] | Ex-40 | 428 | 1.24 | QC-ACN-AA-XB |
| 267 | Isomer 1 | Ex-2 | 504 | 1.33 | QC-ACN-TFA-XB |
| 268 | Isomer 2 | Ex-2 | 504 | 1.46 | QC-ACN-TFA-XB |

TABLE 5-continued

| Ex. No. | Structure | Starting Material | LCMS MH+ | Ret Time (min) | HPLC Method |
|---|---|---|---|---|---|
| 269 | 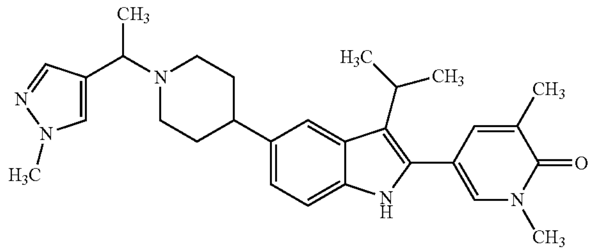 [SMILES: Cc1cc(-c2[nH]c3ccc(C4CCN(C(C)c5cnn(C)c5)CC4)cc3c2C(C)C)cn(C)c1=O] | Ex-2 | 472 | 1.17 | QC-ACN-TFA-XB |
| 270 | 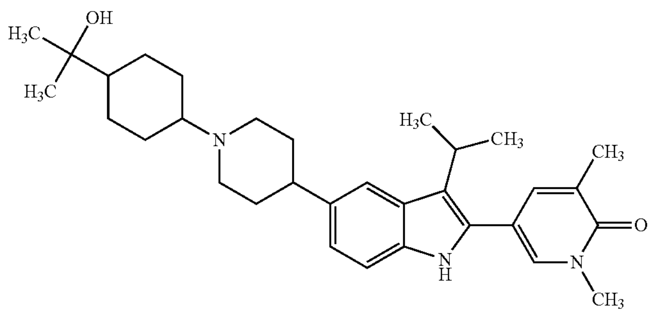 [SMILES: Cc1cc(-c2[nH]c3ccc(C4CCN(C5CCC(C(C)(C)O)CC5)CC4)cc3c2C(C)C)cn(C)c1=O] | Ex-2 | 504.2 | 1.37 | QC-ACN-AA-XB |

Example 271

5-(5-(1-(2-(dimethylamino)acetyl)piperidin-4-yl)-3-isopropyl-1H-indol-2-yl)-1,3-dimethylpyridin-2(1H)-one

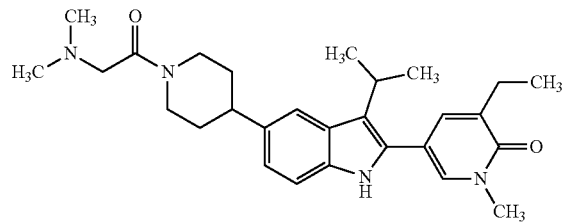

(271)

General Method C: A mixture containing 2-(dimethylamino) acetic acid (12.38 mg, 0.120 mmol), 5-(3-isopropyl-5-(piperidin-4-yl)-1H-indol-2-yl)-1,3-dimethylpyridin-2(1H)-one, HCl (32 mg, 0.080 mmol), and HCTU (49.6 mg, 0.120 mmol) was suspended in THF (1 mL), followed by the addition of TEA (0.045 mL, 0.32 mmol). The reaction mixture was stirred for 7 h and concentrated to dryness under a stream of nitrogen. The residue was suspended in aqueous 0.1 N NaOH (5 mL) and stirred for 30 min. The solids were filtered, rinsed sequentially with additional 0.1 N NaOH and water, and dried to afford 5-(5-(1-(2-(dimethylamino)acetyl)piperidin-4-yl)-3-isopropyl-1H-indol-2-yl)-1,3-dimethylpyridin-2(1H)-one (35 mg, 0.074 mmol, 93% yield). LCMS MEV: 449.2. HPLC Ret. Time 0.67 min. Method B1. $^1$H NMR (400 MHz, CHLOROFORM-d) δ 7.91-7.86 (m, 1H), 7.61-7.57 (m, 1H), 7.36-7.30 (m, 2H), 7.06 (dd, J=8.4, 1.5 Hz, 1H), 4.81 (br d, J=13.5 Hz, 1H), 4.27 (br d, J=13.5 Hz, 1H), 3.64 (s, 3H), 3.26-3.13 (m, 1H), 2.93-2.84 (m, 1H), 2.84-2.80 (s, 2H), 2.76-2.67 (m, 1H), 2.35 (s, 6H, 2.24 (s, 3H), 1.99 (br m, J=12.7 Hz, 1H), 1.81-1.59 (m, 4H), 1.47 (d, J=7.0 Hz, 6H).

Example 272

5-(5-(1-(1-aminocyclopropanecarbonyl)piperidin-4-yl)-3-isopropyl-1H-indol-2-yl)-1,3-dimethylpyridin-2(1H)-one

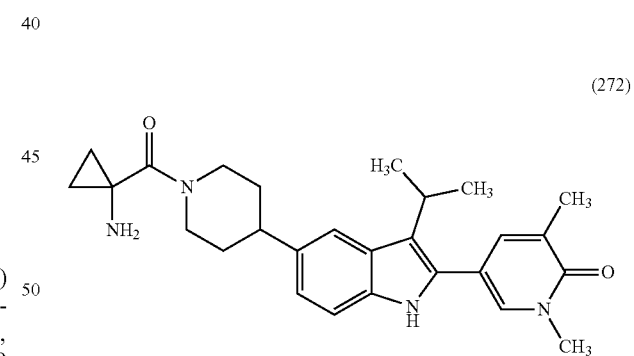

(272)

A mixture containing 1-((tert-butoxycarbonyl)amino)cyclopropanecarboxylic acid (15.3 mg, 0.075 mmol), 5-(3-isopropyl-5-(piperidin-4-yl)-1H-indol-2-yl)-1,3-dimethylpyridin-2(1H)-one, HCl (20 mg, 0.050 mmol), and HCTU (31.0 mg, 0.075 mmol) was suspended in THF (0.5 mL) and TEA (0.035 mL, 0.250 mmol) was added. The reaction mixture was stirred for 20 h, diluted with ethyl acetate (4 mL) and washed with 1N NaOH (2×1 mL) and saturated aqueous NaCl solution (1 mL) and concentrated. The residue was treated with TFA (1 mL) for 30 min to facilitate the removal of the Boc groups. The reaction mixture was re-concentrated to dryness and re-dissolved in DMF (2 mL). The sample was filtered through an Acrodisc, 13 mm, 0.45 micron nylon membrane syringe filter. The crude material was purified via preparative LC/MS. Fractions containing the product were combined and dried via centrifugal evaporation to afford 5-(5-(1-(1-aminocyclopropanecarbonyl)piperidin-4-yl)-3-isopropyl-1H-indol-2-yl)-1,3-dimethylpyridin-2(1H)-one (2.6 mg, 12%). LCMS MH+: 449.2. HPLC Ret. Time 1.21 min. Method-QC-ACN-AA-XB. $^1$H NMR (500 MHz, DMSO-$d_6$) δ 10.79 (s, 1H), 7.66-7.59 (m, 1H), 7.47 (s, 1H), 7.43 (br s, 1H), 7.23 (br d, J=8.3 Hz, 1H), 6.95 (br d, J=8.2 Hz, 1H), 4.44 (br d, J=12.5 Hz, 2H), 3.66-3.59 (m, 3H), 3.19-3.09 (m, 2H), 2.90-2.71 (m, 2H), 2.54 (s, 1H), 2.07 (s, 3H), 1.86-1.75 (m, 3H), 1.69-1.48 (m, 2H), 1.37 (br d, J=6.8 Hz, 6H), 0.83 (br s, 2H), 0.67 (br s, 2H).

The following examples were prepared according to the general method for Examples 271 or Example 272, using the indicated starting material.

TABLE 6

| Ex. No. | Structure | Starting Material | LCMS MH+ | Ret Time (min) | HPLC Method |
|---|---|---|---|---|---|
| 273 | 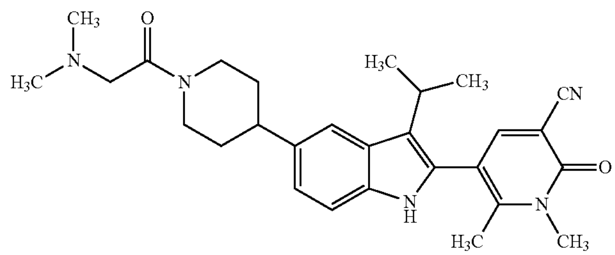 [SMILES: Cc1c(-c2[nH]c3ccc(C4CCN(C(=O)CN(C)C)CC4)cc3c2C(C)C)cc(C#N)c(=O)n1C] | Ex-23 | 473.9 | 1.33 | QC-ACN-AA-XB |
| 274 | 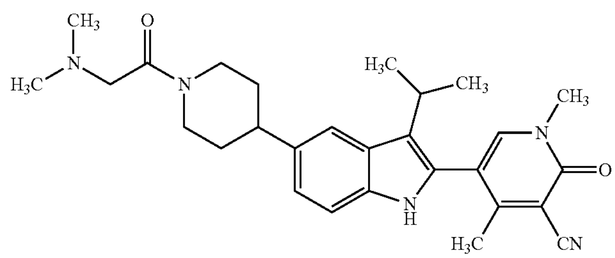 [SMILES: Cc1c(-c2[nH]c3ccc(C4CCN(C(=O)CN(C)C)CC4)cc3c2C(C)C)cn(C)c(=O)c1C#N] | Ex-24 | 474.2 | 1.36 | QC-ACN-AA-XB |
| 275 | 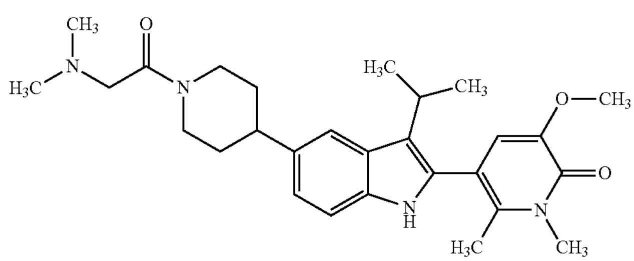 | Ex-28 | 479.2 | 0.65 | QC-ACN-TFA-XB |
| 276 | 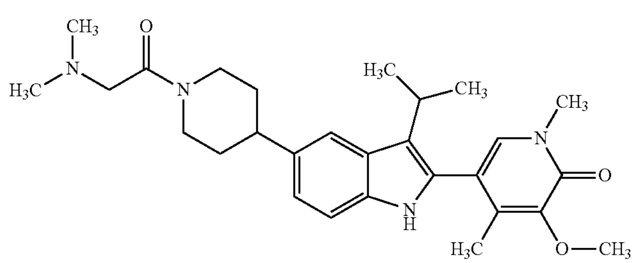 | Ex-29 | 479.1 | 1.18 | QC-ACN-AA-XB |
| 277 | 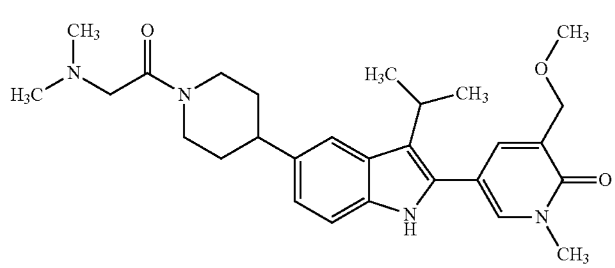 [SMILES: COCc1cc(-c2[nH]c3ccc(C4CCN(C(=O)CN(C)C)CC4)cc3c2C(C)C)cn(C)c1=O] | Ex-353 | 479.4 | 1.29 | QC-ACN-TFA-XB |

TABLE 6-continued

| Ex. No. | Structure | Starting Material | LCMS MH+ | Ret Time (min) | HPLC Method |
|---|---|---|---|---|---|
| 278 | 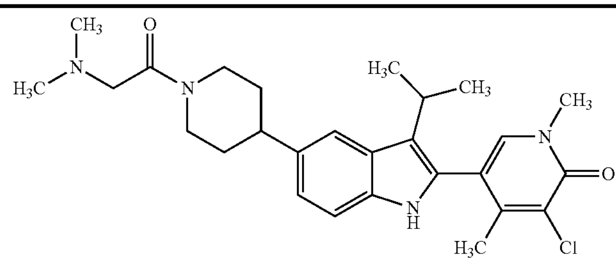 | Ex-31 | 483 | 1.54 | QC-ACN-AA-XB |
| 279 | 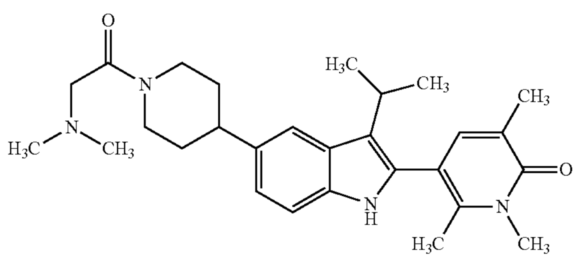 [SMILES: Cc1cc(-c2[nH]c3ccc(C4CCN(C(=O)CN(C)C)CC4)cc3c2C(C)C)c(C)n(C)c1=O] | Ex-3 | 463.4 | 1.28 | QC-ACN-AA-XB |
| 280 | 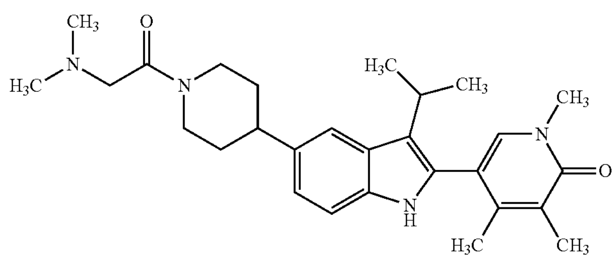 | Ex-14 | 463.2 | 1.44 | QC-ACN-AA-XB |
| 281 | 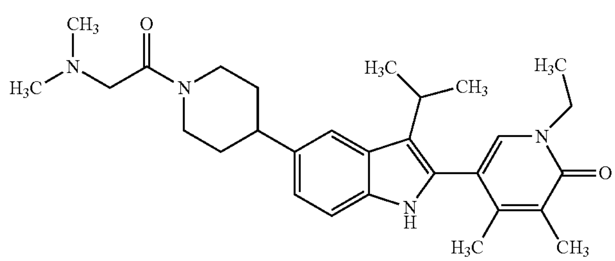 [SMILES: CCn1cc(-c2[nH]c3ccc(C4CCN(C(=O)CN(C)C)CC4)cc3c2C(C)C)c(C)c(C)c1=O] | Ex-26 | 477.1 | 1.3 | QC-ACN-AA-XB |
| 282 | 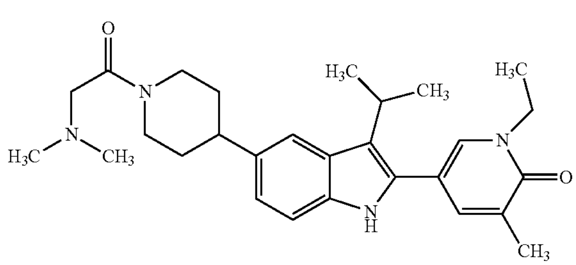 [SMILES: CCn1cc(-c2[nH]c3ccc(C4CCN(C(=O)CN(C)C)CC4)cc3c2C(C)C)cc(C)c1=O] | Ex-15 | 463.2 | 1.45 | QC-ACN-AA-XB |
| 283 | 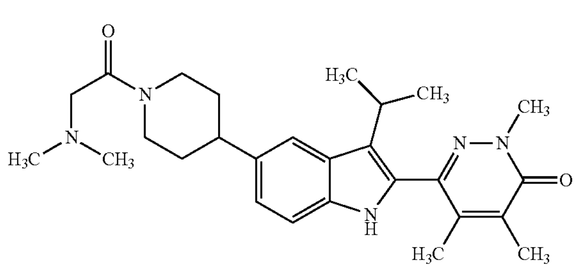 [SMILES: Cc1c(-c2[nH]c3ccc(C4CCN(C(=O)CN(C)C)CC4)cc3c2C(C)C)nn(C)c(=O)c1C] | Ex-17 | 464.4 | 0.69 | QC-ACN-TFA-XB |

TABLE 6-continued
| Ex. No. | Structure | Starting Material | LCMS MH+ | Ret Time (min) | HPLC Method |
|---|---|---|---|---|---|
| 284 | 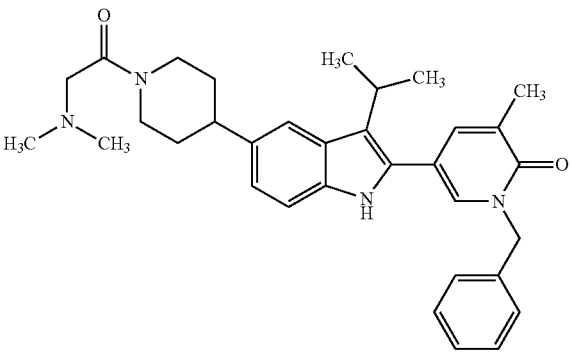 [SMILES: Cc1cc(-c2[nH]c3ccc(C4CCN(C(=O)CN(C)C)CC4)cc3c2C(C)C)cn(Cc2ccccc2)c1=O] | Ex-46 | 525.6 | 1.66 | QC-ACN-AA-XB |
| 285 | 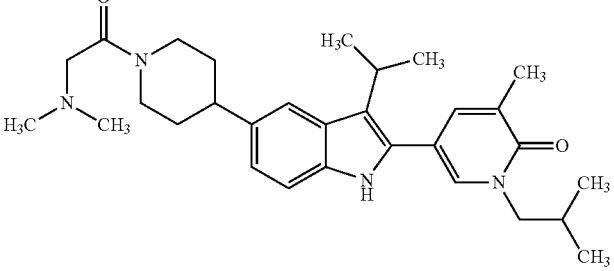 | Ex-36 | 491 | 1.56 | QC-ACN-AA-XB |
| 286 | 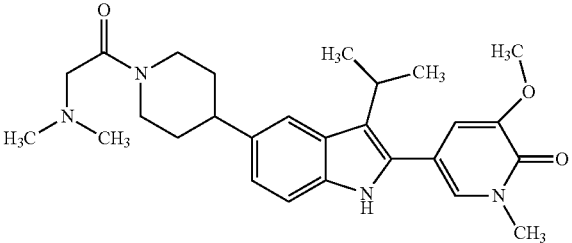 [SMILES: COc1cc(-c2[nH]c3ccc(C4CCN(C(=O)CN(C)C)CC4)cc3c2C(C)C)cn(C)c1=O] | Ex-20 | 465.4 | 0.62 | QC-ACN-TFA-XB |
| 287 | 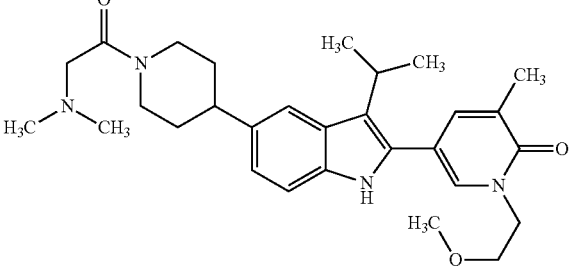 | Ex-39 | 493 | 1.37 | QC-ACN-AA-XB |
| 288 | 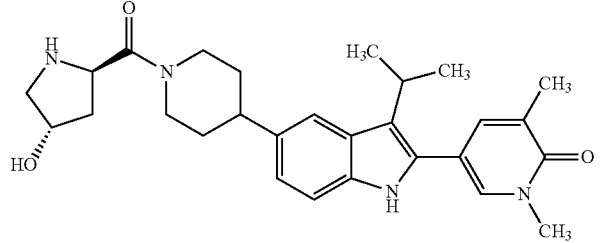 [SMILES: Cc1cc(-c2[nH]c3ccc(C4CCN(C(=O)[C@H]5C[C@H](O)CN5)CC4)cc3c2C(C)C)cn(C)c1=O] | Ex-2 | 477.3 | 1.17 | QC-ACN-AA-XB |

TABLE 6-continued

| Ex. No. | Structure | Starting Material | LCMS MH+ | Ret Time (min) | HPLC Method |
|---|---|---|---|---|---|
| 289 | 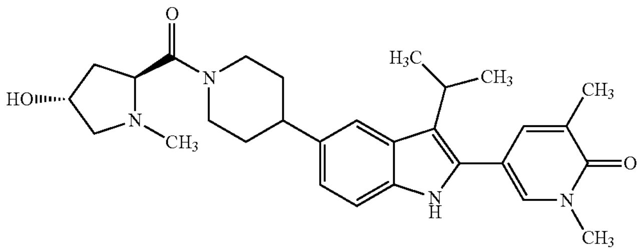 [SMILES: Cc1cc(-c2[nH]c3ccc(C4CCN(C(=O)[C@@H]5C[C@@H](O)CN5C)CC4)cc3c2C(C)C)cn(C)c1=O] | Ex-2 | 491.2 | 1.2 | QC-ACN-AA-XB |
| 290 | 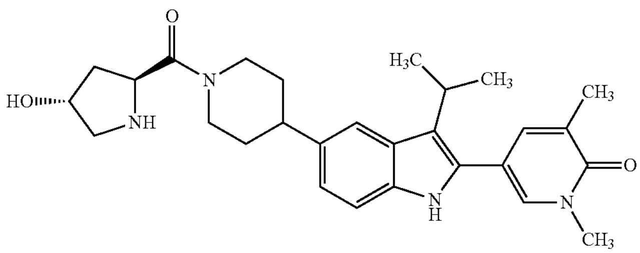 [SMILES: Cc1cc(-c2[nH]c3ccc(C4CCN(C(=O)[C@@H]5C[C@@H](O)CN5)CC4)cc3c2C(C)C)cn(C)c1=O] | Ex-2 | 477.3 | 1.08 | QC-ACN-AA-XB |
| 291 | 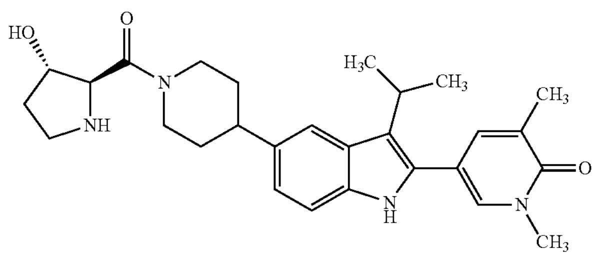 [SMILES: Cc1cc(-c2[nH]c3ccc(C4CCN(C(=O)[C@H]5NCC[C@@H]5O)CC4)cc3c2C(C)C)cn(C)c1=O] | Ex-2 | 477.2 | 1.16 | QC-ACN-AA-XB |
| 292 | 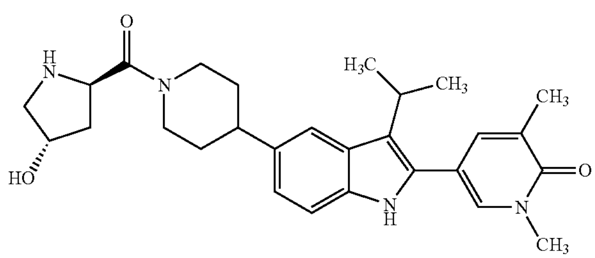 [SMILES: Cc1cc(-c2[nH]c3ccc(C4CCN(C(=O)[C@H]5C[C@H](O)CN5)CC4)cc3c2C(C)C)cn(C)c1=O] | Ex-2 | 477.4 | 1.14 | QC-ACN-TFA-XB |
| 293 | 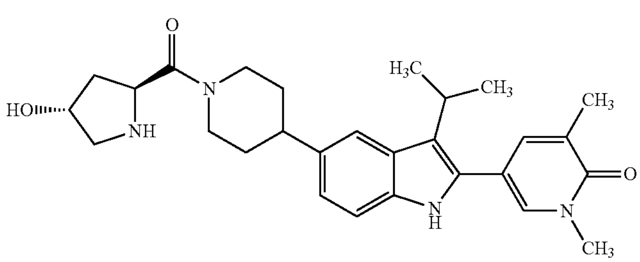 [SMILES: Cc1cc(-c2[nH]c3ccc(C4CCN(C(=O)[C@@H]5C[C@@H](O)CN5)CC4)cc3c2C(C)C)cn(C)c1=O] | Ex-2 | 477.4 | 1.19 | QC-ACN-AA-XB |
| 294 | 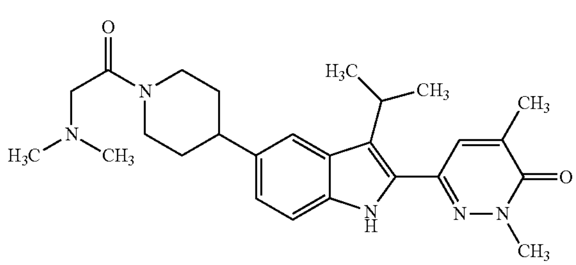 [SMILES: Cc1cc(-c2[nH]c3ccc(C4CCN(C(=O)CN(C)C)CC4)cc3c2C(C)C)nn(C)c1=O] | Ex-11 | 450.2 | 1.22 | QC-ACN-TFA-XB |

TABLE 6-continued

| Ex. No. | Structure | Starting Material | LCMS MH+ | Ret Time (min) | HPLC Method |
|---|---|---|---|---|---|
| 295 | 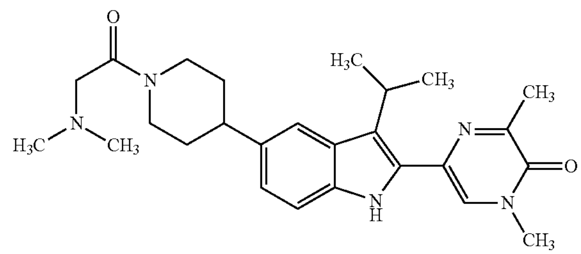 [SMILES: Cc1nc(-c2[nH]c3ccc(C4CCN(C(=O)CN(C)C)CC4)cc3c2C(C)C)cn(C)c1=O] | Ex-12 | 450.4 | 1.26 | QC-ACN-AA-XB |
| 296 | 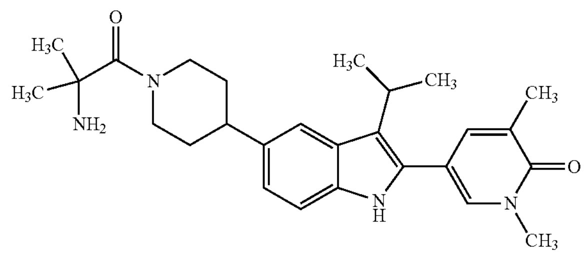 [SMILES: Cc1cc(-c2[nH]c3ccc(C4CCN(C(=O)C(C)(C)N)CC4)cc3c2C(C)C)cn(C)c1=O] | Ex-2 | 449.5 | 0.67 | QC-ACN-TFA-XB |
| 297 | 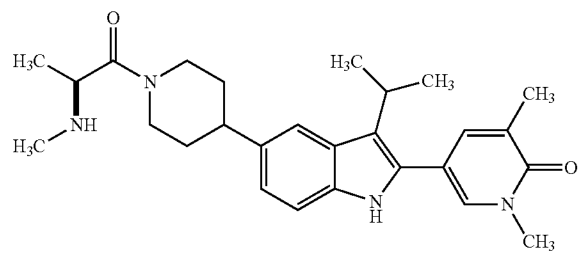 [SMILES: CN[C@@H](C)C(=O)N1CCC(c2ccc3[nH]c(-c4cc(C)c(=O)n(C)c4)c(C(C)C)c3c2)CC1] | Ex-2 | 449.2 | 1.21 | QC-ACN-AA-XB |
| 298 | 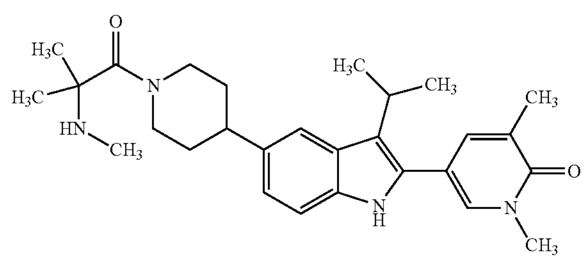 [SMILES: CNC(C)(C)C(=O)N1CCC(c2ccc3[nH]c(-c4cc(C)c(=O)n(C)c4)c(C(C)C)c3c2)CC1] | Ex-2 | 463.4 | 1.4 | QC-ACN-AA-XB |
| 299 | 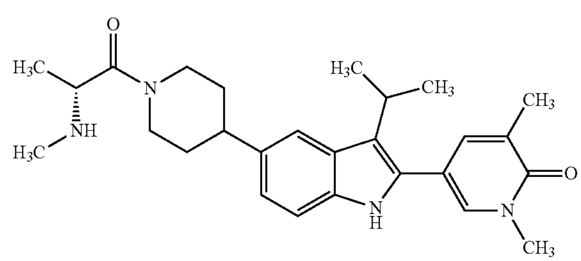 [SMILES: CN[C@H](C)C(=O)N1CCC(c2ccc3[nH]c(-c4cc(C)c(=O)n(C)c4)c(C(C)C)c3c2)CC1] | Ex-2 | 449.2 | 1.21 | QC-ACN-TFA-XB |
| 300 | 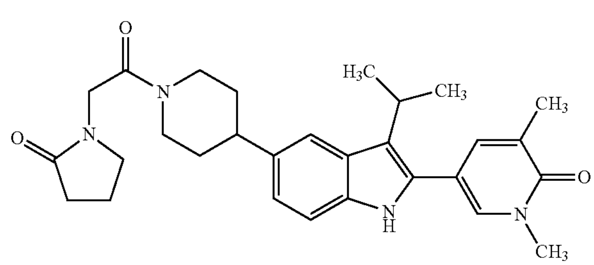 [SMILES: Cc1cc(-c2[nH]c3ccc(C4CCN(C(=O)CN5CCCC5=O)CC4)cc3c2C(C)C)cn(C)c1=O] | Ex-2 | 489.1 | 1.42 | QC-ACN-AA-XB |

TABLE 6-continued

| Ex. No. | Structure | Starting Material | LCMS MH+ | Ret Time (min) | HPLC Method |
|---|---|---|---|---|---|
| 301 | 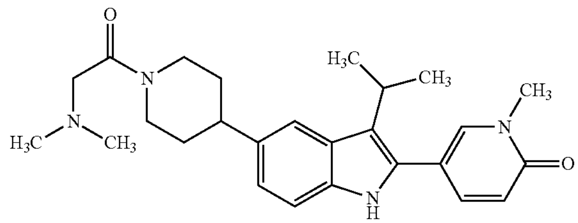 [SMILES: CC(C)c1c(-c2ccc(=O)n(C)c2)[nH]c2ccc(C3CCN(C(=O)CN(C)C)CC3)cc12] | Ex-1 | 435.1 | 1.06 | QC-ACN-TFA-XB |
| 302 | 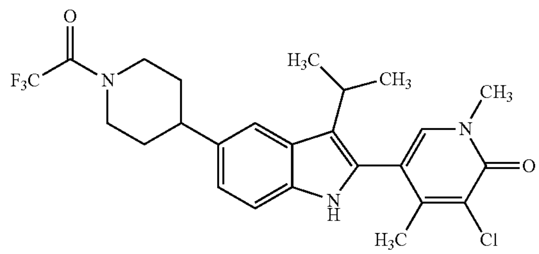 | Ex-31 | 494.2 | 2.13 | QC-ACN-AA-XB |
| 303 | 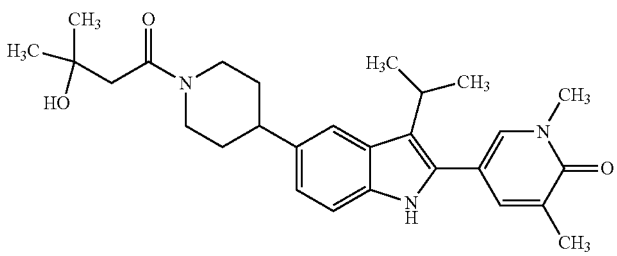 [SMILES: Cc1cc(-c2[nH]c3ccc(C4CCN(C(=O)CC(C)(C)O)CC4)cc3c2C(C)C)cn(C)c1=O] | Ex-2 | 464.3 | 1.68 | QC-ACN-AA-XB |
| 304 | 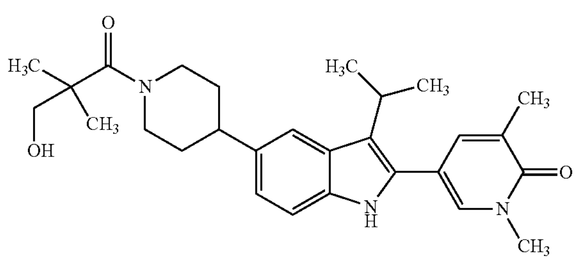 [SMILES: Cc1cc(-c2[nH]c3ccc(C4CCN(C(=O)C(C)(C)CO)CC4)cc3c2C(C)C)cn(C)c1=O] | Ex-2 | 464 | 1.7 | QC-ACN-AA-XB |
| 305 | 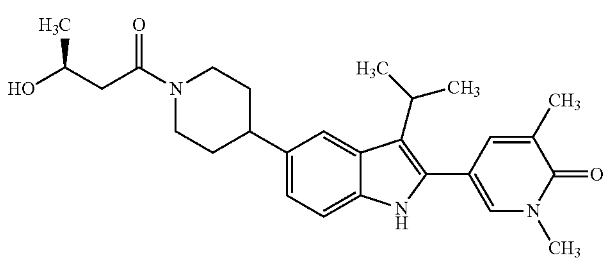 [SMILES: Cc1cc(-c2[nH]c3ccc(C4CCN(C(=O)C[C@H](C)O)CC4)cc3c2C(C)C)cn(C)c1=O] | Ex-2 | 450 | 1.51 | QC-ACN-TFA-XB |
| 306 | 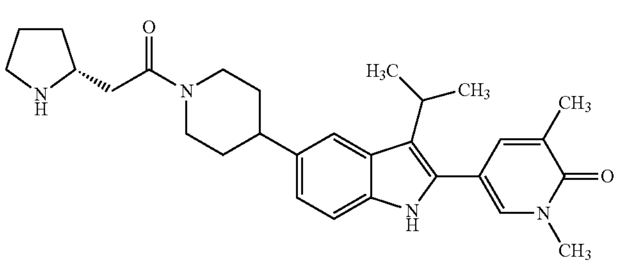 [SMILES: Cc1cc(-c2[nH]c3ccc(C4CCN(C(=O)C[C@H]5CCCN5)CC4)cc3c2C(C)C)cn(C)c1=O] | Ex-2 | 475.4 | 1.27 | QC-ACN-TFA-XB |

TABLE 6-continued

| Ex. No. | Structure | Starting Material | LCMS MH+ | Ret Time (min) | HPLC Method |
|---|---|---|---|---|---|
| 307 | 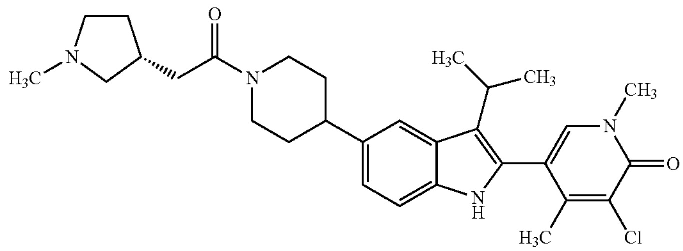 [SMILES: Cc1c(-c2[nH]c3ccc(C4CCN(C(=O)C[C@H]5CCN(C)C5)CC4)cc3c2C(C)C)cn(C)c(=O)c1Cl] | Ex-31 | 524.4 | 0.74 | QC-ACN-TFA-XB |
| 308 | 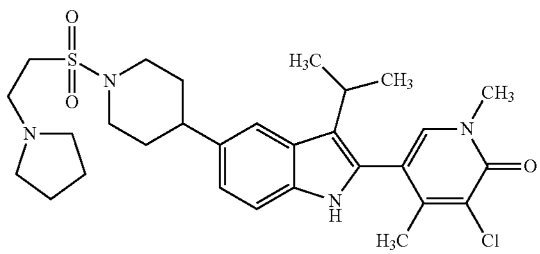 [SMILES: Cc1c(-c2[nH]c3ccc(C4CCN(S(=O)(=O)CCN5CCCC5)CC4)cc3c2C(C)C)cn(C)c(=O)c1Cl] | Ex-31 | 559.3 | 1.74 | QC-ACN-AA-XB |

Example 309

3-chloro-5-(5-(1-(2-hydroxy-2-methylpropyl)piperidin-4-yl)-3-isopropyl-1H-indol-2-yl)-1,4-dimethylpyridin-2(1H)-one

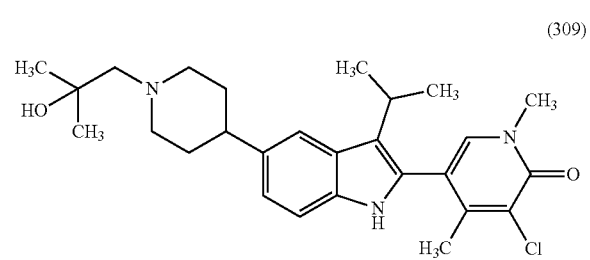 [SMILES: Cc1c(-c2[nH]c3ccc(C4CCN(CC(C)(C)O)CC4)cc3c2C(C)C)cn(C)c(=O)c1Cl]

(309)

General Method D: Tert-butyl 4-(2-(5-chloro-1,4-dimethyl-6-oxo-1,6-dihydropyridin-3-yl)-3-isopropyl-1H-indol-5-yl)piperidine-1-carboxylate (25 mg, 0.050 mmol) was deprotected with 2:1 trifluoroacetic acid/dichloromethane (1.2 mL, 0.050 mmol) for 45 min. Toluene (0.2 mL) was added to the reaction mixture and excess solvent was evaporated. The resulting residue was stirred with isobutylene oxide (0.023 mL, 0.251 mmol) and potassium carbonate (41.6 mg, 0.301 mmol) in methanol (0.502 mL) at room temperature for 19 h. The reaction mixture was partitioned between water and ethyl acetate (~3.5 mL total volume). The phases were separated, and the aqueous phase was extracted with ethyl acetate (2×1 mL). The organic phases were combined and excess solvent was evaporated off. DMF (1 mL) was added to the resulting yellow residue, and the crude material was purified via preparative LC/MS. Fractions containing the product were combined and dried via centrifugal evaporation. The yield of 3-chloro-5-(5-(1-(2-hydroxy-2-methylpropyl)piperidin-4-yl)-3-isopropyl-1H-indol-2-yl)-1,4-dimethylpyridin-2(1H)-one was 19.8 mg (82%), and its estimated purity by LCMS analysis was 98%. LCMS MH+: 470.3. HPLC Ret. Time 1.26 min. Method: QC-ACN-TFA-XB. $^1$H NMR: (500 MHz, DMSO-$d_6$) δ 10.77 (s, 1H), 7.71 (s, 1H), 7.47 (s, 1H), 7.22 (d, J=8.3 Hz, 1H), 6.99 (d, J=8.2 Hz, 1H), 3.05 (d, J=11.2 Hz, 2H), 2.90 (dt, J=14.0, 7.0 Hz, 1H), 2.30-2.22 (m, 4H), 2.06 (s, 3H), 1.90 (s, 2H), 1.78-1.68 (m, 4H), 1.30 (d, J=6.5 Hz, 6H), 1.11 (s, 6H).

The following examples were prepared in a manner similar to Example 309, using the indicated starting material.

TABLE 7

| Ex. No. | Structure | Starting Material | LCMS MH+ | Ret Time (min) | HPLC Method |
|---|---|---|---|---|---|
| 310 | 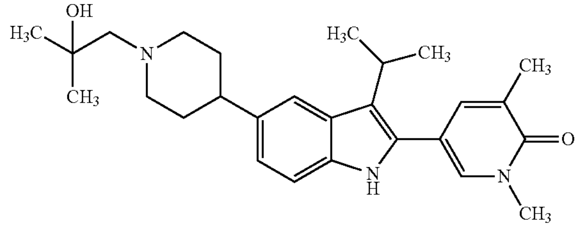 | Ex-2 | 436 | 1.45 | QC-ACN-TFA-XB |

TABLE 7-continued

| Ex. No. | Structure | Starting Material | LCMS MH+ | Ret Time (min) | HPLC Method |
|---|---|---|---|---|---|
| 311 | 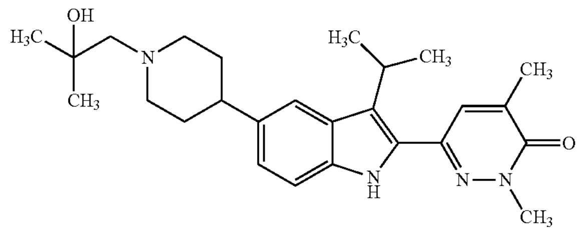 [SMILES: Cc1cc(-c2[nH]c3ccc(C4CCN(CC(C)(C)O)CC4)cc3c2C(C)C)nn(C)c1=O] | Ex-11 | 437 | 1.18 | QC-ACN-TFA-XB |
| 312 | 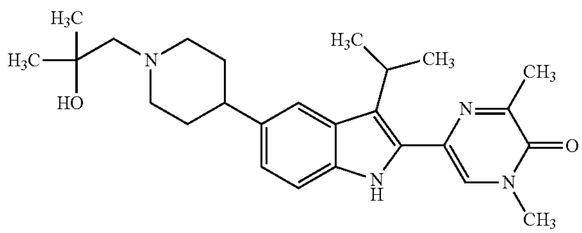 [SMILES: Cc1nc(-c2[nH]c3ccc(C4CCN(CC(C)(C)O)CC4)cc3c2C(C)C)cn(C)c1=O] | Ex-12 | 437 | 1.28 | QC-ACN-AA-XB |
| 313 | 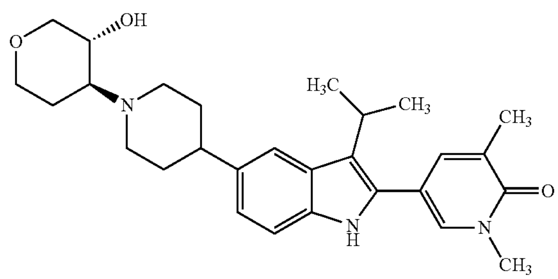 [SMILES: Cc1cc(-c2[nH]c3ccc(C4CCN([C@H]5CCOC[C@@H]5O)CC4)cc3c2C(C)C)cn(C)c1=O] | Ex-2 | 464 | 1.25 | QC-ACN-AA-XB |
| 314 | 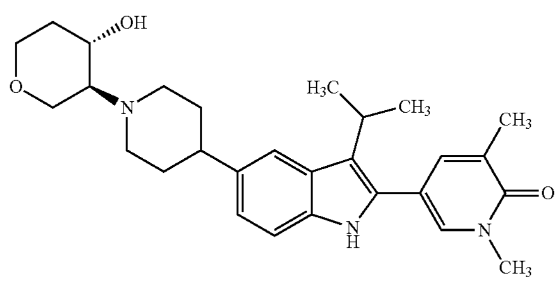 [SMILES: Cc1cc(-c2[nH]c3ccc(C4CCN([C@H]5COCC[C@@H]5O)CC4)cc3c2C(C)C)cn(C)c1=O] | Ex-2 | 464 | 1.42 | QC-ACN-AA-XB |
| 315 | 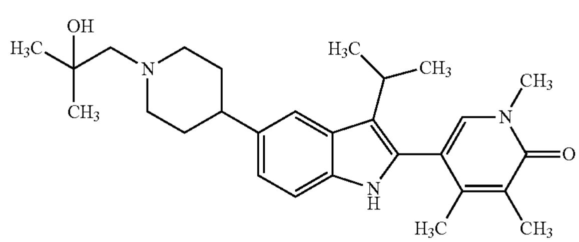 [SMILES: Cc1c(-c2[nH]c3ccc(C4CCN(CC(C)(C)O)CC4)cc3c2C(C)C)cn(C)c(=O)c1C] | Ex-14 | 450.3 | 0.68 | QC-ACN-TFA-XB |
| 316 | 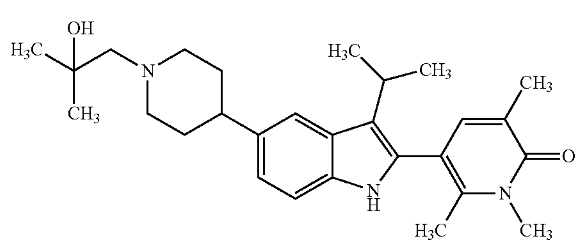 | Ex-3 | 450.3 | 0.68 | QC-ACN-TFA-XB |

TABLE 7-continued

| Ex. No. | Structure | Starting Material | LCMS MH+ | Ret Time (min) | HPLC Method |
|---|---|---|---|---|---|
| 317 | 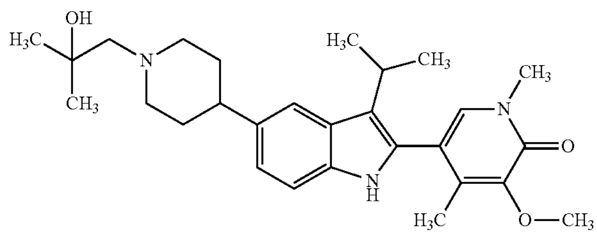 [SMILES: COc1c(C)c(-c2[nH]c3ccc(C4CCN(CC(C)(C)O)CC4)cc3c2C(C)C)cn(C)c1=O] | Ex-29 | 466.0 | 0.65 | QC-ACN-TFA-XB |
| 318 | 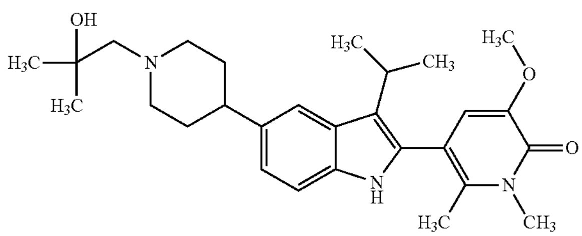 [SMILES: COc1cc(-c2[nH]c3ccc(C4CCN(CC(C)(C)O)CC4)cc3c2C(C)C)c(C)n(C)c1=O] | Ex-28 | 466.1 | 0.64 | QC-ACN-TFA-XB |
| 319 | 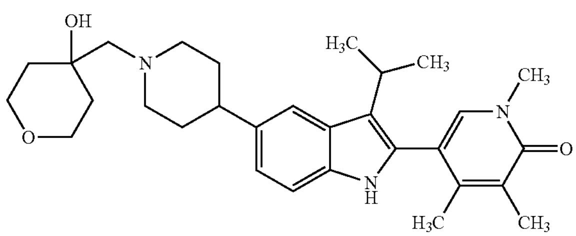 [SMILES: Cc1c(-c2[nH]c3ccc(C4CCN(CC5(O)CCOCC5)CC4)cc3c2C(C)C)cn(C)c(=O)c1C] | Ex-14 | 492.3 | 0.67 | QC-ACN-TFA-XB |
| 320 | 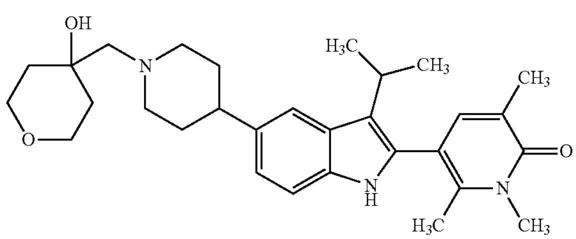 [SMILES: Cc1cc(-c2[nH]c3ccc(C4CCN(CC5(O)CCOCC5)CC4)cc3c2C(C)C)c(C)n(C)c1=O] | Ex-3 | 492.3 | 0.67 | QC-ACN-TFA-XB |
| 321 | 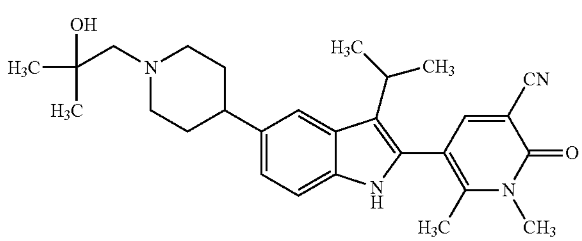 [SMILES: Cc1c(-c2[nH]c3ccc(C4CCN(CC(C)(C)O)CC4)cc3c2C(C)C)cc(C#N)c(=O)n1C] | Ex-23 | 461.1 | 0.67 | QC-ACN-TFA-XB |
| 322 | 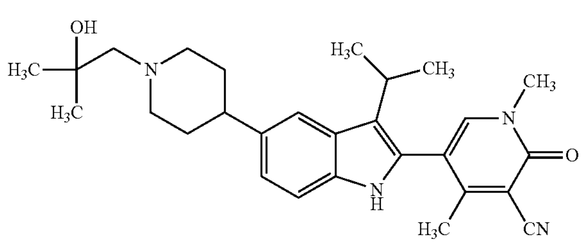 [SMILES: Cc1c(-c2[nH]c3ccc(C4CCN(CC(C)(C)O)CC4)cc3c2C(C)C)cn(C)c(=O)c1C#N] | Ex-24 | 461.0 | 0.70 | QC-ACN-TFA-XB |

TABLE 7-continued

| Ex. No. | Structure | Starting Material | LCMS MH+ | Ret Time (min) | HPLC Method |
|---|---|---|---|---|---|
| 323 | 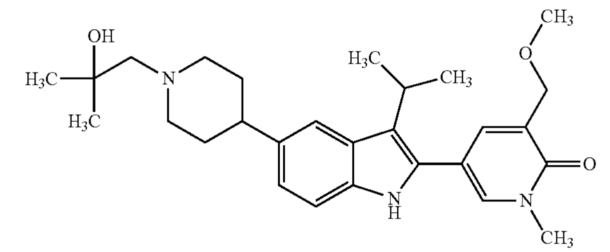 [SMILES: COCc1cc(-c2[nH]c3ccc(C4CCN(CC(C)(C)O)CC4)cc3c2C(C)C)cn(C)c1=O] | Ex-353 | 466 | 1.15 | QC-ACN-AA-XB |
| 324 | 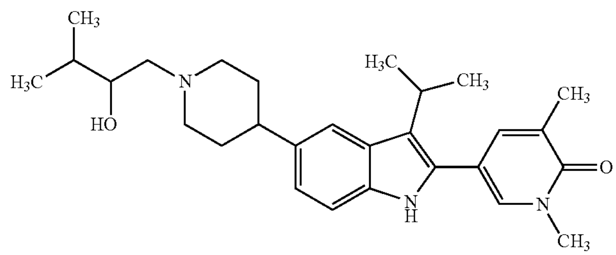 [SMILES: Cc1cc(-c2[nH]c3ccc(C4CCN(CC(O)C(C)C)CC4)cc3c2C(C)C)cn(C)c1=O] | Ex-2 | 450 | 1.38 | QC-ACN-AA-XB |
| 325 | 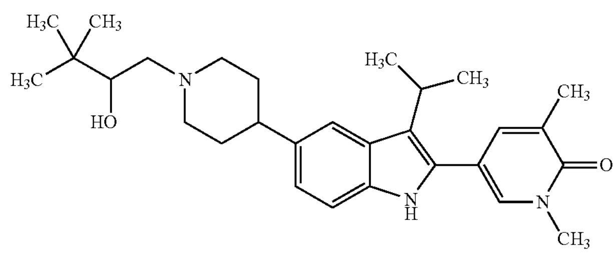 [SMILES: Cc1cc(-c2[nH]c3ccc(C4CCN(CC(O)C(C)(C)C)CC4)cc3c2C(C)C)cn(C)c1=O] | Ex-2 | 464.4 | 0.74 | QC-ACN-AA-XB B1 |
| 326 | 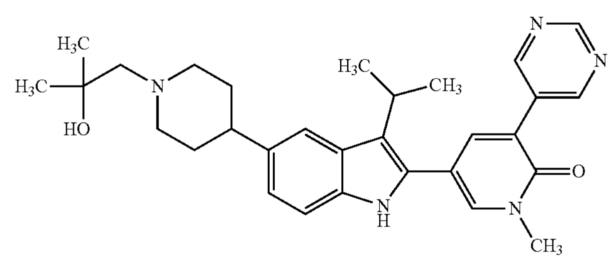 [SMILES: CC(C)c1c(-c2cc(-c3cncnc3)c(=O)n(C)c2)[nH]c2ccc(C3CCN(CC(C)(C)O)CC3)cc12] | Ex-54 | 500 | 1.11 | QC-ACN-TFA-XB |
| 327 | 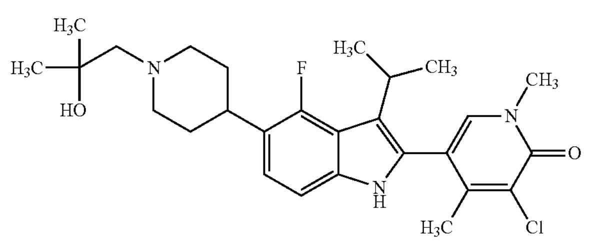 [SMILES: Cc1c(-c2[nH]c3ccc(C4CCN(CC(C)(C)O)CC4)c(F)c3c2C(C)C)cn(C)c(=O)c1Cl] | Ex-31 | 489 | 1.41 | QC-ACN-TFA-XB |
| 328 | 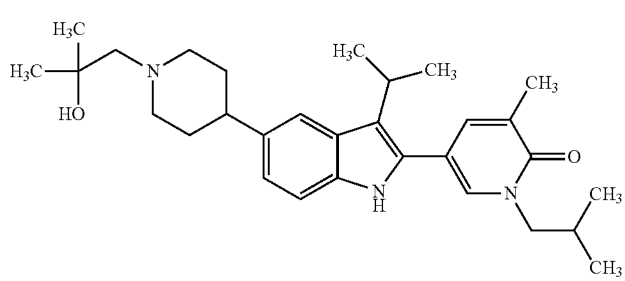 [SMILES: Cc1cc(-c2[nH]c3ccc(C4CCN(CC(C)(C)O)CC4)cc3c2C(C)C)cn(CC(C)C)c1=O] | Ex-36 | 478 | 1.57 | QC-ACN-TFA-XB |

TABLE 7-continued

| Ex. No. | Structure | Starting Material | LCMS MH+ | Ret Time (min) | HPLC Method |
|---|---|---|---|---|---|
| 329 | 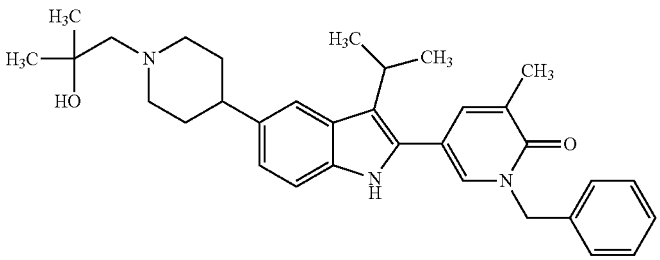 [SMILES: Cc1cc(-c2[nH]c3ccc(C4CCN(CC(C)(C)O)CC4)cc3c2C(C)C)cn(Cc2ccccc2)c1=O] | Ex-46 | 512 | 1.72 | QC-ACN-AA-XB |

The following examples were prepared according to the general procedures for the above examples.

TABLE 8

| Ex. No. | Structure | LCMS MH+ | Ret Time (min) | HPLC Method |
|---|---|---|---|---|
| 330 | 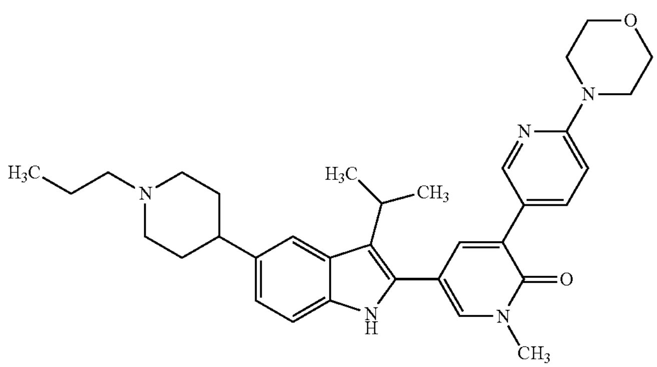 [SMILES: CCCN1CCC(c2ccc3[nH]c(-c4cc(-c5ccc(N6CCOCC6)nc5)c(=O)n(C)c4)c(C(C)C)c3c2)CC1] | 554.2 | 1.4 | QC-ACN-AA-XB |
| 331 | 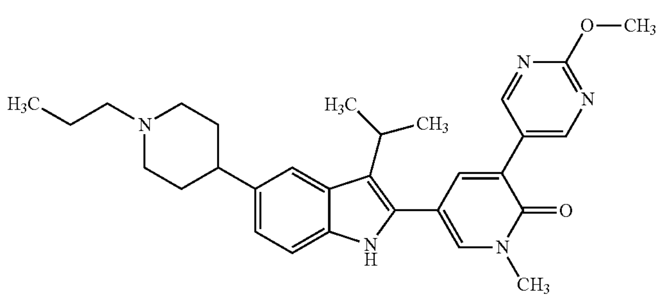 [SMILES: CCCN1CCC(c2ccc3[nH]c(-c4cc(-c5cnc(OC)nc5)c(=O)n(C)c4)c(C(C)C)c3c2)CC1] | 500 | 1.7 | QC-ACN-AA-XB |
| 332 | 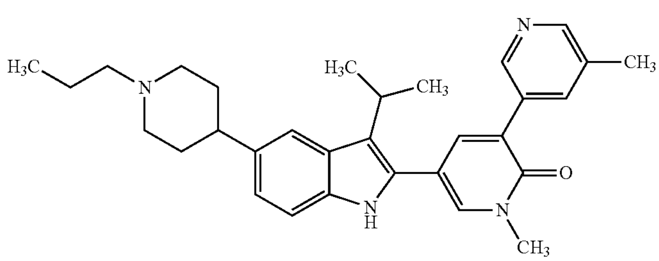 [SMILES: CCCN1CCC(c2ccc3[nH]c(-c4cc(-c5cncc(C)c5)c(=O)n(C)c4)c(C(C)C)c3c2)CC1] | 484 | 1.3 | QC-ACN-AA-XB |

TABLE 8-continued

| Ex. No. | Structure | LCMS MH+ | Ret Time (min) | HPLC Method |
|---|---|---|---|---|
| 333 | 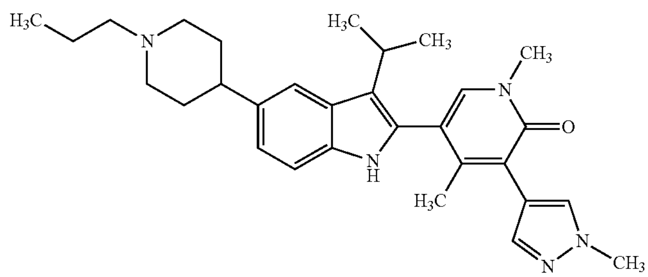 [SMILES: CCCN1CCC(c2ccc3[nH]c(-c4cn(C)c(=O)c(-c5cnn(C)c5)c4C)c(C(C)C)c3c2)CC1] | 486 | 1.22 | QC-ACN-TFA-XB |
| 334 | 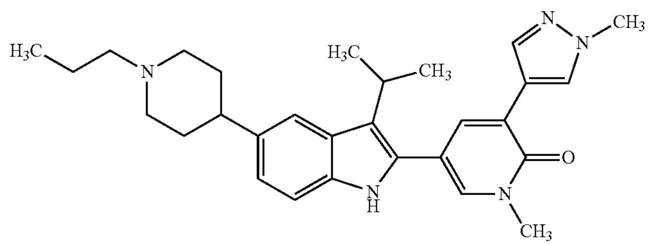 [SMILES: CCCN1CCC(c2ccc3[nH]c(-c4cc(-c5cnn(C)c5)c(=O)n(C)c4)c(C(C)C)c3c2)CC1] | 472 | 1.35 | QC-ACN-TFA-XB |
| 335 | 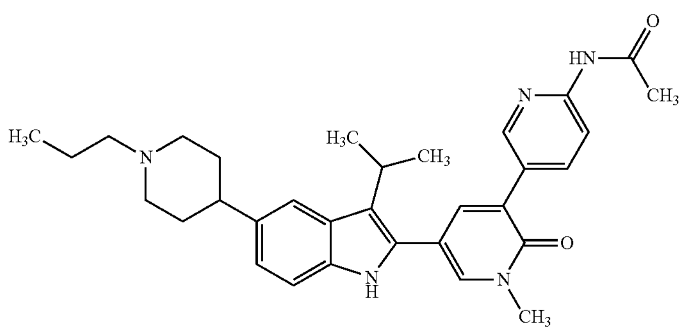 [SMILES: CCCN1CCC(c2ccc3[nH]c(-c4cc(-c5ccc(NC(C)=O)nc5)c(=O)n(C)c4)c(C(C)C)c3c2)CC1] | 526 | 1.12 | QC-ACN-TFA-XB |
| 336 | 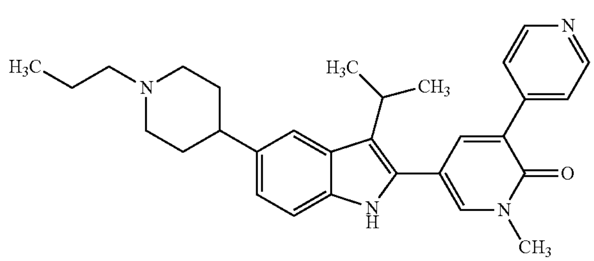 [SMILES: CCCN1CCC(c2ccc3[nH]c(-c4cc(-c5ccncc5)c(=O)n(C)c4)c(C(C)C)c3c2)CC1] | 469 | 1.03 | QC-ACN-TFA-XB |
| 337 | 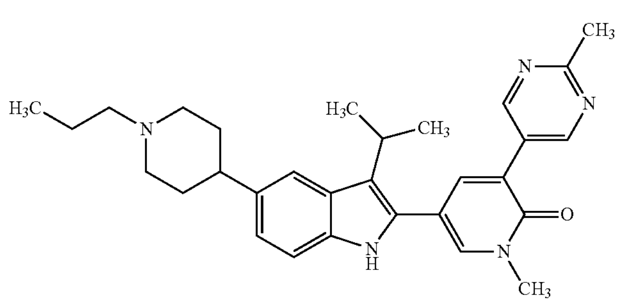 [SMILES: CCCN1CCC(c2ccc3[nH]c(-c4cc(-c5cnc(C)nc5)c(=O)n(C)c4)c(C(C)C)c3c2)CC1] | 484 | 1.34 | QC-ACN-AA-XB |

TABLE 8-continued
| Ex. No. | Structure | LCMS MH+ | Ret Time (min) | HPLC Method |
|---|---|---|---|---|
| 338 | 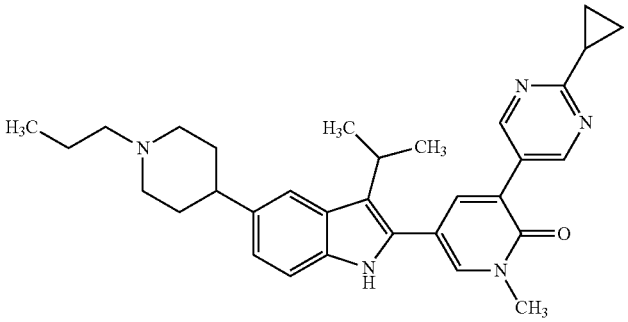 [SMILES: CCCN1CCC(c2ccc3[nH]c(-c4cc(-c5cnc(C6CC6)nc5)c(=O)n(C)c4)c(C(C)C)c3c2)CC1] | 510 | 1.5 | QC-ACN-AA-XB |
| 339 | 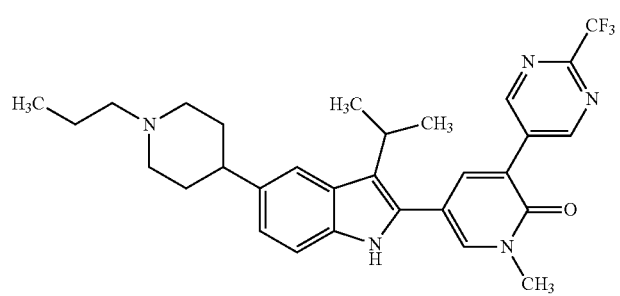 [SMILES: CCCN1CCC(c2ccc3[nH]c(-c4cc(-c5cnc(C(F)(F)F)nc5)c(=O)n(C)c4)c(C(C)C)c3c2)CC1] | 538 | 1.65 | QC-ACN-AA-XB |
| 340 | 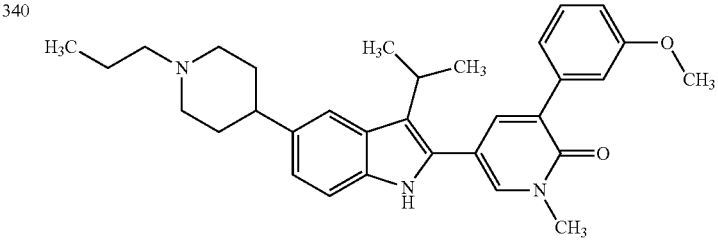 | 498 | 1.55 | QC-ACN-TFA-XB |
| 341 | 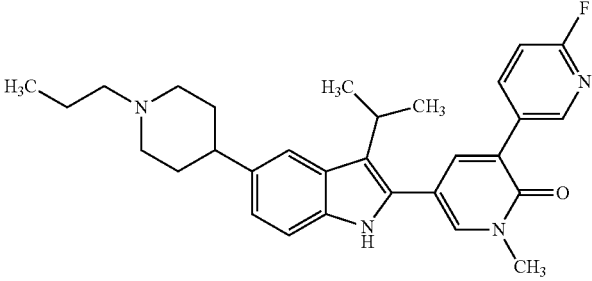 [SMILES: CCCN1CCC(c2ccc3[nH]c(-c4cc(-c5ccc(F)nc5)c(=O)n(C)c4)c(C(C)C)c3c2)CC1] | 488 | 1.45 | QC-ACN-AA-XB |
| 342 | 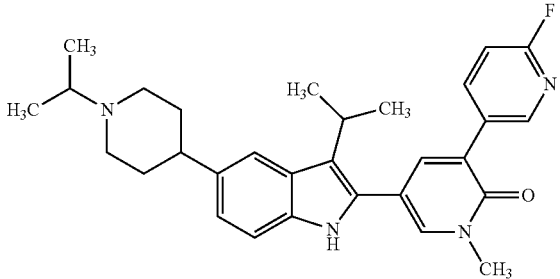 [SMILES: CC(C)c1c(-c2cc(-c3ccc(F)nc3)c(=O)n(C)c2)[nH]c2ccc(C3CCN(C(C)C)CC3)cc12] | 487 | 1.39 | QC-ACN-AA-XB |

TABLE 8-continued

| Ex. No. | Structure | LCMS MH+ | Ret Time (min) | HPLC Method |
|---|---|---|---|---|
| 343 | 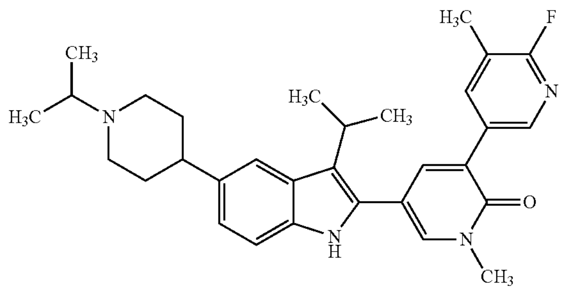 [SMILES: Cc1cc(-c2cc(-c3[nH]c4ccc(C5CCN(C(C)C)CC5)cc4c3C(C)C)cn(C)c2=O)cnc1F] | 501 | 1.45 | QC-ACN-TFA-XB |
| 344 | 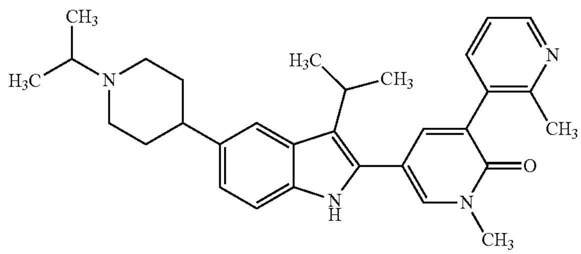 [SMILES: Cc1ncccc1-c1cc(-c2[nH]c3ccc(C4CCN(C(C)C)CC4)cc3c2C(C)C)cn(C)c1=O] | 483 | 1.08 | QC-ACN-TFA-XB |
| 345 | 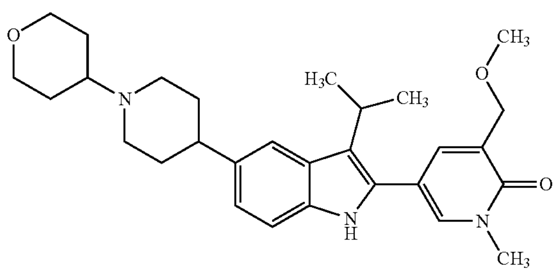 [SMILES: COCc1cc(-c2[nH]c3ccc(C4CCN(C5CCOCC5)CC4)cc3c2C(C)C)cn(C)c1=O] | 478 | 1.35 | QC-ACN-AA-XB |
| 346 | 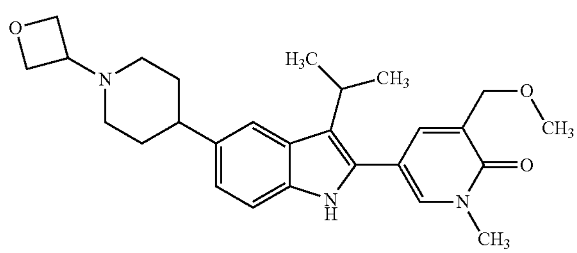 [SMILES: COCc1cc(-c2[nH]c3ccc(C4CCN(C5COC5)CC4)cc3c2C(C)C)cn(C)c1=O] | 450 | 1.52 | QC-ACN-AA-XB |
| 347 | 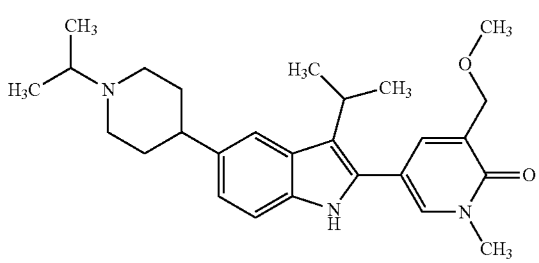 [SMILES: COCc1cc(-c2[nH]c3ccc(C4CCN(C(C)C)CC4)cc3c2C(C)C)cn(C)c1=O] | 436 | 1.2 | QC-ACN-AA-XB |
| 348 | 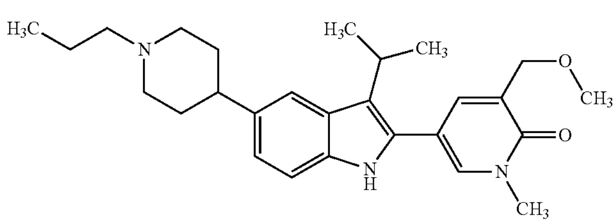 [SMILES: CCCN1CCC(c2ccc3[nH]c(-c4cc(COC)c(=O)n(C)c4)c(C(C)C)c3c2)CC1] | 436 | 1.44 | QC-ACN-AA-XB |

TABLE 8-continued
| Ex. No. | Structure | LCMS MH+ | Ret Time (min) | HPLC Method |
|---|---|---|---|---|
| 349 | 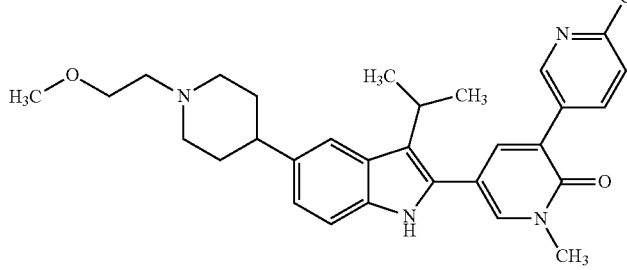 | 499 | 1.09 | QC-ACN-TFA-XB |
| 350 | 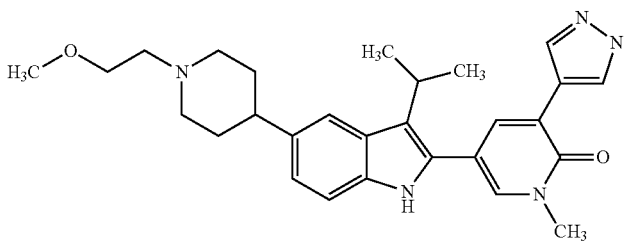 | 488 | 1.42 | QC-ACN-AA-XB |
| 351 | 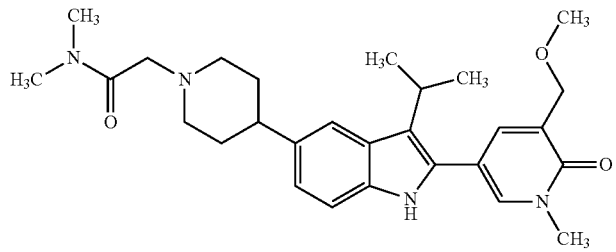 [SMILES: COCc1cc(-c2[nH]c3ccc(C4CCN(CC(=O)N(C)C)CC4)cc3c2C(C)C)cn(C)c1=O] | 479.3 | 1.12 | QC-ACN-TFA-XB |
| 352 | 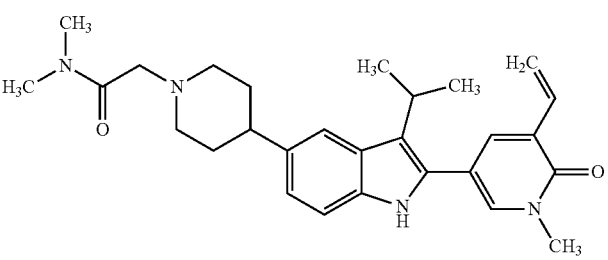 [SMILES: C=Cc1cc(-c2[nH]c3ccc(C4CCN(CC(=O)N(C)C)CC4)cc3c2C(C)C)cn(C)c1=O] | 461.1 | 1.28 | QC-ACN-TFA-XB |
The following example was prepared according to the general procedures of Examples 1 and 2 using the indicated fragment.
TABLE 9
| Ex. No. | Structure | Fragment | LCMS MH+ | Ret Time (min) | HPLC Method |
|---|---|---|---|---|---|
| 353 | 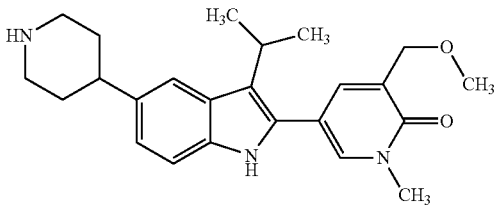 [SMILES: COCc1cc(-c2[nH]c3ccc(C4CCNCC4)cc3c2C(C)C)cn(C)c1=O] | F-31A | 394.2 | 0.62 | A1 |

Biological Assays

The pharmacological properties of the compounds of this invention may be confirmed by a number of biological assays. The exemplified biological assays, which follow, have been carried out with compounds of the invention.

TLR7/8/9 Inhibition Reporter Assays

HEK-Blue™-cells (Invivogen) overexpressing human TLR7, TLR8 or TLR9 receptors were used for screening inhibitors of these receptors using an inducible SEAP (secreted embryonic alkaline phosphatase) reporter gene under the control of the IFN-β minimal promoter fused to five NF-κB and AP-1-binding sites. Briefly, cells are seeded into Greiner 384 well plates (15000 cells per well for TLR7, 20,000 for TLR8 and 25,000 for TLR9) and then treated with test compounds in DMSO to yield a final dose response concentration range of 0.05 nM-50 μM. After a 30 minute compound pre-treatment at room temperature, the cells are then stimulated with a TLR7 ligand (gardiquimod at a final concentration of 7.5 μM), TLR8 ligand (R848 at a final concentration of 15.9 μM) or TLR9 ligand (ODN2006 at a final concentration of 5 nM) to activate NF-κB and AP-1 which induce the production of SEAP. After a 22 hour incubation at 37° C., 5% $CO_2$, SEAP levels are determined with the addition of HEK-Blue™ Detection reagent (Invivogen), a cell culture medium that allows for detection of SEAP, according to manufacturer's specifications. The percent inhibition is determined as the % reduction in the HEK-Blue signal present in wells treated with agonist plus DMSO alone compared to wells treated with a known inhibitor.

TABLE 10

TLR7/8/9 Inhibition Data

| Ex No. | TLR7 $IC_{50}$ (nM) | TLR8 $IC_{50}$ (nM) | TLR9 $IC_{50}$ (nM) |
|---|---|---|---|
| 1 | 27.5 | 15.4 | 621 |
| 2 | 1.6 | 5.1 | 4335 |
| 3 | 8.4 | 3.4 | 979 |
| 4 | 82.8 | 38.4 | 756 |
| 5 | 178.7 | 107.0 | 763 |
| 6 | 12.8 | 13.3 | 580 |
| 8 | 72.7 | 43.5 | 957 |
| 9 | 50.8 | 11.5 | 879 |
| 10 | 329.5 | 38.4 | 1540 |
| 11 | 5.3 | 3.3 | 4851 |
| 12 | 24.7 | 29.0 | 5225 |
| 13 | 18.2 | 33.9 | 593 |
| 14 | 3.5 | 3.6 | 1652 |
| 15 | 1.9 | 3.3 | 179 |
| 16 | 301.9 | 172.7 | 914 |
| 17 | 21.1 | 12.2 | 597 |
| 18 | 18.3 | 14.7 | 6653 |
| 19 | 25.7 | 39.7 | 792 |
| 20 | 6.0 | 17.0 | 1786 |
| 21 | 104.9 | 263.2 | 6540 |
| 22 | 1.1 | 10.7 | 2549 |
| 23 | 62.8 | 15.1 | 6265 |
| 24 | 75.9 | 10.7 | 3757 |
| 25 | 40.3 | 7.8 | 1372 |
| 26 | 12.0 | 8.9 | 1859 |
| 27 | 164.8 | 18.5 | — |
| 28 | 206.6 | 173.7 | 1206 |
| 29 | 14.1 | 50.9 | 783 |
| 30 | 8.4 | 10.1 | 2386 |
| 31 | 1.0 | 7.0 | 1121 |
| 32 | 1.8 | 17.2 | 1068 |
| 33 | 16.1 | 12.6 | 922 |
| 34 | 7.1 | 48.0 | 1463 |
| 35 | 60.0 | 6.8 | 574 |
| 36 | 9.6 | 81.2 | 1311 |
| 37 | 458.1 | 182.2 | 2432 |
| 38 | 51.2 | 30.3 | 3033 |
| 39 | 7.9 | 7.9 | 3181 |
| 40 | 5.2 | 16.9 | 4448 |
| 41 | 18.0 | 157.6 | 1120 |
| 42 | 40.9 | 134.1 | 6706 |
| 43 | 110.4 | 156.6 | 1562 |
| 44 | 3.8 | 19.4 | 2083 |
| 45 | 12.9 | 48.4 | 4667 |
| 46 | 2.9 | 29.9 | 919 |
| 47 | 31.9 | 41.1 | 1885 |
| 48 | 13946.5 | 50000.0 | 1274 |
| 49 | 2614.0 | 2087.2 | 50000 |
| 50 | 6.8 | 7.7 | 411 |
| 51 | 10.9 | 30.6 | 2585 |
| 52 | 184.6 | 141.6 | 1521 |
| 53 | 11.4 | 10.3 | — |
| 54 | 23.4 | 5.9 | 753 |
| 55 | 13.9 | 202.8 | 2289 |
| 56 | 13.7 | 49.0 | 408 |
| 57 | 68.4 | 81.9 | 1357 |
| 58 | 5.4 | 222.3 | 3480 |
| 59 | 46.6 | 270.4 | 5848 |
| 60 | 90.3 | 210.9 | 3062 |
| 61 | 2193.6 | 2275.1 | 2083 |
| 62 | 3125.0 | 3125.0 | 50000 |
| 63 | 3125.0 | 3125.0 | 50000 |
| 64 | 479.7 | 1082.2 | 7378 |
| 65 | 975.5 | 75.1 | 3104 |
| 66 | 12.6 | 70.5 | 764 |
| 67 | 4.3 | 5.9 | 919 |
| 68 | 8.5 | 9.8 | 5359 |
| 69 | 333.1 | 179.5 | 50000 |
| 70 | 8.6 | 26.1 | 2449 |
| 71 | 2.8 | 5.1 | 11002 |
| 72 | 21.8 | 17.3 | 50000 |
| 73 | 8.0 | 3.3 | 6074 |
| 74 | 20.9 | 4.9 | 4327 |
| 75 | 5.0 | 5.6 | 9325 |
| 76 | 4.4 | 4.7 | 19915 |
| 77 | 123.2 | 50.6 | 7851 |
| 78 | 67.6 | 64.0 | 34764 |
| 79 | 11.1 | 10.8 | 3794 |
| 80 | 127.6 | 140.7 | 48780 |
| 81 | 8.8 | 20.3 | 50000 |
| 82 | 9.5 | 11.9 | 799 |
| 83 | 3.9 | 1.2 | 7140 |
| 84 | 44.3 | 73.6 | 50000 |
| 85 | 2.2 | 4.6 | 8455 |
| 86 | 2.1 | 4.6 | 2543 |
| 87 | 3.1 | 5.7 | 2563 |
| 88 | 67.5 | 53.2 | — |
| 89 | 16.9 | 4.5 | 1958 |
| 90 | 21.7 | 7.0 | 1973 |
| 91 | 2.6 | 5.0 | 4386 |
| 92 | 3.2 | 2.8 | 8512 |
| 93 | 5.0 | 4.9 | 5802 |
| 94 | 8.0 | 1.3 | 2033 |
| 95 | 7.0 | 7.8 | 6092 |
| 96 | 2.0 | 14.3 | 2861 |
| 97 | 5.2 | 9.7 | 2047 |
| 98 | 20.6 | 10.4 | 8752 |
| 99 | 7.1 | 10.3 | 4981 |
| 100 | 21.5 | 2.3 | 3055 |
| 101 | 12.8 | 9.3 | 4876 |
| 102 | 33.2 | 32.4 | 50000 |
| 103 | 9.6 | 1.3 | 2083 |
| 104 | 13.1 | 3.5 | 2699 |
| 105 | 5.1 | 10.7 | 5517 |
| 106 | 6.2 | 5.5 | 1248 |
| 107 | 6.6 | 4.4 | 13353 |
| 108 | 32.8 | 2.0 | 7542 |
| 109 | 13.0 | 9.7 | 5306 |
| 110 | 56.1 | 163.5 | 5258 |
| 111 | 48.0 | 157.5 | 3060 |

TABLE 10-continued

TLR7/8/9 Inhibition Data

| Ex No. | TLR7 IC$_{50}$ (nM) | TLR8 IC$_{50}$ (nM) | TLR9 IC$_{50}$ (nM) |
|---|---|---|---|
| 112 | 38.9 | 70.5 | 2363 |
| 113 | 26.4 | 70.7 | 2189 |
| 114 | 42.9 | 43.6 | 10375 |
| 115 | 48.0 | 42.1 | 6594 |
| 116 | 29.6 | 23.8 | 6099 |
| 117 | 2.0 | 5.3 | 13975 |
| 118 | 18.6 | 14.5 | 9636 |
| 119 | 11.4 | 14.9 | 1155 |
| 120 | 7.4 | 11.5 | 851 |
| 121 | 40.7 | 102.3 | 50000 |
| 122 | 4.9 | 15.7 | 14719 |
| 123 | 7.0 | 8.0 | 23803 |
| 124 | 9.7 | 11.3 | 50000 |
| 125 | 3125.0 | 288.7 | 50000 |
| 126 | 3125.0 | 631.4 | 50000 |
| 127 | 3.7 | 5.2 | 33623 |
| 128 | 3.0 | 5.7 | 977 |
| 129 | 5.0 | 8.0 | 2928 |
| 130 | 289.6 | 25.9 | 8506 |
| 131 | 244.6 | 33.4 | 16237 |
| 132 | 9.0 | 15.1 | 25521 |
| 133 | 24.1 | 6.2 | 14874 |
| 134 | 11.9 | 8.7 | 3461 |
| 135 | 5.3 | 5.6 | 18958 |
| 136 | 12.0 | 13.6 | 1954 |
| 137 | 19.9 | 12.3 | 11508 |
| 138 | 17.5 | 5.2 | 7613 |
| 139 | 15.4 | 4.2 | 10356 |
| 140 | 47.8 | 39.7 | 21905 |
| 141 | 27.9 | 37.3 | 4457 |
| 142 | 204.9 | 95.4 | 7649 |
| 143 | 413.2 | 99.7 | 2717 |
| 144 | 59.9 | 4.7 | 11388 |
| 145 | 63.8 | 10.7 | 7175 |
| 146 | 38.8 | 4.5 | 6992 |
| 147 | 56.3 | 4.8 | 5016 |
| 148 | 193.4 | 364.0 | 50000 |
| 149 | 16.0 | 27.3 | 23168 |
| 150 | 1.2 | 4.4 | 11377 |
| 151 | 1.2 | 13.7 | 11046 |
| 152 | 1.4 | 4.6 | 16580 |
| 153 | 3.5 | 12.6 | 7883 |
| 154 | 4.6 | 26.6 | 13839 |
| 155 | 5.3 | 24.2 | 21139 |
| 156 | 4.3 | 7.4 | 11792 |
| 157 | 12.8 | 12.2 | 6387 |
| 158 | 6.6 | 2.6 | 3525 |
| 159 | 10.2 | 19.7 | 16617 |
| 160 | 8.9 | 14.5 | 14739 |
| 161 | 50.5 | 239.5 | 8734 |
| 162 | 8.4 | 99.4 | 4120 |
| 163 | 12.3 | 117.6 | 3887 |
| 164 | 7.0 | 42.4 | 2555 |
| 165 | 45.8 | 113.4 | 10083 |
| 167 | 61.7 | 15.6 | 49253 |
| 168 | 7.9 | 10.3 | 2380 |
| 169 | 11.9 | 6.2 | 1800 |
| 170 | 19.8 | 14.4 | 2075 |
| 171 | 5.1 | 10.4 | 25229 |
| 172 | 29.9 | 6.9 | 151 |
| 173 | 3125.0 | 983.1 | 6611 |
| 174 | 15.7 | 44.8 | 50000 |
| 175 | 275.1 | 87.5 | 15517 |
| 176 | 1.3 | 1.3 | 177 |
| 177 | 154.5 | 51.9 | 9211 |
| 178 | 3.9 | 3.2 | 7087 |
| 179 | 95.1 | 28.8 | 3928 |
| 180 | 7.0 | 8.2 | 5745 |
| 181 | 2.0 | 8.5 | 13516 |
| 182 | 5.9 | 7.3 | 5547 |
| 183 | 28.5 | 31.4 | 9652 |
| 184 | 71.8 | 34.2 | 2124 |
| 185 | 61.3 | 19.0 | 4325 |
| 186 | 112.2 | 75.5 | 6730 |
| 187 | 85.4 | 30.1 | 655 |
| 188 | 14.1 | 11.1 | 526 |
| 189 | 25.5 | 25.0 | 47836 |
| 190 | 25.6 | 53.8 | 2265 |
| 191 | 6.9 | 21.5 | 8842 |
| 192 | 6.4 | 12.0 | 2824 |
| 193 | 12.6 | 11.7 | 8916 |
| 194 | 10.2 | 6.3 | 2979 |
| 195 | 3.9 | 2.6 | 5191 |
| 196 | 3.0 | 2.4 | 4978 |
| 197 | 4.6 | 2.4 | 8342 |
| 198 | 9.1 | 13.4 | 50000 |
| 199 | 1.9 | 4.2 | 1550 |
| 200 | 4.3 | 2.2 | 3739 |
| 201 | 4.0 | 4.4 | 959 |
| 202 | 11.3 | 13.5 | 5634 |
| 203 | 271.7 | 28.7 | 16865 |
| 204 | 14.6 | 18.0 | 50000 |
| 205 | 500.8 | 19.8 | 8709 |
| 206 | 18.9 | 2.6 | 4495 |
| 207 | 20.8 | 11.7 | 46799 |
| 208 | 31.1 | 7.0 | 3109 |
| 209 | 34.3 | 18.0 | 17495 |
| 210 | 24.7 | 2.7 | 5031 |
| 211 | 34.6 | 17.1 | 50000 |
| 212 | 17.1 | 17.4 | 12619 |
| 213 | 15.6 | 16.5 | 2906 |
| 214 | 13.9 | 7.9 | 5692 |
| 215 | 66.1 | 54.9 | 17176 |
| 217 | 659.5 | 162.8 | 10935 |
| 219 | 48.0 | 9.1 | 22305 |
| 220 | 24.5 | 1.4 | 2785 |
| 221 | 67.0 | 9.3 | 25379 |
| 222 | 15.6 | 0.9 | 3067 |
| 223 | 10.0 | 13.6 | 5907 |
| 224 | 1.8 | 4.5 | 14025 |
| 225 | 4.6 | 3.6 | 6989 |
| 226 | 3.8 | 7.0 | 10444 |
| 227 | 3.8 | 4.1 | 3037 |
| 228 | 3.6 | 4.3 | 4269 |
| 229 | 5.7 | 4.2 | 50000 |
| 230 | 11.2 | 23.1 | 5513 |
| 231 | 7.0 | 22.3 | 3227 |
| 232 | 2.9 | 1.1 | 6010 |
| 233 | 57.7 | 97.0 | — |
| 234 | 40.2 | 52.3 | — |
| 235 | 11.0 | 5.2 | 1767 |
| 236 | 4.6 | 9.8 | 980 |
| 237 | 181.1 | 19.8 | 2104 |
| 238 | 7.2 | 11.8 | 8334 |
| 239 | 5.4 | 5.3 | 5808 |
| 240 | 1.0 | 3.7 | 2588 |
| 241 | 8.3 | 4.8 | 4866 |
| 242 | 3.2 | 5.1 | 2680 |
| 243 | 1.4 | 9.1 | 1772 |
| 244 | 6.0 | 1.8 | 954 |
| 245 | 7.3 | 2.0 | 851 |
| 246 | 2.9 | 1.7 | 387 |
| 247 | 3.0 | 4.1 | 864 |
| 248 | 5.6 | 16.9 | 30048 |
| 249 | 14.1 | 1.1 | 1765 |
| 250 | 6.3 | 4.8 | 3006 |
| 251 | 3.5 | 8.1 | 3527 |
| 252 | 4.2 | 2.7 | 2657 |
| 253 | 6.1 | 5.2 | 1241 |
| 254 | 5.5 | 2.1 | 2666 |
| 255 | 4.8 | 2.3 | 1819 |
| 256 | 12.4 | 1.7 | 1473 |
| 257 | 15.6 | 1.1 | 1979 |
| 258 | 4.5 | 1.1 | 832 |
| 259 | 6.1 | 0.6 | 983 |
| 260 | 23.2 | 3.1 | 2237 |
| 261 | 8.8 | 7.1 | 3361 |
| 262 | 47.7 | 52.3 | 2121 |
| 263 | 10.8 | 24.1 | 1565 |
| 264 | 13.5 | 927.2 | 6088 |

TABLE 10-continued

TLR7/8/9 Inhibition Data

| Ex No. | TLR7 IC$_{50}$ (nM) | TLR8 IC$_{50}$ (nM) | TLR9 IC$_{50}$ (nM) |
|---|---|---|---|
| 265 | 20.1 | 42.6 | 5026 |
| 266 | 11.6 | 15.8 | 4481 |
| 267 | 2.2 | 6.6 | 3535 |
| 268 | 2.4 | 6.6 | 2626 |
| 269 | 35.5 | 4.6 | 5904 |
| 270 | 2.1 | 4.7 | 4159 |
| 271 | 5.3 | 8.3 | 13527 |
| 272 | 7.9 | 53.0 | — |
| 273 | 90.2 | 16.0 | 2078 |
| 274 | 183.3 | 15.3 | 1589 |
| 275 | 193.8 | 95.7 | 3194 |
| 276 | 52.2 | 80.2 | 4764 |
| 277 | 9.3 | 21.0 | 15626 |
| 278 | 5.3 | 21.0 | 3202 |
| 279 | 23.1 | 5.9 | 7059 |
| 280 | 6.1 | 9.0 | 4569 |
| 281 | 47.4 | 29.6 | 5697 |
| 282 | 5.2 | 7.0 | 6273 |
| 283 | 512.1 | 46.8 | 6246 |
| 284 | 6.5 | 21.8 | 1655 |
| 285 | 14.6 | 99.1 | 3414 |
| 286 | 5.0 | 5.6 | 289 |
| 287 | 7.8 | 8.6 | 18171 |
| 288 | 17.4 | 61.7 | 2498 |
| 289 | 5.9 | 12.3 | 5283 |
| 290 | 8.3 | 17.1 | 1085 |
| 291 | 12.3 | 11.2 | 1417 |
| 292 | 7.2 | 40.7 | 492 |
| 293 | 21.6 | 74.9 | 12500 |
| 294 | 12.5 | 16.9 | 3316 |
| 295 | 114.2 | 61.9 | 9687 |
| 296 | 1.1 | 3.0 | 4308 |
| 297 | 4.4 | 5.5 | 3994 |
| 298 | 168.6 | 147.7 | 21284 |
| 299 | 3.7 | 4.3 | 504 |
| 300 | 42.6 | 42.5 | 50000 |
| 301 | 25.7 | 36.5 | 1830 |
| 302 | 20.4 | 213.8 | 50000 |
| 303 | 9.6 | 49.9 | 50000 |
| 304 | 7.8 | 80.0 | 50000 |
| 305 | 11.0 | 97.5 | 50000 |
| 306 | 16.5 | 26.9 | 547 |
| 307 | 7.5 | 11.2 | 2748 |
| 308 | 2.0 | 22.1 | 5655 |
| 309 | 13.7 | 5.3 | 8509 |
| 310 | 2.3 | 1.3 | 5543 |
| 311 | 17.7 | 3.9 | 3145 |
| 312 | 35.1 | 22.2 | 3171 |
| 313 | 4.7 | 3.1 | 8036 |
| 314 | 5.2 | 5.1 | 10069 |
| 315 | 6.7 | 1.8 | 4938 |
| 316 | 10.2 | 1.9 | 3086 |
| 317 | 19.3 | 7.2 | 3585 |
| 318 | 360.6 | 22.3 | 3433 |
| 319 | 10.9 | 1.6 | 4328 |
| 320 | 14.2 | 1.7 | 2310 |
| 321 | 36.7 | 1.6 | 4370 |
| 322 | 45.7 | 1.0 | 4789 |
| 323 | 18.4 | 13.9 | 7177 |
| 324 | 2.5 | 2.8 | 11550 |
| 325 | 8.7 | 4.3 | 3002 |
| 326 | 6.1 | 0.6 | 1661 |
| 327 | 6.0 | 1.6 | 3279 |
| 328 | 49.1 | 54.7 | 5969 |
| 329 | 15.8 | 32.4 | — |
| 330 | 7.7 | 432.2 | 705 |
| 331 | 6.3 | 9.6 | 2713 |
| 332 | 4.9 | 1.1 | 789 |
| 333 | 92.2 | 11.1 | 3009 |
| 334 | 8.6 | 0.8 | 487 |
| 335 | 2.4 | 5.9 | 529 |
| 336 | 10.2 | 1.2 | 553 |
| 337 | 1.8 | 11.9 | 2492 |
| 338 | 1.1 | 13.5 | 772 |
| 339 | 28.9 | 2143.7 | 1023 |
| 340 | 4.5 | 16.6 | 1210 |
| 341 | 16.2 | 4.3 | 714 |
| 342 | 12.9 | 16.0 | 3333 |
| 343 | 18.3 | 14.2 | 1168 |
| 344 | 11.5 | 26.5 | 322 |
| 345 | 11.1 | 16.9 | 7048 |
| 346 | 37.9 | 86.8 | 16676 |
| 347 | 7.2 | 28.6 | 13597 |
| 348 | 7.1 | 25.3 | 10830 |
| 349 | 14.5 | 72.6 | 782 |
| 350 | 14.4 | 1.4 | 2139 |
| 351 | 78.5 | 134.6 | 11923 |
| 352 | 21.5 | 31.5 | 2416 |

What is claimed is:

1. A compound of Formula (I)

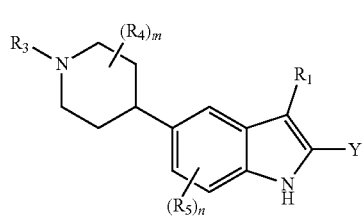

or a salt thereof, wherein:

Y is

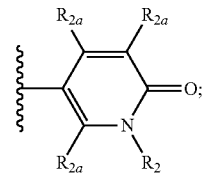

R$_1$ is —CH$_2$CH$_3$ or —CH(CH$_3$)$_2$;

R$_2$ is —CH$_3$, —CH$_2$CH$_3$, —CH(CH$_3$)$_2$, —CH$_2$CH(CH$_3$)$_2$, —CH$_2$CH$_2$OH, —CH$_2$CH$_2$CH$_2$OH, —CH$_2$C(CH$_3$)$_2$OH, —CH$_2$CHF$_2$, —CH$_2$CF$_3$, —CH$_2$CH$_2$OCH$_3$, —CH$_2$(cyclopropyl), —CH$_2$(phenyl), —CH$_2$C(O)NH$_2$, tetrahydrofuranyl, or phenyl;

each R$_{2a}$ is independently H, F, Cl, —CN, —NH$_2$, C$_{1-5}$ alkyl, —CF$_3$, —CH$_2$OH, —OCH$_3$, —CH$_2$OCH$_3$, —CH$_2$CH$_2$(cyclopropyl), —C(O)OCH$_3$, —C(O)N(CH$_3$)$_2$, —C(O)NH(CH$_2$CH$_2$CH$_3$), —CH=CH$_2$, —C(CH$_3$)=CH$_2$, —CH=CH(cyclopropyl), —C(O)(pyrrolidinyl), or a cyclic group selected from pyrrolidinyl, pyrazolyl, phenyl, pyridinyl, and pyrimidinyl, each substituted with zero, 1, or 2 R$_y$;

each R$_y$ is independently F, —CN, —CH$_3$, —CF$_3$, —OCH$_3$, —NHC(O)CH$_3$, —C(O)NH$_2$, —C(O)NH(CH$_3$), cyclopropyl, or morpholinyl;

R$_3$ is H, —CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH$_2$CH$_2$CH(CH$_3$)$_2$, —CH$_2$CH$_2$CF$_3$, —CH$_2$CH$_2$CH$_2$CF$_3$, —CH$_2$CH$_2$CH(CF$_3$)$_2$, —CH$_2$CH$_2$OH, —CH$_2$CH$_2$CH$_2$OH, —C(CH$_3$)$_2$OH, —CH$_2$C(CH$_3$)$_2$OH, —CH$_2$CH$_2$C(CH$_3$)$_2$OH, —CH$_2$CH(OH)CH (CH$_3$)$_2$, —CH$_2$CH(OH)CH$_2$OH, —CH(CH$_2$CH$_2$OH)$_2$, —CH$_2$CN, —CH$_2$CH$_2$CN, —CH$_2$CH$_2$OCH$_3$, —CH$_2$CH$_2$CH$_2$OCH$_3$, —(CH$_2$CH$_2$O)$_{2-3}$OCH$_3$, —CH$_2$CH$_2$NH(CH$_3$), —C(CH$_3$)$_2$C(O)OH, —CH$_2$C(O)NH$_2$, —CH$_2$C(O)NH(CH$_3$), —CH$_2$C(O)N(CH$_3$)$_2$, —CH$_2$C(O)NH(CH$_2$CH$_3$), —CH$_2$C(O)NH(CH$_2$CH(CH$_3$)OH), —CH$_2$C(O)NH(CH$_2$C(CH$_3$)$_2$OH), —CH(CH$_3$)C(O)NH$_2$, —C(CH$_3$)$_2$C(O)NH$_2$, —CH$_2$CH$_2$C(O)NH$_2$, —CH$_2$CH$_2$S(O)$_2$CH$_3$, —C(O)CH$_3$, —C(O)CF$_3$, —C(O)CH$_2$N(CH$_3$)$_2$, —C(O)C(CH$_3$)$_2$NH$_2$, —C(O)CH(CH$_3$)NH(CH$_3$), —C(O)C(CH$_3$)$_2$NH(CH$_3$), —C(O)CH$_2$CH(CH$_3$)OH, —C(O)CH$_2$C(CH$_3$)$_2$OH, —C(O)C(CH$_3$)$_2$CH$_2$OH, —NHC(O)CH$_3$, —CH$_2$(methyl triazolyl), —CH$_2$(trifluoromethyl phenyl), —CH$_2$(difluoromethyl, fluorophenyl), —CH$_2$(fluoro, chlorophenyl), —CH$_2$(difluorocyclopropyl), —CH$_2$CH$_2$(pyrrolidin-dionyl), —CH$_2$(oxetanyl), —CH$_2$(tetrahydropyranyl), —CH$_2$C(O)(hydroxypyrrolidinyl), —CH$_2$C(O)(pyrazolidinonyl), —CH$_2$C(O)(pyrrolidinyl), —CH$_2$(dimethyl pyrazolyl), —CH$_2$(methyl pyrazolyl), —CH$_2$(pyrazolyl), —CH$_2$(cyclopropyl), —CH$_2$(tetrahydrofuranyl), —CH$_2$(i-propyl pyrazolyl), —CH$_2$(n-propyl pyrazolyl), —CH(CH$_3$)(methyl pyrazolyl), —C(O)(aminocyclopropyl), —C(O)(hydroxypyrrolidinyl), —C(O)(methyl, hydroxypyrrolidinyl), —C(O)CH$_2$(pyrrolidinonyl), —C(O)CH$_2$(pyrrolidinyl), —C(O)O(methyl pyrrolidinyl), —S(O)$_2$CH$_2$CH$_2$(pyrrolidinyl), —CH$_2$(hydroxytetrahydropyranyl), or a cyclic group selected from cyclopentyl, cyclohexyl, oxetanyl, azetidinyl, pyrrolidinonyl, tetrahydrofuranyl, tetrahydrofuranonyl, tetrahydropyranyl, piperidinyl, and dioxotetrahydrothiophenyl, each substituted with zero, 1, or 2 R$_{3a}$;
each R$_{3a}$ is independently F, —OH, —CH$_3$, —CH(CH$_3$)$_2$, —CF$_3$, or —C(O)NH$_2$;
R$_5$ is F;
m is zero; and
n is zero or 1.

2. The compound according to claim 1 or a salt thereof, wherein:
R$_1$ is —CH(CH$_3$)$_2$;
R$_2$ is —CH$_3$, —CH$_2$CH$_3$, —CH(CH$_3$)$_2$, —CH$_2$CH(CH$_3$)$_2$, —CH$_2$CH$_2$OH, —CH$_2$CH$_2$CH$_2$OH, —CH$_2$C(CH$_3$)$_2$OH, —CH$_2$CHF$_2$, —CH$_2$CF$_3$, or —CH$_2$CH$_2$OCH$_3$;
each R$_{2a}$ is independently H, F, Cl, —CN, —NH$_2$, C$_{1-5}$ alkyl, —CF$_3$, —CH$_2$OH, —OCH$_3$, —CH$_2$OCH$_3$, —CH$_2$CH$_2$(cyclopropyl), —C(O)OCH$_3$, —C(O)N(CH$_3$)$_2$, —C(O)NH(CH$_2$CH$_2$CH$_3$), —CH=CH$_2$, —C(CH$_3$)=CH$_2$, —CH=CH(cyclopropyl), —C(O)(pyrrolidinyl), or a cyclic group selected from phenyl, pyridinyl, and pyrimidinyl, each substituted with zero, 1, or 2 R$_y$;
R$_3$ is H, —CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH$_2$CH$_2$CH(CH$_3$)$_2$, —CH$_2$CH$_2$CF$_3$, —CH$_2$CH$_2$CH$_2$CF$_3$, —CH$_2$CH$_2$CH(CF$_3$)$_2$, —CH$_2$CH$_2$OH, —CH$_2$CH$_2$CH$_2$OH, —C(CH$_3$)$_2$OH, —CH$_2$C(CH$_3$)$_2$OH, —CH$_2$CH$_2$C(CH$_3$)$_2$OH, —CH$_2$CH(OH)CH(CH$_3$)$_2$, —CH$_2$CH(OH)CH$_2$OH, —CH(CH$_2$CH$_2$OH)$_2$, —CH$_2$CN, —CH$_2$CH$_2$CN, —CH$_2$CH$_2$OCH$_3$, —CH$_2$CH$_2$CH$_2$OCH$_3$, —(CH$_2$CH$_2$O)$_{2-3}$OCH$_3$, —CH$_2$CH$_2$NH(CH$_3$), —C(CH$_3$)$_2$C(O)OH, —CH$_2$C(O)NH$_2$, —CH$_2$C(O)NH(CH$_3$), —CH$_2$C(O)N(CH$_3$)$_2$, —CH$_2$C(O)NH(CH$_2$CH$_3$), —CH$_2$C(O)NH(CH$_2$CH(CH$_3$)OH), —CH$_2$C(O)NH(CH$_2$C(CH$_3$)$_2$OH), —CH(CH$_3$)C(O)NH$_2$, —C(CH$_3$)$_2$C(O)NH$_2$, —CH$_2$CH$_2$C(O)NH$_2$, —CH$_2$CH$_2$S(O)$_2$CH$_3$, —C(O)CH$_3$, —C(O)CF$_3$, —C(O)CH$_2$N(CH$_3$)$_2$, —C(O)C(CH$_3$)$_2$NH$_2$, —C(O)CH(CH$_3$)NH(CH$_3$), —C(O)C(CH$_3$)$_2$NH(CH$_3$), —C(O)CH$_2$CH(CH$_3$)OH, —C(O)CH$_2$C(CH$_3$)$_2$OH, —C(O)CH$_2$C(CH$_3$)$_2$CH$_2$OH, —NHC(O)CH$_3$, —CH$_2$(methyl triazolyl), —CH$_2$(trifluoromethyl phenyl), —CH$_2$(difluoromethyl, fluorophenyl), —CH$_2$(fluoro, chlorophenyl), —CH$_2$(difluorocyclopropyl), —CH$_2$CH$_2$(pyrrolidin-dionyl), —CH$_2$(oxetanyl), —CH$_2$(tetrahydropyranyl), —CH$_2$C(O)(hydroxypyrrolidinyl), —CH$_2$C(O)(pyrazolidinonyl), —CH$_2$C(O)(pyrrolidinyl), —CH$_2$(dimethyl pyrazolyl), —CH$_2$(methyl pyrazolyl), —CH$_2$(pyrazolyl), —CH$_2$(cyclopropyl), —CH$_2$(tetrahydrofuranyl), —CH$_2$(i-propyl pyrazolyl), —CH$_2$(n-propyl pyrazolyl), —CH(CH$_3$)(methyl pyrazolyl), —C(O)(aminocyclopropyl), —C(O)(hydroxypyrrolidinyl), —C(O)(methyl, hydroxypyrrolidinyl), —C(O)CH$_2$(pyrrolidinonyl), —C(O)CH$_2$(pyrrolidinyl), —C(O)O(methyl pyrrolidinyl), —S(O)$_2$CH$_2$CH$_2$(pyrrolidinyl), or —CH$_2$(hydroxytetrahydropyranyl).

3. A pharmaceutical composition comprising a compound according to claim 1 or a pharmaceutically-acceptable salt thereof; and a pharmaceutically acceptable carrier.

4. The compound according to claim 1 or a salt thereof, wherein:
R$_3$ is H, —CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH$_2$CH$_2$CH(CH$_3$)$_2$, —CH$_2$CH$_2$CF$_3$, —CH$_2$CH$_2$CH$_2$CF$_3$, —CH$_2$CH$_2$CH(CF$_3$)$_2$, —CH$_2$CH$_2$OH, —CH$_2$CH$_2$CH$_2$OH, —C(CH$_3$)$_2$OH, —CH$_2$C(CH$_3$)$_2$OH, —CH$_2$CH$_2$C(CH$_3$)$_2$OH, —CH$_2$CH(OH)CH(CH$_3$)$_2$, —CH$_2$CH(OH)CH$_2$OH, —CH(CH$_2$CH$_2$OH)$_2$, —CH$_2$CN, —CH$_2$CH$_2$CN, —CH$_2$CH$_2$OCH$_3$, —CH$_2$CH$_2$CH$_2$OCH$_3$, —(CH$_2$CH$_2$O)$_{2-3}$OCH$_3$, —CH$_2$CH$_2$NH(CH$_3$), —C(CH$_3$)$_2$C(O)OH, —CH$_2$C(O)NH$_2$, —CH$_2$C(O)NH(CH$_3$), —CH$_2$C(O)N(CH$_3$)$_2$, —CH$_2$C(O)NH(CH$_2$CH$_3$), —CH$_2$C(O)NH(CH$_2$CH(CH$_3$)OH), —CH$_2$C(O)NH(CH$_2$C(CH$_3$)$_2$OH), —CH(CH$_3$)C(O)NH$_2$, —C(CH$_3$)$_2$C(O)NH$_2$, —CH$_2$CH$_2$C(O)NH$_2$, —CH$_2$CH$_2$S(O)$_2$CH$_3$, —C(O)CH$_3$, —C(O)CF$_3$, —C(O)CH$_2$N(CH$_3$)$_2$, —C(O)C(CH$_3$)$_2$NH$_2$, —C(O)CH(CH$_3$)NH(CH$_3$), —C(O)C(CH$_3$)$_2$NH(CH$_3$), —C(O)CH$_2$CH(CH$_3$)OH, —C(O)CH$_2$C(CH$_3$)$_2$OH, —C(O)C(CH$_3$)$_2$CH$_2$OH, or —NHC(O)CH$_3$.

5. The compound according to claim 1 or a salt thereof, wherein:
R$_1$ is —CH(CH$_3$)$_2$; and
R$_3$ is H, —CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH$_2$CH$_2$CH(CH$_3$)$_2$, —CH$_2$CH$_2$CF$_3$, —CH$_2$CH$_2$CH$_2$CF$_3$, —CH$_2$CH$_2$CH(CF$_3$)$_2$, —CH$_2$CN, —CH$_2$CH$_2$CN, —CH$_2$CH$_2$NH(CH$_3$), —CH$_2$C(O)NH$_2$, —CH$_2$C(O)NH(CH$_3$), —CH$_2$C(O)N(CH$_3$)$_2$, —CH$_2$C(O)NH(CH$_2$CH$_3$), —CH(CH$_3$)C(O)NH$_2$, —C(CH$_3$)$_2$C(O)NH$_2$, —CH$_2$CH$_2$C(O)NH$_2$, —CH$_2$CH$_2$S(O)$_2$CH$_3$, —C(O)CH$_3$, —C(O)CF$_3$, —C(O)CH$_2$N(CH$_3$)$_2$, —C(O)C(CH$_3$)$_2$NH$_2$, —C(O)CH(CH$_3$)NH(CH$_3$), or —C(O)C(CH$_3$)$_2$NH(CH$_3$).

6. A compound selected from:
5-(3-isopropyl-5-(piperidin-4-yl)-1H-indol-2-yl)-1-methylpyridin-2(1H)-on (1);
5-(3-isopropyl-5-(piperidin-4-yl)-1H-indol-2-yl)-1,3-dimethylpyridin-2(1H)-one (2);
5-(3-isopropyl-5-(piperidin-4-yl)-1H-indol-2-yl)-1,3,6-trimethylpyridin-2(1H)-one (3);
5-(3-isopropyl-5-(piperidin-4-yl)-1H-indol-2-yl)-1,6-dimethylpyridin-2(1H)-one (6);

5-(3-isopropyl-5-(piperidin-4-yl)-1H-indol-2-yl)-1,4-dimethylpyridin-2(1H)-one (8);
3-amino-5-(3-isopropyl-5-(piperidin-4-yl)-1H-indol-2-yl)-1-methylpyridin-2(1H)-one (9);
3-fluoro-5-(3-isopropyl-5-(piperidin-4-yl)-1H-indol-2-yl)-1-methylpyridin-2(1H)-one (13);
5-(3-isopropyl-5-(piperidin-4-yl)-1H-indol-2-yl)-1,3,4-trimethylpyridin-2(1H)-one (14);
1-ethyl-5-(3-isopropyl-5-(piperidin-4-yl)-1H-indol-2-yl)-3-methylpyridin-2(1H)-one (15);
1-isopropyl-5-(3-isopropyl-5-(piperidin-4-yl)-1H-indol-2-yl)pyridin-2(1H)-one (16);
3-amino-5-(3-isopropyl-5-(piperidin-4-yl)-1H-indol-2-yl)-1,4-dimethylpyridin-2(1H)-one (19);
5-(3-isopropyl-5-(piperidin-4-yl)-1H-indol-2-yl)-3-methoxy-1-methylpyridin-2(1H)-one (20);
3-chloro-5-(3-isopropyl-5-(piperidin-4-yl)-1H-indol-2-yl)-1-methylpyridin-2(1H)-one (22);
5-(3-isopropyl-5-(piperidin-4-yl)-1H-indol-2-yl)-1,6-dimethyl-2-oxo-1,2-dihydropyridine-3-carbonitrile (23);
5-(3-isopropyl-5-(piperidin-4-yl)-1H-indol-2-yl)-1,4-dimethyl-2-oxo-1,2-dihydropyridine-3-carbonitrile (24);
3-ethyl-5-(3-isopropyl-5-(piperidin-4-yl)-1H-indol-2-yl)-1,6-dimethylpyridin-2(1H)-one (25);
1-ethyl-5-(3-isopropyl-5-(piperidin-4-yl)-1H-indol-2-yl)-3,4-dimethylpyridin-2(1H)-one (26);
5-(3-isopropyl-5-(piperidin-4-yl)-1H-indol-2-yl)-3-methoxy-1,6-dimethylpyridin-2(1H)-one (28);
5-(3-isopropyl-5-(piperidin-4-yl)-1H-indol-2-yl)-3-methoxy-1,4-dimethylpyridin-2(1H)-one (29);
1-(2-hydroxyethyl)-5-(3-isopropyl-5-(piperidin-4-yl)-1H-indol-2-yl)-3-methylpyridin-2(1H)-one (30);
3-chloro-5-(3-isopropyl-5-(piperidin-4-yl)-1H-indol-2-yl)-1,4-dimethylpyridin-2(1H)-one (31);
3-chloro-1-ethyl-5-(3-isopropyl-5-(piperidin-4-yl)-1H-indol-2-yl)pyridin-2(1H)-one (32);
3-chloro-5-(3-isopropyl-5-(piperidin-4-yl)-1H-indol-2-yl)-1,6-dimethylpyridin-2(1H)-one (33);
1-(cyclopropylmethyl)-5-(3-isopropyl-5-(piperidin-4-yl)-1H-indol-2-yl)-3-methylpyridin-2(1H)-one (34);
1,3-diethyl-5-(3-isopropyl-5-(piperidin-4-yl)-1H-indol-2-yl)-6-methylpyridin-2(1H)-one (35);
1-isobutyl-5-(3-isopropyl-5-(piperidin-4-yl)-1H-indol-2-yl)-3-methylpyridin-2(1H)-one (36);
methyl 5-(3-isopropyl-5-(piperidin-4-yl)-1H-indol-2-yl)-1-methyl-2-oxo-1,2-dihydropyridine-3-carboxylate (37);
1-(3-hydroxypropyl)-5-(3-isopropyl-5-(piperidin-4-yl)-1H-indol-2-yl)-3-methylpyridin-2(1H)-one (38);
5-(3-isopropyl-5-(piperidin-4-yl)-1H-indol-2-yl)-1-(2-methoxyethyl)-3-methylpyridin-2(1H)-one (39);
1-(2,2-difluoroethyl)-5-(3-isopropyl-5-(piperidin-4-yl)-1H-indol-2-yl)-3-methylpyridin-2(1H)-one (40);
5-(3-isopropyl-5-(piperidin-4-yl)-1H-indol-2-yl)-1-methyl-3-(trifluoromethyl)pyridin-2(1H)-one (41);
5-(3-isopropyl-5-(piperidin-4-yl)-1H-indol-2-yl)-3-methyl-1-(tetrahydrofuran-3-yl) pyridin-2(1H)-one (42);
1-(2-hydroxy-2-methylpropyl)-5-(3-isopropyl-5-(piperidin-4-yl)-1H-indol-2-yl)-3-methylpyridin-2(1H)-one (43);
5-(3-isopropyl-5-(piperidin-4-yl)-1H-indol-2-yl)-3-methyl-1-phenylpyridin-2(1H)-one (44);
5-(3-isopropyl-5-(piperidin-4-yl)-1H-indol-2-yl)-3-methyl-1-(2,2,2-trifluoroethyl)pyridin-2(1H)-one (45);
1-benzyl-5-(3-isopropyl-5-(piperidin-4-yl)-1H-indol-2-yl)-3-methylpyridin-2(1H)-one (46);
5-(3-isopropyl-5-(piperidin-4-yl)-1H-indol-2-yl)-1-methyl-2-oxo-1,2-dihydropyridine-3-carbonitrile (47);
1-(2-hydroxy-2-methylpropyl)-5-(3-isopropyl-5-(piperidin-4-yl)-1H-indol-2-yl)pyridin-2(1H)-one (48);
2-(5-(3-isopropyl-5-(piperidin-4-yl)-1H-indol-2-yl)-2-oxopyridin-1(2H)-yl)acetamide (49);
5-(3-isopropyl-5-(piperidin-4-yl)-1H-indol-2-yl)-1-methyl-[3,3'-bipyridin]-2(1H)-one (50);
5-(3-isopropyl-5-(piperidin-4-yl)-1H-indol-2-yl)-1-methyl-3-(prop-1-en-2-yl)pyridin-2(1H)-one (51);
(E)-3-(2-cyclopropylvinyl)-5-(3-isopropyl-5-(piperidin-4-yl)-1H-indol-2-yl)-1-methylpyridin-2(1H)-one (52);
5-(3-isopropyl-5-(piperidin-4-yl)-1H-indol-2-yl)-1-methyl-3-phenylpyridin-2(1H)-one (53);
5-(3-isopropyl-5-(piperidin-4-yl)-1H-indol-2-yl)-1-methyl-3-(pyrimidin-5-yl)pyridin-2(1H)-one (54);
5-(3-isopropyl-5-(piperidin-4-yl)-1H-indol-2-yl)-1-methyl-3-(p-tolyl)pyridin-2(1H)-one (55);
3-(5-(3-isopropyl-5-(piperidin-4-yl)-1H-indol-2-yl)-1-methyl-2-oxo-1,2-dihydropyridin-3-yl)benzonitrile (56);
5-(3-isopropyl-5-(piperidin-4-yl)-1H-indol-2-yl)-2'-methoxy-1-methyl-[3,3'-bipyridin]-2(1H)-one (57);
3-(5-(3-isopropyl-5-(piperidin-4-yl)-1H-indol-2-yl)-1-methyl-2-oxo-1,2-dihydropyridin-3-yl)benzamide (58);
3-(5-(3-isopropyl-5-(piperidin-4-yl)-1H-indol-2-yl)-1-methyl-2-oxo-1,2-dihydropyridin-3-yl)-N-methylbenzamide (59);
N-(3-(5-(3-isopropyl-5-(piperidin-4-yl)-1H-indol-2-yl)-1-methyl-2-oxo-1,2-dihydropyridin-3-yl)phenyl)acetamide (60);
3-(3,3-dimethylbutyl)-5-(3-isopropyl-5-(piperidin-4-yl)-1H-indol-2-yl)-1-methylpyridin-2(1H)-one (61);
3-(2-cyclopropylethyl)-5-(3-isopropyl-5-(piperidin-4-yl)-1H-indol-2-yl)-1-methylpyridin-2(1H)-one (62);
5-(3-isopropyl-5-(piperidin-4-yl)-1H-indol-2-yl)-N,N,1-trimethyl-2-oxo-1,2-dihydropyridine-3-carboxamide (63);
5-(3-isopropyl-5-(piperidin-4-yl)-1H-indol-2-yl)-1-methyl-2-oxo-N-propyl-1,2-dihydropyridine-3-carboxamide (64);
5-(3-isopropyl-5-(piperidin-4-yl)-1H-indol-2-yl)-1,4-dimethyl-[3,3'-bipyridin]-2(1H)-one (65);
3-isopropyl-5-(3-isopropyl-5-(piperidin-4-yl)-1H-indol-2-yl)-1-methylpyridin-2(1H)-one (66);
3-ethyl-5-(3-isopropyl-5-(piperidin-4-yl)-1H-indol-2-yl)-1-methylpyridin-2(1H)-one (67);
1,3-diethyl-5-(3-isopropyl-5-(piperidin-4-yl)-1H-indol-2-yl)pyridin-2(1H)-one (68);
5-(3-isopropyl-5-(piperidin-4-yl)-1H-indol-2-yl)-1-methyl-3-(pyrrolidine-1-carbonyl) pyridin-2(1H)-one (69);
3-(hydroxymethyl)-5-(3-isopropyl-5-(piperidin-4-yl)-1H-indol-2-yl)-1-methylpyridin-2(1H)-one (70);
2-(4-(2-(1,5-dimethyl-6-oxo-1,6-dihydropyridin-3-yl)-3-isopropyl-1H-indol-5-yl)piperidin-1-yl)-N,N-dimethylacetamide (71);
5-(3-isopropyl-5-(1-((1-methyl-1H-1,2,4-triazol-3-yl)methyl)piperidin-4-yl)-1H-indol-2-yl)-1,3-dimethylpyridin-2(1H)-one (72);
5-(5-(1-(3-hydroxy-3-methylbutyl)piperidin-4-yl)-3-isopropyl-1H-indol-2-yl)-1,3,4-trimethylpyridin-2(1H)-one (73);
5-(5-(1-(3-hydroxy-3-methylbutyl)piperidin-4-yl)-3-isopropyl-1H-indol-2-yl)-1,3,6-trimethylpyridin-2(1H)-one (74);

5-(5-(1-isobutylpiperidin-4-yl)-3-isopropyl-1H-indol-2-yl)-1,3-dimethylpyridin-2(1H)-one (75);

3-(4-(2-(1,5-dimethyl-6-oxo-1,6-dihydropyridin-3-yl)-3-isopropyl-1H-indol-5-yl)piperidin-1-yl)propanenitrile (76);

5-(3-isopropyl-5-(1-(4-(trifluoromethoxy) benzyl)piperidin-4-yl)-1H-indol-2-yl)-1,3-dimethylpyridin-2(1H)-one (77);

5-(5-(1-(5-(difluoromethoxy)-2-fluorobenzyl)piperidin-4-yl)-3-isopropyl-1H-indol-2-yl)-1,3-dimethylpyridin-2(1H)-one (78);

5-(3-isopropyl-5-(1-(4,4,4-trifluorobutyl)piperidin-4-yl)-1H-indol-2-yl)-1,3-dimethylpyridin-2(1H)-one (79);

5-(5-(1-(5-chloro-2-fluorobenzyl)piperidin-4-yl)-3-isopropyl-1H-indol-2-yl)-1,3-dimethylpyridin-2(1H)-one (80);

5-(5-(1-(1,1-dioxidotetrahydrothiophen-3-yl)piperidin-4-yl)-3-isopropyl-1H-indol-2-yl)-1,3-dimethylpyridin-2(1H)-one (81);

3-(4-(2-(1,5-dimethyl-6-oxo-1,6-dihydropyridin-3-yl)-3-isopropyl-1H-indol-5-yl) piperidin-1-yl)propanamide (82);

5-(5-(1-((2,2-difluorocyclopropyl)methyl)piperidin-4-yl)-3-isopropyl-1H-indol-2-yl)-1,3-dimethylpyridin-2(1H)-one (83);

1-(2-(4-(2-(1,5-dimethyl-6-oxo-1,6-dihydropyridin-3-yl)-3-isopropyl-1H-indol-5-yl)piperidin-1-yl)ethyl)pyrrolidine-2,5-dione (84);

5-(5-(1-(3-hydroxypropyl)piperidin-4-yl)-3-isopropyl-1H-indol-2-yl)-1,3-dimethylpyridin-2(1H)-one (85);

5-(5-(1-isopentylpiperidin-4-yl)-3-isopropyl-1H-indol-2-yl)-1,3-dimethylpyridin-2(1H)-one (86);

5-(5-(1-cyclohexylpiperidin-4-yl)-3-isopropyl-1H-indol-2-yl)-1,3-dimethylpyridin-2(1H)-one (87);

5-(3-isopropyl-5-(1-(4,4,4-trifluoro-3-(trifluoromethyl)butyl)piperidin-4-yl)-1H-indol-2-yl)-1,3-dimethylpyridin-2(1H)-one (88);

5-(5-(1-isobutylpiperidin-4-yl)-3-isopropyl-1H-indol-2-yl)-1-methyl-3-phenylpyridin-2(1H)-one (89);

5-(5-(1-isopentylpiperidin-4-yl)-3-isopropyl-1H-indol-2-yl)-1-methyl-3-phenylpyridin-2(1H)-one (90);

3-chloro-5-(5-(1-isopentylpiperidin-4-yl)-3-isopropyl-1H-indol-2-yl)-1,4-dimethylpyridin-2(1H)-one (91);

3-chloro-5-(3-isopropyl-5-(1-(oxetan-3-ylmethyl)piperidin-4-yl)-1H-indol-2-yl)-1,4-dimethylpyridin-2(1H)-one (92);

3-chloro-5-(3-isopropyl-5-(1-((tetrahydro-2H-pyran-4-yl)methyl)piperidin-4-yl)-1H-indol-2-yl)-1,4-dimethylpyridin-2(1H)-one (93);

5-(3-isopropyl-5-(1-(oxetan-3-ylmethyl)piperidin-4-yl)-1H-indol-2-yl)-1-methyl-3-(pyrimidin-5-yl)pyridin-2(1H)-one (94);

3-chloro-5-(3-isopropyl-5-(1-(2-methoxyethyl)piperidin-4-yl)-1H-indol-2-yl)-1,4-dimethylpyridin-2(1H)-one (95);

2-(4-(2-(5-chloro-1,4-dimethyl-6-oxo-1,6-dihydropyridin-3-yl)-3-isopropyl-1H-indol-5-yl)piperidin-1-yl)acetonitrile (96);

3-chloro-5-(5-(1-cyclopentylpiperidin-4-yl)-3-isopropyl-1H-indol-2-yl)-1,4-dimethylpyridin-2(1H)-one (97);

3-chloro-5-(3-isopropyl-5-(1-(2-(2-(2-methoxyethoxy)ethoxy)ethyl) piperidin-4-yl)-1H-indol-2-yl)-1,4-dimethylpyridin-2(1H)-one (98);

3-chloro-5-(3-isopropyl-5-(1-(3-methoxypropyl)piperidin-4-yl)-1H-indol-2-yl)-1,4-dimethylpyridin-2(1H)-one (99);

5-(3-isopropyl-5-(1-((tetrahydro-2H-pyran-4-yl)methyl)piperidin-4-yl)-1H-indol-2-yl)-1-methyl-3-(pyrimidin-5-yl)pyridin-2(1H)-one (100);

3-chloro-5-(3-isopropyl-5-(1-(2-(2-methoxyethoxy)ethyl)piperidin-4-yl)-1H-indol-2-yl)-1,4-dimethylpyridin-2(1H)-one (101);

3-chloro-5-(3-isopropyl-5-(1-(3,3,3-trifluoropropyl) piperidin-4-yl)-1H-indol-2-yl)-1,4-dimethylpyridin-2(1H)-one (102);

5-(3-isopropyl-5-(1-(2-methoxyethyl)piperidin-4-yl)-1H-indol-2-yl)-1-methyl-3-(pyrimidin-5-yl)pyridin-2(1H)-one (103);

5-(3-isopropyl-5-(1-(4,4,4-trifluorobutyl)piperidin-4-yl)-1H-indol-2-yl)-1-methyl-3-(pyrimidin-5-yl)pyridin-2(1H)-one (104);

3-chloro-5-(3-isopropyl-5-(1-(4,4,4-trifluorobutyl)piperidin-4-yl)-1H-indol-2-yl)-1,4-dimethylpyridin-2(1H)-one (105);

3-chloro-5-(5-(1-isobutylpiperidin-4-yl)-3-isopropyl-1H-indol-2-yl)-1,4-dimethylpyridin-2(1H)-one (106);

3-chloro-5-(3-isopropyl-5-(1-(2-(methylsulfonyl)ethyl)piperidin-4-yl)-1H-indol-2-yl)-1,4-dimethylpyridin-2(1H)-one (107);

5-(3-isopropyl-5-(1-(2-(methylsulfonyl)ethyl)piperidin-4-yl)-1H-indol-2-yl)-1-methyl-3-(pyrimidin-5-yl) pyridin-2(1H)-one (108);

5-(5-(1-isobutylpiperidin-4-yl)-3-isopropyl-1H-indol-2-yl)-1-(2-methoxyethyl)-3-methylpyridin-2(1H)-one (109);

1-isobutyl-5-(3-isopropyl-5-(1-(4,4,4-trifluorobutyl)piperidin-4-yl)-1H-indol-2-yl)-3-methylpyridin-2(1H)-one (110);

1-benzyl-5-(3-isopropyl-5-(1-(4,4,4-trifluorobutyl)piperidin-4-yl)-1H-indol-2-yl)-3-methylpyridin-2(1H)-one (111);

1-isobutyl-5-(5-(1-isobutylpiperidin-4-yl)-3-isopropyl-1H-indol-2-yl)-3-methylpyridin-2(1H)-one (112);

1-benzyl-5-(5-(1-isobutylpiperidin-4-yl)-3-isopropyl-1H-indol-2-yl)-3-methylpyridin-2(1H)-one (113);

2-(4-(3-isopropyl-2-(1-methyl-6-oxo-1,6-dihydropyridin-3-yl)-1H-indol-5-yl)piperidin-1-yl)-N,N-dimethylacetamide (114);

2-(4-(2-(1,5-dimethyl-6-oxo-1,6-dihydropyridin-3-yl)-3-isopropyl-1H-indol-5-yl)piperidin-1-yl)-N-methylacetamide (117);

(S)-5-(5-(1-(2-(3-hydroxypyrrolidin-1-yl)-2-oxoethyl)piperidin-4-yl)-3-isopropyl-1H-indol-2-yl)-1,3-dimethylpyridin-2(1H)-one (119);

(R)-5-(5-(1-(2-(3-hydroxypyrrolidin-1-yl)-2-oxoethyl) piperidin-4-yl)-3-isopropyl-1H-indol-2-yl)-1,3-dimethylpyridin-2(1H)-one (120);

5-(3-isopropyl-5-(1-(2-oxo-2-(3-oxopyrazolidin-1-yl) ethyl)piperidin-4-yl)-1H-indol-2-yl)-1,3-dimethylpyridin-2(1H)-one (121);

5-(3-isopropyl-5-(1-(2-oxo-2-(pyrrolidin-1-yl)ethyl) piperidin-4-yl)-1H-indol-2-yl)-1,3-dimethylpyridin-2(1H)-one (122);

(R)-5-(3-isopropyl-5-(1-(2-oxopyrrolidin-3-yl)piperidin-4-yl)-1H-indol-2-yl)-1,3-dimethylpyridin-2(1H)-one (123);

2-(4-(2-(1,5-dimethyl-6-oxo-1,6-dihydropyridin-3-yl)-3-isopropyl-1H-indol-5-yl) piperidin-1-yl)-N-(2-hydroxy-2-methylpropyl)acetamide (124);

(R)-2-(4-(2-(1,5-dimethyl-6-oxo-1,6-dihydropyridin-3-yl)-3-isopropyl-1H-indol-5-yl) piperidin-1-yl)-N-(2-hydroxypropyl)acetamide (125);

(S)-2-(4-(2-(1,5-dimethyl-6-oxo-1,6-dihydropyridin-3-yl)-3-isopropyl-1H-indol-5-yl) piperidin-1-yl)-N-(2-hydroxypropyl)acetamide (126);

5-(3-isopropyl-5-(1-(1-methyl-2-oxopyrrolidin-3-yl)piperidin-4-yl)-1H-indol-2-yl)-1,3-dimethylpyridin-2(1H)-one (127);

2-(4-(3-isopropyl-2-(5-methoxy-1-methyl-6-oxo-1,6-dihydropyridin-3-yl)-1H-indol-5-yl) piperidin-1-yl)-N,N-dimethylacetamide (128);

2-(4-(3-isopropyl-2-(5-methoxy-1-methyl-6-oxo-1,6-dihydropyridin-3-yl)-1H-indol-5-yl) piperidin-1-yl)-N-methylacetamide (129);

2-(4-(2-(1-ethyl-5-methyl-6-oxo-1,6-dihydropyridin-3-yl)-3-isopropyl-1H-indol-5-yl) piperidin-1-yl)-N-methylacetamide (132);

2-(4-(2-(1-ethyl-5-methyl-6-oxo-1,6-dihydropyridin-3-yl)-3-isopropyl-1H-indol-5-yl) piperidin-1-yl)-N,N-dimethylacetamide (133);

2-(4-(3-isopropyl-2-(1,4,5-trimethyl-6-oxo-1,6-dihydropyridin-3-yl)-1H-indol-5-yl) piperidin-1-yl)-N,N-dimethylacetamide (134);

2-(4-(3-isopropyl-2-(1,4,5-trimethyl-6-oxo-1,6-dihydropyridin-3-yl)-1H-indol-5-yl) piperidin-1-yl)-N-methylacetamide (135);

2-(4-(2-(1-ethyl-4,5-dimethyl-6-oxo-1,6-dihydropyridin-3-yl)-3-isopropyl-1H-indol-5-yl) piperidin-1-yl)-N,N-dimethylacetamide (136);

2-(4-(2-(1-ethyl-4,5-dimethyl-6-oxo-1,6-dihydropyridin-3-yl)-3-isopropyl-1H-indol-5-yl) piperidin-1-yl)-N-methylacetamide (137);

2-(4-(3-isopropyl-2-(1,2,5-trimethyl-6-oxo-1,6-dihydropyridin-3-yl)-1H-indol-5-yl)piperidin-1-yl)-N,N-dimethylacetamide (138);

2-(4-(3-isopropyl-2-(1,2,5-trimethyl-6-oxo-1,6-dihydropyridin-3-yl)-1H-indol-5-yl) piperidin-1-yl)-N-methylacetamide (139);

2-(4-(3-isopropyl-2-(5-methoxy-1,4-dimethyl-6-oxo-1,6-dihydropyridin-3-yl)-1H-indol-5-yl)piperidin-1-yl)-N-methylacetamide (140);

2-(4-(3-isopropyl-2-(5-methoxy-1,4-dimethyl-6-oxo-1,6-dihydropyridin-3-yl)-1H-indol-5-yl)piperidin-1-yl)-N,N-dimethylacetamide (141);

2-(4-(3-isopropyl-2-(5-methoxy-1,2-dimethyl-6-oxo-1,6-dihydropyridin-3-yl)-1H-indol-5-yl)piperidin-1-yl)-N-methylacetamide (142);

2-(4-(3-isopropyl-2-(5-methoxy-1,2-dimethyl-6-oxo-1,6-dihydropyridin-3-yl)-1H-indol-5-yl)piperidin-1-yl)-N,N-dimethylacetamide (143);

2-(4-(2-(5-cyano-1,2-dimethyl-6-oxo-1,6-dihydropyridin-3-yl)-3-isopropyl-1H-indol-5-yl)piperidin-1-yl)-N-methylacetamide (144);

2-(4-(2-(5-cyano-1,2-dimethyl-6-oxo-1,6-dihydropyridin-3-yl)-3-isopropyl-1H-indol-5-yl)piperidin-1-yl)-N,N-dimethylacetamide (145);

2-(4-(2-(5-cyano-1,4-dimethyl-6-oxo-1,6-dihydropyridin-3-yl)-3-isopropyl-1H-indol-5-yl)piperidin-1-yl)-N-methylacetamide (146);

2-(4-(2-(5-cyano-1,4-dimethyl-6-oxo-1,6-dihydropyridin-3-yl)-3-isopropyl-1H-indol-5-yl)piperidin-1-yl)-N,N-dimethylacetamide (147);

2-(4-(2-(1,5-dimethyl-6-oxo-1,6-dihydropyridin-3-yl)-3-isopropyl-1H-indol-5-yl) piperidin-1-yl)-2-methylpropanoic acid (148);

5-(3-isopropyl-5-(1-(5-methyl-2-oxotetrahydrofuran-3-yl)piperidin-4-yl)-1H-indol-2-yl)-1,3-dimethylpyridin-2(1H)-one (149);

2-(4-(2-(1,5-dimethyl-6-oxo-1,6-dihydropyridin-3-yl)-3-isopropyl-1H-indol-5-yl) piperidin-1-yl)acetamide (150);

2-(4-(2-(1,5-dimethyl-6-oxo-1,6-dihydropyridin-3-yl)-3-isopropyl-1H-indol-5-yl)piperidin-1-yl)-2-methylpropanamide (151);

2-(4-(2-(5-chloro-1,4-dimethyl-6-oxo-1,6-dihydropyridin-3-yl)-3-isopropyl-1H-indol-5-yl)piperidin-1-yl)-N,N-dimethylacetamide (152);

2-(4-(2-(5-chloro-1,4-dimethyl-6-oxo-1,6-dihydropyridin-3-yl)-3-isopropyl-1H-indol-5-yl)piperidin-1-yl)-N-methylacetamide (153);

2-(4-(2-(5-chloro-1,4-dimethyl-6-oxo-1,6-dihydropyridin-3-yl)-3-isopropyl-1H-indol-5-yl)piperidin-1-yl)-2-methylpropanamide (154);

2-(4-(2-(5-chloro-1,4-dimethyl-6-oxo-1,6-dihydropyridin-3-yl)-3-isopropyl-1H-indol-5-yl)piperidin-1-yl)-N-ethylacetamide (155);

2-(4-(2-(5-chloro-1,4-dimethyl-6-oxo-1,6-dihydropyridin-3-yl)-3-isopropyl-1H-indol-5-yl)piperidin-1-yl) propanamide (156);

2-(4-(2-(5-chloro-1,4-dimethyl-6-oxo-1,6-dihydropyridin-3-yl)-3-ethyl-1H-indol-5-yl) piperidin-1-yl)-N,N-dimethylacetamide (157);

2-(4-(2-(5-chloro-1,4-dimethyl-6-oxo-1,6-dihydropyridin-3-yl)-4-fluoro-3-isopropyl-1H-indol-5-yl)piperidin-1-yl)-N,N-dimethylacetamide (158);

2-(4-(3-isopropyl-2-(1-(2-methoxyethyl)-5-methyl-6-oxo-1,6-dihydropyridin-3-yl)-1H-indol-5-yl)piperidin-1-yl)-N,N-dimethylacetamide (159);

2-(4-(3-isopropyl-2-(1-(2-methoxyethyl)-5-methyl-6-oxo-1,6-dihydropyridin-3-yl)-1H-indol-5-yl)piperidin-1-yl)-N-methylacetamide (160);

2-(4-(2-(1-isobutyl-5-methyl-6-oxo-1,6-dihydropyridin-3-yl)-3-isopropyl-1H-indol-5-yl) piperidin-1-yl)-N-methylacetamide (161);

2-(4-(2-(1-benzyl-5-methyl-6-oxo-1,6-dihydropyridin-3-yl)-3-isopropyl-1H-indol-5-yl) piperidin-1-yl)-N-methylacetamide (162);

2-(4-(2-(1-isobutyl-5-methyl-6-oxo-1,6-dihydropyridin-3-yl)-3-isopropyl-1H-indol-5-yl) piperidin-1-yl)-N,N-dimethylacetamide (163);

2-(4-(2-(1-benzyl-5-methyl-6-oxo-1,6-dihydropyridin-3-yl)-3-isopropyl-1H-indol-5-yl) piperidin-1-yl)-N,N-dimethylacetamide (164);

2-(4-(3-isopropyl-2-(5-methyl-6-oxo-1-(2,2,2-trifluoroethyl)-1,6-dihydropyridin-3-yl)-1H-indol-5-yl)piperidin-1-yl)-N,N-dimethylacetamide (165);

2-(4-(2-(1-(2,2-difluoroethyl)-5-methyl-6-oxo-1,6-dihydropyridin-3-yl)-3-isopropyl-1H-indol-5-yl)piperidin-1-yl)-N,N-dimethylacetamide (166);

2-(4-(2-(1-(2-hydroxyethyl)-5-methyl-6-oxo-1,6-dihydropyridin-3-yl)-3-isopropyl-1H-indol-5-yl)piperidin-1-yl)-N,N-dimethylacetamide (167);

2-(4-(2-(5-ethyl-1-methyl-6-oxo-1,6-dihydropyridin-3-yl)-3-isopropyl-1H-indol-5-yl)piperidin-1-yl)-N,N-dimethylacetamide (168);

2-(4-(3-isopropyl-2-(1-methyl-2-oxo-1,2-dihydro-[3,3'-bipyridin]-5-yl)-1H-indol-5-yl)piperidin-1-yl)-N,N-dimethylacetamide (169);

2-(4-(3-isopropyl-2-(1-methyl-6-oxo-5-phenyl-1,6-dihydropyridin-3-yl)-1H-indol-5-yl)piperidin-1-yl)-N,N-dimethylacetamide (170);

5-(3-isopropyl-5-(1-(oxetan-3-yl)piperidin-4-yl)-1H-indol-2-yl)-1,3-dimethylpyridin-2(1H)-one (171);

5-(3-isopropyl-5-(1-(2-(methylamino)ethyl)piperidin-4-yl)-1H-indol-2-yl)-1-methylpyridin-2(1H)-one (172);

5-(3-isopropyl-5-(1-propylpiperidin-4-yl)-1H-indol-2-yl)-1-methyl-3-(piperidin-1-yl) pyridin-2(1H)-one (173);

5-(5-(1-(1-acetylazetidin-3-yl)piperidin-4-yl)-3-isopropyl-1H-indol-2-yl)-3-chloro-1,4-dimethylpyridin-2(1H)-one (174);

5-(3-isopropyl-5-(1-(oxetan-3-yl)piperidin-4-yl)-1H-indol-2-yl)-1-methylpyridin-2(1H)-one (175);

5-(3-isopropyl-5-(1-(2-(methylamino)ethyl)piperidin-4-yl)-1H-indol-2-yl)-1,3-dimethylpyridin-2(1H)-one (176);

5-(3-isopropyl-5-(1-(tetrahydrofuran-3-yl)piperidin-4-yl)-1H-indol-2-yl)-1-methylpyridin-2(1H)-one (177);

5-(3-isopropyl-5-(1-(tetrahydro-2H-pyran-4-yl) piperidin-4-yl)-1H-indol-2-yl)-1,3-dimethylpyridin-2(1H)-one (178);

5-(3-isopropyl-5-(1-(oxetan-3-yl)piperidin-4-yl)-1H-indol-2-yl)-1-methylpyridin-2(1H)-one (179);

5-(3-isopropyl-5-(1-(tetrahydrofuran-3-yl)piperidin-4-yl)-1H-indol-2-yl)-1,3-dimethylpyridin-2(1H)-one (180);

5-(3-isopropyl-5-(1-methylpiperidin-4-yl)-1H-indol-2-yl)-1,3-dimethylpyridin-2(1H)-one (181);

5-(3-isopropyl-5-(1-isopropylpiperidin-4-yl)-1H-indol-2-yl)-1,3-dimethylpyridin-2(1H)-one (182);

5-(3-isopropyl-5-(1-((1-methyl-1H-pyrazol-3-yl)methyl)piperidin-4-yl)-1H-indol-2-yl)-1,3-dimethylpyridin-2(1H)-one (195);

5-(3-isopropyl-5-(1-((1-methyl-1H-pyrazol-4-yl)methyl)piperidin-4-yl)-1H-indol-2-yl)-1,3-dimethylpyridin-2(1H)-one (196);

5-(3-isopropyl-5-(1-((1-methyl-1H-pyrazol-5-yl) methyl)piperidin-4-yl)-1H-indol-2-yl)-1,3-dimethylpyridin-2(1H)-one (197);

5-(3-isopropyl-5-(1-((1-methyl-1H-1,2,4-triazol-5-yl)methyl)piperidin-4-yl)-1H-indol-2-yl)-1,3-dimethylpyridin-2(1H)-one (198);

5-(5-(1-(4,4-difluorocyclohexyl)piperidin-4-yl)-3-isopropyl-1H-indol-2-yl)-1,3-dimethylpyridin-2(1H)-one (199);

5-(5-(1-((4H-pyrazol-3-yl)methyl)piperidin-4-yl)-3-isopropyl-1H-indol-2-yl)-1,3-dimethylpyridin-2(1H)-one (200);

5-(3-isopropyl-5-(1-(tetrahydro-2H-pyran-4-yl)piperidin-4-yl)-1H-indol-2-yl)-3-methoxy-1-methylpyridin-2(1H)-one (201);

5-(3-isopropyl-5-(1-(oxetan-3-yl)piperidin-4-yl)-1H-indol-2-yl)-3-methoxy-1-methylpyridin-2(1H)-one (202);

1-ethyl-5-(3-isopropyl-5-(1-(oxetan-3-yl)piperidin-4-yl)-1H-indol-2-yl)-3-methylpyridin-2(1H)-one (204);

5-(3-isopropyl-5-(1-(tetrahydro-2H-pyran-4-yl)piperidin-4-yl)-1H-indol-2-yl)-1,3,4-trimethylpyridin-2(1H)-one (206);

5-(3-isopropyl-5-(1-(oxetan-3-yl)piperidin-4-yl)-1H-indol-2-yl)-1,3,4-trimethylpyridin-2(1H)-one (207);

1-ethyl-5-(3-isopropyl-5-(1-(tetrahydro-2H-pyran-4-yl)piperidin-4-yl)-1H-indol-2-yl)-3,4-dimethylpyridin-2(1H)-one (208);

1-ethyl-5-(3-isopropyl-5-(1-(oxetan-3-yl)piperidin-4-yl)-1H-indol-2-yl)-3,4-dimethylpyridin-2(1H)-one (209);

5-(3-isopropyl-5-(1-(tetrahydro-2H-pyran-4-yl) piperidin-4-yl)-1H-indol-2-yl)-1,3,6-trimethylpyridin-2(1H)-one (210);

5-(3-isopropyl-5-(1-(oxetan-3-yl)piperidin-4-yl)-1H-indol-2-yl)-1,3,6-trimethylpyridin-2(1H)-one (211);

5-(3-isopropyl-5-(1-isopropylpiperidin-4-yl)-1H-indol-2-yl)-1,3,4-trimethylpyridin-2(1H)-one (212);

1-ethyl-5-(3-isopropyl-5-(1-isopropylpiperidin-4-yl)-1H-indol-2-yl)-3,4-dimethylpyridin-2(1H)-one (213);

5-(3-isopropyl-5-(1-isopropylpiperidin-4-yl)-1H-indol-2-yl)-1,3,6-trimethylpyridin-2(1H)-one (214);

5-(3-isopropyl-5-(1-(oxetan-3-yl) piperidin-4-yl)-1H-indol-2-yl)-3-methoxy-1,4-dimethylpyridin-2(1H)-one (215);

5-(3-isopropyl-5-(1-(tetrahydro-2H-pyran-4-yl)piperidin-4-yl)-1H-indol-2-yl)-3-methoxy-1,4-dimethylpyridin-2(1H)-one (216);

5-(3-isopropyl-5-(1-(oxetan-3-yl)piperidin-4-yl)-1H-indol-2-yl)-3-methoxy-1,6-dimethylpyridin-2(1H)-one (217);

5-(3-isopropyl-5-(1-(tetrahydro-2H-pyran-4-yl)piperidin-4-yl)-1H-indol-2-yl)-3-methoxy-1,6-dimethylpyridin-2(1H)-one (218);

5-(3-isopropyl-5-(1-(oxetan-3-yl)piperidin-4-yl)-1H-indol-2-yl)-1,6-dimethyl-2-oxo-1,2-dihydropyridine-3-carbonitrile (219);

5-(3-isopropyl-5-(1-(tetrahydro-2H-pyran-4-yl)piperidin-4-yl)-1H-indol-2-yl)-1,6-dimethyl-2-oxo-1,2-dihydropyridine-3-carbonitrile (220);

5-(3-isopropyl-5-(1-(oxetan-3-yl)piperidin-4-yl)-1H-indol-2-yl)-1,4-dimethyl-2-oxo-1,2-dihydropyridine-3-carbonitrile (221);

5-(3-isopropyl-5-(1-(tetrahydro-2H-pyran-4-yl)piperidin-4-yl)-1H-indol-2-yl)-1,4-dimethyl-2-oxo-1,2-dihydropyridine-3-carbonitrile (222);

5-(5-(1-(cyclopropylmethyl)piperidin-4-yl)-3-isopropyl-1H-indol-2-yl)-1,3-dimethylpyridin-2(1H)-one (223);

5-(3-isopropyl-5-(1-propylpiperidin-4-yl)-1H-indol-2-yl)-1,3-dimethylpyridin-2(1H)-one (224);

5-(3-isopropyl-5-(1-((tetrahydrofuran-3-yl)methyl)piperidin-4-yl)-1H-indol-2-yl)-1,3-dimethylpyridin-2(1H)-one (225);

3-chloro-5-(3-isopropyl-5-(1-(tetrahydro-2H-pyran-4-yl)piperidin-4-yl)-1H-indol-2-yl)-1-methylpyridin-2(1H)-one (226);

3-chloro-5-(3-isopropyl-5-(1-((1-isopropyl-1H-pyrazol-4-yl)methyl)piperidin-4-yl)-1H-indol-2-yl)-1-methylpyridin-2(1H)-one (227);

5-(3-isopropyl-5-(1-((1-propyl-1H-pyrazol-4-yl)methyl)piperidin-4-yl)-1H-indol-2-yl)-1,3-dimethylpyridin-2(1H)-one (228);

N-(4-(4-(2-(1,5-dimethyl-6-oxo-1,6-dihydropyridin-3-yl)-3-isopropyl-1H-indol-5-yl)piperidin-1-yl) cyclohexyl)acetamide (229);

5-(3-isopropyl-5-(1-(4-(trifluoromethyl)cyclohexyl) piperidin-4-yl)-1H-indol-2-yl)-1,3-dimethylpyridin-2(1H)-one (230);

5-(3-isopropyl-5-(1-(4-(trifluoromethyl)cyclohexyl)piperidin-4-yl)-1H-indol-2-yl)-1,3-dimethylpyridin-2(1H)-one (231);

5-(5-(1-((1,3-dimethyl-1H-pyrazol-4-yl)methyl)piperidin-4-yl)-3-isopropyl-1H-indol-2-yl)-1,3-dimethylpyridin-2(1H)-one (232);

5-(3-isopropyl-5-(1-(4-isopropylcyclohexyl)piperidin-4-yl)-1H-indol-2-yl)-1,3-dimethylpyridin-2(1H)-one (233);

5-(3-isopropyl-5-(1-(4-isopropylcyclohexyl)piperidin-4-yl)-1H-indol-2-yl)-1,3-dimethylpyridin-2(1H)-one (234);

5-(3-isopropyl-5-(1-isopropylpiperidin-4-yl)-1H-indol-2-yl)-1-methyl-[3,3'-bipyridin]-2(1H)-one (235); 5-(5-(1-

(2-hydroxyethyl)piperidin-4-yl)-3-isopropyl-1H-indol-2-yl)-1-methyl-[3,3'-bipyridin]-2(1H)-one (236);

5-(3-isopropyl-5-(1-isopropylpiperidin-4-yl)-1H-indol-2-yl)-1,4-dimethyl-[3,3'-bipyridin]-2(1H)-one (237);

3-chloro-5-(3-isopropyl-5-(1-isopropylpiperidin-4-yl)-1H-indol-2-yl)-1,4-dimethylpyridin-2(1H)-one (238);

3-chloro-5-(3-isopropyl-5-(1-(tetrahydro-2H-pyran-4-yl)piperidin-4-yl)-1H-indol-2-yl)-1,4-dimethylpyridin-2(1H)-one (241);

3-chloro-5-(3-isopropyl-5-(1-methylpiperidin-4-yl)-1H-indol-2-yl)-1,4-dimethylpyridin-2(1H)-one (240);

5-(5-(1-acetylpiperidin-4-yl)-3-isopropyl-1H-indol-2-yl)-3-chloro-1,4-dimethylpyridin-2(1H)-one (241);

3-chloro-5-(3-isopropyl-5-(1-propylpiperidin-4-yl)-1H-indol-2-yl)-1,4-dimethylpyridin-2(1H)-one (242);

3-chloro-5-(5-(1-(1,5-dihydroxypentan-3-yl)piperidin-4-yl)-3-isopropyl-1H-indol-2-yl)-1,4-dimethylpyridin-2(1H)-one (243);

5-(3-isopropyl-5-(1-isopropylpiperidin-4-yl)-1H-indol-2-yl)-1-methyl-3-(pyrimidin-5-yl)pyridin-2(1H)-one (244);

5-(3-isopropyl-5-(1-propylpiperidin-4-yl)-1H-indol-2-yl)-1-methyl-[3,3'-bipyridin]-2(1H)-one (245);

5-(3-isopropyl-5-(1-methylpiperidin-4-yl)-1H-indol-2-yl)-1-methyl-3-(pyrimidin-5-yl) pyridin-2(1H)-one (246);

5-(3-isopropyl-5-(1-methylpiperidin-4-yl)-1H-indol-2-yl)-1-methyl-[3,3'-bipyridin]-2(1H)-one (247);

3-chloro-5-(3-isopropyl-5-(1-(oxetan-3-yl)piperidin-4-yl)-1H-indol-2-yl)-1,4-dimethylpyridin-2(1H)-one (248);

5-(3-isopropyl-5-(1-propylpiperidin-4-yl)-1H-indol-2-yl)-1-methyl-3-(pyrimidin-5-yl)pyridin-2(1H)-one (249);

3-chloro-5-(3-isopropyl-5-(1-((tetrahydrofuran-2-yl)methyl)piperidin-4-yl)-1H-indol-2-yl)-1,4-dimethylpyridin-2(1H)-one (250);

5-(5-(1-butylpiperidin-4-yl)-3-isopropyl-1H-indol-2-yl)-3-chloro-1,4-dimethylpyridin-2(1H)-one (251);

3-chloro-5-(3-isopropyl-5-(1-((tetrahydrofuran-3-yl)methyl)piperidin-4-yl)-1H-indol-2-yl)-1,4-dimethylpyridin-2(1H)-one (252);

3-chloro-5-(5-(1-(2,3-dihydroxypropyl)piperidin-4-yl)-3-isopropyl-1H-indol-2-yl)-1,4-dimethylpyridin-2(1H)-one (253);

3-chloro-5-(3-isopropyl-5-(1-((tetrahydrofuran-3-yl)methyl)piperidin-4-yl)-1H-indol-2-yl)-1,4-dimethylpyridin-2(1H)-one (254-255);

5-(5-(1-isobutylpiperidin-4-yl)-3-isopropyl-1H-indol-2-yl)-1-methyl-3-(pyrimidin-5-yl)pyridin-2(1H)-one (256);

5-(3-isopropyl-5-(1-((tetrahydrofuran-3-yl)methyl)piperidin-4-yl)-1H-indol-2-yl)-1-methyl-3-(pyrimidin-5-yl)pyridin-2(1H)-one (257);

5-(4-fluoro-3-isopropyl-5-(1-propylpiperidin-4-yl)-1H-indol-2-yl)-1-methyl-3-(pyrimidin-5-yl)pyridin-2(1H)-one (258);

5-(4-fluoro-3-isopropyl-5-(1-((tetrahydrofuran-3-yl)methyl)piperidin-4-yl)-1H-indol-2-yl)-1-methyl-3-(pyrimidin-5-yl)pyridin-2(1H)-one (259);

1-ethyl-5-(3-isopropyl-5-(1-propylpiperidin-4-yl)-1H-indol-2-yl)-3-(pyrimidin-5-yl)pyridin-2(1H)-one (260);

5-(3-isopropyl-5-(1-(tetrahydro-2H-pyran-4-yl)piperidin-4-yl)-1H-indol-2-yl)-1-(2-methoxyethyl)-3-methylpyridin-2(1H)-one (261);

1-isobutyl-5-(3-isopropyl-5-(1-(tetrahydro-2H-pyran-4-yl)piperidin-4-yl)-1H-indol-2-yl)-3-methylpyridin-2(1H)-one (262);

1-benzyl-5-(3-isopropyl-5-(1-(tetrahydro-2H-pyran-4-yl)piperidin-4-yl)-1H-indol-2-yl)-3-methylpyridin-2(1H)-one (263);

1-(2-hydroxyethyl)-5-(3-isopropyl-5-(1-methylpiperidin-4-yl)-1H-indol-2-yl)-3-methylpyridin-2(1H)-one (264);

5-(3-isopropyl-5-(1-methylpiperidin-4-yl)-1H-indol-2-yl)-3-methyl-1-(2,2,2-trifluoroethyl)pyridin-2(1H)-one (265);

1-(2,2-difluoroethyl)-5-(3-isopropyl-5-(1-methylpiperidin-4-yl)-1H-indol-2-yl)-3-methylpyridin-2(1H)-one (266);

5-(5-(1-(4-(2-hydroxypropan-2-yl)cyclohexyl)piperidin-4-yl)-3-isopropyl-1H-indol-2-yl)-1,3-dimethylpyridin-2(1H)-one (267-268);

5-(3-isopropyl-5-(1-(1-(1-methyl-1H-pyrazol-4-yl)ethyl)piperidin-4-yl)-1H-indol-2-yl)-1,3-dimethylpyridin-2(1H)-one (269);

5-(5-(1-(4-(2-hydroxypropan-2-yl)cyclohexyl)piperidin-4-yl)-3-isopropyl-1H-indol-2-yl)-1,3-dimethylpyridin-2(1H)-one (270);

5-(5-(1-(2-(dimethylamino)acetyl)piperidin-4-yl)-3-isopropyl-1H-indol-2-yl)-1,3-dimethylpyridin-2(1H)-one (271);

5-(5-(1-(1-aminocyclopropanecarbonyl)piperidin-4-yl)-3-isopropyl-1H-indol-2-yl)-1,3-dimethylpyridin-2(1H)-one (272);

5-(5-(1-(dimethylglycyl)piperidin-4-yl)-3-isopropyl-1H-indol-2-yl)-1,6-dimethyl-2-oxo-1,2-dihydropyridine-3-carbonitrile (273);

5-(5-(1-(dimethylglycyl)piperidin-4-yl)-3-isopropyl-1H-indol-2-yl)-1,4-dimethyl-2-oxo-1,2-dihydropyridine-3-carbonitrile (274);

5-(5-(1-(dimethylglycyl)piperidin-4-yl)-3-isopropyl-1H-indol-2-yl)-3-methoxy-1,6-dimethylpyridin-2(1H)-one (275);

5-(5-(1-(dimethylglycyl)piperidin-4-yl)-3-isopropyl-1H-indol-2-yl)-3-methoxy-1,4-dimethylpyridin-2(1H)-one (276);

5-(5-(1-(dimethylglycyl)piperidin-4-yl)-3-isopropyl-1H-indol-2-yl)-3-(methoxymethyl)-1-methylpyridin-2(1H)-one (277);

3-chloro-5-(5-(1-(dimethylglycyl)piperidin-4-yl)-3-isopropyl-1H-indol-2-yl)-1,4-dimethylpyridin-2(1H)-one (278);

5-(5-(1-(dimethylglycyl)piperidin-4-yl)-3-isopropyl-1H-indol-2-yl)-1,3,6-trimethylpyridin-2(1H)-one (279);

5-(5-(1-(dimethylglycyl)piperidin-4-yl)-3-isopropyl-1H-indol-2-yl)-1,3,4-trimethylpyridin-2(1H)-one (280);

5-(5-(1-(dimethylglycyl) piperidin-4-yl)-3-isopropyl-1H-indol-2-yl)-1-ethyl-3,4-dimethylpyridin-2(1H)-one (281);

5-(5-(1-(dimethylglycyl)piperidin-4-yl)-3-isopropyl-1H-indol-2-yl)-1-ethyl-3-methylpyridin-2(1H)-one (282);

1-benzyl-5-(5-(1-(dimethylglycyl)piperidin-4-yl)-3-isopropyl-1H-indol-2-yl)-3-methylpyridin-2(1H)-one (284);

5-(5-(1-(dimethylglycyl) piperidin-4-yl)-3-isopropyl-1H-indol-2-yl)-1-isobutyl-3-methylpyridin-2(1H)-one (285);

5-(5-(1-(dimethylglycyl)piperidin-4-yl)-3-isopropyl-1H-indol-2-yl)-3-methoxy-1-methylpyridin-2(1H)-one (286);

5-(5-(1-(dimethylglycyl)piperidin-4-yl)-3-isopropyl-1H-indol-2-yl)-1-(2-methoxyethyl)-3-methylpyridin-2(1H)-one (287);

5-(5-(1-((2R,4S)-4-hydroxypyrrolidine-2-carbonyl)piperidin-4-yl)-3-isopropyl-1H-indol-2-yl)-1,3-dimethylpyridin-2(1H)-one (288);

5-(5-(1-((2S,4R)-4-hydroxy-1-methylpyrrolidine-2-carbonyl)piperidin-4-yl)-3-isopropyl-1H-indol-2-yl)-1,3-dimethylpyridin-2(1H)-one (289);

5-(5-(1-((2S,4R)-4-hydroxypyrrolidine-2-carbonyl)piperidin-4-yl)-3-isopropyl-1H-indol-2-yl)-1,3-dimethylpyridin-2(1H)-one (290);

5-(5-(1-((2S,3S)-3-hydroxypyrrolidine-2-carbonyl)piperidin-4-yl)-3-isopropyl-1H-indol-2-yl)-1,3-dimethylpyridin-2(1H)-one (291);

5-(5-(1-((2R,4S)-4-hydroxypyrrolidine-2-carbonyl)piperidin-4-yl)-3-isopropyl-1H-indol-2-yl)-1,3-dimethylpyridin-2(1H)-one (292);

5-(5-(1-((2S,4R)-4-hydroxypyrrolidine-2-carbonyl)piperidin-4-yl)-3-isopropyl-1H-indol-2-yl)-1,3-dimethylpyridin-2(1H)-one (293);

5-(5-(1-(2-amino-2-methylpropanoyl)piperidin-4-yl)-3-isopropyl-1H-indol-2-yl)-1,3-dimethylpyridin-2(1H)-one (296);

5-(3-isopropyl-5-(1-(methyl-L-alanyl)piperidin-4-yl)-1H-indol-2-yl)-1,3-dimethylpyridin-2(1H)-one (297);

5-(3-isopropyl-5-(1-(2-methyl-2-(methylamino)propanoyl)piperidin-4-yl)-1H-indol-2-yl)-1,3-dimethylpyridin-2(1H)-one (298);

5-(3-isopropyl-5-(1-(methyl-D-alanyl)piperidin-4-yl)-1H-indol-2-yl)-1,3-dimethylpyridin-2(1H)-one (299);

5-(3-isopropyl-5-(1-(2-(2-oxopyrrolidin-1-yl)acetyl)piperidin-4-yl)-1H-indol-2-yl)-1,3-dimethylpyridin-2(1H)-one (300);

5-(5-(1-(dimethylglycyl)piperidin-4-yl)-3-isopropyl-1H-indol-2-yl)-1-methylpyridin-2(1H)-one (301);

3-chloro-5-(3-isopropyl-5-(1-(2,2,2-trifluoroacetyl) piperidin-4-yl)-1H-indol-2-yl)-1,4-dimethylpyridin-2(1H)-one (302);

5-(5-(1-(3-hydroxy-3-methylbutanoyl)piperidin-4-yl)-3-isopropyl-1H-indol-2-yl)-1,3-dimethylpyridin-2(1H)-one (303);

5-(5-(1-(3-hydroxy-2,2-dimethylpropanoyl)piperidin-4-yl)-3-isopropyl-1H-indol-2-yl)-1,3-dimethylpyridin-2(1H)-one (304);

(S)-5-(5-(1-(3-hydroxybutanoyl) piperidin-4-yl)-3-isopropyl-1H-indol-2-yl)-1,3-dimethylpyridin-2(1H)-one (305);

(R)-5-(3-isopropyl-5-(1-(2-(pyrrolidin-2-yl)acetyl)piperidin-4-yl)-1H-indol-2-yl)-1,3-dimethylpyridin-2(1H)-one (306);

(S)-1-methylpyrrolidin-3-yl 4-(2-(5-chloro-1,4-dimethyl-6-oxo-1,6-dihydropyridin-3-yl)-3-isopropyl-1H-indol-5-yl)piperidine-1-carboxylate (307);

3-chloro-5-(3-isopropyl-5-(1-((2-(pyrrolidin-1-yl)ethyl) sulfonyl) piperidin-4-yl)-1H-indol-2-yl)-1,4-dimethylpyridin-2(1H)-one (308);

3-chloro-5-(5-(1-(2-hydroxy-2-methylpropyl)piperidin-4-yl)-3-isopropyl-1H-indol-2-yl)-1,4-dimethylpyridin-2(1H)-one (309);

5-(5-(1-(2-hydroxy-2-methylpropyl)piperidin-4-yl)-3-isopropyl-1H-indol-2-yl)-1,3-dimethylpyridin-2(1H)-one (310);

5-(5-(1-((3R,4S)-3-hydroxytetrahydro-2H-pyran-4-yl)piperidin-4-yl)-3-isopropyl-1H-indol-2-yl)-1,3-dimethylpyridin-2(1H)-one (313);

5-(5-(1-((3S,4S)-4-hydroxytetrahydro-2H-pyran-3-yl)piperidin-4-yl)-3-isopropyl-1H-indol-2-yl)-1,3-dimethylpyridin-2(1H)-one (314);

5-(5-(1-(2-hydroxy-2-methylpropyl)piperidin-4-yl)-3-isopropyl-1H-indol-2-yl)-1,3,4-trimethylpyridin-2(1H)-one (315);

5-(5-(1-(2-hydroxy-2-methylpropyl)piperidin-4-yl)-3-isopropyl-1H-indol-2-yl)-1,3,6-trimethylpyridin-2(1H)-one (316);

5-(5-(1-(2-hydroxy-2-methylpropyl) piperidin-4-yl)-3-isopropyl-1H-indol-2-yl)-3-methoxy-1,4-dimethylpyridin-2(1H)-one (317);

5-(5-(1-(2-hydroxy-2-methylpropyl)piperidin-4-yl)-3-isopropyl-1H-indol-2-yl)-3-methoxy-1,6-dimethylpyridin-2(1H)-one (318);

5-(5-(1-((4-hydroxytetrahydro-2H-pyran-4-yl)methyl)piperidin-4-yl)-3-isopropyl-1H-indol-2-yl)-1,3,4-trimethylpyridin-2(1H)-one (319);

5-(5-(1-((4-hydroxytetrahydro-2H-pyran-4-yl)methyl)piperidin-4-yl)-3-isopropyl-1H-indol-2-yl)-1,3,6-trimethylpyridin-2(1H)-one (320);

5-(5-(1-(2-hydroxy-2-methylpropyl)piperidin-4-yl)-3-isopropyl-1H-indol-2-yl)-1,6-dimethyl-2-oxo-1,2-dihydropyridine-3-carbonitrile (321);

5-(5-(1-(2-hydroxy-2-methylpropyl)piperidin-4-yl)-3-isopropyl-1H-indol-2-yl)-1,4-dimethyl-2-oxo-1,2-dihydropyridine-3-carbonitrile (322);

5-(5-(1-(2-hydroxy-2-methylpropyl)piperidin-4-yl)-3-isopropyl-1H-indol-2-yl)-3-(methoxymethyl)-1-methylpyridin-2(1H)-one (323);

5-(5-(1-(2-hydroxy-3-methylbutyl) piperidin-4-yl)-3-isopropyl-1H-indol-2-yl)-1,3-dimethylpyridin-2(1H)-one (324);

5-(5-(1-(2-hydroxy-3,3-dimethylbutyl)piperidin-4-yl)-3-isopropyl-1H-indol-2-yl)-1,3-dimethylpyridin-2(1H)-one (325);

5-(5-(1-(2-hydroxy-2-methylpropyl)piperidin-4-yl)-3-isopropyl-1H-indol-2-yl)-1-methyl-3-(pyrimidin-5-yl)pyridin-2(1H)-one (326);

3-chloro-5-(4-fluoro-5-(1-(2-hydroxy-2-methylpropyl)piperidin-4-yl)-3-isopropyl-1H-indol-2-yl)-1,4-dimethylpyridin-2(1H)-one (327);

5-(5-(1-(2-hydroxy-2-methylpropyl)piperidin-4-yl)-3-isopropyl-1H-indol-2-yl)-1-isobutyl-3-methylpyridin-2(1H)-one (328);

1-benzyl-5-(5-(1-(2-hydroxy-2-methylpropyl)piperidin-4-yl)-3-isopropyl-1H-indol-2-yl)-3-methylpyridin-2(1H)-one (329);

5-(3-isopropyl-5-(1-propylpiperidin-4-yl)-1H-indol-2-yl)-1-methyl-6'-morpholino-[3,3'-bipyridin]-2(1H)-one (330);

5-(3-isopropyl-5-(1-propylpiperidin-4-yl)-1H-indol-2-yl)-3-(2-methoxypyrimidin-5-yl)-1-methylpyridin-2(1H)-one (331);

5-(3-isopropyl-5-(1-propylpiperidin-4-yl)-1H-indol-2-yl)-1,5'-dimethyl-[3,3'-bipyridin]-2(1H)-one (332);

5-(3-isopropyl-5-(1-propylpiperidin-4-yl)-1H-indol-2-yl)-1,4-dimethyl-3-(1-methyl-1H-pyrazol-4-yl)pyridin-2(1H)-one (333);

5-(3-isopropyl-5-(1-propylpiperidin-4-yl)-1H-indol-2-yl)-1-methyl-3-(1-methyl-1H-pyrazol-4-yl) pyridin-2(1H)-one (334);

N-(5'-(3-isopropyl-5-(1-propylpiperidin-4-yl)-1H-indol-2-yl)-1'-methyl-2'-oxo-1',2'-dihydro-[3,3'-bipyridin]-6-yl)acetamide (335);

5-(3-isopropyl-5-(1-propylpiperidin-4-yl)-1H-indol-2-yl)-1-methyl-[3,4'-bipyridin]-2(1H)-one (336);

5-(3-isopropyl-5-(1-propylpiperidin-4-yl)-1H-indol-2-yl)-1-methyl-3-(2-methylpyrimidin-5-yl)pyridin-2(1H)-one (337);

3-(2-cyclopropylpyrimidin-5-yl)-5-(3-isopropyl-5-(1-propylpiperidin-4-yl)-1H-indol-2-yl)-1-methylpyridin-2(1H)-one (338);

5-(3-isopropyl-5-(1-propylpiperidin-4-yl)-1H-indol-2-yl)-1-methyl-3-(2-(trifluoromethyl)pyrimidin-5-yl)pyridin-2(1H)-one (339);

5-(3-isopropyl-5-(1-propylpiperidin-4-yl)-1H-indol-2-yl)-3-(3-methoxyphenyl)-1-methylpyridin-2(1H)-one (340);

6'-fluoro-5-(3-isopropyl-5-(1-propylpiperidin-4-yl)-1H-indol-2-yl)-1-methyl-[3,3'-bipyridin]-2(1H)-one (341);

6'-fluoro-5-(3-isopropyl-5-(1-isopropylpiperidin-4-yl)-1H-indol-2-yl)-1-methyl-[3,3'-bipyridin]-2(1H)-one (342);

6'-fluoro-5-(3-isopropyl-5-(1-isopropylpiperidin-4-yl)-1H-indol-2-yl)-1,5'-dimethyl-[3,3'-bipyridin]-2(1H)-one (343);

5-(3-isopropyl-5-(1-isopropylpiperidin-4-yl)-1H-indol-2-yl)-1,2'-dimethyl-[3,3'-bipyridin]-2(1H)-one (244);

5-(3-isopropyl-5-(1-(tetrahydro-2H-pyran-4-yl)piperidin-4-yl)-1H-indol-2-yl)-3-(methoxymethyl)-1-methylpyridin-2(1H)-one (345);

5-(3-isopropyl-5-(1-(oxetan-3-yl) piperidin-4-yl)-1H-indol-2-yl)-3-(methoxymethyl)-1-methylpyridin-2(1H)-one (346);

5-(3-isopropyl-5-(1-isopropylpiperidin-4-yl)-1H-indol-2-yl)-3-(methoxymethyl)-1-methylpyridin-2(1H)-one (347);

5-(3-isopropyl-5-(1-propylpiperidin-4-yl)-1H-indol-2-yl)-3-(methoxymethyl)-1-methylpyridin-2(1H)-one (348);

5-(3-isopropyl-5-(1-(2-methoxyethyl)piperidin-4-yl)-1H-indol-2-yl)-1,6'-dimethyl-[3,3'-bipyridin]-2(1H)-one (349);

5-(3-isopropyl-5-(1-(2-methoxyethyl)piperidin-4-yl)-1H-indol-2-yl)-1-methyl-3-(1-methyl-1H-pyrazol-4-yl)pyridin-2(1H)-one (350);

2-(4-(3-isopropyl-2-(5-(methoxymethyl)-1-methyl-6-oxo-1,6-dihydropyridin-3-yl)-1H-indol-5-yl)piperidin-1-yl)-N,N-dimethylacetamide (351);

2-(4-(3-isopropyl-2-(1-methyl-6-oxo-5-vinyl-1,6-dihydropyridin-3-yl)-1H-indol-5-yl)piperidin-1-yl)-N,N-dimethylacetamide (352); and 5-(3-isopropyl-5-(piperidin-4-yl)-1H-indol-2-yl)-3-(methoxymethyl)-1-methylpyridin-2(1H)-one (353).

7. A method of treating an autoimmune disease or a chronic inflammatory disease, comprising administering to a mammalian patent a compound according to claim 1 or a pharmaceutically acceptable salt thereof, wherein said autoimmune disease or chronic inflammatory disease is selected from systemic lupus erythematosus (SLE), rheumatoid arthritis, multiple sclerosis (MS), and Sjögren's syndrome.

* * * * *

UNITED STATES PATENT AND TRADEMARK OFFICE
CERTIFICATE OF CORRECTION

PATENT NO.         : 11,447,466 B2                                        Page 1 of 1
APPLICATION NO.    : 16/635593
DATED              : September 20, 2022
INVENTOR(S)        : Alaric Dyckman et al.

It is certified that error appears in the above-identified patent and that said Letters Patent is hereby corrected as shown below:

In the Claims

Claim 6, Column 217, Line 9 (Approx.), delete "(241);" and insert -- (239); --.

Claim 6, Column 219, Line 53, delete "3-yl 4-(2-" and insert -- 3-yl-4-(2- --.

Signed and Sealed this
Sixteenth Day of September, 2025

Coke Morgan Stewart
*Acting Director of the United States Patent and Trademark Office*